(12) United States Patent
Tavazoie et al.

(10) Patent No.: US 10,337,065 B2
(45) Date of Patent: Jul. 2, 2019

(54) TRNA QUANTIFICATION

(71) Applicant: The Rockefeller University, New York, NY (US)

(72) Inventors: Sohail Tavazoie, New York, NY (US); Hani Goodarzi, New York, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 0 days.

(21) Appl. No.: 15/487,192

(22) Filed: Apr. 13, 2017

(65) Prior Publication Data

US 2017/0298433 A1 Oct. 19, 2017

Related U.S. Application Data

(60) Provisional application No. 62/321,973, filed on Apr. 13, 2016.

(51) Int. Cl.
*C12Q 1/6809* (2018.01)
*C12Q 1/6869* (2018.01)
*C12Q 1/6876* (2018.01)

(52) U.S. Cl.
CPC ......... *C12Q 1/6876* (2013.01); *C12Q 1/6809* (2013.01); *C12Q 2600/178* (2013.01)

(58) Field of Classification Search
CPC .................. C12Q 1/6869; C12N 2800/22
See application file for complete search history.

(56) References Cited

PUBLICATIONS

Pavon-Eternod et al. tRNA over-expression in breast cancer and functional consequences. Nucleic Acids Research, vol. 37, No. 21, pp. 7268-7280, Sep. 2009, including supplemental Tables S1-5 and S8. (Year: 2009).*
Borodina et al. Ligation detection reaction-TaqMan procedure for single nucleotide polymorphism detection on genomic DNA. Analytical Biochemistry, vol. 333, pp. 309-319, 2004. (Year: 2004).*
Fuglsang. Codon optimizer: a freeware tool for codon optimization. Protein Expression and Purification, vol. 31, pp. 247-249, 2003. (Year: 2003).*
Dittmar, K.A. et al., Tissue-Specific Differences in Human Transfer RNA Expression, Dec. 2006, PLoS Genetics 2, e221, pp. 2107-2115.
Geslain, R. et al., Functional Analysis of Human tRNA Isodecoders. J. Mol. Biol., Feb. 26, 2010, 396(3): 821 DOI:101016/jmb.2009.12.018, pp. 1-20.
Zheng, G. et al., efficient and quantitative high-throughput tRNA sequencing, Nature Methods, Sep. 2015, 12(9): pp. 835-837 online methods.

* cited by examiner

*Primary Examiner* — Jennifer Dunston
(74) *Attorney, Agent, or Firm* — Hoffmann & Baron, LLP

(57) ABSTRACT

In one embodiment, the present invention relates to a method for optimizing cell-type specific protein expression. In another embodiment, the present invention relates to a method for creating a tRNA profile of a cell.

19 Claims, 43 Drawing Sheets
(43 of 43 Drawing Sheet(s) Filed in Color)

Specification includes a Sequence Listing.

Figure 5A  Figure 5B

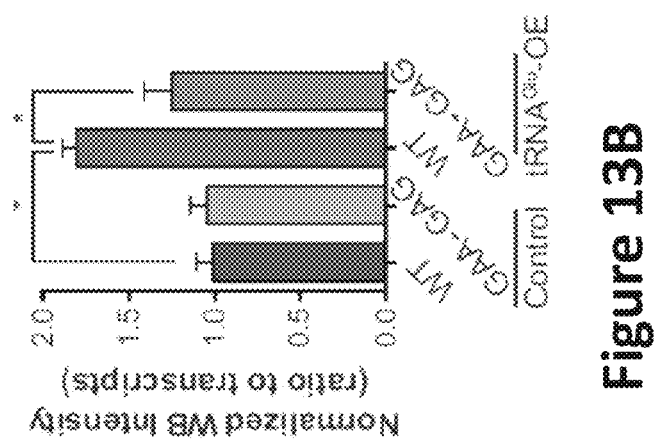
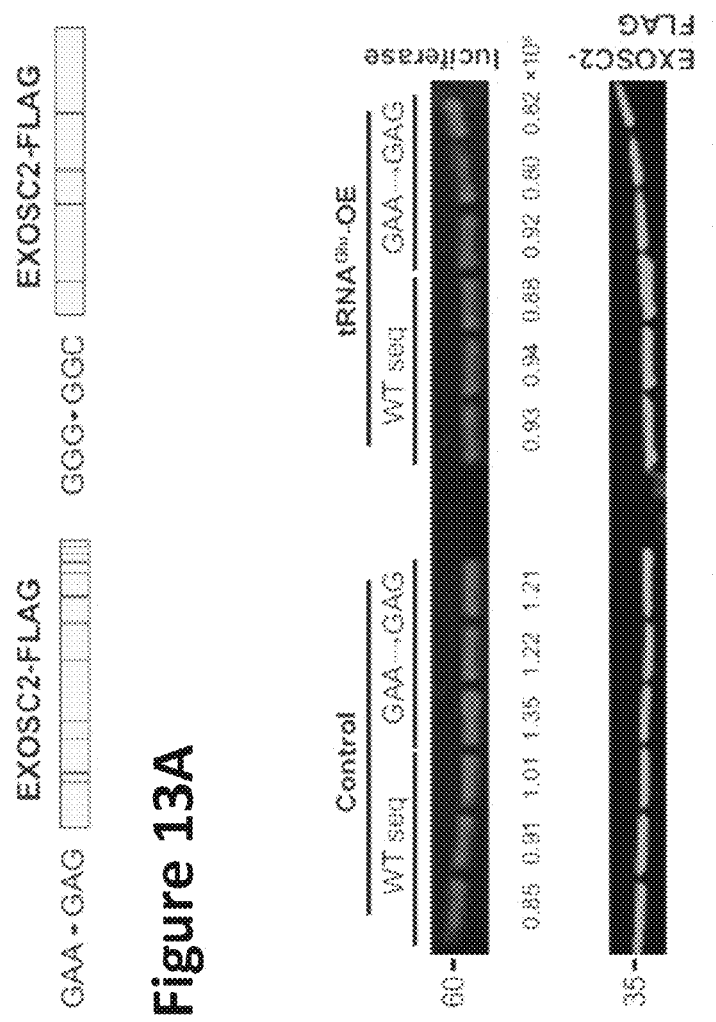
Figure 13A
Figure 13B
Figure 13C chr6.trna105-Ala-AGC_33-35

True-seq smRNA RNA PCR Primer (RP1)
AATGATACGGCGACCACCGAGATCTACACGTTCAGAGTTCTACAGTCCGA
                                              3'-CTCAAGATGTCAGGTCGTAGCCCCACATCCCACATCCGATCGCYACGAATCGTACRTR
                                                                5'-GGGGGTATAGCTTCAGCGGTAGAGCGCGTGCTTAGCATGCAC RNA PCR Primer, Index 1 (RPI1)
                                                                                                             GGTACCTTAAGAGACCCCACGGTTCCTTGAGGTCAAGTTAGTCCTAGAGCATACGGCAGAAGACGAAC-5'
CTCCGGGCCCAAGTTAGGGGTCGTGGAGGTGGTACCTTAAGAGAGCCCACG-'5
GAGGCCTGGGTTCAATCCCCAATACCTCCA-3'

Figure 15

```
                            SEQUENCE LISTING

<160> NUMBER OF SEQ ID NOS: 397

<210> SEQ ID NO 1
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1
gagttctaca gtccgacgat c                                             21

<210> SEQ ID NO 2
<211> LENGTH: 19
<212> TYPE: DNA
<213> ORGANISM: Artificial Sequence
<220> FEATURE:
<223> OTHER INFORMATION: Synthetic sequence

<400> SEQUENCE: 2
ccatggaatt ctcgggtgc                                                19

<210> SEQ ID NO 3
<211> LENGTH: 19
<212> TYPE: DNA
<213> ORGANISM: Artificial Sequence
<220> FEATURE:
<223> OTHER INFORMATION: Synthetic sequence

<400> SEQUENCE: 3
cacgacgctc ttccgatct                                                19

<210> SEQ ID NO 4
<211> LENGTH: 18
<212> TYPE: DNA
<213> ORGANISM: Artificial Sequence
<220> FEATURE:
<223> OTHER INFORMATION: Synthetic sequence

<400> SEQUENCE: 4
ttctttgcag tgtcgtgg                                                 18

<210> SEQ ID NO 5
<211> LENGTH: 51
<212> TYPE: DNA
<213> ORGANISM: Artificial Sequence
<220> FEATURE:
<223> OTHER INFORMATION: Synthetic sequence

<400> SEQUENCE: 5
ggtagtagcg acgggcggtg tgtacaaagg gcagatcgga agagcgtcgt g            51

<210> SEQ ID NO 6
<211> LENGTH: 50
<212> TYPE: DNA
<213> ORGANISM: Artificial Sequence
```

```
<220> FEATURE:
<223> OTHER INFORMATION: Synthetic sequence

<400> SEQUENCE: 6
ttctttgcag tgtcgtggcc gatccgaggg cctcactaaa ccatccaatc          50

<210> SEQ ID NO 7
<211> LENGTH: 19
<212> TYPE: DNA
<213> ORGANISM: Artificial Sequence
<220> FEATURE:
<223> OTHER INFORMATION: Synthetic sequence

<400> SEQUENCE: 7
tggctcgcaa gcctcttag                                            19

<210> SEQ ID NO 8
<211> LENGTH: 23
<212> TYPE: DNA
<213> ORGANISM: Artificial Sequence
<220> FEATURE:
<223> OTHER INFORMATION: Synthetic sequence

<400> SEQUENCE: 8
tgtgtccgta gtgattgtat ccc                                       23

<210> SEQ ID NO 9
<211> LENGTH: 23
<212> TYPE: DNA
<213> ORGANISM: Artificial Sequence
<220> FEATURE:
<223> OTHER INFORMATION: Synthetic sequence

<400> SEQUENCE: 9
ggacaaacaa ctaccagctt tca                                       23

<210> SEQ ID NO 10
<211> LENGTH: 20
<212> TYPE: DNA
<213> ORGANISM: Artificial Sequence
<220> FEATURE:
<223> OTHER INFORMATION: Synthetic sequence

<400> SEQUENCE: 10
gcgaccttct gtcgaagact                                           20

<210> SEQ ID NO 11
<211> LENGTH: 22
<212> TYPE: DNA
<213> ORGANISM: Artificial Sequence
<220> FEATURE:
<223> OTHER INFORMATION: Synthetic sequence

<400> SEQUENCE: 11
aatgaatccc aacagtccct ct                                        22

<210> SEQ ID NO 12
<211> LENGTH: 20
<212> TYPE: DNA
<213> ORGANISM: Artificial Sequence
<220> FEATURE:
<223> OTHER INFORMATION: Synthetic sequence

<400> SEQUENCE: 12
cagctcggta aaccaggcag                                           20
```

```
<210> SEQ ID NO 13
<211> LENGTH: 23
<212> TYPE: DNA
<213> ORGANISM: Artificial Sequence
<220> FEATURE:
<223> OTHER INFORMATION: Synthetic sequence

<400> SEQUENCE: 13
cggttcatgc tattattcag ccg                                              23

<210> SEQ ID NO 14
<211> LENGTH: 20
<212> TYPE: DNA
<213> ORGANISM: Artificial Sequence
<220> FEATURE:
<223> OTHER INFORMATION: Synthetic sequence

<400> SEQUENCE: 14
ccgttccttg tccgaagtgg                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic sequence

<400> SEQUENCE: 15
accaaccaga tccgcctaac                                                  20

<210> SEQ ID NO 16
<211> LENGTH: 22
<212> TYPE: DNA
<213> ORGANISM: Artificial Sequence
<220> FEATURE:
<223> OTHER INFORMATION: Synthetic sequence

<400> SEQUENCE: 16
cgacgacctt gttttttgtag ca                                              22

<210> SEQ ID NO 17
<211> LENGTH: 23
<212> TYPE: DNA
<213> ORGANISM: Artificial Sequence
<220> FEATURE:
<223> OTHER INFORMATION: Synthetic sequence

<400> SEQUENCE: 17
aactgcatca tctcgctggt aac                                              23

<210> SEQ ID NO 18
<211> LENGTH: 23
<212> TYPE: DNA
<213> ORGANISM: Artificial Sequence
<220> FEATURE:
<223> OTHER INFORMATION: Synthetic sequence

<400> SEQUENCE: 18
cttgtcgtca tcgtctttgt agt                                              23

<210> SEQ ID NO 19
<211> LENGTH: 17
<212> TYPE: DNA
<213> ORGANISM: Artificial Sequence
<220> FEATURE:
<223> OTHER INFORMATION: Synthetic sequence
```

```
<400> SEQUENCE: 19
ctgaccggca agctgga                                                    17

<210> SEQ ID NO 20
<211> LENGTH: 27
<212> TYPE: DNA
<213> ORGANISM: Artificial Sequence
<220> FEATURE:
<223> OTHER INFORMATION: Synthetic sequence

<400> SEQUENCE: 20
gactctagaa ttattacacg gcgatct                                         27

<210> SEQ ID NO 21
<211> LENGTH: 21
<212> TYPE: DNA
<213> ORGANISM: Artificial Sequence
<220> FEATURE:
<223> OTHER INFORMATION: Synthetic sequence

<400> SEQUENCE: 21
gagttctaca gtccgacgat c                                               21

<210> SEQ ID NO 22
<211> LENGTH: 19
<212> TYPE: DNA
<213> ORGANISM: Artificial Sequence
<220> FEATURE:
<223> OTHER INFORMATION: Synthetic sequence

<400> SEQUENCE: 22
ccatggaatt ctcgggtgc                                                  19

<210> SEQ ID NO 23
<211> LENGTH: 58
<212> TYPE: DNA
<213> ORGANISM: Artificial Sequence
<220> FEATURE:
<223> OTHER INFORMATION: mm10_Ala_AGC-1_33_R

<400> SEQUENCE: 23
gcacccgaga attccatgga tggagatgct ggggctcgaa cccagrcybc rhrcaygc       58

<210> SEQ ID NO 24
<211> LENGTH: 57
<212> TYPE: DNA
<213> ORGANISM: Artificial Sequence
<220> FEATURE:
<223> OTHER INFORMATION: mm10_Ala_AGC-2_33_R

<400> SEQUENCE: 24
gcacccgaga attccatggt ggaggatgtg ggcatcgatc ccawkcctcd yrcatgc        57

<210> SEQ ID NO 25
<211> LENGTH: 57
<212> TYPE: DNA
<213> ORGANISM: Artificial Sequence
<220> FEATURE:
<223> OTHER INFORMATION: mm10_Ala_CGC-2_32_R

<400> SEQUENCE: 25
gcacccgaga attccatggt ggagatgccg ggagtcgaac ccgggccsca yacatgc        57

<210> SEQ ID NO 26
```

```
<211> LENGTH: 57
<212> TYPE: DNA
<213> ORGANISM: Artificial Sequence
<220> FEATURE:
<223> OTHER INFORMATION: mm10_Ala_CGC_32_R

<400> SEQUENCE: 26
gcacccgaga attccatggt ggagatgccg ggagtcgaac ccgggccsca yacatgc      57

<210> SEQ ID NO 27
<211> LENGTH: 57
<212> TYPE: DNA
<213> ORGANISM: Artificial Sequence
<220> FEATURE:
<223> OTHER INFORMATION: mm10_Ala_TGC_32_R

<400> SEQUENCE: 27
gcacccgaga attccatggt ggagatgccg ggaatcgaac ccggkccyca trcatgc      57

<210> SEQ ID NO 28
<211> LENGTH: 57
<212> TYPE: DNA
<213> ORGANISM: Artificial Sequence
<220> FEATURE:
<223> OTHER INFORMATION: mm10_Arg_ACG_32_R

<400> SEQUENCE: 28
gcacccgaga attccatggc gagccagcca ggagtcgaac ctggatcttc tgatccg      57

<210> SEQ ID NO 29
<211> LENGTH: 57
<212> TYPE: DNA
<213> ORGANISM: Artificial Sequence
<220> FEATURE:
<223> OTHER INFORMATION: mm10_Arg_CCG_32_R

<400> SEQUENCE: 29
gcacccgaga attccatggc gaccacgaag ggactcgaac cctcatcyyc sgmtccg      57

<210> SEQ ID NO 30
<211> LENGTH: 57
<212> TYPE: DNA
<213> ORGANISM: Artificial Sequence
<220> FEATURE:
<223> OTHER INFORMATION: mm10_Arg_CCT_32_R

<400> SEQUENCE: 30
gcacccgaga attccatggc accccaggtg ggactcgaac ccacatccct ggcttag      57

<210> SEQ ID NO 31
<211> LENGTH: 57
<212> TYPE: DNA
<213> ORGANISM: Artificial Sequence
<220> FEATURE:
<223> OTHER INFORMATION: mm10_Arg_TCG_32_R

<400> SEQUENCE: 31
gcacccgaga attccatggc aaccacgaag ggattcgaac cctcatcttc tgatccg      57

<210> SEQ ID NO 32
<211> LENGTH: 57
<212> TYPE: DNA
<213> ORGANISM: Artificial Sequence
<220> FEATURE:
<223> OTHER INFORMATION: mm10_Arg_TCT_32_R

<400> SEQUENCE: 32
```
gcacccgaga attccatgga gggggcacct ggatttgaac cagggycyck tratctg        57

<210> SEQ ID NO 33
<211> LENGTH: 57
<212> TYPE: DNA
<213> ORGANISM: Artificial Sequence
<220> FEATURE:
<223> OTHER INFORMATION: mm10_Asn_GTT_33_R

<400> SEQUENCE: 33
gcacccgaga attccatggc gtccctgggt gggctcgaac caccaccty yrgttaa        57

<210> SEQ ID NO 34
<211> LENGTH: 57
<212> TYPE: DNA
<213> ORGANISM: Artificial Sequence
<220> FEATURE:
<223> OTHER INFORMATION: mm10_Asp_GTC_32_R

<400> SEQUENCE: 34
gcacccgaga attccatggc tccccgtcgg ggaatcgaac cccggtwtcc ygygtga        57

<210> SEQ ID NO 35
<211> LENGTH: 57
<212> TYPE: DNA
<213> ORGANISM: Artificial Sequence
<220> FEATURE:
<223> OTHER INFORMATION: mm10_Cys_GCA_32_R

<400> SEQUENCE: 35
gcacccgaga attccatgga gggggcacct ggatttgaac cagggycyck tratctg        57

<210> SEQ ID NO 36
<211> LENGTH: 57
<212> TYPE: DNA
<213> ORGANISM: Artificial Sequence
<220> FEATURE:
<223> OTHER INFORMATION: mm10_Gln_CTG_32_R

<400> SEQUENCE: 36
gcacccgaga attccatgga ggtcccaccg agatttgaac tcggrtcgct ggattca        57

<210> SEQ ID NO 37
<211> LENGTH: 57
<212> TYPE: DNA
<213> ORGANISM: Artificial Sequence
<220> FEATURE:
<223> OTHER INFORMATION: mm10_Gln_TTG_32_R

<400> SEQUENCE: 37
gcacccgaga attccatgga ggtcccaccg agatttgaac tcggatygct ggaytca        57

<210> SEQ ID NO 38
<211> LENGTH: 57
<212> TYPE: DNA
<213> ORGANISM: Artificial Sequence
<220> FEATURE:
<223> OTHER INFORMATION: mm10_Glu_CTC_32_R

<400> SEQUENCE: 38
gcacccgaga attccatggt tccctgaccg ggaatcgaac ccgggcmryg whggtga        57

<210> SEQ ID NO 39
<211> LENGTH: 57
<212> TYPE: DNA

```
<213> ORGANISM: Artificial Sequence
<220> FEATURE:
<223> OTHER INFORMATION: mm10_Glu_TTC-1_32_R

<400> SEQUENCE: 39
gcacccgaga attccatggt tcccacaccg ggagtcgaac ccgggccgcc tgggtga      57

<210> SEQ ID NO 40
<211> LENGTH: 57
<212> TYPE: DNA
<213> ORGANISM: Artificial Sequence
<220> FEATURE:
<223> OTHER INFORMATION: mm10_Glu_TTC-2_32_R

<400> SEQUENCE: 40
gcacccgaga attccatggt tccctgaccg ggaatcgaac ccgggccgcg gcggtga      57

<210> SEQ ID NO 41
<211> LENGTH: 57
<212> TYPE: DNA
<213> ORGANISM: Artificial Sequence
<220> FEATURE:
<223> OTHER INFORMATION: mm10_Gly_ACC_33_R

<400> SEQUENCE: 41
gcacccgaga attccatggt gtttccgccc ggtttcgaac cggggccttt cgcttgg      57

<210> SEQ ID NO 42
<211> LENGTH: 57
<212> TYPE: DNA
<213> ORGANISM: Artificial Sequence
<220> FEATURE:
<223> OTHER INFORMATION: mm10_Gly_CCC-1_32_R

<400> SEQUENCE: 42
gcacccgaga attccatggt gcgccgcccg ggaatcgaac ccgggtcgca agaatgg      57

<210> SEQ ID NO 43
<211> LENGTH: 57
<212> TYPE: DNA
<213> ORGANISM: Artificial Sequence
<220> FEATURE:
<223> OTHER INFORMATION: mm10_Gly_CCC-2_32_R

<400> SEQUENCE: 43
gcacccgaga attccatggt gcattggccg ggaatcgaac ccgggtcmcc crhgtgg      57

<210> SEQ ID NO 44
<211> LENGTH: 57
<212> TYPE: DNA
<213> ORGANISM: Artificial Sequence
<220> FEATURE:
<223> OTHER INFORMATION: mm10_Gly_CCC-3_32_R

<400> SEQUENCE: 44
gcacccgaga attccatggt gcgccgcccg ggaatcgaac ccgggtcgca agaatgg      57

<210> SEQ ID NO 45
<211> LENGTH: 57
<212> TYPE: DNA
<213> ORGANISM: Artificial Sequence
<220> FEATURE:
<223> OTHER INFORMATION: mm10_Gly_CCC_32_R

<400> SEQUENCE: 45
gcacccgaga attccatggt gcattggccg ggaatcgaac ccgggtcmcc crhgtgg      57
```

<210> SEQ ID NO 46
<211> LENGTH: 57
<212> TYPE: DNA
<213> ORGANISM: Artificial Sequence
<220> FEATURE:
<223> OTHER INFORMATION: mm10_Gly_GCC_32_R

<400> SEQUENCE: 46
gcacccgaga attccatggt gcattggccg ggaatcgaac ccgggcctcc cgwgtgg    57

<210> SEQ ID NO 47
<211> LENGTH: 57
<212> TYPE: DNA
<213> ORGANISM: Artificial Sequence
<220> FEATURE:
<223> OTHER INFORMATION: mm10_Gly_TCC_32_R

<400> SEQUENCE: 47
gcacccgaga attccatggt gcgttggccg ggaatcgaac ccgggtcaac tgcttgg    57

<210> SEQ ID NO 48
<211> LENGTH: 57
<212> TYPE: DNA
<213> ORGANISM: Artificial Sequence
<220> FEATURE:
<223> OTHER INFORMATION: mm10_His_ATG_33_R

<400> SEQUENCE: 48
gcacccgaga attccatggc gagccagaca ggagtcgaac ctagatcttc tgatcca    57

<210> SEQ ID NO 49
<211> LENGTH: 57
<212> TYPE: DNA
<213> ORGANISM: Artificial Sequence
<220> FEATURE:
<223> OTHER INFORMATION: mm10_His_GTG_32_R

<400> SEQUENCE: 49
gcacccgaga attccatggt gccgtgactc ggattcgaac cgaggttgct gcrgcca    57

<210> SEQ ID NO 50
<211> LENGTH: 57
<212> TYPE: DNA
<213> ORGANISM: Artificial Sequence
<220> FEATURE:
<223> OTHER INFORMATION: mm10_Ile_AAT_33_R

<400> SEQUENCE: 50
gcacccgaga attccatggt ggcccgtacg gggatcgaac ccgyrccttg gcgttat    57

<210> SEQ ID NO 51
<211> LENGTH: 57
<212> TYPE: DNA
<213> ORGANISM: Artificial Sequence
<220> FEATURE:
<223> OTHER INFORMATION: mm10_Ile_GAT_34_R

<400> SEQUENCE: 51
gcacccgaga attccatggt gacctgtacg gggaacgaac ccacgacttg gcattat    57

<210> SEQ ID NO 52
<211> LENGTH: 57
<212> TYPE: DNA
<213> ORGANISM: Artificial Sequence
<220> FEATURE:

<223> OTHER INFORMATION: mm10_Ile_TAT-1_33_R

<400> SEQUENCE: 52
gcacccgaga attccatggt gctccaggtg aggctcgaac tcacacctcg gcattat      57

<210> SEQ ID NO 53
<211> LENGTH: 55
<212> TYPE: DNA
<213> ORGANISM: Artificial Sequence
<220> FEATURE:
<223> OTHER INFORMATION: mm10_Ile_TAT-2_33_R

<400> SEQUENCE: 53
gcacccgaga attccatggt agttccactg gggctcaaac tcaggccttc tgcat        55

<210> SEQ ID NO 54
<211> LENGTH: 57
<212> TYPE: DNA
<213> ORGANISM: Artificial Sequence
<220> FEATURE:
<223> OTHER INFORMATION: mm10_Leu_AAG-1_32_R

<400> SEQUENCE: 54
gcacccgaga attccatggg gactcgtcca agctttgaac ccaggcttct cagacct      57

<210> SEQ ID NO 55
<211> LENGTH: 60
<212> TYPE: DNA
<213> ORGANISM: Artificial Sequence
<220> FEATURE:
<223> OTHER INFORMATION: mm10_Leu_AAG-2_32_R

<400> SEQUENCE: 55
gcacccgaga attccatggc ggtgggattc gaacccacgc ccccgaagag actggagcct   60

<210> SEQ ID NO 56
<211> LENGTH: 60
<212> TYPE: DNA
<213> ORGANISM: Artificial Sequence
<220> FEATURE:
<223> OTHER INFORMATION: mm10_Leu_CAA_32_R

<400> SEQUENCE: 56
gcacccgaga attccatggg tgggattcga acccacgcct ccabdcggag accagaactt   60

<210> SEQ ID NO 57
<211> LENGTH: 60
<212> TYPE: DNA
<213> ORGANISM: Artificial Sequence
<220> FEATURE:
<223> OTHER INFORMATION: mm10_Leu_CAG_32_R

<400> SEQUENCE: 57
gcacccgaga attccatgga gtgggattcg aacccacgcc tccaggggag actgcgacct   60

<210> SEQ ID NO 58
<211> LENGTH: 60
<212> TYPE: DNA
<213> ORGANISM: Artificial Sequence
<220> FEATURE:
<223> OTHER INFORMATION: mm10_Leu_TAA-1_32_R

<400> SEQUENCE: 58
gcacccgaga attccatggg tggggttcga acccacgcag ryasmhrycc attggatctt   60

```
<210> SEQ ID NO 59
<211> LENGTH: 57
<212> TYPE: DNA
<213> ORGANISM: Artificial Sequence
<220> FEATURE:
<223> OTHER INFORMATION: mm10_Leu_TAA-2_34_R

<400> SEQUENCE: 59
gcacccgaga attccatggt attagggaga ggatttgaac ctctggaaca aggtttt      57

<210> SEQ ID NO 60
<211> LENGTH: 60
<212> TYPE: DNA
<213> ORGANISM: Artificial Sequence
<220> FEATURE:
<223> OTHER INFORMATION: mm10_Leu_TAG_32_R

<400> SEQUENCE: 60
gcacccgaga attccatggc ggtgggattc gaacccacgc csycgaarsg actggagcct   60

<210> SEQ ID NO 61
<211> LENGTH: 57
<212> TYPE: DNA
<213> ORGANISM: Artificial Sequence
<220> FEATURE:
<223> OTHER INFORMATION: mm10_Lys_CTT-1_33_R

<400> SEQUENCE: 61
gcacccgaga attccatggt gcccaacgtg gggcttgaac ccaygcyctg rgattaa      57

<210> SEQ ID NO 62
<211> LENGTH: 57
<212> TYPE: DNA
<213> ORGANISM: Artificial Sequence
<220> FEATURE:
<223> OTHER INFORMATION: mm10_Lys_CTT-2_33_R

<400> SEQUENCE: 62
gcacccgaga attccatggc gcccaacgtg gggctcgaac ccaygccctr rgaytaa      57

<210> SEQ ID NO 63
<211> LENGTH: 57
<212> TYPE: DNA
<213> ORGANISM: Artificial Sequence
<220> FEATURE:
<223> OTHER INFORMATION: mm10_Lys_CTT_33_R

<400> SEQUENCE: 63
gcacccgaga attccatggc gcccaacgtg gggctcgaac ccaygcyctr rgaytaa      57

<210> SEQ ID NO 64
<211> LENGTH: 57
<212> TYPE: DNA
<213> ORGANISM: Artificial Sequence
<220> FEATURE:
<223> OTHER INFORMATION: mm10_Lys_TTT-1_32_R

<400> SEQUENCE: 64
gcacccgaga attccatggt gctcgatgtg gggcttgaac cttwrwcctw agattaa      57

<210> SEQ ID NO 65
<211> LENGTH: 57
<212> TYPE: DNA
<213> ORGANISM: Artificial Sequence
<220> FEATURE:
<223> OTHER INFORMATION: mm10_Lys_TTT-2_32_R
```

<400> SEQUENCE: 65
gcacccgaga attccatggc gcccgaacag ggacttgaac cctgrccctc agattaa    57

<210> SEQ ID NO 66
<211> LENGTH: 57
<212> TYPE: DNA
<213> ORGANISM: Artificial Sequence
<220> FEATURE:
<223> OTHER INFORMATION: mm10_Lys_TTT_32_R

<400> SEQUENCE: 66
gcacccgaga attccatggc gcccgaacag ggacttgaac cctwrwcctw agattaa    57

<210> SEQ ID NO 67
<211> LENGTH: 57
<212> TYPE: DNA
<213> ORGANISM: Artificial Sequence
<220> FEATURE:
<223> OTHER INFORMATION: mm10_Met_CAT-1_32_R

<400> SEQUENCE: 67
gcacccgaga attccatggt agcagaggat ggtttcgatc catcgcctct gggttat    57

<210> SEQ ID NO 68
<211> LENGTH: 57
<212> TYPE: DNA
<213> ORGANISM: Artificial Sequence
<220> FEATURE:
<223> OTHER INFORMATION: mm10_Met_CAT-2_33_R

<400> SEQUENCE: 68
gcacccgaga attccatggt gcccctctg aggttcgaac tcawgyctyc sgsttat    57

<210> SEQ ID NO 69
<211> LENGTH: 57
<212> TYPE: DNA
<213> ORGANISM: Artificial Sequence
<220> FEATURE:
<223> OTHER INFORMATION: mm10_Phe_GAA_33_R

<400> SEQUENCE: 69
gcacccgaga attccatggt gccgaaaccc gggatcgaac cagggccttt agatctt    57

<210> SEQ ID NO 70
<211> LENGTH: 57
<212> TYPE: DNA
<213> ORGANISM: Artificial Sequence
<220> FEATURE:
<223> OTHER INFORMATION: mm10_Pro_AGG_32_R

<400> SEQUENCE: 70
gcacccgaga attccatggg ggctcgtccg ggatttgaac ccgggcctct crcaccc    57

<210> SEQ ID NO 71
<211> LENGTH: 57
<212> TYPE: DNA
<213> ORGANISM: Artificial Sequence
<220> FEATURE:
<223> OTHER INFORMATION: mm10_Pro_CGG_32_R

<400> SEQUENCE: 71
gcacccgaga attccatggg ggctcgtccg ggatttgaac ccgggcctct cgcaccc    57

<210> SEQ ID NO 72
<211> LENGTH: 57

<212> TYPE: DNA
<213> ORGANISM: Artificial Sequence
<220> FEATURE:
<223> OTHER INFORMATION: mm10_Pro_TGG_32_R

<400> SEQUENCE: 72
gcacccgaga attccatggg ggctcgtccg ggatttgaac ccgggcctct cdvaccc        57

<210> SEQ ID NO 73
<211> LENGTH: 60
<212> TYPE: DNA
<213> ORGANISM: Artificial Sequence
<220> FEATURE:
<223> OTHER INFORMATION: mm10_SeC(e)_TCA_36_R

<400> SEQUENCE: 73
gcacccgaga attccatggg tggaattgaa ccactctgtc gctaaacagc tacaggtttg     60

<210> SEQ ID NO 74
<211> LENGTH: 56
<212> TYPE: DNA
<213> ORGANISM: Artificial Sequence
<220> FEATURE:
<223> OTHER INFORMATION: mm10_SeC_TCA_32_R

<400> SEQUENCE: 74
gcacccgaga attccatggc gcccaatgtg gggctcgaac ccacaccctg agattg         56

<210> SEQ ID NO 75
<211> LENGTH: 60
<212> TYPE: DNA
<213> ORGANISM: Artificial Sequence
<220> FEATURE:
<223> OTHER INFORMATION: mm10_Ser_AGA_32_R

<400> SEQUENCE: 75
gcacccgaga attccatggg gcaggattcg aacctgcgcg gggaracccc aatggatttc     60

<210> SEQ ID NO 76
<211> LENGTH: 60
<212> TYPE: DNA
<213> ORGANISM: Artificial Sequence
<220> FEATURE:
<223> OTHER INFORMATION: mm10_Ser_CGA_32_R

<400> SEQUENCE: 76
gcacccgaga attccatgga gcaggattcg aacctgcgcg ggraramccc attggatttc     60

<210> SEQ ID NO 77
<211> LENGTH: 60
<212> TYPE: DNA
<213> ORGANISM: Artificial Sequence
<220> FEATURE:
<223> OTHER INFORMATION: mm10_Ser_GCT_32_R

<400> SEQUENCE: 77
gcacccgaga attccatggg atgggattcg aaccacgcr trcsragcac artggattag     60

<210> SEQ ID NO 78
<211> LENGTH: 57
<212> TYPE: DNA
<213> ORGANISM: Artificial Sequence
<220> FEATURE:
<223> OTHER INFORMATION: mm10_Ser_GGA_34_R

<400> SEQUENCE: 78
gcacccgaga attccatggt gccgaaaccc gggatcaaac cagggccttt agatctc        57

<210> SEQ ID NO 79
<211> LENGTH: 60
<212> TYPE: DNA
<213> ORGANISM: Artificial Sequence
<220> FEATURE:
<223> OTHER INFORMATION: mm10_Ser_TGA_32_R

<400> SEQUENCE: 79
gcacccgaga attccatggg gcaggattcg aacctgcgcg ggaraccccc astggatttc       60

<210> SEQ ID NO 80
<211> LENGTH: 60
<212> TYPE: DNA
<213> ORGANISM: Artificial Sequence
<220> FEATURE:
<223> OTHER INFORMATION: mm10_Sup_TTA_33_R

<400> SEQUENCE: 80
gcacccgaga attccatggg tggggtttga acccacgcag gcatccgccc attggatcta       60

<210> SEQ ID NO 81
<211> LENGTH: 57
<212> TYPE: DNA
<213> ORGANISM: Artificial Sequence
<220> FEATURE:
<223> OTHER INFORMATION: mm10_Thr_AGT_33_R

<400> SEQUENCE: 81
gcacccgaga attccatgga ggcaccgctg ggattcgaac ccaggtctcc tgtttac        57

<210> SEQ ID NO 82
<211> LENGTH: 57
<212> TYPE: DNA
<213> ORGANISM: Artificial Sequence
<220> FEATURE:
<223> OTHER INFORMATION: mm10_Thr_CGT-1_33_R

<400> SEQUENCE: 82
gcacccgaga attccatgga ggcccggctg gggttcgaac ccgbgtctyc kgtttac        57

<210> SEQ ID NO 83
<211> LENGTH: 57
<212> TYPE: DNA
<213> ORGANISM: Artificial Sequence
<220> FEATURE:
<223> OTHER INFORMATION: mm10_Thr_CGT-2_33_R

<400> SEQUENCE: 83
gcacccgaga attccatgga aggggcacta ggaactgaac ctagacctcc aacctac        57

<210> SEQ ID NO 84
<211> LENGTH: 57
<212> TYPE: DNA
<213> ORGANISM: Artificial Sequence
<220> FEATURE:
<223> OTHER INFORMATION: mm10_Thr_TGT_33_R

<400> SEQUENCE: 84
gcacccgaga attccatgga ggccccagcg agatttgaac tcgwgycycy kgtttac        57

<210> SEQ ID NO 85
<211> LENGTH: 57
<212> TYPE: DNA
<213> ORGANISM: Artificial Sequence
<220> FEATURE:
<223> OTHER INFORMATION: mm10_Trp_CCA_32_R

<400> SEQUENCE: 85
gcacccgaga attccatggt gaccccgacg tgatttgaac acgcaccttc tgatctg     57

<210> SEQ ID NO 86
<211> LENGTH: 57
<212> TYPE: DNA
<213> ORGANISM: Artificial Sequence
<220> FEATURE:
<223> OTHER INFORMATION: mm10_Tyr_GTA_33_R

<400> SEQUENCE: 86
gcacccgaga attccatggt ccttcgagcc ggattcgaac cagcgcctaa ggatcta     57

<210> SEQ ID NO 87
<211> LENGTH: 57
<212> TYPE: DNA
<213> ORGANISM: Artificial Sequence
<220> FEATURE:
<223> OTHER INFORMATION: mm10_Val_AAC-1_32_R

<400> SEQUENCE: 87
gcacccgaga attccatggt gtttccgccc ggtttcgaac cggggcctyt cgcgtgt     57

<210> SEQ ID NO 88
<211> LENGTH: 56
<212> TYPE: DNA
<213> ORGANISM: Artificial Sequence
<220> FEATURE:
<223> OTHER INFORMATION: mm10_Val_AAC-2_33_R

<400> SEQUENCE: 88
gcacccgaga attccatggc tatggtactg ggaattgaac ccaggctttt gcatgt      56

<210> SEQ ID NO 89
<211> LENGTH: 57
<212> TYPE: DNA
<213> ORGANISM: Artificial Sequence
<220> FEATURE:
<223> OTHER INFORMATION: mm10_Val_CAC-1_32_R

<400> SEQUENCE: 89
gcacccgaga attccatggt gtttctgctg ggttttgaac cggggcctyt ygcrtgt     57

<210> SEQ ID NO 90
<211> LENGTH: 57
<212> TYPE: DNA
<213> ORGANISM: Artificial Sequence
<220> FEATURE:
<223> OTHER INFORMATION: mm10_Val_CAC-2_32_R

<400> SEQUENCE: 90
gcacccgaga attccatggt gtttccgccc ggtttcgaac cggggcctyt ygcrtgt     57

<210> SEQ ID NO 91
<211> LENGTH: 57
<212> TYPE: DNA
<213> ORGANISM: Artificial Sequence
<220> FEATURE:
<223> OTHER INFORMATION: mm10_Val_CAC_32_R

<400> SEQUENCE: 91
gcacccgaga attccatggt gtttccgccc ggtttcgaac cggggcctyt ygcrtgt     57

<210> SEQ ID NO 92
<211> LENGTH: 57
<212> TYPE: DNA
<213> ORGANISM: Artificial Sequence
<220> FEATURE:
<223> OTHER INFORMATION: mm10_Val_GAC_34_R

<400> SEQUENCE: 92
gcacccgaga attccatggc ataaacactg gggtttgaac ccagactttc tgcaggt    57

<210> SEQ ID NO 93
<211> LENGTH: 57
<212> TYPE: DNA
<213> ORGANISM: Artificial Sequence
<220> FEATURE:
<223> OTHER INFORMATION: mm10_Val_TAC_32_R

<400> SEQUENCE: 93
gcacccgaga attccatggt ggttccactg gggctcgaac ccaggccttc tgcgtgt    57

<210> SEQ ID NO 94
<211> LENGTH: 55
<212> TYPE: DNA
<213> ORGANISM: Artificial Sequence
<220> FEATURE:
<223> OTHER INFORMATION: mm10_Ala_AGC-1_33_L

<400> SEQUENCE: 94
tarrcrmrcr ctctaccaac tgagccacat ccccgatcgt cggactgtag aactc    55

<210> SEQ ID NO 95
<211> LENGTH: 55
<212> TYPE: DNA
<213> ORGANISM: Artificial Sequence
<220> FEATURE:
<223> OTHER INFORMATION: mm10_Ala_AGC-2_33_L

<400> SEQUENCE: 95
taagcrhgcg ctctaccatt tgagctaatc ccccgatcgt cggactgtag aactc    55

<210> SEQ ID NO 96
<211> LENGTH: 54
<212> TYPE: DNA
<213> ORGANISM: Artificial Sequence
<220> FEATURE:
<223> OTHER INFORMATION: mm10_Ala_CGC-2_32_L

<400> SEQUENCE: 96
gaagcrygyg ctctacctct gagctacatc cccgatcgtc ggactgtaga actc    54

<210> SEQ ID NO 97
<211> LENGTH: 54
<212> TYPE: DNA
<213> ORGANISM: Artificial Sequence
<220> FEATURE:
<223> OTHER INFORMATION: mm10_Ala_CGC_32_L

<400> SEQUENCE: 97
gaagcaygyg ctctacctct gagctacatc cccgatcgtc ggactgtaga actc    54

<210> SEQ ID NO 98
<211> LENGTH: 54
<212> TYPE: DNA
<213> ORGANISM: Artificial Sequence
<220> FEATURE:
<223> OTHER INFORMATION: mm10_Ala_TGC_32_L

<400> SEQUENCE: 98
aaagcatgyg ctctaccact gagctacatc cccgatcgtc ggactgtaga actc    54

<210> SEQ ID NO 99
<211> LENGTH: 54
<212> TYPE: DNA
<213> ORGANISM: Artificial Sequence
<220> FEATURE:
<223> OTHER INFORMATION: mm10_Arg_ACG_32_L

<400> SEQUENCE: 99
tagtcagacg cgtttccatt gcgccactgg cccgatcgtc ggactgtaga actc    54

<210> SEQ ID NO 100
<211> LENGTH: 54
<212> TYPE: DNA
<213> ORGANISM: Artificial Sequence
<220> FEATURE:
<223> OTHER INFORMATION: mm10_Arg_CCG_32_L

<400> SEQUENCE: 100
garkcsgayg cctttccatt aggccacgcg gccgatcgtc ggactgtaga actc    54

<210> SEQ ID NO 101
<211> LENGTH: 54
<212> TYPE: DNA
<213> ORGANISM: Artificial Sequence
<220> FEATURE:
<223> OTHER INFORMATION: mm10_Arg_CCT_32_L

<400> SEQUENCE: 101
gaggccartg cctttccatt aggccactgg ggcgatcgtc ggactgtaga actc    54

<210> SEQ ID NO 102
<211> LENGTH: 54
<212> TYPE: DNA
<213> ORGANISM: Artificial Sequence
<220> FEATURE:
<223> OTHER INFORMATION: mm10_Arg_TCG_32_L

<400> SEQUENCE: 102
aagtcagacg cctttccatt aggccacgtg gtcgatcgtc ggactgtaga actc    54

<210> SEQ ID NO 103
<211> LENGTH: 54
<212> TYPE: DNA
<213> ORGANISM: Artificial Sequence
<220> FEATURE:
<223> OTHER INFORMATION: mm10_Arg_TCT_32_L

<400> SEQUENCE: 103
aagtccaryg cgcttccatt gcgccacaga gccgatcgtc ggactgtaga actc    54

<210> SEQ ID NO 104
<211> LENGTH: 55
<212> TYPE: DNA
<213> ORGANISM: Artificial Sequence
<220> FEATURE:
<223> OTHER INFORMATION: mm10_Asn_GTT_33_L

<400> SEQUENCE: 104
cagcwraacr cgctaccgat tgcgccacag agacgatcgt cggactgtag aactc    55

<210> SEQ ID NO 105

<211> LENGTH: 54
<212> TYPE: DNA
<213> ORGANISM: Artificial Sequence
<220> FEATURE:
<223> OTHER INFORMATION: mm10_Asp_GTC_32_L

<400> SEQUENCE: 105
caggcrggga tactaccact atactaacga ggagatcgtc ggactgtaga actc             54

<210> SEQ ID NO 106
<211> LENGTH: 54
<212> TYPE: DNA
<213> ORGANISM: Artificial Sequence
<220> FEATURE:
<223> OTHER INFORMATION: mm10_Cys_GCA_32_L

<400> SEQUENCE: 106
cakycaaatr ctctaccct gagctatacc cccgatcgtc ggactgtaga actc             54

<210> SEQ ID NO 107
<211> LENGTH: 54
<212> TYPE: DNA
<213> ORGANISM: Artificial Sequence
<220> FEATURE:
<223> OTHER INFORMATION: mm10_Gln_CTG_32_L

<400> SEQUENCE: 107
gagtccagag tgctaccatt acaccatgga accgatcgtc ggactgtaga actc             54

<210> SEQ ID NO 108
<211> LENGTH: 54
<212> TYPE: DNA
<213> ORGANISM: Artificial Sequence
<220> FEATURE:
<223> OTHER INFORMATION: mm10_Gln_TTG_32_L

<400> SEQUENCE: 108
aagtccagsg tgctaccatt acaccatggg accgatcgtc ggactgtaga actc             54

<210> SEQ ID NO 109
<211> LENGTH: 54
<212> TYPE: DNA
<213> ORGANISM: Artificial Sequence
<220> FEATURE:
<223> OTHER INFORMATION: mm10_Glu_CTC_32_L

<400> SEQUENCE: 109
gawcrmyrav tcctaccact agaccaccag ggagatcgtc ggactgtaga actc             54

<210> SEQ ID NO 110
<211> LENGTH: 54
<212> TYPE: DNA
<213> ORGANISM: Artificial Sequence
<220> FEATURE:
<223> OTHER INFORMATION: mm10_Glu_TTC-1_32_L

<400> SEQUENCE: 110
aaaccaggaa tcctaccgct agaccatgtg ggagatcgtc ggactgtaga actc             54

<210> SEQ ID NO 111
<211> LENGTH: 54
<212> TYPE: DNA
<213> ORGANISM: Artificial Sequence
<220> FEATURE:
<223> OTHER INFORMATION: mm10_Glu_TTC-2_32_L

<400> SEQUENCE: 111
aagcgccgaa tcctgccact agaccaccag ggagatcgtc ggactgtaga actc    54

<210> SEQ ID NO 112
<211> LENGTH: 54
<212> TYPE: DNA
<213> ORGANISM: Artificial Sequence
<220> FEATURE:
<223> OTHER INFORMATION: mm10_Gly_ACC_33_L

<400> SEQUENCE: 112
taggcgaacg cgctaccact acactacgga aacgatcgtc ggactgtaga actc    54

<210> SEQ ID NO 113
<211> LENGTH: 54
<212> TYPE: DNA
<213> ORGANISM: Artificial Sequence
<220> FEATURE:
<223> OTHER INFORMATION: mm10_Gly_CCC-1_32_L

<400> SEQUENCE: 113
gaatcttgca tgataccact acaccagcgg cgcgatcgtc ggactgtaga actc    54

<210> SEQ ID NO 114
<211> LENGTH: 54
<212> TYPE: DNA
<213> ORGANISM: Artificial Sequence
<220> FEATURE:
<223> OTHER INFORMATION: mm10_Gly_CCC-2_32_L

<400> SEQUENCE: 114
gaggcgagaa ttctaccatt gaaccaccaa tgcgatcgtc ggactgtaga actc    54

<210> SEQ ID NO 115
<211> LENGTH: 54
<212> TYPE: DNA
<213> ORGANISM: Artificial Sequence
<220> FEATURE:
<223> OTHER INFORMATION: mm10_Gly_CCC-3_32_L

<400> SEQUENCE: 115
gaatcttgca tgataccact acaccagcgg cgcgatcgtc ggactgtaga actc    54

<210> SEQ ID NO 116
<211> LENGTH: 54
<212> TYPE: DNA
<213> ORGANISM: Artificial Sequence
<220> FEATURE:
<223> OTHER INFORMATION: mm10_Gly_CCC_32_L

<400> SEQUENCE: 116
gaggcgagaa ttctaccatt gaaccaccaa tgcgatcgtc ggactgtaga actc    54

<210> SEQ ID NO 117
<211> LENGTH: 54
<212> TYPE: DNA
<213> ORGANISM: Artificial Sequence
<220> FEATURE:
<223> OTHER INFORMATION: mm10_Gly_GCC_32_L

<400> SEQUENCE: 117
caggcragaa ttctaccact gaaccaccaa tgcgatcgtc ggactgtaga actc    54

<210> SEQ ID NO 118
<211> LENGTH: 54
<212> TYPE: DNA

<213> ORGANISM: Artificial Sequence
<220> FEATURE:
<223> OTHER INFORMATION: mm10_Gly_TCC_32_L

<400> SEQUENCE: 118
aaggcagcta tgctaccact ataccaccaa cgcgatcgtc ggactgtaga actc    54

<210> SEQ ID NO 119
<211> LENGTH: 54
<212> TYPE: DNA
<213> ORGANISM: Artificial Sequence
<220> FEATURE:
<223> OTHER INFORMATION: mm10_His_ATG_33_L

<400> SEQUENCE: 119
tagtcagacg tgtttccatt gcaccactgg tccgatcgtc ggactgtaga actc    54

<210> SEQ ID NO 120
<211> LENGTH: 54
<212> TYPE: DNA
<213> ORGANISM: Artificial Sequence
<220> FEATURE:
<223> OTHER INFORMATION: mm10_His_GTG_32_L

<400> SEQUENCE: 120
caaygcagag tactaccact atacgatcac ggcgatcgtc ggactgtaga actc    54

<210> SEQ ID NO 121
<211> LENGTH: 55
<212> TYPE: DNA
<213> ORGANISM: Artificial Sequence
<220> FEATURE:
<223> OTHER INFORMATION: mm10_Ile_AAT_33_L

<400> SEQUENCE: 121
tagcaccayr ctctaccaac tgagctaacc ggccgatcgt cggactgtag aactc    55

<210> SEQ ID NO 122
<211> LENGTH: 55
<212> TYPE: DNA
<213> ORGANISM: Artificial Sequence
<220> FEATURE:
<223> OTHER INFORMATION: mm10_Ile_GAT_34_L

<400> SEQUENCE: 122
cagcaccatg ctctaccaac tgagctaact ggccgatcgt cggactgtag aactc    55

<210> SEQ ID NO 123
<211> LENGTH: 55
<212> TYPE: DNA
<213> ORGANISM: Artificial Sequence
<220> FEATURE:
<223> OTHER INFORMATION: mm10_Ile_TAT-1_33_L

<400> SEQUENCE: 123
aagtaccgcg cgctaccgat tgcgccactg gagcgatcgt cggactgtag aactc    55

<210> SEQ ID NO 124
<211> LENGTH: 56
<212> TYPE: DNA
<213> ORGANISM: Artificial Sequence
<220> FEATURE:
<223> OTHER INFORMATION: mm10_Ile_TAT-2_33_L

<400> SEQUENCE: 124
ataaagcaga tgtgatacca ctaccctatg gaaccgatcg tcggactgta gaactc    56

<210> SEQ ID NO 125
<211> LENGTH: 54
<212> TYPE: DNA
<213> ORGANISM: Artificial Sequence
<220> FEATURE:
<223> OTHER INFORMATION: mm10_Leu_AAG-1_32_L

<400> SEQUENCE: 125
taagtgagaa tcatacccct agaccaacaa gccgatcgtc ggactgtaga actc    54

<210> SEQ ID NO 126
<211> LENGTH: 54
<212> TYPE: DNA
<213> ORGANISM: Artificial Sequence
<220> FEATURE:
<223> OTHER INFORMATION: mm10_Leu_AAG-2_32_L

<400> SEQUENCE: 126
taatccagcg ccttaccgct cggccacgct accgatcgtc ggactgtaga actc    54

<210> SEQ ID NO 127
<211> LENGTH: 54
<212> TYPE: DNA
<213> ORGANISM: Artificial Sequence
<220> FEATURE:
<223> OTHER INFORMATION: mm10_Leu_CAA_32_L

<400> SEQUENCE: 127
gagtctggcg ccttaccact cggccatcct gacgatcgtc ggactgtaga actc    54

<210> SEQ ID NO 128
<211> LENGTH: 54
<212> TYPE: DNA
<213> ORGANISM: Artificial Sequence
<220> FEATURE:
<223> OTHER INFORMATION: mm10_Leu_CAG_32_L

<400> SEQUENCE: 128
gaacrcagcg ccttaccgct cggccatcct gacgatcgtc ggactgtaga actc    54

<210> SEQ ID NO 129
<211> LENGTH: 54
<212> TYPE: DNA
<213> ORGANISM: Artificial Sequence
<220> FEATURE:
<223> OTHER INFORMATION: mm10_Leu_TAA-1_32_L

<400> SEQUENCE: 129
aagtccaacg ccttaccact cggccatcct ggtgatcgtc ggactgtaga actc    54

<210> SEQ ID NO 130
<211> LENGTH: 55
<212> TYPE: DNA
<213> ORGANISM: Artificial Sequence
<220> FEATURE:
<223> OTHER INFORMATION: mm10_Leu_TAA-2_34_L

<400> SEQUENCE: 130
aagtcttacg caattccggc tctgccaccc taatgatcgt cggactgtag aactc    55

<210> SEQ ID NO 131
<211> LENGTH: 54
<212> TYPE: DNA
<213> ORGANISM: Artificial Sequence
<220> FEATURE:

<223> OTHER INFORMATION: mm10_Leu_TAG_32_L

<400> SEQUENCE: 131
aaatccagcg ccttaccgct cggccacgct accgatcgtc ggactgtaga actc    54

<210> SEQ ID NO 132
<211> LENGTH: 55
<212> TYPE: DNA
<213> ORGANISM: Artificial Sequence
<220> FEATURE:
<223> OTHER INFORMATION: mm10_Lys_CTT-1_33_L

<400> SEQUENCE: 132
gagtcycatg ctgtaccgac tgagctagct gggcgatcgt cggactgtag aactc    55

<210> SEQ ID NO 133
<211> LENGTH: 55
<212> TYPE: DNA
<213> ORGANISM: Artificial Sequence
<220> FEATURE:
<223> OTHER INFORMATION: mm10_Lys_CTT-2_33_L

<400> SEQUENCE: 133
gaktcycahg ctctaccgac tgagctagcc gggcgatcgt cggactgtag aactc    55

<210> SEQ ID NO 134
<211> LENGTH: 55
<212> TYPE: DNA
<213> ORGANISM: Artificial Sequence
<220> FEATURE:
<223> OTHER INFORMATION: mm10_Lys_CTT_33_L

<400> SEQUENCE: 134
gaktcycahg ctctaccgac tgagctagcc gggcgatcgt cggactgtag aactc    55

<210> SEQ ID NO 135
<211> LENGTH: 55
<212> TYPE: DNA
<213> ORGANISM: Artificial Sequence
<220> FEATURE:
<223> OTHER INFORMATION: mm10_Lys_TTT-1_32_L

<400> SEQUENCE: 135
aagtytwatr ctctactgac tgagctatcc aggtgatcgt cggactgtag aactc    55

<210> SEQ ID NO 136
<211> LENGTH: 55
<212> TYPE: DNA
<213> ORGANISM: Artificial Sequence
<220> FEATURE:
<223> OTHER INFORMATION: mm10_Lys_TTT-2_32_L

<400> SEQUENCE: 136
aagtctgatg ctctaccgac tgagctatcc gggcgatcgt cggactgtag aactc    55

<210> SEQ ID NO 137
<211> LENGTH: 55
<212> TYPE: DNA
<213> ORGANISM: Artificial Sequence
<220> FEATURE:
<223> OTHER INFORMATION: mm10_Lys_TTT_32_L

<400> SEQUENCE: 137
aagtytwatr ctctaccgac tgagctatcc gggcgatcgt cggactgtag aactc    55

-continued

<210> SEQ ID NO 138
<211> LENGTH: 54
<212> TYPE: DNA
<213> ORGANISM: Artificial Sequence
<220> FEATURE:
<223> OTHER INFORMATION: mm10_Met_CAT-1_32_L

<400> SEQUENCE: 138
gggcccagca cgcttccgct gcgccactct gctgatcgtc ggactgtaga actc        54

<210> SEQ ID NO 139
<211> LENGTH: 55
<212> TYPE: DNA
<213> ORGANISM: Artificial Sequence
<220> FEATURE:
<223> OTHER INFORMATION: mm10_Met_CAT-2_33_L

<400> SEQUENCE: 139
gagacsgrcr cgctgcctac tgcgctaagg aggcgatcgt cggactgtag aactc       55

<210> SEQ ID NO 140
<211> LENGTH: 55
<212> TYPE: DNA
<213> ORGANISM: Artificial Sequence
<220> FEATURE:
<223> OTHER INFORMATION: mm10_Phe_GAA_33_L

<400> SEQUENCE: 140
cagtctaacg ctctcccaac tgagctattt cggcgatcgt cggactgtag aactc       55

<210> SEQ ID NO 141
<211> LENGTH: 54
<212> TYPE: DNA
<213> ORGANISM: Artificial Sequence
<220> FEATURE:
<223> OTHER INFORMATION: mm10_Pro_AGG_32_L

<400> SEQUENCE: 141
taagygagaa tcatacccct agaccaacga gccgatcgtc ggactgtaga actc        54

<210> SEQ ID NO 142
<211> LENGTH: 54
<212> TYPE: DNA
<213> ORGANISM: Artificial Sequence
<220> FEATURE:
<223> OTHER INFORMATION: mm10_Pro_CGG_32_L

<400> SEQUENCE: 142
gaagcgagaa tcatacccct agaccaacga gccgatcgtc ggactgtaga actc        54

<210> SEQ ID NO 143
<211> LENGTH: 54
<212> TYPE: DNA
<213> ORGANISM: Artificial Sequence
<220> FEATURE:
<223> OTHER INFORMATION: mm10_Pro_TGG_32_L

<400> SEQUENCE: 143
aaawhgagaa tcatacccct agaccaacga gccgatcgtc ggactgtaga actc        54

<210> SEQ ID NO 144
<211> LENGTH: 56
<212> TYPE: DNA
<213> ORGANISM: Artificial Sequence
<220> FEATURE:
<223> OTHER INFORMATION: mm10_SeC(e)_TCA_36_L

<400> SEQUENCE: 144
aagcctgcac cccagaccac tgaggatcat ccgggcgatc gtcggactgt agaacc         56

<210> SEQ ID NO 145
<211> LENGTH: 53
<212> TYPE: DNA
<213> ORGANISM: Artificial Sequence
<220> FEATURE:
<223> OTHER INFORMATION: mm10_SeC_TCA_32_L

<400> SEQUENCE: 145
agtctcatgc tctcccactg agctagctgg gtgatcgtcg gactgtagaa ctc           53

<210> SEQ ID NO 146
<211> LENGTH: 54
<212> TYPE: DNA
<213> ORGANISM: Artificial Sequence
<220> FEATURE:
<223> OTHER INFORMATION: mm10_Ser_AGA_32_L

<400> SEQUENCE: 146
tagtccatcg ccttaccact cggccacgac tacgatcgtc ggactgtaga actc          54

<210> SEQ ID NO 147
<211> LENGTH: 54
<212> TYPE: DNA
<213> ORGANISM: Artificial Sequence
<220> FEATURE:
<223> OTHER INFORMATION: mm10_Ser_CGA_32_L

<400> SEQUENCE: 147
gagtccaacg ccttaccact cggccatcac agcgatcgtc ggactgtaga actc          54

<210> SEQ ID NO 148
<211> LENGTH: 54
<212> TYPE: DNA
<213> ORGANISM: Artificial Sequence
<220> FEATURE:
<223> OTHER INFORMATION: mm10_Ser_GCT_32_L

<400> SEQUENCE: 148
cagtccatcg ccttaccact cggccacctc gtcgatcgtc ggactgtaga actc          54

<210> SEQ ID NO 149
<211> LENGTH: 55
<212> TYPE: DNA
<213> ORGANISM: Artificial Sequence
<220> FEATURE:
<223> OTHER INFORMATION: mm10_Ser_GGA_34_L

<400> SEQUENCE: 149
cagtctaatg ctctcccaac tgagctattt cagcgatcgt cggactgtag aactc         55

<210> SEQ ID NO 150
<211> LENGTH: 54
<212> TYPE: DNA
<213> ORGANISM: Artificial Sequence
<220> FEATURE:
<223> OTHER INFORMATION: mm10_Ser_TGA_32_L

<400> SEQUENCE: 150
aagtccatcg ccttaccact cggccacgac tacgatcgtc ggactgtaga actc          54

<210> SEQ ID NO 151
<211> LENGTH: 54

-continued

```
<212> TYPE: DNA
<213> ORGANISM: Artificial Sequence
<220> FEATURE:
<223> OTHER INFORMATION: mm10_Sup_TTA_33_L

<400> SEQUENCE: 151
aagtccaagg ccttaccact cagccatccc agtgatcgtc ggactgtaga actc          54

<210> SEQ ID NO 152
<211> LENGTH: 55
<212> TYPE: DNA
<213> ORGANISM: Artificial Sequence
<220> FEATURE:
<223> OTHER INFORMATION: mm10_Thr_AGT_33_L

<400> SEQUENCE: 152
gagacmgrcg ctttaccagc ttggccacgg cgccgatcgt cggactgtag aactc         55

<210> SEQ ID NO 153
<211> LENGTH: 55
<212> TYPE: DNA
<213> ORGANISM: Artificial Sequence
<220> FEATURE:
<223> OTHER INFORMATION: mm10_Thr_CGT-1_33_L

<400> SEQUENCE: 153
gagacmgrcg ctttaccagc ttggccacgg cgccgatcgt cggactgtag aactc         55

<210> SEQ ID NO 154
<211> LENGTH: 54
<212> TYPE: DNA
<213> ORGANISM: Artificial Sequence
<220> FEATURE:
<223> OTHER INFORMATION: mm10_Thr_CGT-2_33_L

<400> SEQUENCE: 154
gaggcaagtg ttcatccact gaactacatc cctgatcgtc ggactgtaga actc          54

<210> SEQ ID NO 155
<211> LENGTH: 55
<212> TYPE: DNA
<213> ORGANISM: Artificial Sequence
<220> FEATURE:
<223> OTHER INFORMATION: mm10_Thr_TGT_33_L

<400> SEQUENCE: 155
aagacmrgyg ctctaccacc tgagctatgg agccgatcgt cggactgtag aactc         55

<210> SEQ ID NO 156
<211> LENGTH: 54
<212> TYPE: DNA
<213> ORGANISM: Artificial Sequence
<220> FEATURE:
<223> OTHER INFORMATION: mm10_Trp_CCA_32_L

<400> SEQUENCE: 156
gagtcagacg cgctaccgtt gcgccacgag gtcgatcgtc ggactgtaga actc          54

<210> SEQ ID NO 157
<211> LENGTH: 55
<212> TYPE: DNA
<213> ORGANISM: Artificial Sequence
<220> FEATURE:
<223> OTHER INFORMATION: mm10_Tyr_GTA_33_L

<400> SEQUENCE: 157
```
cagtcctccg ctctaccaac tgagctatcg aagggatcgt cggactgtag aactc       55

<210> SEQ ID NO 158
<211> LENGTH: 54
<212> TYPE: DNA
<213> ORGANISM: Artificial Sequence
<220> FEATURE:
<223> OTHER INFORMATION: mm10_Val_AAC-1_32_L

<400> SEQUENCE: 158
taggcgaryg tgataccact acactacgga aacgatcgtc ggactgtaga actc       54

<210> SEQ ID NO 159
<211> LENGTH: 54
<212> TYPE: DNA
<213> ORGANISM: Artificial Sequence
<220> FEATURE:
<223> OTHER INFORMATION: mm10_Val_AAC-2_33_L

<400> SEQUENCE: 159
taggcaaatg ctctaccact gagctatatc accgatcgtc ggactgtaga actc       54

<210> SEQ ID NO 160
<211> LENGTH: 54
<212> TYPE: DNA
<213> ORGANISM: Artificial Sequence
<220> FEATURE:
<223> OTHER INFORMATION: mm10_Val_CAC-1_32_L

<400> SEQUENCE: 160
gaggcraryg tgataccgct acactacaga aacgatcgtc ggactgtaga actc       54

<210> SEQ ID NO 161
<211> LENGTH: 54
<212> TYPE: DNA
<213> ORGANISM: Artificial Sequence
<220> FEATURE:
<223> OTHER INFORMATION: mm10_Val_CAC-2_32_L

<400> SEQUENCE: 161
gaggcgarcg tgataccact acactacgga aacgatcgtc ggactgtaga actc       54

<210> SEQ ID NO 162
<211> LENGTH: 54
<212> TYPE: DNA
<213> ORGANISM: Artificial Sequence
<220> FEATURE:
<223> OTHER INFORMATION: mm10_Val_CAC_32_L

<400> SEQUENCE: 162
gaggcraryg tgataccact acactacgga aacgatcgtc ggactgtaga actc       54

<210> SEQ ID NO 163
<211> LENGTH: 55
<212> TYPE: DNA
<213> ORGANISM: Artificial Sequence
<220> FEATURE:
<223> OTHER INFORMATION: mm10_Val_GAC_34_L

<400> SEQUENCE: 163
caagcaagca ctttaccaat tgagctatat ccacgatcgt cggactgtag aactc       55

<210> SEQ ID NO 164
<211> LENGTH: 54
<212> TYPE: DNA
<213> ORGANISM: Artificial Sequence
<220> FEATURE:
<223> OTHER INFORMATION: mm10_Val_TAC_32_L

<400> SEQUENCE: 164
aaagcagacg tgataccgct acactatgga accgatcgtc ggactgtaga actc         54

<210> SEQ ID NO 165
<211> LENGTH: 57
<212> TYPE: DNA
<213> ORGANISM: Artificial Sequence
<220> FEATURE:
<223> OTHER INFORMATION: Ala_AGC-1_32_R

<400> SEQUENCE: 165
gcacccgaga attccatggt ggaggtgctg gggattgaac ccgggcctcr trcatgc      57

<210> SEQ ID NO 166
<211> LENGTH: 57
<212> TYPE: DNA
<213> ORGANISM: Artificial Sequence
<220> FEATURE:
<223> OTHER INFORMATION: Ala_AGC-2_33_R

<400> SEQUENCE: 166
gcacccgaga attccatggt ggagaatgcg ggcatcgatc ccgctcctct ygcrtgc      57

<210> SEQ ID NO 167
<211> LENGTH: 57
<212> TYPE: DNA
<213> ORGANISM: Artificial Sequence
<220> FEATURE:
<223> OTHER INFORMATION: Ala_AGC-3_32_R

<400> SEQUENCE: 167
gcacccgaga attccatggt ggaggtgctg gggattgaac ccgggcctcr tgcatgc      57

<210> SEQ ID NO 168
<211> LENGTH: 57
<212> TYPE: DNA
<213> ORGANISM: Artificial Sequence
<220> FEATURE:
<223> OTHER INFORMATION: Ala_CGC_32_R

<400> SEQUENCE: 168
gcacccgaga attccatggt ggagatgccg gggatcgaac ccgggcctcr yacatgc      57

<210> SEQ ID NO 169
<211> LENGTH: 57
<212> TYPE: DNA
<213> ORGANISM: Artificial Sequence
<220> FEATURE:
<223> OTHER INFORMATION: Ala_TGC_32_R

<400> SEQUENCE: 169
gcacccgaga attccatggt ggaggtgccg gggatcgaac ccggryctca yacrtgc      57

<210> SEQ ID NO 170
<211> LENGTH: 57
<212> TYPE: DNA
<213> ORGANISM: Artificial Sequence
<220> FEATURE:
<223> OTHER INFORMATION: Arg_ACG_32_R

<400> SEQUENCE: 170
gcacccgaga attccatggc gagccagcca ggagtcgaac ctagatcttc tgatccg      57

-continued

```
<210> SEQ ID NO 171
<211> LENGTH: 57
<212> TYPE: DNA
<213> ORGANISM: Artificial Sequence
<220> FEATURE:
<223> OTHER INFORMATION: Arg_CCG-1_32_R

<400> SEQUENCE: 171
gcacccgaga attccatggc gaccacgaag ggactcgaac cctcatcttc tgatccg      57

<210> SEQ ID NO 172
<211> LENGTH: 57
<212> TYPE: DNA
<213> ORGANISM: Artificial Sequence
<220> FEATURE:
<223> OTHER INFORMATION: Arg_CCG-2_33_R

<400> SEQUENCE: 172
gcacccgaga attccatggc gacccagatg ggactcgaac ccacatcccc agctccg      57

<210> SEQ ID NO 173
<211> LENGTH: 57
<212> TYPE: DNA
<213> ORGANISM: Artificial Sequence
<220> FEATURE:
<223> OTHER INFORMATION: Arg_CCT_32_R

<400> SEQUENCE: 173
gcacccgaga attccatggt accccaggtg ggactcgaac ccacatccct ggcttag      57

<210> SEQ ID NO 174
<211> LENGTH: 57
<212> TYPE: DNA
<213> ORGANISM: Artificial Sequence
<220> FEATURE:
<223> OTHER INFORMATION: Arg_TCG_32_R

<400> SEQUENCE: 174
gcacccgaga attccatggc gaccacggag ggattcgaac cctcatctty tgatccg      57

<210> SEQ ID NO 175
<211> LENGTH: 57
<212> TYPE: DNA
<213> ORGANISM: Artificial Sequence
<220> FEATURE:
<223> OTHER INFORMATION: Arg_TCT_32_R

<400> SEQUENCE: 175
gcacccgaga attccatggc gactctggtg ggactcgaac ccgcacctyt grattag      57

<210> SEQ ID NO 176
<211> LENGTH: 57
<212> TYPE: DNA
<213> ORGANISM: Artificial Sequence
<220> FEATURE:
<223> OTHER INFORMATION: Asn_ATT_34_R

<400> SEQUENCE: 176
gcacccgaga attccatggc gtccctgggt ggtcttgaac tactcccgtt cggttaa      57

<210> SEQ ID NO 177
<211> LENGTH: 57
<212> TYPE: DNA
<213> ORGANISM: Artificial Sequence
<220> FEATURE:
<223> OTHER INFORMATION: Asn_GTT-1_33_R
```

<400> SEQUENCE: 177
gcacccgaga attccatggc gtccctgggt gggctcgaac caccacytth ygkttaa    57

<210> SEQ ID NO 178
<211> LENGTH: 57
<212> TYPE: DNA
<213> ORGANISM: Artificial Sequence
<220> FEATURE:
<223> OTHER INFORMATION: Asn_GTT-2_33_R

<400> SEQUENCE: 178
gcacccgaga attccatggc gtccctgggt gggctcgaac cacyabytth yrgttaa    57

<210> SEQ ID NO 179
<211> LENGTH: 57
<212> TYPE: DNA
<213> ORGANISM: Artificial Sequence
<220> FEATURE:
<223> OTHER INFORMATION: Asn_GTT-3_33_R

<400> SEQUENCE: 179
gcacccgaga attccatggc atccctggat gggcttgcac caccacctttt cagttaa   57

<210> SEQ ID NO 180
<211> LENGTH: 57
<212> TYPE: DNA
<213> ORGANISM: Artificial Sequence
<220> FEATURE:
<223> OTHER INFORMATION: Asp_GTC-1_32_R

<400> SEQUENCE: 180
gcacccgaga attccatggc tccctgttgg ggactcgacc tcctwtctca yrcatga    57

<210> SEQ ID NO 181
<211> LENGTH: 57
<212> TYPE: DNA
<213> ORGANISM: Artificial Sequence
<220> FEATURE:
<223> OTHER INFORMATION: Asp_GTC-2_32_R

<400> SEQUENCE: 181
gcacccgaga attccatggc tccccgtcgg ggaatcgaac cccgwtctcc cgcgtga    57

<210> SEQ ID NO 182
<211> LENGTH: 57
<212> TYPE: DNA
<213> ORGANISM: Artificial Sequence
<220> FEATURE:
<223> OTHER INFORMATION: Cys_GCA_32_R

<400> SEQUENCE: 182
gcacccgaga attccatgga gggggcaccc ggatttgaac cggggcytyt tgatytg    57

<210> SEQ ID NO 183
<211> LENGTH: 56
<212> TYPE: DNA
<213> ORGANISM: Artificial Sequence
<220> FEATURE:
<223> OTHER INFORMATION: Gln_CTG-1_33_R

<400> SEQUENCE: 183
gcacccgaga attccatggt gacagaacca gattcaaatc aagttctctg acttca     56

<210> SEQ ID NO 184

```
<211> LENGTH: 57
<212> TYPE: DNA
<213> ORGANISM: Artificial Sequence
<220> FEATURE:
<223> OTHER INFORMATION: Gln_CTG-2_32_R

<400> SEQUENCE: 184
gcacccgaga attccatgga ggttccaccg agacttgaac tcggrtbrcy gkattca        57

<210> SEQ ID NO 185
<211> LENGTH: 56
<212> TYPE: DNA
<213> ORGANISM: Artificial Sequence
<220> FEATURE:
<223> OTHER INFORMATION: Gln_CTG-3_32_R

<400> SEQUENCE: 185
gcacccgaga attccatgga agcagtgccg ggatttgaac ccagcccttc tgacca         56

<210> SEQ ID NO 186
<211> LENGTH: 57
<212> TYPE: DNA
<213> ORGANISM: Artificial Sequence
<220> FEATURE:
<223> OTHER INFORMATION: Gln_TTG-1_33_R

<400> SEQUENCE: 186
gcacccgaga attccatggc tgggactata ggaattgaac ctayccctga gamtcca        57

<210> SEQ ID NO 187
<211> LENGTH: 57
<212> TYPE: DNA
<213> ORGANISM: Artificial Sequence
<220> FEATURE:
<223> OTHER INFORMATION: Gln_TTG-2_32_R

<400> SEQUENCE: 187
gcacccgaga attccatgga ggtcccaccg agatttgaac tcggatygct ggattca        57

<210> SEQ ID NO 188
<211> LENGTH: 57
<212> TYPE: DNA
<213> ORGANISM: Artificial Sequence
<220> FEATURE:
<223> OTHER INFORMATION: Gln_TTG-3_33_R

<400> SEQUENCE: 188
gcacccgaga attccatggt gaccatgaaa ggacttgaac cctcatcttc tgaccca        57

<210> SEQ ID NO 189
<211> LENGTH: 57
<212> TYPE: DNA
<213> ORGANISM: Artificial Sequence
<220> FEATURE:
<223> OTHER INFORMATION: Glu_CTC-1_32_R

<400> SEQUENCE: 189
gcacccgaga attccatggt tccctgaccg ggaatcgagt ctgggymryr gtggtga        57

<210> SEQ ID NO 190
<211> LENGTH: 54
<212> TYPE: DNA
<213> ORGANISM: Artificial Sequence
<220> FEATURE:
<223> OTHER INFORMATION: Glu_CTC-2_33_R

<400> SEQUENCE: 190
```

-continued gcacccgaga attccatggt ccccctgatct ggaatcaacc agtcccggcg gtga         54

<210> SEQ ID NO 191
<211> LENGTH: 57
<212> TYPE: DNA
<213> ORGANISM: Artificial Sequence
<220> FEATURE:
<223> OTHER INFORMATION: Glu_CTC-3_32_R

<400> SEQUENCE: 191
gcacccgaga attccatggt tccctgaccg ggaatcgaac ccgggcmgcr gcggtga      57

<210> SEQ ID NO 192
<211> LENGTH: 57
<212> TYPE: DNA
<213> ORGANISM: Artificial Sequence
<220> FEATURE:
<223> OTHER INFORMATION: Glu_TTC-1_32_R

<400> SEQUENCE: 192
gcacccgaga attccatggt tcccataccg ggagtcgaac ccgggccrcc tgggtga      57

<210> SEQ ID NO 193
<211> LENGTH: 56
<212> TYPE: DNA
<213> ORGANISM: Artificial Sequence
<220> FEATURE:
<223> OTHER INFORMATION: Glu_TTC-2_31_R

<400> SEQUENCE: 193
gcacccgaga attccatggt ctctaaccag gaattgaacc tgggctgtca tgacga       56

<210> SEQ ID NO 194
<211> LENGTH: 57
<212> TYPE: DNA
<213> ORGANISM: Artificial Sequence
<220> FEATURE:
<223> OTHER INFORMATION: Glu_TTC-3_32_R

<400> SEQUENCE: 194
gcacccgaga attccatggt tccctgatct ggaatcgaac tcgagyywcg gcggtga      57

<210> SEQ ID NO 195
<211> LENGTH: 57
<212> TYPE: DNA
<213> ORGANISM: Artificial Sequence
<220> FEATURE:
<223> OTHER INFORMATION: Glu_TTC-4_31_R

<400> SEQUENCE: 195
gcacccgaga attccatggt tccctgactg ggaattgaac ctggrctrwa gcamtga      57

<210> SEQ ID NO 196
<211> LENGTH: 57
<212> TYPE: DNA
<213> ORGANISM: Artificial Sequence
<220> FEATURE:
<223> OTHER INFORMATION: Glu_TTC-5_32_R

<400> SEQUENCE: 196
gcacccgaga attccatggt tccctgaccg ggaatcgaac ccgggccgcg gcggtga      57

<210> SEQ ID NO 197
<211> LENGTH: 57
<212> TYPE: DNA

<213> ORGANISM: Artificial Sequence
<220> FEATURE:
<223> OTHER INFORMATION: Gly_CCC-1_32_R

<400> SEQUENCE: 197
gcacccgaga attccatggt gcgccgcccg ggaatcgaac ccgggtcgca agaatgg    57

<210> SEQ ID NO 198
<211> LENGTH: 57
<212> TYPE: DNA
<213> ORGANISM: Artificial Sequence
<220> FEATURE:
<223> OTHER INFORMATION: Gly_CCC-2_32_R

<400> SEQUENCE: 198
gcacccgaga attccatggt gcattggccg ggaattgaac ccgggtctcc yrcrtgg    57

<210> SEQ ID NO 199
<211> LENGTH: 57
<212> TYPE: DNA
<213> ORGANISM: Artificial Sequence
<220> FEATURE:
<223> OTHER INFORMATION: Gly_CCC-3_33_R

<400> SEQUENCE: 199
gcacccgaga attccatggt gcattggccg ggaattgaac ccgggtctcc cgcgtgg    57

<210> SEQ ID NO 200
<211> LENGTH: 57
<212> TYPE: DNA
<213> ORGANISM: Artificial Sequence
<220> FEATURE:
<223> OTHER INFORMATION: Gly_GCC_32_R

<400> SEQUENCE: 200
gcacccgaga attccatggt gcattggccg ggaatcgaac ccgggcckcc ygcrtgg    57

<210> SEQ ID NO 201
<211> LENGTH: 57
<212> TYPE: DNA
<213> ORGANISM: Artificial Sequence
<220> FEATURE:
<223> OTHER INFORMATION: Gly_TCC_32_R

<400> SEQUENCE: 201
gcacccgaga attccatggt gcgttggccg ggaatcgaac ccgggtcaac tgcttgg    57

<210> SEQ ID NO 202
<211> LENGTH: 57
<212> TYPE: DNA
<213> ORGANISM: Artificial Sequence
<220> FEATURE:
<223> OTHER INFORMATION: His_GTG_32_R

<400> SEQUENCE: 202
gcacccgaga attccatggt gccgtgactc ggattcgaac cgaggttgct gyggcca    57

<210> SEQ ID NO 203
<211> LENGTH: 57
<212> TYPE: DNA
<213> ORGANISM: Artificial Sequence
<220> FEATURE:
<223> OTHER INFORMATION: Ile_AAT_33_R

<400> SEQUENCE: 203
gcacccgaga attccatggt ggcccgtacg gggatcgaac ccgcgccttr gcgttat    57

<210> SEQ ID NO 204
<211> LENGTH: 57
<212> TYPE: DNA
<213> ORGANISM: Artificial Sequence
<220> FEATURE:
<223> OTHER INFORMATION: Ile_GAT_33_R

<400> SEQUENCE: 204
gcacccgaga attccatggt ggccggtgcg ggagtcgagc ccgcgccttg gtgttat      57

<210> SEQ ID NO 205
<211> LENGTH: 57
<212> TYPE: DNA
<213> ORGANISM: Artificial Sequence
<220> FEATURE:
<223> OTHER INFORMATION: Ile_TAT_33_R

<400> SEQUENCE: 205
gcacccgaga attccatggt gctccaggtg aggctcgaac tcacacctcg gcattat      57

<210> SEQ ID NO 206
<211> LENGTH: 60
<212> TYPE: DNA
<213> ORGANISM: Artificial Sequence
<220> FEATURE:
<223> OTHER INFORMATION: Leu_AAG-1_32_R

<400> SEQUENCE: 206
gcacccgaga attccatggc ggtgggattg aaacccatgc cycyraagag actggagsct   60

<210> SEQ ID NO 207
<211> LENGTH: 60
<212> TYPE: DNA
<213> ORGANISM: Artificial Sequence
<220> FEATURE:
<223> OTHER INFORMATION: Leu_AAG-2_32_R

<400> SEQUENCE: 207
gcacccgaga attccatggc ggtgggattc gaacccacgc cyccgaagag actggagcct   60

<210> SEQ ID NO 208
<211> LENGTH: 57
<212> TYPE: DNA
<213> ORGANISM: Artificial Sequence
<220> FEATURE:
<223> OTHER INFORMATION: Leu_AAG-3_33_R

<400> SEQUENCE: 208
gcacccgaga attccatggt gagccagcca ggagtcaagg ctggatcttc tgattct      57

<210> SEQ ID NO 209
<211> LENGTH: 57
<212> TYPE: DNA
<213> ORGANISM: Artificial Sequence
<220> FEATURE:
<223> OTHER INFORMATION: Leu_CAA-1_34_R

<400> SEQUENCE: 209
gcacccgaga attccatggt gccccctctg aggcttgaac tcaggccttc agatttt      57

<210> SEQ ID NO 210
<211> LENGTH: 60
<212> TYPE: DNA
<213> ORGANISM: Artificial Sequence
<220> FEATURE:

<223> OTHER INFORMATION: Leu_CAA-2_32_R

<400> SEQUENCE: 210
gcacccgaga attccatggg tgggattcga acccacgcct ccatvyggag accagaactt    60

<210> SEQ ID NO 211
<211> LENGTH: 60
<212> TYPE: DNA
<213> ORGANISM: Artificial Sequence
<220> FEATURE:
<223> OTHER INFORMATION: Leu_CAG-1_32_R

<400> SEQUENCE: 211
gcacccgaga attccatgga gtgggattcg aacccacgcc tccaggggag actgcgacct    60

<210> SEQ ID NO 212
<211> LENGTH: 60
<212> TYPE: DNA
<213> ORGANISM: Artificial Sequence
<220> FEATURE:
<223> OTHER INFORMATION: Leu_CAG-2_32_R

<400> SEQUENCE: 212
gcacccgaga attccatggg ccagggctag ggtttgaacc cagatctacc tacctgttct    60

<210> SEQ ID NO 213
<211> LENGTH: 60
<212> TYPE: DNA
<213> ORGANISM: Artificial Sequence
<220> FEATURE:
<223> OTHER INFORMATION: Leu_TAA-1_32_R

<400> SEQUENCE: 213
gcacccgaga attccatggg tggggttcga acccacgcgg ryayvsrycc attggatctt    60

<210> SEQ ID NO 214
<211> LENGTH: 57
<212> TYPE: DNA
<213> ORGANISM: Artificial Sequence
<220> FEATURE:
<223> OTHER INFORMATION: Leu_TAA-2_33_R

<400> SEQUENCE: 214
gcacccgaga attccatggt gttaatgaga ggagttgaac ctctgttata aartttt    57

<210> SEQ ID NO 215
<211> LENGTH: 60
<212> TYPE: DNA
<213> ORGANISM: Artificial Sequence
<220> FEATURE:
<223> OTHER INFORMATION: Leu_TAA-3_33_R

<400> SEQUENCE: 215
gcacccgaga attccatggg tggggtttaa acccacacag ccactactcc attggatctt    60

<210> SEQ ID NO 216
<211> LENGTH: 60
<212> TYPE: DNA
<213> ORGANISM: Artificial Sequence
<220> FEATURE:
<223> OTHER INFORMATION: Leu_TAG_32_R

<400> SEQUENCE: 216
gcacccgaga attccatggc ggtgggattc gaacccacgc chycgaarsg actggagcct    60

<210> SEQ ID NO 217
<211> LENGTH: 57
<212> TYPE: DNA
<213> ORGANISM: Artificial Sequence
<220> FEATURE:
<223> OTHER INFORMATION: Lys_CTT-1_33_R

<400> SEQUENCE: 217
gcacccgaga attccatggt gtccaatgtg gggcttgaac ccaykccctg agattaa    57

<210> SEQ ID NO 218
<211> LENGTH: 57
<212> TYPE: DNA
<213> ORGANISM: Artificial Sequence
<220> FEATURE:
<223> OTHER INFORMATION: Lys_CTT-2_33_R

<400> SEQUENCE: 218
gcacccgaga attccatggc gcccaacgtg gggctcgaac ccayrccctg rgatkaa    57

<210> SEQ ID NO 219
<211> LENGTH: 57
<212> TYPE: DNA
<213> ORGANISM: Artificial Sequence
<220> FEATURE:
<223> OTHER INFORMATION: Lys_TTT-1_32_R

<400> SEQUENCE: 219
gcacccgaga attccatggc gcccgaacag ggacttgaac cctrwccwtc arattaa    57

<210> SEQ ID NO 220
<211> LENGTH: 57
<212> TYPE: DNA
<213> ORGANISM: Artificial Sequence
<220> FEATURE:
<223> OTHER INFORMATION: Lys_TTT-2_32_R

<400> SEQUENCE: 220
gcacccgaga attccatggc acccaaacag ggacttgaac cctrgccctc arattaa    57

<210> SEQ ID NO 221
<211> LENGTH: 57
<212> TYPE: DNA
<213> ORGANISM: Artificial Sequence
<220> FEATURE:
<223> OTHER INFORMATION: Met_CAT-1_33_R

<400> SEQUENCE: 221
gcacccgaga attccatggt gccctctctg aggctcgaac tcawgcyttc agattat    57

<210> SEQ ID NO 222
<211> LENGTH: 57
<212> TYPE: DNA
<213> ORGANISM: Artificial Sequence
<220> FEATURE:
<223> OTHER INFORMATION: Met_CAT-2_32_R

<400> SEQUENCE: 222
gcacccgaga attccatggt agcagaggat ggtttcgatc catcrcctct gggttat    57

<210> SEQ ID NO 223
<211> LENGTH: 57
<212> TYPE: DNA
<213> ORGANISM: Artificial Sequence
<220> FEATURE:
<223> OTHER INFORMATION: Phe_GAA_33_R

```
<400> SEQUENCE: 223
gcacccgaga attccatggt gccgaaaccc gggatcgaac cagrgcytkh agasctt          57

<210> SEQ ID NO 224
<211> LENGTH: 57
<212> TYPE: DNA
<213> ORGANISM: Artificial Sequence
<220> FEATURE:
<223> OTHER INFORMATION: Pro_AGG_32_R

<400> SEQUENCE: 224
gcacccgaga attccatggg ggctcgtccg ggatttgaac ccgggcctct cgcaycc          57

<210> SEQ ID NO 225
<211> LENGTH: 57
<212> TYPE: DNA
<213> ORGANISM: Artificial Sequence
<220> FEATURE:
<223> OTHER INFORMATION: Pro_CGG_32_R

<400> SEQUENCE: 225
gcacccgaga attccatggg ggctcgtccg ggatttgaac ccgggcctct crcaccc          57

<210> SEQ ID NO 226
<211> LENGTH: 57
<212> TYPE: DNA
<213> ORGANISM: Artificial Sequence
<220> FEATURE:
<223> OTHER INFORMATION: Pro_TGG_32_R

<400> SEQUENCE: 226
gcacccgaga attccatggg ggctcgtccg ggatttgaac ccgggcctct cgwaccc          57

<210> SEQ ID NO 227
<211> LENGTH: 60
<212> TYPE: DNA
<213> ORGANISM: Artificial Sequence
<220> FEATURE:
<223> OTHER INFORMATION: SeC(e)_TCA_35_R

<400> SEQUENCE: 227
gcacccgaga attccatggg tggaattgaa ccactctgtc rctagacagc tacaggtttg       60

<210> SEQ ID NO 228
<211> LENGTH: 57
<212> TYPE: DNA
<213> ORGANISM: Artificial Sequence
<220> FEATURE:
<223> OTHER INFORMATION: SeC_TCA_33_R

<400> SEQUENCE: 228
gcacccgaga attccatggt gaccacaaag ggactcaaac cctcatcttc tgatctg          57

<210> SEQ ID NO 229
<211> LENGTH: 60
<212> TYPE: DNA
<213> ORGANISM: Artificial Sequence
<220> FEATURE:
<223> OTHER INFORMATION: Ser_AGA-1_33_R

<400> SEQUENCE: 229
gcacccgaga attccatgga gcaggattca aacctgcaca gagagaaacc aacgaatttc       60

<210> SEQ ID NO 230
<211> LENGTH: 60
```

```
<212> TYPE: DNA
<213> ORGANISM: Artificial Sequence
<220> FEATURE:
<223> OTHER INFORMATION: Ser_AGA-2_32_R

<400> SEQUENCE: 230
gcacccgaga attccatggg gcaggattcg aacctgcgcg gggaracccc aatggrtttc    60

<210> SEQ ID NO 231
<211> LENGTH: 55
<212> TYPE: DNA
<213> ORGANISM: Artificial Sequence
<220> FEATURE:
<223> OTHER INFORMATION: Ser_AGA-3_33_R

<400> SEQUENCE: 231
gcacccgaga attccatgga gggggcacct ggatttgaac cagggcctct tgatc         55

<210> SEQ ID NO 232
<211> LENGTH: 60
<212> TYPE: DNA
<213> ORGANISM: Artificial Sequence
<220> FEATURE:
<223> OTHER INFORMATION: Ser_CGA_32_R

<400> SEQUENCE: 232
gcacccgaga attccatgga gcaggatttg aacctgcgcg gggarmcccc attggatttc    60

<210> SEQ ID NO 233
<211> LENGTH: 60
<212> TYPE: DNA
<213> ORGANISM: Artificial Sequence
<220> FEATURE:
<223> OTHER INFORMATION: Ser_GCT_32_R

<400> SEQUENCE: 233
gcacccgaga attccatggg atgggattcg aacccacgcg tgcaragcac aatggattag    60

<210> SEQ ID NO 234
<211> LENGTH: 60
<212> TYPE: DNA
<213> ORGANISM: Artificial Sequence
<220> FEATURE:
<223> OTHER INFORMATION: Ser_TGA-1_32_R

<400> SEQUENCE: 234
gcacccgaga attccatggg gcaggattcg aacctgcgcg gggaracccc astggatttc    60

<210> SEQ ID NO 235
<211> LENGTH: 57
<212> TYPE: DNA
<213> ORGANISM: Artificial Sequence
<220> FEATURE:
<223> OTHER INFORMATION: Ser_TGA-2_30_R

<400> SEQUENCE: 235
gcacccgaga attccatggt gaaaaggag ggaatcgaac cccccagac tggtttc         57

<210> SEQ ID NO 236
<211> LENGTH: 57
<212> TYPE: DNA
<213> ORGANISM: Artificial Sequence
<220> FEATURE:
<223> OTHER INFORMATION: Thr_AGT_33_R

<400> SEQUENCE: 236
```
gcacccgaga attccatgga ggccccgctg ggattcgaac ccaggtctcc tgtttac 57

<210> SEQ ID NO 237
<211> LENGTH: 57
<212> TYPE: DNA
<213> ORGANISM: Artificial Sequence
<220> FEATURE:
<223> OTHER INFORMATION: Thr_CGT-1_32_R

<400> SEQUENCE: 237
gcacccgaga attccatggt ggccctggtt ggctttgatc tcttgccyct ggkttac 57

<210> SEQ ID NO 238
<211> LENGTH: 57
<212> TYPE: DNA
<213> ORGANISM: Artificial Sequence
<220> FEATURE:
<223> OTHER INFORMATION: Thr_CGT-2_33_R

<400> SEQUENCE: 238
gcacccgaga attccatgga ggcccggctg gggttcgaac ccgbgtctyc kgtttac 57

<210> SEQ ID NO 239
<211> LENGTH: 57
<212> TYPE: DNA
<213> ORGANISM: Artificial Sequence
<220> FEATURE:
<223> OTHER INFORMATION: Thr_TGT_33_R

<400> SEQUENCE: 239
gcacccgaga attccatgga ggcccagcg agatttgaac tcgwgycycy kgtttac 57

<210> SEQ ID NO 240
<211> LENGTH: 57
<212> TYPE: DNA
<213> ORGANISM: Artificial Sequence
<220> FEATURE:
<223> OTHER INFORMATION: Trp_CCA-1_34_R

<400> SEQUENCE: 240
gcacccgaga attccatgga tgcagaactg ggaattgaac ccaggcacat gactgtg 57

<210> SEQ ID NO 241
<211> LENGTH: 57
<212> TYPE: DNA
<213> ORGANISM: Artificial Sequence
<220> FEATURE:
<223> OTHER INFORMATION: Trp_CCA-2_32_R

<400> SEQUENCE: 241
gcacccgaga attccatggt gaccccgacg tgatttgaac acgcaccttc tgatctg 57

<210> SEQ ID NO 242
<211> LENGTH: 57
<212> TYPE: DNA
<213> ORGANISM: Artificial Sequence
<220> FEATURE:
<223> OTHER INFORMATION: Trp_CCA-3_33_R

<400> SEQUENCE: 242
gcacccgaga attccatggt gaccccgacg tgatttgaac acgcaccttc tgatctg 57

<210> SEQ ID NO 243
<211> LENGTH: 57
<212> TYPE: DNA
<213> ORGANISM: Artificial Sequence
<220> FEATURE:
<223> OTHER INFORMATION: Tyr_ATA_34_R

<400> SEQUENCE: 243
gcacccgaga attccatggt ccttcaagct ggaatcgaac cagcacctaa ggaccta            57

<210> SEQ ID NO 244
<211> LENGTH: 57
<212> TYPE: DNA
<213> ORGANISM: Artificial Sequence
<220> FEATURE:
<223> OTHER INFORMATION: Tyr_GTA-1_33_R

<400> SEQUENCE: 244
gcacccgaga attccatggt ccttcgagcc ggaatcgaac cagcrcctaa gratcta            57

<210> SEQ ID NO 245
<211> LENGTH: 57
<212> TYPE: DNA
<213> ORGANISM: Artificial Sequence
<220> FEATURE:
<223> OTHER INFORMATION: Tyr_GTA-2_32_R

<400> SEQUENCE: 245
gcacccgaga attccatgga gggagaacct ggatttgaac cagggcctct tgctcta            57

<210> SEQ ID NO 246
<211> LENGTH: 57
<212> TYPE: DNA
<213> ORGANISM: Artificial Sequence
<220> FEATURE:
<223> OTHER INFORMATION: Val_AAC-1_33_R

<400> SEQUENCE: 246
gcacccgaga attccatggt gtttctgcct ggtttcaaac caaggccttt cgcgtgt            57

<210> SEQ ID NO 247
<211> LENGTH: 57
<212> TYPE: DNA
<213> ORGANISM: Artificial Sequence
<220> FEATURE:
<223> OTHER INFORMATION: Val_AAC-2_32_R

<400> SEQUENCE: 247
gcacccgaga attccatggt gtttccgccc ggtttcgaac cggggccttt cgcgtgt            57

<210> SEQ ID NO 248
<211> LENGTH: 57
<212> TYPE: DNA
<213> ORGANISM: Artificial Sequence
<220> FEATURE:
<223> OTHER INFORMATION: Val_AAC-3_33_R

<400> SEQUENCE: 248
gcacccgaga attccatggt ggaagtgctg gggatcgaac ccagacctca tgaatgt            57

<210> SEQ ID NO 249
<211> LENGTH: 55
<212> TYPE: DNA
<213> ORGANISM: Artificial Sequence
<220> FEATURE:
<223> OTHER INFORMATION: Val_CAC-1_33_R

<400> SEQUENCE: 249
gcacccgaga attccatggc gtttccacct ggtttcgaac cagrgcytts mdcgt              55

<210> SEQ ID NO 250
<211> LENGTH: 55
<212> TYPE: DNA
<213> ORGANISM: Artificial Sequence
<220> FEATURE:
<223> OTHER INFORMATION: Val_CAC-2_32_R

<400> SEQUENCE: 250
gcacccgaga attccatggt gtttccgccc ggtttcgaac cggggcyttt cgcgt      55

<210> SEQ ID NO 251
<211> LENGTH: 57
<212> TYPE: DNA
<213> ORGANISM: Artificial Sequence
<220> FEATURE:
<223> OTHER INFORMATION: Val_TAC-1_32_R

<400> SEQUENCE: 251
gcacccgaga attccatggt gtttccgctg ggttttgacc cgaggccttty ygcgtgt    57

<210> SEQ ID NO 252
<211> LENGTH: 57
<212> TYPE: DNA
<213> ORGANISM: Artificial Sequence
<220> FEATURE:
<223> OTHER INFORMATION: Val_TAC-2_32_R

<400> SEQUENCE: 252
gcacccgaga attccatggt ggttccactg gggctcgaac ccaggccttc tgcgtgt     57

<210> SEQ ID NO 253
<211> LENGTH: 57
<212> TYPE: DNA
<213> ORGANISM: Artificial Sequence
<220> FEATURE:
<223> OTHER INFORMATION: mAla-TGC_31_R

<400> SEQUENCE: 253
gcacccgaga attccatggt aaggactgca aaaccccact ctgcatcaac tgaacgc     57

<210> SEQ ID NO 254
<211> LENGTH: 53
<212> TYPE: DNA
<213> ORGANISM: Artificial Sequence
<220> FEATURE:
<223> OTHER INFORMATION: mArg-TCG_31_R

<400> SEQUENCE: 254
gcacccgaga attccatggt tggtaaatat gattatcata atttaatgag tcg          53

<210> SEQ ID NO 255
<211> LENGTH: 58
<212> TYPE: DNA
<213> ORGANISM: Artificial Sequence
<220> FEATURE:
<223> OTHER INFORMATION: mAsn-GTT_34_R

<400> SEQUENCE: 255
gcacccgaga attccatggc tagaccaatg ggacttaaac ccacaaacac ttagttaa    58

<210> SEQ ID NO 256
<211> LENGTH: 56
<212> TYPE: DNA
<213> ORGANISM: Artificial Sequence
<220> FEATURE:
<223> OTHER INFORMATION: mAsp-GTC_31_R

<400> SEQUENCE: 256
gcacccgaga attccatggt aagatatata ggatttagcc tataatttaa ctttga        56

<210> SEQ ID NO 257
<211> LENGTH: 56
<212> TYPE: DNA
<213> ORGANISM: Artificial Sequence
<220> FEATURE:
<223> OTHER INFORMATION: mCys-GCA_29_R

<400> SEQUENCE: 257
gcacccgaga attccatgga agccccggca ggtttgaagc tgcttcttcg aatttg        56

<210> SEQ ID NO 258
<211> LENGTH: 57
<212> TYPE: DNA
<213> ORGANISM: Artificial Sequence
<220> FEATURE:
<223> OTHER INFORMATION: mGlu-TTC_31_R

<400> SEQUENCE: 258
gcacccgaga attccatggt attctcgcac ggactacaac cacgaccaat gatatga       57

<210> SEQ ID NO 259
<211> LENGTH: 57
<212> TYPE: DNA
<213> ORGANISM: Artificial Sequence
<220> FEATURE:
<223> OTHER INFORMATION: mGln-TTG_34_R

<400> SEQUENCE: 259
gcacccgaga attccatggc taggactatg agaatcgaac ccatccctga gaatcca       57

<210> SEQ ID NO 260
<211> LENGTH: 56
<212> TYPE: DNA
<213> ORGANISM: Artificial Sequence
<220> FEATURE:
<223> OTHER INFORMATION: mGly-TCC_31_R

<400> SEQUENCE: 260
gcacccgaga attccatggt actcttttt gaatgttgtc aaaactagtt aattgg         56

<210> SEQ ID NO 261
<211> LENGTH: 57
<212> TYPE: DNA
<213> ORGANISM: Artificial Sequence
<220> FEATURE:
<223> OTHER INFORMATION: mHis-GTG_31_R

<400> SEQUENCE: 261
gcacccgaga attccatggg gtaaataagg ggtcgtaagc ctctgttgtc agattca       57

<210> SEQ ID NO 262
<211> LENGTH: 58
<212> TYPE: DNA
<213> ORGANISM: Artificial Sequence
<220> FEATURE:
<223> OTHER INFORMATION: mIle-GAT_30_R

<400> SEQUENCE: 262
gcacccgaga attccatggt agaaataagg gggtttaagc tcctattatt tactctat     58

<210> SEQ ID NO 263

```
<211> LENGTH: 57
<212> TYPE: DNA
<213> ORGANISM: Artificial Sequence
<220> FEATURE:
<223> OTHER INFORMATION: mLeu-TAG_33_R

<400> SEQUENCE: 263
gcacccgaga attccatggt acttttattt ggagttgcac caaaattttt ggggcct        57

<210> SEQ ID NO 264
<211> LENGTH: 58
<212> TYPE: DNA
<213> ORGANISM: Artificial Sequence
<220> FEATURE:
<223> OTHER INFORMATION: mLeu-TAA_36_R

<400> SEQUENCE: 264
gcacccgaga attccatggt gttaagaaga ggaattgaac ctctgactgt aaagtttt      58

<210> SEQ ID NO 265
<211> LENGTH: 60
<212> TYPE: DNA
<213> ORGANISM: Artificial Sequence
<220> FEATURE:
<223> OTHER INFORMATION: mLys-TTT_28_R

<400> SEQUENCE: 265
gcacccgaga attccatggt cactgtaaag aggtgttggt tctcttaatc tttaacttaa    60

<210> SEQ ID NO 266
<211> LENGTH: 56
<212> TYPE: DNA
<213> ORGANISM: Artificial Sequence
<220> FEATURE:
<223> OTHER INFORMATION: mMet-CAT_31_R

<400> SEQUENCE: 266
gcacccgaga attccatggt agtacgggaa gggtataacc aacattttcg gggtat         56

<210> SEQ ID NO 267
<211> LENGTH: 55
<212> TYPE: DNA
<213> ORGANISM: Artificial Sequence
<220> FEATURE:
<223> OTHER INFORMATION: mPhe-GAA_35_R

<400> SEQUENCE: 267
gcacccgaga attccatggt gtttatgggg tgatgtgagc ccgtctaaac atttt          55

<210> SEQ ID NO 268
<211> LENGTH: 55
<212> TYPE: DNA
<213> ORGANISM: Artificial Sequence
<220> FEATURE:
<223> OTHER INFORMATION: mPro-TGG_32_R

<400> SEQUENCE: 268
gcacccgaga attccatggt cagagaaaaa gtctttaact ccaccattag caccc          55

<210> SEQ ID NO 269
<211> LENGTH: 58
<212> TYPE: DNA
<213> ORGANISM: Artificial Sequence
<220> FEATURE:
<223> OTHER INFORMATION: mSer-GCT_20_R

<400> SEQUENCE: 269
```

-continued

<210> SEQ ID NO 270
<211> LENGTH: 57
<212> TYPE: DNA
<213> ORGANISM: Artificial Sequence
<220> FEATURE:
<223> OTHER INFORMATION: mSer-TGA_31_R

<400> SEQUENCE: 270
gcacccgaga attccatggc aaaaaggaa ggaatcgaac cccccaaagc tggtttc    57

<210> SEQ ID NO 271
<211> LENGTH: 53
<212> TYPE: DNA
<213> ORGANISM: Artificial Sequence
<220> FEATURE:
<223> OTHER INFORMATION: mThr-TGT_32_R

<400> SEQUENCE: 271
gcacccgaga attccatggt gtccttggaa aaaggttttc atctccggtt tac    53

<210> SEQ ID NO 272
<211> LENGTH: 54
<212> TYPE: DNA
<213> ORGANISM: Artificial Sequence
<220> FEATURE:
<223> OTHER INFORMATION: mTrp-TCA_33_R

<400> SEQUENCE: 272
gcacccgaga attccatggc agaaattaag tattgcaact tactgagggc tttg    54

<210> SEQ ID NO 273
<211> LENGTH: 55
<212> TYPE: DNA
<213> ORGANISM: Artificial Sequence
<220> FEATURE:
<223> OTHER INFORMATION: mTyr-GTA_30_R

<400> SEQUENCE: 273
gcacccgaga attccatggt ggtaaaaaga ggcctaaccc ctgtctttag attta    55

<210> SEQ ID NO 274
<211> LENGTH: 56
<212> TYPE: DNA
<213> ORGANISM: Artificial Sequence
<220> FEATURE:
<223> OTHER INFORMATION: mVal-TAC_32_R

<400> SEQUENCE: 274
gcacccgaga attccatggt cagagcggtc aagttaagtt gaaatctcct aagtgt    56

<210> SEQ ID NO 275
<211> LENGTH: 54
<212> TYPE: DNA
<213> ORGANISM: Artificial Sequence
<220> FEATURE:
<223> OTHER INFORMATION: Ala_AGC-1_32_L

<400> SEQUENCE: 275
taagcaygcg ctctaccact gagctacacc cccgatcgtc ggactgtaga actc    54

<210> SEQ ID NO 276
<211> LENGTH: 55
<212> TYPE: DNA

```
<213> ORGANISM: Artificial Sequence
<220> FEATURE:
<223> OTHER INFORMATION: Ala_AGC-2_33_L

<400> SEQUENCE: 276
taagwrrgcr ctctaccact tgagctaatt ccccgatcgt cggactgtag aactc      55

<210> SEQ ID NO 277
<211> LENGTH: 54
<212> TYPE: DNA
<213> ORGANISM: Artificial Sequence
<220> FEATURE:
<223> OTHER INFORMATION: Ala_AGC-3_32_L

<400> SEQUENCE: 277
taagcrygcg ctctaccact gatctacacc cccgatcgtc ggactgtaga actc       54

<210> SEQ ID NO 278
<211> LENGTH: 54
<212> TYPE: DNA
<213> ORGANISM: Artificial Sequence
<220> FEATURE:
<223> OTHER INFORMATION: Ala_CGC_32_L

<400> SEQUENCE: 278
gaagcrygcg ctctaccact gagctacatc cccgatcgtc ggactgtaga actc       54

<210> SEQ ID NO 279
<211> LENGTH: 54
<212> TYPE: DNA
<213> ORGANISM: Artificial Sequence
<220> FEATURE:
<223> OTHER INFORMATION: Ala_TGC_32_L

<400> SEQUENCE: 279
aaagcatwyg ctctaccact gagctacacc cccgatcgtc ggactgtaga actc       54

<210> SEQ ID NO 280
<211> LENGTH: 54
<212> TYPE: DNA
<213> ORGANISM: Artificial Sequence
<220> FEATURE:
<223> OTHER INFORMATION: Arg_ACG_32_L

<400> SEQUENCE: 280
tagtcagacg cgtttccatt gcgccactgg cccgatcgtc ggactgtaga actc       54

<210> SEQ ID NO 281
<211> LENGTH: 54
<212> TYPE: DNA
<213> ORGANISM: Artificial Sequence
<220> FEATURE:
<223> OTHER INFORMATION: Arg_CCG-1_32_L

<400> SEQUENCE: 281
gaatcagacg cctttccatt aggccacgcg gccgatcgtc ggactgtaga actc       54

<210> SEQ ID NO 282
<211> LENGTH: 54
<212> TYPE: DNA
<213> ORGANISM: Artificial Sequence
<220> FEATURE:
<223> OTHER INFORMATION: Arg_CCG-2_33_L

<400> SEQUENCE: 282
gaggctgatg cctttccatt aggccactgg gtcgatcgtc ggactgtaga actc       54
```

<210> SEQ ID NO 283
<211> LENGTH: 54
<212> TYPE: DNA
<213> ORGANISM: Artificial Sequence
<220> FEATURE:
<223> OTHER INFORMATION: Arg_CCT_32_L

<400> SEQUENCE: 283
gaggccartr cctttccatt aggccactgg ggcgatcgtc ggactgtaga actc    54

<210> SEQ ID NO 284
<211> LENGTH: 54
<212> TYPE: DNA
<213> ORGANISM: Artificial Sequence
<220> FEATURE:
<223> OTHER INFORMATION: Arg_TCG_32_L

<400> SEQUENCE: 284
aagtcagacg cctttccatt aggccacgtg gtcgatcgtc ggactgtaga actc    54

<210> SEQ ID NO 285
<211> LENGTH: 54
<212> TYPE: DNA
<213> ORGANISM: Artificial Sequence
<220> FEATURE:
<223> OTHER INFORMATION: Arg_TCT_32_L

<400> SEQUENCE: 285
aagtccaryg cgcttccatt gcgccacaga gccgatcgtc ggactgtaga actc    54

<210> SEQ ID NO 286
<211> LENGTH: 55
<212> TYPE: DNA
<213> ORGANISM: Artificial Sequence
<220> FEATURE:
<223> OTHER INFORMATION: Asn_ATT_34_L

<400> SEQUENCE: 286
tagccgaacg ctctaccgat tgcgccacag agacgatcgt cggactgtag aactc    55

<210> SEQ ID NO 287
<211> LENGTH: 55
<212> TYPE: DNA
<213> ORGANISM: Artificial Sequence
<220> FEATURE:
<223> OTHER INFORMATION: Asn_GTT-1_33_L

<400> SEQUENCE: 287
crgccgaawg cgctaccgat tgcgccacag agacgatcgt cggactgtag aactc    55

<210> SEQ ID NO 288
<211> LENGTH: 55
<212> TYPE: DNA
<213> ORGANISM: Artificial Sequence
<220> FEATURE:
<223> OTHER INFORMATION: Asn_GTT-2_33_L

<400> SEQUENCE: 288
cagcwraayg cgctaccgat tgcgccacag agacgatcgt cggactgtag aactc    55

<210> SEQ ID NO 289
<211> LENGTH: 55
<212> TYPE: DNA
<213> ORGANISM: Artificial Sequence
<220> FEATURE:

```
<223> OTHER INFORMATION: Asn_GTT-3_33_L

<400> SEQUENCE: 289
cagtcaaacg cgctaccgat tgcgccacag agacgatcgt cggactgtag aactc         55

<210> SEQ ID NO 290
<211> LENGTH: 54
<212> TYPE: DNA
<213> ORGANISM: Artificial Sequence
<220> FEATURE:
<223> OTHER INFORMATION: Asp_GTC-1_32_L

<400> SEQUENCE: 290
caggcagara tactaccact atagtaacaa ggagatcgtc ggactgtaga actc          54

<210> SEQ ID NO 291
<211> LENGTH: 54
<212> TYPE: DNA
<213> ORGANISM: Artificial Sequence
<220> FEATURE:
<223> OTHER INFORMATION: Asp_GTC-2_32_L

<400> SEQUENCE: 291
cagrcrggga tactaccact atactaacga ggagatcgtc ggactgtaga actc          54

<210> SEQ ID NO 292
<211> LENGTH: 54
<212> TYPE: DNA
<213> ORGANISM: Artificial Sequence
<220> FEATURE:
<223> OTHER INFORMATION: Cys_GCA_32_L

<400> SEQUENCE: 292
cagtcaartg ctctacccct gagctatacc cccgatcgtc ggactgtaga actc          54

<210> SEQ ID NO 293
<211> LENGTH: 54
<212> TYPE: DNA
<213> ORGANISM: Artificial Sequence
<220> FEATURE:
<223> OTHER INFORMATION: Gln_CTG-1_33_L

<400> SEQUENCE: 293
gagttcatga tcttaccact ctaccatact gccgatcgtc ggactgtaga actc          54

<210> SEQ ID NO 294
<211> LENGTH: 54
<212> TYPE: DNA
<213> ORGANISM: Artificial Sequence
<220> FEATURE:
<223> OTHER INFORMATION: Gln_CTG-2_32_L

<400> SEQUENCE: 294
gagtccarrg tgctaccatt acaccatgga accgatcgtc ggactgtaga actc          54

<210> SEQ ID NO 295
<211> LENGTH: 53
<212> TYPE: DNA
<213> ORGANISM: Artificial Sequence
<220> FEATURE:
<223> OTHER INFORMATION: Gln_CTG-3_32_L

<400> SEQUENCE: 295
gagcgaatgc cctacctctg ggctacactg ccgatcgtcg gactgtagaa ctc           53
```

```
<210> SEQ ID NO 296
<211> LENGTH: 55
<212> TYPE: DNA
<213> ORGANISM: Artificial Sequence
<220> FEATURE:
<223> OTHER INFORMATION: Gln_TTG-1_33_L

<400> SEQUENCE: 296
aaattctcyr tgctacctat tacaccatgt cctagatcgt cggactgtag aactc        55

<210> SEQ ID NO 297
<211> LENGTH: 54
<212> TYPE: DNA
<213> ORGANISM: Artificial Sequence
<220> FEATURE:
<223> OTHER INFORMATION: Gln_TTG-2_32_L

<400> SEQUENCE: 297
aagyccagag tgctaccatt acaccatggg gccgatcgtc ggactgtaga actc          54

<210> SEQ ID NO 298
<211> LENGTH: 54
<212> TYPE: DNA
<213> ORGANISM: Artificial Sequence
<220> FEATURE:
<223> OTHER INFORMATION: Gln_TTG-3_33_L

<400> SEQUENCE: 298
aagtgagatg tctttcccct aggccacatg gtcgatcgtc ggactgtaga actc          54

<210> SEQ ID NO 299
<211> LENGTH: 54
<212> TYPE: DNA
<213> ORGANISM: Artificial Sequence
<220> FEATURE:
<223> OTHER INFORMATION: Glu_CTC-1_32_L

<400> SEQUENCE: 299
gagwkcyraa tccttccgct agaccacccg ggggatcgtc ggactgtaga actc          54

<210> SEQ ID NO 300
<211> LENGTH: 54
<212> TYPE: DNA
<213> ORGANISM: Artificial Sequence
<220> FEATURE:
<223> OTHER INFORMATION: Glu_CTC-2_33_L

<400> SEQUENCE: 300
gagcgccaaa ctttgccact agactaccag ggagatcgtc ggactgtaga actc          54

<210> SEQ ID NO 301
<211> LENGTH: 54
<212> TYPE: DNA
<213> ORGANISM: Artificial Sequence
<220> FEATURE:
<223> OTHER INFORMATION: Glu_CTC-3_32_L

<400> SEQUENCE: 301
gagcrccgaa tcctaccact agaccaccag ggagatcgtc ggactgtaga actc          54

<210> SEQ ID NO 302
<211> LENGTH: 54
<212> TYPE: DNA
<213> ORGANISM: Artificial Sequence
<220> FEATURE:
<223> OTHER INFORMATION: Glu_TTC-1_32_L
```

<400> SEQUENCE: 302
aaaccaggaa tcctaccgct agaccatgtg ggagatcgtc ggactgtaga actc    54

<210> SEQ ID NO 303
<211> LENGTH: 52
<212> TYPE: DNA
<213> ORGANISM: Artificial Sequence
<220> FEATURE:
<223> OTHER INFORMATION: Glu_TTC-2_31_L

<400> SEQUENCE: 303
aagcaccaac tcctaccact agaccacagg ggatcgtcgg actgtagaac tc    52

<210> SEQ ID NO 304
<211> LENGTH: 54
<212> TYPE: DNA
<213> ORGANISM: Artificial Sequence
<220> FEATURE:
<223> OTHER INFORMATION: Glu_TTC-3_32_L

<400> SEQUENCE: 304
aagcgccraa ttttgccact agactaccag ggagatcgtc ggactgtaga actc    54

<210> SEQ ID NO 305
<211> LENGTH: 53
<212> TYPE: DNA
<213> ORGANISM: Artificial Sequence
<220> FEATURE:
<223> OTHER INFORMATION: Glu_TTC-4_31_L

<400> SEQUENCE: 305
aarcacsrag ttttgccact agaccacagg gtgatcgtcg gactgtagaa ctc    53

<210> SEQ ID NO 306
<211> LENGTH: 54
<212> TYPE: DNA
<213> ORGANISM: Artificial Sequence
<220> FEATURE:
<223> OTHER INFORMATION: Glu_TTC-5_32_L

<400> SEQUENCE: 306
aagcgccgaa tcctgccact agaccaccag ggagatcgtc ggactgtaga actc    54

<210> SEQ ID NO 307
<211> LENGTH: 54
<212> TYPE: DNA
<213> ORGANISM: Artificial Sequence
<220> FEATURE:
<223> OTHER INFORMATION: Gly_CCC-1_32_L

<400> SEQUENCE: 307
gaatcttgca tgataccact acaccagcgg cgcgatcgtc ggactgtaga actc    54

<210> SEQ ID NO 308
<211> LENGTH: 54
<212> TYPE: DNA
<213> ORGANISM: Artificial Sequence
<220> FEATURE:
<223> OTHER INFORMATION: Gly_CCC-2_32_L

<400> SEQUENCE: 308
gaggcgagaa ttctaccact gaaccaccaa tgcgatcgtc ggactgtaga actc    54

<210> SEQ ID NO 309
<211> LENGTH: 54

```
<212> TYPE: DNA
<213> ORGANISM: Artificial Sequence
<220> FEATURE:
<223> OTHER INFORMATION: Gly_CCC-3_33_L

<400> SEQUENCE: 309
gaggcgagaa ttctaccact gaaccaccaa tgcgatcgtc ggactgtaga actc    54

<210> SEQ ID NO 310
<211> LENGTH: 54
<212> TYPE: DNA
<213> ORGANISM: Artificial Sequence
<220> FEATURE:
<223> OTHER INFORMATION: Gly_GCC_32_L

<400> SEQUENCE: 310
caggcragaa ttctaccact gaaccaccaa tgcgatcgtc ggactgtaga actc    54

<210> SEQ ID NO 311
<211> LENGTH: 54
<212> TYPE: DNA
<213> ORGANISM: Artificial Sequence
<220> FEATURE:
<223> OTHER INFORMATION: Gly_TCC_32_L

<400> SEQUENCE: 311
aaggcarcta tgctaccact ataccaccaa cgcgatcgtc ggactgtaga actc    54

<210> SEQ ID NO 312
<211> LENGTH: 54
<212> TYPE: DNA
<213> ORGANISM: Artificial Sequence
<220> FEATURE:
<223> OTHER INFORMATION: His_GTG_32_L

<400> SEQUENCE: 312
carcrcagag tactaccact atacgatcac ggcgatcgtc ggactgtaga actc    54

<210> SEQ ID NO 313
<211> LENGTH: 55
<212> TYPE: DNA
<213> ORGANISM: Artificial Sequence
<220> FEATURE:
<223> OTHER INFORMATION: Ile_AAT_33_L

<400> SEQUENCE: 313
tagcrccacg ctctaccaac tgagctaacc ggccgatcgt cggactgtag aactc    55

<210> SEQ ID NO 314
<211> LENGTH: 55
<212> TYPE: DNA
<213> ORGANISM: Artificial Sequence
<220> FEATURE:
<223> OTHER INFORMATION: Ile_GAT_33_L

<400> SEQUENCE: 314
cagcaccacg ctctaccaac tgagctaacc ggccgatcgt cggactgtag aactc    55

<210> SEQ ID NO 315
<211> LENGTH: 55
<212> TYPE: DNA
<213> ORGANISM: Artificial Sequence
<220> FEATURE:
<223> OTHER INFORMATION: Ile_TAT_33_L

<400> SEQUENCE: 315
```
aagtaccgcg cgctaccgat tgcgccactg gagcgatcgt cggactgtag aactc      55

<210> SEQ ID NO 316
<211> LENGTH: 54
<212> TYPE: DNA
<213> ORGANISM: Artificial Sequence
<220> FEATURE:
<223> OTHER INFORMATION: Leu_AAG-1_32_L

<400> SEQUENCE: 316
taatscagtg tcttaccgct cggccatgct accgatcgtc ggactgtaga actc      54

<210> SEQ ID NO 317
<211> LENGTH: 54
<212> TYPE: DNA
<213> ORGANISM: Artificial Sequence
<220> FEATURE:
<223> OTHER INFORMATION: Leu_AAG-2_32_L

<400> SEQUENCE: 317
taatccagcg ccttaccgct cggccacgct accgatcgtc ggactgtaga actc      54

<210> SEQ ID NO 318
<211> LENGTH: 54
<212> TYPE: DNA
<213> ORGANISM: Artificial Sequence
<220> FEATURE:
<223> OTHER INFORMATION: Leu_AAG-3_33_L

<400> SEQUENCE: 318
tagtcagacg catttccatt gagccactgg cccgatcgtc ggactgtaga actc      54

<210> SEQ ID NO 319
<211> LENGTH: 55
<212> TYPE: DNA
<213> ORGANISM: Artificial Sequence
<220> FEATURE:
<223> OTHER INFORMATION: Leu_CAA-1_34_L

<400> SEQUENCE: 319
gagactgatg cgctacctac tgcactaagg aggcgatcgt cggactgtag aactc     55

<210> SEQ ID NO 320
<211> LENGTH: 54
<212> TYPE: DNA
<213> ORGANISM: Artificial Sequence
<220> FEATURE:
<223> OTHER INFORMATION: Leu_CAA-2_32_L

<400> SEQUENCE: 320
gagtctggcg ccttaccact cggccatcct gacgatcgtc ggactgtaga actc      54

<210> SEQ ID NO 321
<211> LENGTH: 54
<212> TYPE: DNA
<213> ORGANISM: Artificial Sequence
<220> FEATURE:
<223> OTHER INFORMATION: Leu_CAG-1_32_L

<400> SEQUENCE: 321
gaacgcagcg ccttaccgct cggccatcct gacgatcgtc ggactgtaga actc      54

<210> SEQ ID NO 322
<211> LENGTH: 53
<212> TYPE: DNA
<213> ORGANISM: Artificial Sequence -continued

```
<220> FEATURE:
<223> OTHER INFORMATION: Leu_CAG-2_32_L

<400> SEQUENCE: 322
gagcaggtcc ttaaccacta aactccactg ccgatcgtcg gactgtagaa ctc         53

<210> SEQ ID NO 323
<211> LENGTH: 54
<212> TYPE: DNA
<213> ORGANISM: Artificial Sequence
<220> FEATURE:
<223> OTHER INFORMATION: Leu_TAA-1_32_L

<400> SEQUENCE: 323
aagtccaacg ccttaccact cggccatcct ggtgatcgtc ggactgtaga actc        54

<210> SEQ ID NO 324
<211> LENGTH: 55
<212> TYPE: DNA
<213> ORGANISM: Artificial Sequence
<220> FEATURE:
<223> OTHER INFORMATION: Leu_TAA-2_33_L

<400> SEQUENCE: 324
aagtyttatg caatgccggc tctgccatct taacgatcgt cggactgtag aactc       55

<210> SEQ ID NO 325
<211> LENGTH: 54
<212> TYPE: DNA
<213> ORGANISM: Artificial Sequence
<220> FEATURE:
<223> OTHER INFORMATION: Leu_TAA-3_33_L

<400> SEQUENCE: 325
aagtccaatg ccttaccact cagccaaatg agtgatcgtc ggactgtaga actc        54

<210> SEQ ID NO 326
<211> LENGTH: 54
<212> TYPE: DNA
<213> ORGANISM: Artificial Sequence
<220> FEATURE:
<223> OTHER INFORMATION: Leu_TAG_32_L

<400> SEQUENCE: 326
aaatccagcg ccttaccgct cggccacgct accgatcgtc ggactgtaga actc        54

<210> SEQ ID NO 327
<211> LENGTH: 55
<212> TYPE: DNA
<213> ORGANISM: Artificial Sequence
<220> FEATURE:
<223> OTHER INFORMATION: Lys_CTT-1_33_L

<400> SEQUENCE: 327
gagtctcayg ctttatcgac tgagctattt ggttgatcgt cggactgtag aactc       55

<210> SEQ ID NO 328
<211> LENGTH: 55
<212> TYPE: DNA
<213> ORGANISM: Artificial Sequence
<220> FEATURE:
<223> OTHER INFORMATION: Lys_CTT-2_33_L

<400> SEQUENCE: 328
grgtcyyatg ctctaccgac tgagctagcc gggcgatcgt cggactgtag aactc       55
```

<210> SEQ ID NO 329
<211> LENGTH: 55
<212> TYPE: DNA
<213> ORGANISM: Artificial Sequence
<220> FEATURE:
<223> OTHER INFORMATION: Lys_TTT-1_32_L

<400> SEQUENCE: 329
aagtcyratg ctctaccgac tgagctatcc gggcgatcgt cggactgtag aactc      55

<210> SEQ ID NO 330
<211> LENGTH: 55
<212> TYPE: DNA
<213> ORGANISM: Artificial Sequence
<220> FEATURE:
<223> OTHER INFORMATION: Lys_TTT-2_32_L

<400> SEQUENCE: 330
aagtcyratg ctctacctac tgagctaccc aggtgatcgt cggactgtag aactc      55

<210> SEQ ID NO 331
<211> LENGTH: 55
<212> TYPE: DNA
<213> ORGANISM: Artificial Sequence
<220> FEATURE:
<223> OTHER INFORMATION: Met_CAT-1_33_L

<400> SEQUENCE: 331
garactgacg cgctgcctgc tgcgctaaga gggcgatcgt cggactgtag aactc      55

<210> SEQ ID NO 332
<211> LENGTH: 54
<212> TYPE: DNA
<213> ORGANISM: Artificial Sequence
<220> FEATURE:
<223> OTHER INFORMATION: Met_CAT-2_32_L

<400> SEQUENCE: 332
gggcccagya cgcttccgct gcgccactct gctgatcgtc ggactgtaga actc       54

<210> SEQ ID NO 333
<211> LENGTH: 55
<212> TYPE: DNA
<213> ORGANISM: Artificial Sequence
<220> FEATURE:
<223> OTHER INFORMATION: Phe_GAA_33_L

<400> SEQUENCE: 333
crgtctaacr ctctcccaac tgagctattt cggcgatcgt cggactgtag aactc      55

<210> SEQ ID NO 334
<211> LENGTH: 54
<212> TYPE: DNA
<213> ORGANISM: Artificial Sequence
<220> FEATURE:
<223> OTHER INFORMATION: Pro_AGG_32_L

<400> SEQUENCE: 334
taagcgagaa tcataccct agaccaacga gccgatcgtc ggactgtaga actc        54

<210> SEQ ID NO 335
<211> LENGTH: 54
<212> TYPE: DNA
<213> ORGANISM: Artificial Sequence
<220> FEATURE:
<223> OTHER INFORMATION: Pro_CGG_32_L -continued

<400> SEQUENCE: 335
gaagcgagaa tcatacccct agaccaacga gccgatcgtc ggactgtaga actc    54

<210> SEQ ID NO 336
<211> LENGTH: 54
<212> TYPE: DNA
<213> ORGANISM: Artificial Sequence
<220> FEATURE:
<223> OTHER INFORMATION: Pro_TGG_32_L

<400> SEQUENCE: 336
aaawcgagaa tcatacccct agaccaacga gccgatcgtc ggactgtaga actc    54

<210> SEQ ID NO 337
<211> LENGTH: 57
<212> TYPE: DNA
<213> ORGANISM: Artificial Sequence
<220> FEATURE:
<223> OTHER INFORMATION: SeC(e)_TCA_35_L

<400> SEQUENCE: 337
aagcctgcac cccagaccac tgaggatcat ccgggcgatc gtcggactgt agaactc    57

<210> SEQ ID NO 338
<211> LENGTH: 54
<212> TYPE: DNA
<213> ORGANISM: Artificial Sequence
<220> FEATURE:
<223> OTHER INFORMATION: SeC_TCA_33_L

<400> SEQUENCE: 338
aagtcagaca cctttccatt aggccacacg gtcgatcgtc ggactgtaga actc    54

<210> SEQ ID NO 339
<211> LENGTH: 54
<212> TYPE: DNA
<213> ORGANISM: Artificial Sequence
<220> FEATURE:
<223> OTHER INFORMATION: Ser_AGA-1_33_L

<400> SEQUENCE: 339
tagctcgttg ccttaccact cagctacaac tcagatcgtc ggactgtaga actc    54

<210> SEQ ID NO 340
<211> LENGTH: 54
<212> TYPE: DNA
<213> ORGANISM: Artificial Sequence
<220> FEATURE:
<223> OTHER INFORMATION: Ser_AGA-2_32_L

<400> SEQUENCE: 340
tagtccatcg ccttaccact cggccacgac tacgatcgtc ggactgtaga actc    54

<210> SEQ ID NO 341
<211> LENGTH: 56
<212> TYPE: DNA
<213> ORGANISM: Artificial Sequence
<220> FEATURE:
<223> OTHER INFORMATION: Ser_AGA-3_33_L

<400> SEQUENCE: 341
tctagtcaaa ttctctaccc ctgagccata cacccgatcg tcggactgta gaactc    56

<210> SEQ ID NO 342

-continued

<210> SEQ ID NO 342
<211> LENGTH: 54
<212> TYPE: DNA
<213> ORGANISM: Artificial Sequence
<220> FEATURE:
<223> OTHER INFORMATION: Ser_CGA_32_L

<400> SEQUENCE: 342
gagtccaacg ccttaccact cggccatcac agcgatcgtc ggactgtaga actc      54

<210> SEQ ID NO 343
<211> LENGTH: 54
<212> TYPE: DNA
<213> ORGANISM: Artificial Sequence
<220> FEATURE:
<223> OTHER INFORMATION: Ser_GCT_32_L

<400> SEQUENCE: 343
cagtccatcg ccttaccact cggccacctc gtcgatcgtc ggactgtaga actc      54

<210> SEQ ID NO 344
<211> LENGTH: 54
<212> TYPE: DNA
<213> ORGANISM: Artificial Sequence
<220> FEATURE:
<223> OTHER INFORMATION: Ser_TGA-1_32_L

<400> SEQUENCE: 344
aagtccatcg ccttaccact cggccacgac tacgatcgtc ggactgtaga actc      54

<210> SEQ ID NO 345
<211> LENGTH: 51
<212> TYPE: DNA
<213> ORGANISM: Artificial Sequence
<220> FEATURE:
<223> OTHER INFORMATION: Ser_TGA-2_30_L

<400> SEQUENCE: 345
aagccaatcc atacctctg tgaccttctc gatcgtcgga ctgtagaact c      51

<210> SEQ ID NO 346
<211> LENGTH: 55
<212> TYPE: DNA
<213> ORGANISM: Artificial Sequence
<220> FEATURE:
<223> OTHER INFORMATION: Thr_AGT_33_L

<400> SEQUENCE: 346
tagacaggyg ctttaccagc taagccacgg cgccgatcgt cggactgtag aactc      55

<210> SEQ ID NO 347
<211> LENGTH: 54
<212> TYPE: DNA
<213> ORGANISM: Artificial Sequence
<220> FEATURE:
<223> OTHER INFORMATION: Thr_CGT-1_32_L

<400> SEQUENCE: 347
grgmccagcr ctcttccgct gcgctactgt gccgatcgtc ggactgtaga actc      54

<210> SEQ ID NO 348
<211> LENGTH: 55
<212> TYPE: DNA
<213> ORGANISM: Artificial Sequence
<220> FEATURE:
<223> OTHER INFORMATION: Thr_CGT-2_33_L

<400> SEQUENCE: 348
gagacmgrcg ctttaccaac ttggccaccg cgccgatcgt cggactgtag aactc    55

<210> SEQ ID NO 349
<211> LENGTH: 55
<212> TYPE: DNA
<213> ORGANISM: Artificial Sequence
<220> FEATURE:
<223> OTHER INFORMATION: Thr_TGT_33_L

<400> SEQUENCE: 349
aagacmrgyg ctctaccacc tgagctatgg agccgatcgt cggactgtag aactc    55

<210> SEQ ID NO 350
<211> LENGTH: 55
<212> TYPE: DNA
<213> ORGANISM: Artificial Sequence
<220> FEATURE:
<223> OTHER INFORMATION: Trp_CCA-1_34_L

<400> SEQUENCE: 350
gagcccacag gctttccagc ttggccatcc ttccgatcgt cggactgtag aactc    55

<210> SEQ ID NO 351
<211> LENGTH: 54
<212> TYPE: DNA
<213> ORGANISM: Artificial Sequence
<220> FEATURE:
<223> OTHER INFORMATION: Trp_CCA-2_32_L

<400> SEQUENCE: 351
gagtcagacg cgctaccgtt gcgccacgag gtcgatcgtc ggactgtaga actc    54

<210> SEQ ID NO 352
<211> LENGTH: 54
<212> TYPE: DNA
<213> ORGANISM: Artificial Sequence
<220> FEATURE:
<223> OTHER INFORMATION: Trp_CCA-3_33_L

<400> SEQUENCE: 352
gagtcagacg cgctgccgtt gcgccacgag gtcgatcgtc ggactgtaga actc    54

<210> SEQ ID NO 353
<211> LENGTH: 55
<212> TYPE: DNA
<213> ORGANISM: Artificial Sequence
<220> FEATURE:
<223> OTHER INFORMATION: Tyr_ATA_34_L

<400> SEQUENCE: 353
tagtcctctg ctctaccagc tgaactattg aagggatcgt cggactgtag aactc    55

<210> SEQ ID NO 354
<211> LENGTH: 55
<212> TYPE: DNA
<213> ORGANISM: Artificial Sequence
<220> FEATURE:
<223> OTHER INFORMATION: Tyr_GTA-1_33_L

<400> SEQUENCE: 354
cagtcctccg ctctaccagc tgagctatcg aagggatcgt cggactgtag aactc    55

<210> SEQ ID NO 355
<211> LENGTH: 53
<212> TYPE: DNA

```
<213> ORGANISM: Artificial Sequence
<220> FEATURE:
<223> OTHER INFORMATION: Tyr_GTA-2_32_L

<400> SEQUENCE: 355
cagtcaaaag ctctgccctg agctataccc ccgatcgtcg gactgtagaa ctc      53

<210> SEQ ID NO 356
<211> LENGTH: 54
<212> TYPE: DNA
<213> ORGANISM: Artificial Sequence
<220> FEATURE:
<223> OTHER INFORMATION: Val_AAC-1_33_L

<400> SEQUENCE: 356
taggtgaatg tgataccagt acactatgga aacgatcgtc ggactgtaga actc     54

<210> SEQ ID NO 357
<211> LENGTH: 54
<212> TYPE: DNA
<213> ORGANISM: Artificial Sequence
<220> FEATURE:
<223> OTHER INFORMATION: Val_AAC-2_32_L

<400> SEQUENCE: 357
taggcraacg tgataccact acactacgga aacgatcgtc ggactgtaga actc     54

<210> SEQ ID NO 358
<211> LENGTH: 54
<212> TYPE: DNA
<213> ORGANISM: Artificial Sequence
<220> FEATURE:
<223> OTHER INFORMATION: Val_AAC-3_33_L

<400> SEQUENCE: 358
taagcatacg ctctaccact gagctacacc cccgatcgtc ggactgtaga actc     54

<210> SEQ ID NO 359
<211> LENGTH: 57
<212> TYPE: DNA
<213> ORGANISM: Artificial Sequence
<220> FEATURE:
<223> OTHER INFORMATION: Val_CAC-1_33_L

<400> SEQUENCE: 359
gtgagrckaa crtgataacc actacactac agaaacgatc gtcggactgt agaactc   57

<210> SEQ ID NO 360
<211> LENGTH: 56
<212> TYPE: DNA
<213> ORGANISM: Artificial Sequence
<220> FEATURE:
<223> OTHER INFORMATION: Val_CAC-2_32_L

<400> SEQUENCE: 360
gtgaggcgaa yrtgatacca ctacactacg gaaacgatcg tcggactgta gaactc    56

<210> SEQ ID NO 361
<211> LENGTH: 54
<212> TYPE: DNA
<213> ORGANISM: Artificial Sequence
<220> FEATURE:
<223> OTHER INFORMATION: Val_TAC-1_32_L

<400> SEQUENCE: 361
aargcrratg tgataccact acactatgga accgatcgtc ggactgtaga actc     54
```

<210> SEQ ID NO 362
<211> LENGTH: 54
<212> TYPE: DNA
<213> ORGANISM: Artificial Sequence
<220> FEATURE:
<223> OTHER INFORMATION: Val_TAC-2_32_L

<400> SEQUENCE: 362
aaagcagacg tgataccact acactatgga accgatcgtc ggactgtaga actc    54

<210> SEQ ID NO 363
<211> LENGTH: 52
<212> TYPE: DNA
<213> ORGANISM: Artificial Sequence
<220> FEATURE:
<223> OTHER INFORMATION: mAla-TGC_31_L

<400> SEQUENCE: 363
aaatcagcca ctttaattaa gctaagccct tgatcgtcgg actgtagaac tc    52

<210> SEQ ID NO 364
<211> LENGTH: 52
<212> TYPE: DNA
<213> ORGANISM: Artificial Sequence
<220> FEATURE:
<223> OTHER INFORMATION: mArg-TCG_31_L

<400> SEQUENCE: 364
aaatcattcg ttttgtttaa actatatacc agatcgtcgg actgtagaac tc    52

<210> SEQ ID NO 365
<211> LENGTH: 55
<212> TYPE: DNA
<213> ORGANISM: Artificial Sequence
<220> FEATURE:
<223> OTHER INFORMATION: mAsn-GTT_34_L

<400> SEQUENCE: 365
cagctaagca ccctaatcaa ctggcttcaa tctagatcgt cggactgtag aactc    55

<210> SEQ ID NO 366
<211> LENGTH: 52
<212> TYPE: DNA
<213> ORGANISM: Artificial Sequence
<220> FEATURE:
<223> OTHER INFORMATION: mAsp-GTC_31_L

<400> SEQUENCE: 366
caaagttatg aaatggtttt tctaatacct tgatcgtcgg actgtagaac tc    52

<210> SEQ ID NO 367
<211> LENGTH: 50
<212> TYPE: DNA
<213> ORGANISM: Artificial Sequence
<220> FEATURE:
<223> OTHER INFORMATION: mCys-GCA_29_L

<400> SEQUENCE: 367
caattcaata tgaaaatcac ctcggagctg atcgtcggac tgtagaactc    50

<210> SEQ ID NO 368
<211> LENGTH: 52
<212> TYPE: DNA
<213> ORGANISM: Artificial Sequence
<220> FEATURE:

-continued

<223> OTHER INFORMATION: mGlu-TTC_31_L

<400> SEQUENCE: 368
aaaaccatcg ttgtatttca actacaagaa cgatcgtcgg actgtagaac tc          52

<210> SEQ ID NO 369
<211> LENGTH: 55
<212> TYPE: DNA
<213> ORGANISM: Artificial Sequence
<220> FEATURE:
<223> OTHER INFORMATION: mGln-TTG_34_L

<400> SEQUENCE: 369
aaattctccg tgccacctat cacaccccat cctagatcgt cggactgtag aactc         55

<210> SEQ ID NO 370
<211> LENGTH: 52
<212> TYPE: DNA
<213> ORGANISM: Artificial Sequence
<220> FEATURE:
<223> OTHER INFORMATION: mGly-TCC_31_L

<400> SEQUENCE: 370
aagttaacgg tactatttat actaaaagag tgatcgtcgg actgtagaac tc          52

<210> SEQ ID NO 371
<211> LENGTH: 52
<212> TYPE: DNA
<213> ORGANISM: Artificial Sequence
<220> FEATURE:
<223> OTHER INFORMATION: mHis-GTG_31_L

<400> SEQUENCE: 371
caatctgatg ttttggttaa actatattta cgatcgtcgg actgtagaac tc          52

<210> SEQ ID NO 372
<211> LENGTH: 51
<212> TYPE: DNA
<213> ORGANISM: Artificial Sequence
<220> FEATURE:
<223> OTHER INFORMATION: mIle-GAT_30_L

<400> SEQUENCE: 372
caaagtaact cttttatcag acatatttct gatcgtcgga ctgtagaact c           51

<210> SEQ ID NO 373
<211> LENGTH: 54
<212> TYPE: DNA
<213> ORGANISM: Artificial Sequence
<220> FEATURE:
<223> OTHER INFORMATION: mLeu-TAG_33_L

<400> SEQUENCE: 373
aagaccaatg gatagctgtt atcctttaaa agtgatcgtc ggactgtaga actc         54

<210> SEQ ID NO 374
<211> LENGTH: 57
<212> TYPE: DNA
<213> ORGANISM: Artificial Sequence
<220> FEATURE:
<223> OTHER INFORMATION: mLeu-TAA_36_L

<400> SEQUENCE: 374
aagttttatg cgattaccgg gctctgccat cttaacgatc gtcggactgt agaactc       57

<210> SEQ ID NO 375
<211> LENGTH: 50
<212> TYPE: DNA
<213> ORGANISM: Artificial Sequence
<220> FEATURE:
<223> OTHER INFORMATION: mLys-TTT_28_L

<400> SEQUENCE: 375
aaggttaatg ctaagttagc tttacagtgg atcgtcggac tgtagaactc          50

<210> SEQ ID NO 376
<211> LENGTH: 52
<212> TYPE: DNA
<213> ORGANISM: Artificial Sequence
<220> FEATURE:
<223> OTHER INFORMATION: mMet-CAT_31_L

<400> SEQUENCE: 376
gggcccgata gcttatttag ctgaccttac tgatcgtcgg actgtagaac tc        52

<210> SEQ ID NO 377
<211> LENGTH: 56
<212> TYPE: DNA
<213> ORGANISM: Artificial Sequence
<220> FEATURE:
<223> OTHER INFORMATION: mPhe-GAA_35_L

<400> SEQUENCE: 377
cagtgtattg ctttgaggag gtaagctaca taaacgatcg tcggactgta gaactc    56

<210> SEQ ID NO 378
<211> LENGTH: 53
<212> TYPE: DNA
<213> ORGANISM: Artificial Sequence
<220> FEATURE:
<223> OTHER INFORMATION: mPro-TGG_32_L

<400> SEQUENCE: 378
aaagctaaga ttctaattta aactattctc tggatcgtcg gactgtagaa ctc       53

<210> SEQ ID NO 379
<211> LENGTH: 41
<212> TYPE: DNA
<213> ORGANISM: Artificial Sequence
<220> FEATURE:
<223> OTHER INFORMATION: mSer-GCT_20_L

<400> SEQUENCE: 379
cagttcttgt gagctttctc gatcgtcgga ctgtagaact c                    41

<210> SEQ ID NO 380
<211> LENGTH: 52
<212> TYPE: DNA
<213> ORGANISM: Artificial Sequence
<220> FEATURE:
<223> OTHER INFORMATION: mSer-TGA_31_L

<400> SEQUENCE: 380
aagccaaccc catggcctcc atgacttttt cgatcgtcgg actgtagaac tc        52

<210> SEQ ID NO 381
<211> LENGTH: 53
<212> TYPE: DNA
<213> ORGANISM: Artificial Sequence
<220> FEATURE:
<223> OTHER INFORMATION: mThr-TGT_32_L

```
<400> SEQUENCE: 381
aagactggtg tattagttta tactacaagg acgatcgtcg gactgtagaa ctc            53

<210> SEQ ID NO 382
<211> LENGTH: 54
<212> TYPE: DNA
<213> ORGANISM: Artificial Sequence
<220> FEATURE:
<223> OTHER INFORMATION: mTrp-TCA_33_L

<400> SEQUENCE: 382
aaggctcttg gtctgtattt aacctaaatt tctgatcgtc ggactgtaga actc           54

<210> SEQ ID NO 383
<211> LENGTH: 51
<212> TYPE: DNA
<213> ORGANISM: Artificial Sequence
<220> FEATURE:
<223> OTHER INFORMATION: mTyr-GTA_30_L

<400> SEQUENCE: 383
cagtccaatg cttcactcag ccattttacc gatcgtcgga ctgtagaact c              51

<210> SEQ ID NO 384
<211> LENGTH: 53
<212> TYPE: DNA
<213> ORGANISM: Artificial Sequence
<220> FEATURE:
<223> OTHER INFORMATION: mVal-TAC_32_L

<400> SEQUENCE: 384
aagttgggtg ctttgtgtta agctacactc tggatcgtcg gactgtagaa ctc            53

<210> SEQ ID NO 385
<211> LENGTH: 58
<212> TYPE: DNA
<213> ORGANISM: Artificial Sequence
<220> FEATURE:
<223> OTHER INFORMATION: shCtrl

<400> SEQUENCE: 385
ccggcaacaa gatgaagagc accaactcga gttggtgctc ttcatcttgt tgttttttg      58

<210> SEQ ID NO 386
<211> LENGTH: 59
<212> TYPE: DNA
<213> ORGANISM: Artificial Sequence
<220> FEATURE:
<223> OTHER INFORMATION: ShtRNAArgCCG

<400> SEQUENCE: 386
ccggttctga tccggaatca gacgcctttc tcgagaaagg cgtctgattc cggatcaga      59

<210> SEQ ID NO 387
<211> LENGTH: 66
<212> TYPE: DNA
<213> ORGANISM: Artificial Sequence
<220> FEATURE:
<223> OTHER INFORMATION: ShtRNAGluUUC

<400> SEQUENCE: 387
ccggaacccg ggccgcggcg gtgaaagcgc tcgagcgctt tcaccgccgc ggcccgggtt     60
tttttg                                                                66
```

```
<210> SEQ ID NO 388
<211> LENGTH: 56
<212> TYPE: DNA
<213> ORGANISM: Artificial Sequence
<220> FEATURE:
<223> OTHER INFORMATION: tRNAArgCCG -OE

<400> SEQUENCE: 388
ttctttgcag tgtcgtggcg accacgaagg gactcgaacc ctcatcttct gatccg        56

<210> SEQ ID NO 389
<211> LENGTH: 57
<212> TYPE: DNA
<213> ORGANISM: Artificial Sequence
<220> FEATURE:
<223> OTHER INFORMATION: tRNAGluUUC -OE

<400> SEQUENCE: 389
ttctttgcag tgtcgtggtt ccctgaccgg gaatcgaacc cgggccgcag gcggtga       57

<210> SEQ ID NO 390
<211> LENGTH: 58
<212> TYPE: DNA
<213> ORGANISM: Artificial Sequence
<220> FEATURE:
<223> OTHER INFORMATION: shEXOSC2 #2

<400> SEQUENCE: 390
ccggcccact ttcatgattt gccatctcga gatggcaaat catgaaagtg ggttttttg    58

<210> SEQ ID NO 391
<211> LENGTH: 58
<212> TYPE: DNA
<213> ORGANISM: Artificial Sequence
<220> FEATURE:
<223> OTHER INFORMATION: shEXOSC2 #3

<400> SEQUENCE: 391
ccgggctgta tgataccagc atcctctcga gaggatgctg gtatcataca gcttttttg    58

<210> SEQ ID NO 392
<211> LENGTH: 58
<212> TYPE: DNA
<213> ORGANISM: Artificial Sequence
<220> FEATURE:
<223> OTHER INFORMATION: shGRIPAP1 -1

<400> SEQUENCE: 392
ccgggctcag gtacattcca tggatctcga gatccatgga atgtacctga gctttttg     58

<210> SEQ ID NO 393
<211> LENGTH: 58
<212> TYPE: DNA
<213> ORGANISM: Artificial Sequence
<220> FEATURE:
<223> OTHER INFORMATION: shGRIPAP1-2

<400> SEQUENCE: 393
ccgggaactt caagctcagg tacatctcga gatgtacctg agcttgaagt tcttttttg    58

<210> SEQ ID NO 394
<211> LENGTH: 57
<212> TYPE: DNA
<213> ORGANISM: Artificial Sequence
<220> FEATURE:
<223> OTHER INFORMATION: Synthetic Sequence
```

-continued

```
<400> SEQUENCE: 394
aatgatacgg cgaccaccga gatctacacg ttcagagttc agagttctac agtccga         57

<210> SEQ ID NO 395
<211> LENGTH: 111
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 395
gcacccgaga attccatggt ggaggtgctg gggattgaac ccgggcctcn tncatgctaa      60
gcaygcgctc taccactgag ctacaccccc gatcgtcgga ctgtagaact c              111

<210> SEQ ID NO 396
<211> LENGTH: 71
<212> TYPE: DNA
<213> ORGANISM: Artificial Sequence
<220> FEATURE:
<223> OTHER INFORMATION: Synthetic Sequence

<400> SEQUENCE: 396
gggggtatag ctcagcggta gagcgcgtgc ttagcatgca cgaggcctgg gttcaatccc      60
caatacctcc a                                                          71

<210> SEQ ID NO 397
<211> LENGTH: 65
<212> TYPE: DNA
<213> ORGANISM: Artificial Sequence
<220> FEATURE:
<223> OTHER INFORMATION: Synthetic Sequence

<400> SEQUENCE: 397
caagcagaag acggcatacg agatcgtgat tgactggagt tccttggcac ccgagaattc      60
catgg                                                                 65
```

TRNA QUANTIFICATION

CROSS-REFERENCE TO RELATED APPLICATIONS

This application claims the benefit of prior U.S. Provisional Application No. 62/321,973, filed Apr. 13, 2016, which is hereby incorporated by reference in its entirety.

STATEMENT OF GOVERNMENT RIGHTS

The present application was made with government support under project number K99CA194077 awarded by the National Institutes of Health (NIH). The United States government has certain rights in the invention(s).

BACKGROUND OF THE INVENTION

Transfer RNAs (tRNAs) and the genetic code underlying protein synthesis are universal to all domains of life (Dever and Green, 2012). Despite this universality, genomes show substantial variations in their preference for specific codons across their coding sequences. The source of this bias, though still debated, likely reflects selection for translational efficiency and accuracy (Drummond and Wilke, 2008; Plotkin and Kudla, 2011; Shah and Gilchrist, 2011). Importantly, even the genes within the same genome show high levels of variation in their codon preferences and synonymous codon usage bias. While rigorous proof remains lacking, there is substantial evidence linking these observed variations to different aspects of cellular biology. Given the link between protein synthesis rates, protein concentration, and optimized growth and function (Han et al., 2014; Li et al., 2014), it is conceivable that the components of translation machinery may affect protein expression levels in a concerted fashion. In *Saccharomyces cerevisiae*, the estimated translational speeds determined across all genes showed a significant correlation between codon usage bias and tRNA abundances, highlighting codon usage as an optimizing factor in overall cellular efficiency (Qian et al., 2012). At the same time, the role of tRNAs as direct modulator of translation efficiency in yeast has been challenged (Pop et al., 2014).

On the other hand, microarray-based analysis of tRNA abundances in various tissues has shown a significant correlation between tRNA content and codon usage bias of highly expressed tissue-specific proteins (Dittmar et al., 2006). Given that protein synthesis rate is correlated with tRNA abundance in transgene overexpression experiments (Zouridis and Hatzimanikatis, 2008), it is further hypothesized that tRNA content may effectively regulate the rate of translation for a subset of endogenous proteins (Gustafsson et al., 2004).

The nature of tRNAs makes them difficult to quantify. They have extensive secondary and tertiary structure and numerous post-transcriptional modifications that interfere with reverse transcription and hybridization. There have been previous attempts to quantify tRNA (see e.g., Dittmar et al, 2006; Zheng et al. 2015). However, such methods have various limitations, including inaccurate results due to cross-hybridization, low efficiency of obtaining full-length cDNA products, and the inability to quantify tRNAs among different species. Thus, there is a need for improved methods of tRNA quantification.

SUMMARY OF THE INVENTION

In one embodiment, the present invention relates to a method for optimizing cell-type specific protein expression. The method includes (a) removing RNA from a source cell of said protein, (b) hybridizing said RNA with a plurality of DNA probes specific for a portion of tRNA to form DNA/tRNA hybrids, (c) ligating the DNA of said hybrids, (d) digesting the tRNA from said ligated hybrids to form ligated DNA, (e) sequencing said ligated DNA to obtain sequences that correlate to the tRNA present in the cell, (f) repeating steps a-e for a destination cell in which the protein is to be expressed, (g) analyzing said sequences to identify tRNAs that are present in an amount at least as abundant in said cell destination cell compared to said source cell, and (h) engineering a polynucleotide sequence for the expression of said protein in said destination cell, wherein said engineering excludes codons that correlate to anticodons of tRNAs in the destination cell that are present in an amount that is less than in said source cell.

In another embodiment, the present invention relates to a method for creating a tRNA profile of a cell, (a) removing RNA from said cell, (b) hybridizing said RNA with a plurality of DNA probes specific for a portion of tRNA to form DNA/tRNA hybrids, (c) ligating the DNA of said hybrids, (d) digesting the tRNA from said ligated hybrids to form ligated DNA, (e) sequencing said ligated DNA to obtain sequences that correlate to the tRNA present in the cell, and (f) analyzing said sequences to identify the amount of each tRNA in said cell.

BRIEF DESCRIPTION OF THE FIGURES

The patent or application contains at least one drawing executed in color. Copies of this patent or patent application publication with color drawing(s) will be provided by the United States Patent and Trademark Office upon request and payment of the necessary fee.

(1A) Whole-genome tRNA profiling was performed for MCF10a, MDA-par, MDA-LM2, CN34-par, and CN-LM1a cell lines. Hierarchical clustering was used to cluster the resulting profiles. The tRNAs are labeled based on their cognate amino acid: A, G: Light green; C: Green; D, E, N, Q: Dark green; I, L, M, V: Blue, F, W, Y: Lilac; H: Dark blue; K, R: Orange; P: Pink; S, T: Red. (1B) Correlation plot for changes in tRNA levels between MDA-LM2 and CN-LM1a. Strong positive correlation suggests these two distinct metastatic derivatives employ similar approach in modulating tRNA levels to obtain their metastatic phenotype. $tRNA^{Arg}_{CCG}$ and $tRNA^{Glu}_{UUC}$ are among the most highly upregulated in both MDA-LM2 and CN-LM1a. Quantitative PCR based tRNA quantification validated the changes in the abundance of (1D) $tRNA^{Arg}_{CCG}$ and (1C) $tRNA^{Glu}_{UUC}$ in metastatic MDA-LM2 and CN-LM1a cells relative to their parental lines. (1E) Relative pre-tRNA abundance for $tRNA^{Arg}_{CCG}$ and $tRNA^{Glu}_{UUC}$ across multiple genetic loci as determined by quantitative RT-PCR. $tRNA^{Glu}_{CUC}$, for which a deregulation was not observed, were also included for comparison. (1F) $tRNA^{Glu}_{UUC}$ and (1G) $tRNA^{Arg}_{CCG}$ were successfully overexpressed and knocked-down as determined by quantitative PCR. Note that manipulation in the level of these two tRNA occurs within the physiological boundaries of the parental or metastatic backgrounds. One-tailed Student's t-test was used to measure statistical significance between the two samples in each experiment. Error bars indicate s.e.m. *, p<0.05, and **, p<0.01.

FIGS. 2A-2D| $tRNA^{Glu}_{UUC}$ and $tRNA^{Arg}_{CCG}$ promote metastatic breast cancer.

Figure 3A:
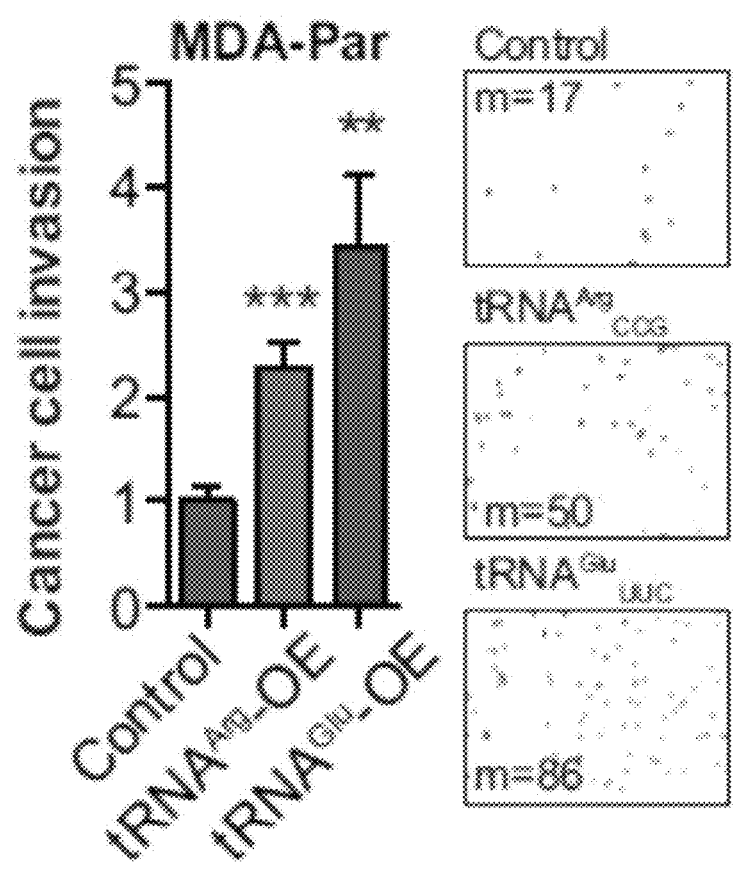

(2A) Bioluminescence imaging plot of lung colonization by MDA-LM2 cells expressing short hairpins targeting tRNA$^{Glu}_{UUC}$, and tRNA$^{Arg}_{CCG}$ or a control hairpin (shControl); n=5 in each cohort. Area-under-the-curve was also calculated for each mouse. (2B) Bioluminescence imaging plot of lung colonization by tRNA$^{Glu}_{UUC}$ and tRNA$^{Arg}_{CCG}$ overexpressing lines, as compared to control in MDA-parental cells; n=5 in each cohort. Area-under-the-curve was also calculated for each mouse. (2C) Primary tumor growth measurement after orthotopic injection of Control, tRNA$^{Glu}_{UUC}$, and tRNA$^{Arg}_{CCG}$ over-expressing cells into the mammary fat pads of mice; n=5 in each cohort. (2D) Orthotopic metastasis bioluminescence imaging plot of mice after primary tumor resection; n=5 in each cohort. For comparing lung colonization, primary tumor growth, and orthotopic metastasis assays, two-way ANOVA was used to measure statistical significance. One-tailed Mann-Whitney test was used to measure statistical significance between the area-under-the curves. Error bars indicate s.e.m. *, $p<0.05$, , $p<0.01$, and *$p<0.001$ FIGS. 3A-3C| In vitro characterization of tRNA$^{Glu}_{UUC}$ and tRNA$^{Arg}_{CCG}$ and their clinical associations with breast cancer progression.

(3A) Over-expression of tRNA$^{Glu}_{UUC}$ and tRNA$^{Arg}_{CCG}$ in MDA-parental cells resulted in a significant increase in cancer cell invasion. Also included are representative fields from the invasion inserts along with the median of cells observed in each cohort. (3B) Conversely, tRNA$^{Glu}_{UUC}$ or tRNA$^{Arg}_{CCG}$ knocked-down in MDA-LM2 cells significantly decreased cancer cell invasion. Also included are representative fields from the invasion inserts along with the median of cells observed in each cohort. (3C) The relative abundance of tRNA$^{Arg}_{CCG}$ and tRNA$^{Glu}_{UUC}$ in primary breast tumor samples from patients who either developed metastatic relapse (n=15) or remained disease-free (n=8), measured using quantitative PCR. One-tailed Mann-Whitney test was used to measure statistical significance between the two cohorts. Error bars indicate s.e.m. *, $p<0.05$, , $p<0.01$, and *$p<0.001$.

FIGS. 4A-4F| Post-transcriptional consequences of over-expressing of tRNA$^{Glu}_{UUC}$ and tRNA$^{Arg}_{CCG}$ (4A) A hallmark of ribosome profiling libraries is a 3-nt periodicity. As an example, we have included the coverage of the 5'-end of reads along the coding sequence with respect to the start (left) or stop codon (right). In comparison, the total RNA library did not show this periodicity. (4B) Given the footprint of ribosome on mRNAs, ribosome protected fragments (RPF) of ~30-nt are expected. Here, as an example, we have shown the RPF length distribution for our control samples. (4C) Genes with higher GAR and CGG contents show significant enrichment among transcripts with increased ribosomal occupancy in tRNA$^{Glu}_{UUC}$ and tRNA$^{Arg}_{CCG}$ overexpressing cells, respectively. (4D) Genes with a high abundance of GAG and GAA (GAR) codons were significantly enriched among the proteins significantly up-regulated (corrected for their transcript changes) in the tRNA$^{Glu}_{UUC}$ over-expression cells. Similarly, genes with higher CGG content showed a significant enrichment among the proteins up-regulated (after correction transcript changes) upon over-expression of tRNA$^{Arg}_{CCG}$. The statistical significance of these enrichments was assessed using mutual-information calculations and associated z-score (based on randomized input vectors). Also included is the $\chi^2$ p-value for the associated contingency table. The heatmap was generated using the –log of hypergeometric p-value for enrichment and log of p-value for depletion (collectively termed the enrichment score). The red and dark-blue borders indicate the statistical significance of the calculated hypergeometric p-values (for details see Goodarzi et al., 2009). (4E) Whole-genome transcript stability measurements show significant enrichment for genes with higher GAR content among those strongly stabilized in tRNA$^{Glu}_{UUC}$ overexpressing line. Similarly, stability of transcripts with higher CGG content is also significantly enhanced in the context of tRNA$^{Arg}_{CCG}$ overexpression. (4F) ERH, AP1S1, and SBDS, were chosen to validate by qRT-PCR the affect of over-expressing or knocking-down corresponding tRNAs on mRNA stability as a function of decay rate.

Figure 5C:
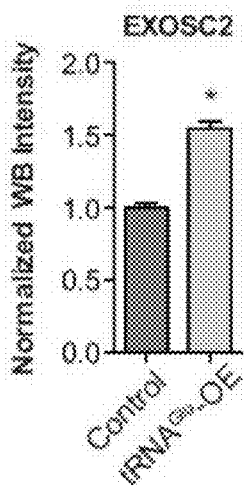
Figure 5C:
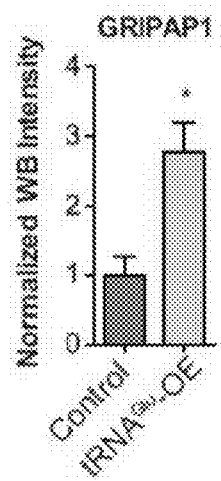
Figure 5C:
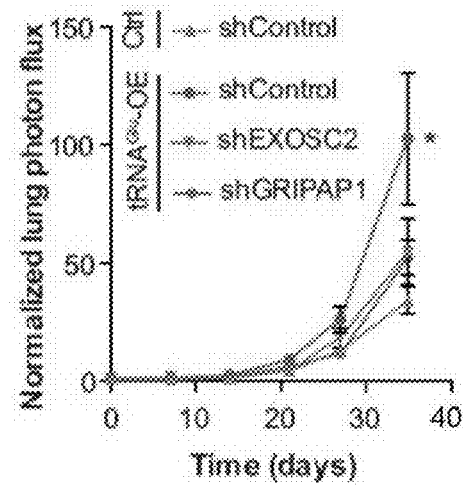
Figure 5C:
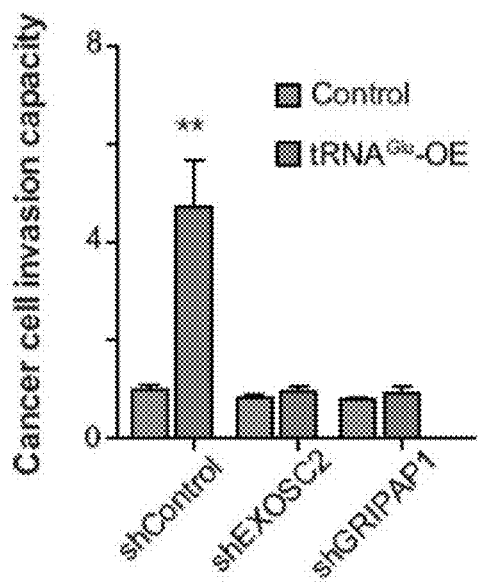
Figure 5C:
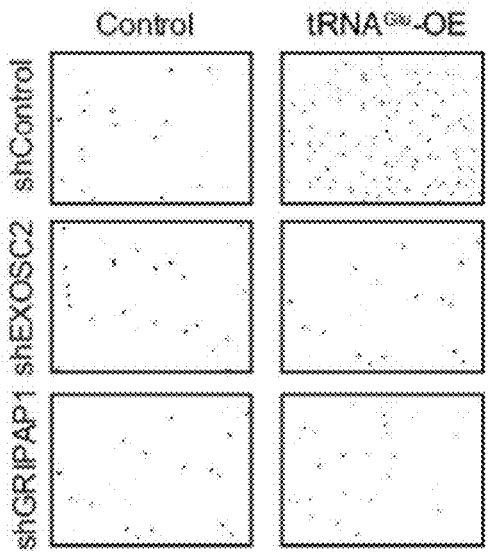

FIGS. 5A-5C| Variations in tRNA$^{Glu}_{UUC}$ level post-transcriptionally modulate expression of breast cancer metastasis promoters EXOSC2 and GRIPAP1.

(5A) EXSOC2 and GRIPAP1 protein levels as measured by quantitative western blotting (see Methods) in respective tRNA$^{Glu}_{UUC}$ over-expressing and control lines. (5B) Bioluminescence imaging plot of lung colonization by EXOSC2 and GRIPAP1 knocked-down cells in MDA-parental over-expressing tRNA$^{Glu}_{UUC}$ relative to control cells expressing a control hairpin, shControl; n=5 in each cohort. Two-way ANOVA was used to measure statistical significance. (5C) Knock-down of EXOSC2 and GRIPAP1 abrogated the enhanced invasion capacity of tRNA$^{Glu}_{UUC}$ overexpressing line. Also included are representative fields from the invasion inserts along with the median of cells observed in each cohort. Error bars indicate s.e.m. *, $p<0.05$, and **, $p<0.01$ by one-tailed Student's t-test.

FIGS. 6A-6D| Codon-specific modulation of EXOSC2 and its clinical association.

(6A) Relative transcript stability measured by qRT-PCR (see Examples and Experimental Procedures) of exogenous wild-type, GGG-to-GCG (Gly) codon mutated, and GAA-to-GAG (Glu) codon mutated transcript in control and tRNA$^{Glu}_{UUC}$ over-expressing backgrounds. While overexpression of tRNA$^{Glu}_{UUC}$ significantly stabilized wild-type and GGG-to-GCG (negative control) transcript, such effect was absent when the specific cognate Glu codon was mutated. (6B) Quantitative western blot demonstrated similar loss of translational enhancement brought about by over-expressing tRNA$^{Glu}_{UUC}$ when the cognate codon was mutated. Error bars indicate s.e.m. *, $p<0.05$ by one-tailed Student's t-test. (6C) Stacked bars representing the fraction of tissue samples from TMA with respectively low, medium, and high intensity of EXOSC2 in normal breast tissues and invasive breast cancer tissues (n=46 and 160, respectively). Also shown are fractions of tissues of different EXOSC2 intensity in breast cancer from patients without metastasis and those with detected metastasis at distant organs (n=107 and 53, respectively). Hypergeometric p-values were calculated to assess the increase in the frequency of samples with higher intensity; *, $p<0.05$. (6D) Shown are representative tissue-microarray immunohistochemical images of stained tissues of median score from normal breast, non-metastatic invasive breast cancer, and metastatic breast cancer tissues. Higher EXOSC2 intensity correlates with later disease progression.

FIGS. 7A-7D| tRNA preference scores were informative of differential ribosome occupancy and protein expression.

(7A) As an example, we have shown the linear regression of MDA-parental and MDA-LM2 ribosome protected fragment to total RNA ratio (RPF/TT). RPF reads were normalized to TT reads to correct for variation in transcript expression in each cell line. (7B) Genes with positive tRNA preference score (based on derivative vs. parental tRNA profiling results) were significantly enriched among transcripts with higher corrected ribosome occupancy values in both MDA-LM2 and CN-LM1a relative to MDA-par and CN34-par, respectively (see Examples and Experimental Procedures). In other words, coding sequences with more favorable codon content, based on changes in tRNA abundance between parental cells and their highly metastatic derivatives, show a more active translation. (7C) Genes with positive tRNA preference score were significantly enriched among the proteins up-regulated in MDA-LM2 cells and CN-LM1a compared to MDA-par and CN34-par, respectively. The significance of these enrichments was determined by calculating mutual-information values and their associated z-scores (based on randomized input values). Also included is the $\chi^2$ p-value for the associated contingency table. The enrichment score, based on which the heatmap was generated, is defined as the −log of hypergeometric p-value for enrichment (gold) and log of p-value for depletion (blue). The red and dark-blue borders indicate the statistical significance of the calculated hypergeometric p-values (Goodarzi et al., 2009). (7D) Normalized relative luciferase activity for CN-optimized and LM2-optimized luciferase constructs.

FIGS. 8A-8G| tRNA profiling approaches and controls.

(8A) For tRNA profiling, total small RNA from growing cells was extracted and subjected to deacylation and 3'-biotinylation. Transfer RNA-specific probe-pairs were hybridized to tRNAs and ligated using T4 DNA ligase. Hybridized and ligated probes were then extracted by streptavidin-based biotin precipitation followed by RNase-mediated elution. Then depending on the assay, either high-throughput sequencing or quantitative PCR assays were used to quantify the levels of each probe in the population. (8B) tRNA Lysine of E. coli was used for benchmarking our approach. Here, we have compared the quantification of probes perfectly designed against tRNA$^{Lys}$ relative to a probe with a mismatch at the ligation site (tRNA$^{Lys}$*). Without 3' biotinylation and enrichment for tRNA hybridized probes, tRNA$^{Lys}$* was measured at ~10% of tRNA$^{Lys}$; the addition of the Streptavidin-mediated precipitation step resulted in another 10-fold increase in signal-to-noise ratio. (8C) A standard curve created using tRNA$^{Lys}$ at different concentrations. (8D) Quantification of three different human tRNAs at different concentrations of input RNA from four separate cell-lines. (8E) We quantified 18S rRNA levels in 23 samples from tumors using first-strand cDNA synthesis followed by quantitative PCR. We then used the probe hybridization/ligation method to quantify 18S rRNA in the same samples. As shown here, we observed a significant agreement between the two distinct measurements. (8F) [32P]-labeled antisense RNA probes (IDT) were used to perform northern blotting for tRNA$^{Glu}_{UUC}$ and tRNA$^{Arg}_{CCG}$ in MDA-Par, MDA-LM2, CN34-Par, and CN-LM1a samples (in biological replicates). Band intensities in each sample were then quantified and normalized to input RNA. In all cases, consistent with our tRNA profiling results, the levels of these tRNAs showed a significant up-regulation. (8G) Relative difference in genomic copy numbers across multiple loci of tRNA$^{Glu}_{UUC}$ and tRNA$^{Arg}_{CCG}$ as measured by quantitative PCR.

FIGS. 9A-9E| Gross histology of lungs extracted from mice injected with MDA-LM2 and MDA-par cells with knock-down or over-expression of specific tRNAs.

(9A-9B) Lungs were extracted, fixed, sectioned, and subjected to hematoxylin and eosin staining. Visible macrometastatic nodules were then counted for each cohort. Shown are representative lung slices from each cohort along with comparison of the number of visible nodules in each cohort. (9C) The proliferation of cells in vitro was performed for tRNA$^{Glu}_{UUC}$ and tRNA$^{Arg}_{CCG}$ over-expressing cells relative to control MDA-parental cells. (9D) Bioluminescence imaging plot of lung metastasis by CN-LM1a cells expressing short hairpins targeting tRNA$^{Glu}_{UUC}$, tRNA$^{Arg}_{CCG}$, or a control hairpin (shControl); n=4-5 in each cohort. Area-under-the-curve was also calculated for each mouse. (9E) Lungs were extracted, fixed, sectioned, and subjected to hematoxylin and eosin staining. Shown are representative lung slices from each cohort. Error bars indicate s.e.m. One-sample t-test was used to calculate the associate p-values; *, $p<0.05$, , $p<0.01$, and *$p<0.001$.

Figure 10B:
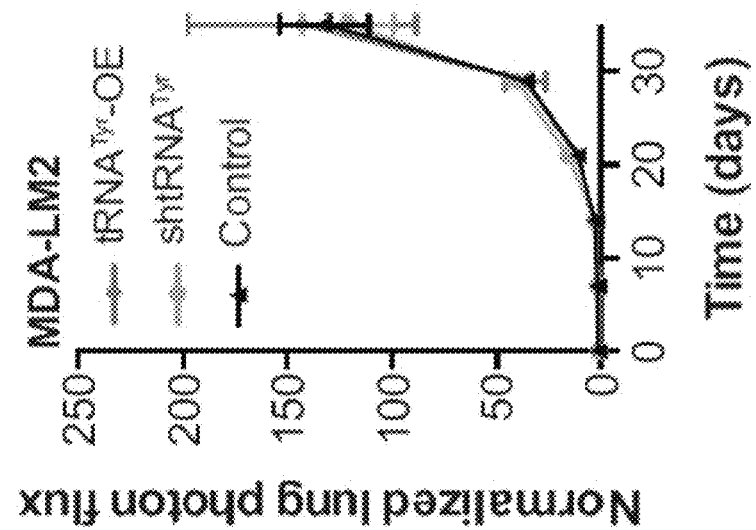
Figure 10A:

FIGS. 10A-10B| Modulations of specific tRNAs affect metastatic progression in breast cancer.

(10A) Bioluminescence imaging plot of lung metastasis by MDA-parental cells simultaneously silencing and over-expressing tRNA$^{Glu}_{UUC}$ and tRNA$^{Arg}_{CCG}$ respectively (in comparison to shControl; n=5 in each cohort). (10B) Bioluminescence imaging plot of lung metastasis by MDA-LM2 cells silencing or over-expressing tRNA$^{Tyr}$ relative to a control hairpin (shControl); n=5 in each cohort.

FIGS. 11A-11G| tRNA$^{Glu}_{UUC}$ and tRNA$^{Arg}_{CCG}$ overexpression alters ribosomal occupancy and translational landscapes.

(11A) Ribosome protected fragment (RPF) reads were normalized to total RNA reads (TT) to correct for variations in transcript levels. Linear regression plots show expected positive Spearman's correlation of RPF/TT ratio between biological replicates on control, tRNA$^{Glu}_{UUC}$, and tRNA$^{Arg}_{CCG}$ overexpressing lines. It should be noted since tRNA$^{Arg}_{CCG}$-OE and tRNA$^{Glu}_{UUC}$-OE samples were prepared independently, they each have their corresponding control samples. (11B) The distribution of ribosome protected fragment (RPF) lengths in each sample. (11C) Observed periodicity of ribosome footprints in tRNA$^{Glu}_{UUC}$ and tRNA$^{Arg}_{CCG}$ overexpressing lines, which is the hallmark of ribosome profiling approach, along with coverage of total RNA along the transcripts as control. (11D) Enrichment/depletion patterns of transcripts with higher GAR and GAA contents in the ribosome profiling measurements. Coding sequences with either high GAR (matching YUC) or GAA (matching UUC) content show a highly significant enrichment among those with increased ribosome occupancy. (11E) Overexpression of tRNA$^{Glu}_{UUC}$ and tRNA$^{Arg}_{CCG}$ in MDA-parental cells resulted in pervasive protein expression modulations relative to the control cells. (11F) Volcano plots depicting the protein expression modulation in MDA-Par cells in which tRNA$^{Glu}_{UUC}$ and tRNA$^{Arg}_{CCG}$ were over-expressed. (11G) Correlation between changes in protein expression levels and those of their corresponding transcripts. Correction for transcript level allows us to focus on tRNA targets that are solely modulated at the translation level.

Figure 12:
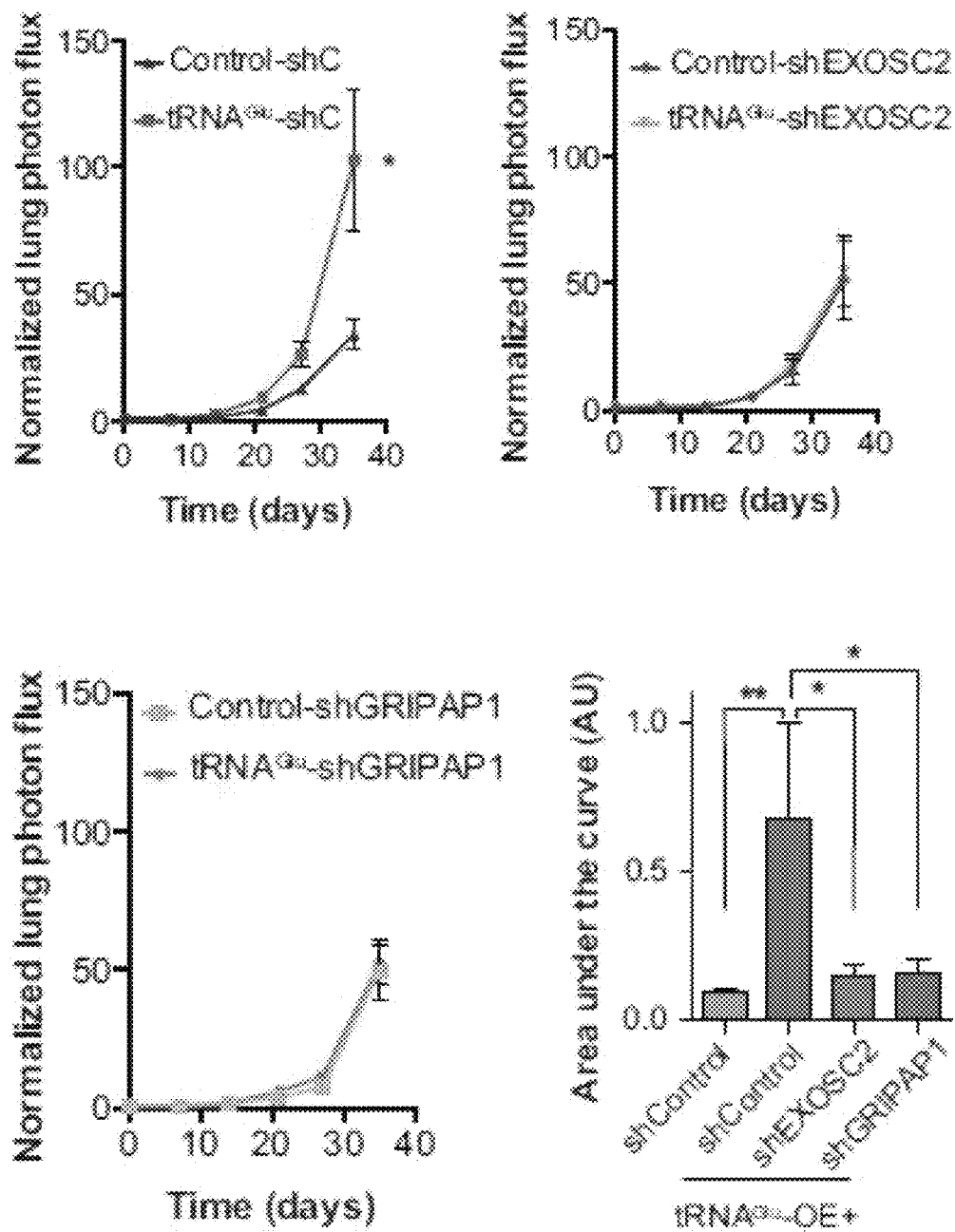

FIG. 12|EXOSC2 and GRIPAP1 act as promoters of breast cancer metastasis.

Bioluminescence imaging plot of lung colonization by MDA-231 cells expressing short-hairpins against EXOSC2 or GRIPAP1 in tRNA$^{Glu}_{UUC}$ overexpressing and control background; n=5 in each cohort. Area-under-the-curve was also calculated for each group. While knock-down of GRIPAP1 and EXOSC2 reversed the lung colonization capacity of tRNA$^{Glu}_{UUC}$ overexpressing cells, it had little to no effect on control cells with parental level of tRNA$^{Glu}_{UUC}$. The p-values were calculated using one-sample one-tailed Mann-Whitney tests; *, $p<0.05$, and **, $p<0.01$.

FIGS. 13A-13D| Codon-specific effect of tRNA$^{Glu}_{UUC}$ modulations and downstream clinical significance.

(13A) Schematic map of mutational positions on synthetic EXOSC2 constructs. (13B) Protein expression level (measured by quantitative WB) corrected for transcript level to demonstrate the translational-specific effect of tRNA$^{Glu}_{UUC}$ overexpression on transcript with or without its cognate codons. The p-values were calculated using one-sample one-tailed Mann-Whitney tests; *, p<0.05, and **, p<0.01. (13C) Shown are quantitative western blots of control and tRNA$^{Glu}_{UUC}$ overexpressing cells transfected with either WT or GAA-to-GAG mutated codons in biological triplicates. Anti-FLAG antibody was used to measure different versions of exogeneous EXOSC2 and anti-Luciferase antibody was used as a loading and transfection control (see Examples). Band intensity was determined by LICOR quantification software. (13D) Shown are representative tissue-microarray immunohistochemical images of normal breast, non-metastatic invasive cancer, and metastatic cancer tissues (5 per cohort). Higher EXOSC2 intensity correlates with later disease progression.

Figure 14A:
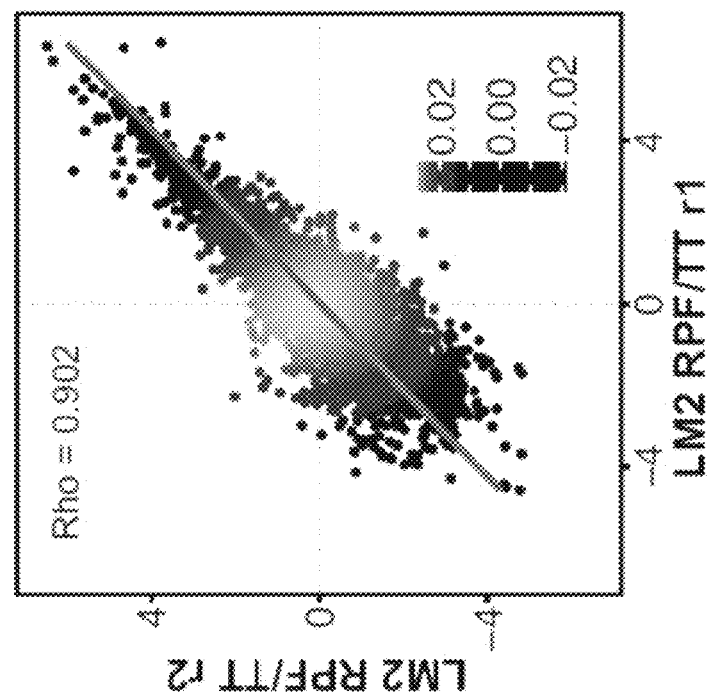
Figure 14A:
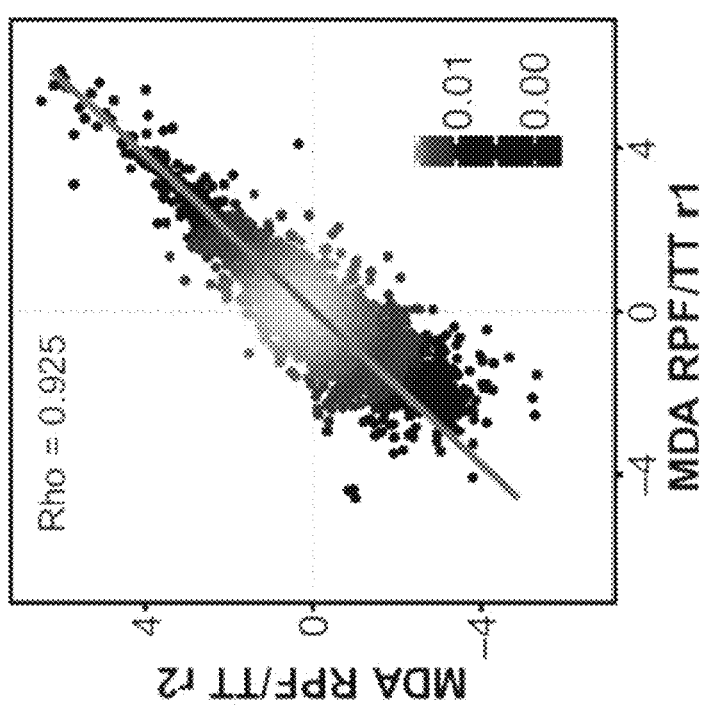
Figure 14C:
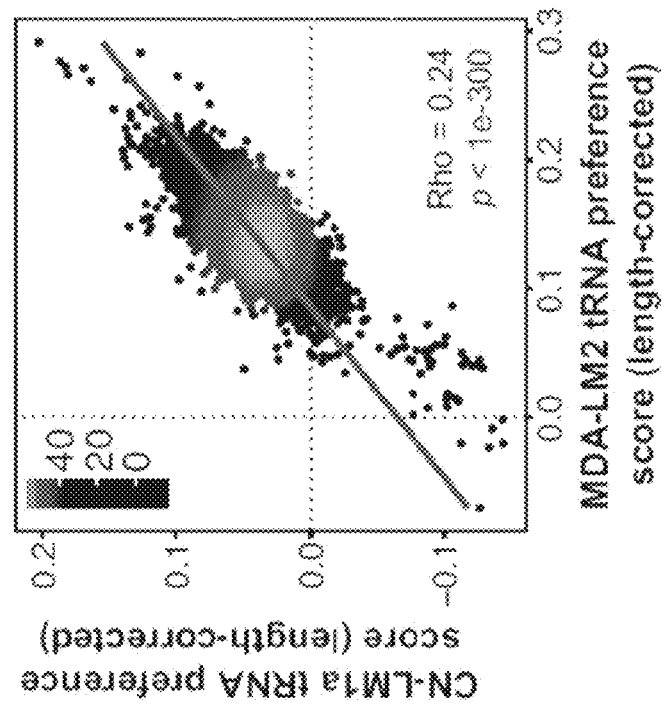
Figure 14B:
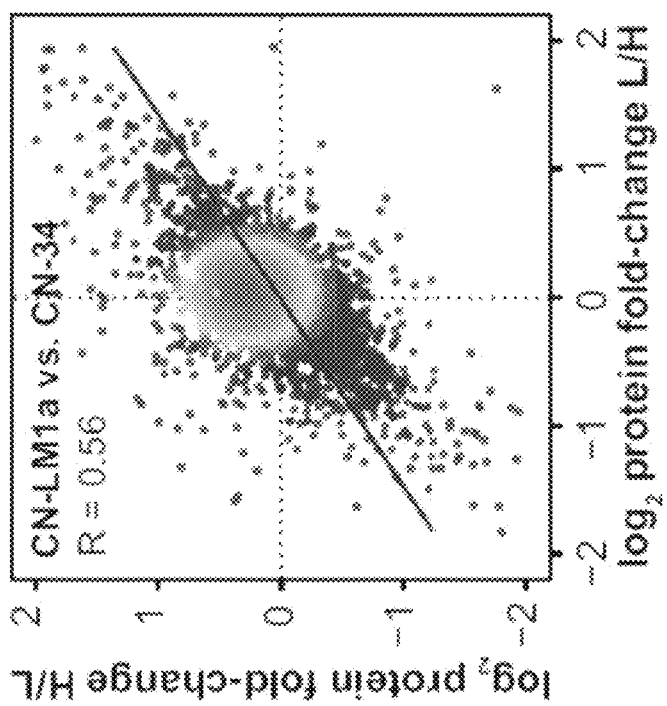

FIGS. 14A-14C| Differential protein expression and tRNA preference scores.

(14A) Correlations between RPF/TT ratios in biological replicates in each background. (14B) As expected, label-swapped biological replicates quantified in our SILAC measurements showed a highly significant correlation. About 3,000 proteins were successfully quantified in both replicates. (14C) Consistent with tRNA modulations being similar between metastatic and parental lines in MDA-231 and CN-34 backgrounds, the tRNA preference scores (corrected for length of coding sequences) calculated for every protein based on differential tRNA expression in each background were highly correlated (Spearman's Rho=0.24, p<1e−300).

FIG. 15 depicts hybridization of probe to the DNA substrate. The sequences are described as follows: True-seq smRNA PCR primer (RP1) SEQ ID NO: 394; upper strand shown in 3' to 5' orientation SEQ ID NO: 395; lower strand shown in 5' to 3' orientation SEQ ID NO: 396; and RNA PCR Primer, Index 1 (RPT1) SEQ ID NO: 397.

DETAILED DESCRIPTION OF THE INVENTION

The present invention relates to tRNA quantification. More specifically, the present invention provides methods for creating a tRNA profile for a particular cell type. Methods of optimizing cell-type specific protein expression are also provided by using the tRNA profile for the cell.

The sequence of nucleotides in the mRNA molecule is read consecutively in groups of three. Each group of three consecutive nucleotides in the mRNA is a codon, and each codon specifies either one amino acid or a stop to the translation process. Since mRNA is a linear polymer of four different nucleotides, there are 64 ($4^3$) possible combinations of three nucleotides. However, only 20 different amino acids are commonly found in proteins. Thus, the mRNA code is redundant and some amino acids are specified by more than one triplet (codon).

The standard genetic code is summarized in the table below.

TABLE 1

| | | 2$^{nd}$ base | | | |
|---|---|---|---|---|---|
| 1$^{st}$ base | U | C | A | G | 3$^{rd}$ base |
| U | UUU Phe | UCU Ser | UAU Tyr | UGU Cys | U |
| | UUC Phe | UCC Ser | UAC Tyr | UGC Cys | C |
| | UUA Leu | UCA Ser | UAA Stop | UGA Stop | A |
| | UUG Leu | UCG Ser | UAG Stop | UGG Trp | G |
| C | CUU Leu | CCU Pro | CAU His | CGU Arg | U |
| | CUC Leu | CCC Pro | CAC His | CGC Arg | C |
| | CUA Leu | CCA Pro | CAA Gln | CGA Arg | A |
| | CUG Leu | CCG Pro | CAG Gln | CGG Arg | G |
| A | AUU Ile | ACU Thr | AAU Asn | AGU Ser | U |
| | AUC Ile | ACC Thr | AAC Asn | AGC Ser | C |
| | AUA Ile | ACA Thr | AAA Lys | AGA Arg | A |
| | AUG Met* | ACG Thr | AAG Lys | AGG Arg | G |
| G | GUU Val | GCU Ala | GAU Asp | GGU Gly | U |
| | GUC Val | GCC Ala | GAC Asp | GGC Gly | C |
| | GUA Val | GCA Ala | GAA Glu | GGA Gly | A |
| | GUG Val | GCG Ala | GAG Glu | GGG Gly | G |

*Met also codes for initiation.

As can be seen, due to the degeneracy of the genetic code, some amino acids are specified by two or more codons.

In addition to the variation from the degeneracy of the genetic code, tRNA isodecoders exist. tRNA isodecoders share the same anticodon, but have differences in their body sequence. In the human genome, more than 270 isodecoder genes are present among the approximately 450 tRNA genes distributed among 49 isoacceptor families.

tRNAs are clover leaf shaped molecules typically 76 to 90 nucleotides in length. tRNAs are charged with an amino acid attached at one end (the stem) of the clover leaf and the anticodon located at the opposite end. During translation, each type of tRNA becomes attached at one end to a specific amino acid, and displays at its other end a specific sequence of three nucleotides—an anticodon—that enables it to recognize, through base pairing, a particular codon in the mRNA. For synthesis of the protein, a succession of tRNA molecules charged with their appropriate amino acids are brought together with an mRNA molecule and matched up by base-pairing through their anticodons with each of its successive codons. The amino acids then are linked together to extend the growing protein chain, and the tRNAs relieved of their amino acids, are released.

In some cell types, certain tRNAs with particular anticodons are more abundant than others. Accordingly, expression of a particular protein can be optimized if a gene is engineered such that it maximizes the codons that correlate with the anticodons of the tRNAs that are more abundantly present in that particular cell type.

All proteins and the genes that encode them are derived from source cells, i.e. those cells in which the proteins are naturally found. If the protein is to be expressed in a cell other than the source cell, i.e. a destination cell, it is possible that the codons for the gene in the destination cell will call for tRNAs that are low in abundance compared to the source cell, and therefore will not be optimally expressed.

With the methods of the invention, a tRNA profile can be developed for the source and destination cells. Using these tRNA profiles, the gene of the protein to be expressed in the destination cells can be engineered to exclude codons that correlate to anticodons of tRNAs that are present in the destination cell in an amount that is less than in the source cell. In this way, the expression of the protein in the destination cell can be optimized.

As used herein, the destination cell includes any cells capable of expressing non-endogenous genes. The destination cell may be a bacterial cell, yeast cell, mammalian cell, plant cell, or insect cell. Examples of mammalian destination cells include chinese hamster ovary (CHO) cells, mouse myeloma cells, HEK 293 (Human embryonic kidney), HT1080, Hep G2, and A549. Examples of yeast cells include *Saccharomyces cerevisiae* and *Pischia pastoris*. An example of a suitable bacterial cell is *E. coli*. Engineered destination cells wherein proteases have been downregulated or tRNA expression profiles have been modified have been contemplated.

The first step in quantifying the tRNA for a particular cell type is to remove the RNA from the source cell. This can be done by any known means. For example, phenol/chloroform extraction may be used to remove the RNA from the source cell. Further examples of RNA extraction/isolation methods can be found in Molecular Cloning, a Laboratory Manual, fourth edition, Cold Spring Harbor Laboratory Press (2012).

In a preferred embodiment, the RNA removed from the source cell would be isolated for short RNA. Short RNA, as defined herein, includes RNA that is composed of less than 300, preferably less than 200, more preferably less than 100 nucleotides. In another preferred embodiment, the step of removing the RNA from the cell includes isolating only tRNAs. Such methods are known in the art. For example, total RNA may be separated according to size with agarose gels, and the size fraction containing the tRNA may be isolated therefrom. Further protocols and methods are described in Molecular Cloning, a Laboratory Manual, fourth edition, Cold Spring Harbor Laboratory Press (2012).

In a preferred embodiment, the RNA that has been removed from the cell is then deacylated. Deacylation can be performed by any known means. For example, the acylated tRNA may be deacylated by incubation at elevated pH and/or elevated temperature, e.g., incubation in 100 mM Tris-HCl (pH 9.0) at 37° C. for 30 min.

After deacylation, the solution can be neutralized by any known means. For example, the solution may be neutralized by the addition of an equal volume of 100 mM Na-acetate/acetic acid (pH 4.8) plus 100 mM NaCl.

Deacylating the tRNA permits the tRNA to be more easily manipulated. For example, deacylation of the RNA promotes proper hybridization discussed below. In addition, deacylation of the RNA permits the RNA to be tagged with a binding ligand. The binding ligand provides a means to capture or bind the tagged tRNA. Examples of binding ligands include biomolecules and small molecules. Examples of binding ligands include biotin, RNA aptamers, haptens, and derivatives thereof.

The tRNA may be tagged at the 5' end or the 3' end. Such tagging methods are known in the art. In one example, the 3' end may be labeled by periodate oxidation and subsequent conjugation with the tag. In another example, the 5' end may be labeled by use of EDC (EDAC, 1-Ethyl-3-[3-dimethyl-aminopropyl]carbodiimide hydrochloride), and conjugation of the tag to the 5' end. Such techniques are described in Bioconjugate Techniques, Third Edition 3rd Edition, by Greg T. Hermanson (Author) Publisher: Academic Press; 3rd edition (Sep. 2, 2013), the contents of which are incorporated herein by reference.

Furthermore, commercially available kits are available for biotinylation of the tRNA. Such kits are available from Pierce Biotechnology and ThermoFisher. In a preferred embodiment, the RNA is tagged at the 3' end with biotin to produce biotinylated RNA.

The RNA can also be purified. Purification can be performed by any known means. For example, RNA can be purified with commercially available kits from Qiagen and Promega, or with methods such as LiCl precipitation. Phenol/chloroform extraction may be used to purify the RNA.

After removal of the RNA from the source cell, the RNA is hybridized with a plurality of DNA probes specific for a portion of tRNA to form DNA/tRNA hybrids. Collectively, the plurality of DNA probes hybridizes to the full length of the tRNA molecule.

Since the nucleotide sequences of tRNA are known for different species, DNA probes specific for a portion of the tRNAs in a cell can be synthesized by any known means. Suitable methods include, for example the phosphoramidite method.

In a preferred embodiment, two DNA probes collectively hybridize to the full length of the tRNA. In addition, it is further preferred that the two probes each hybridize at least one ribonucleotide of the anticodon of the tRNA. Thus, one probe would hybridize the 3' end of the tRNA up to and including one or two nucleotides of the anticodon. Similarly, the second probe would hybridize the 5' end of the tRNA molecule up to and including one or two nucleotides of the anticodon. If the probe hybridizing to the 3' end of the tRNA molecule includes one nucleotide of the anticodon, the 5' end will include the other two nucleotides of the anticodon, or if the probe hybridizing to the 5' end includes two nucleotides of the anticodon, the probe hybridizing to the 3' end of the tRNA molecule will include one nucleotide of the anticodon. A single probe does not hybridize all ribonucleotides of the anticodon.

The disclosure also provides methods of designing DNA probes and compositions relating thereto. The design of the DNA probes provides a robust and efficient way to profile the tRNA abundance of the destination cell. The disclosed method provides the minimum number of probes to provide the maximum amount of hybridization of all the tRNA in the source genome. Each probe may bind more than one specific tRNA sequence.

The DNA probes described herein are more than 80%, more than 90%, or more than 95% complementary to the target tRNA. In some embodiments, the DNA probes may be 100% complementary to the target tRNA.

Furthermore, the DNA probes include additional sequence at the 5' end of the 5' probe and the 3' end of the 3' probe. The sequences provide binding for sequencing primers and sequencing of the DNA probe. For example, universal linker sequences, compatible with Illumina TRUSEQ sequencing primers are added to these (e.g. GAGTTCTACAGTCCGACGATC (SEQ ID NO. 1) to 5' end of the 5' probe and CCATGGAATTCTCGGGTGC (SEQ ID NO. 2) to the 3' end of the 3' probe). The additional sequence allows for primer binding and PCR amplification of the combined DNA probe for downstream analysis, including quantification of tRNA abundance.

Species specific tRNA sequences were obtained from GtRNAdb (Chan, P.P. & Lowe, T. M. (2009) GtRNAdb: A database of transfer RNA genes detected in genomic sequence. Nucl. Acids Res. 37(Database issue):D93-D97). The methods described herein are applicable to any species to generate species specific tRNA probes.

All tRNAs for a given species is grouped into isodecoders, e.g., based on their anticodon sequence. For each group of isodecoders the sequences of the tRNAs are further analyzed by a pair-wise alignment to further group the isodecoders based on sequence similarity to obtain a score for sequence similarities and to create a symmetric matrix having all pairwise alignment scores. For example, the Needleman-Wunsch alignment algorithm may be used to get the score. The symmetric matrix provides a distance matrix that can be used to further classify tRNAs.

The tRNAs are grouped into further subcategories based upon identical anticodon sequence and high sequence similarity using the distance matrix generated above. Any supervised or unsupervised method can be used.

Within the subcategories, consensus sequences for each tRNA subcategory is determined by a multiple alignment algorithm. Such algorithms are known in the art. For example, ClustalW may be used to create the consensus sequences. (ClustalW and ClustalX version 2 (2007) Larkin M A, Blackshields G, Brown N P, Chenna R, McGettigan P A, McWilliam H, Valentin F, Wallace I M, Wilm A, Lopez R, Thompson J D, Gibson T J and Higgins D G Bioinformatics 2007 23(21): 2947-2948; A new bioinformatics analysis tools framework at EMBL-EBI (2010) Goujon M, McWilliam H, Li W, Valentin F, Squizzato S, Paern J, Lopez R Nucleic acids research 2010 July, 38 Suppl: W695-9; Analysis Tool Web Services from the EMBL-EBI. (2013) McWilliam H, Li W, Uludag M, Squizzato S, Park Y M, Buso N, Cowley A P, Lopez R Nucleic acids research 2013 July; 41(Web Server issue):W597-600) The consensus sequences within each subcategory are compared. If the sequence similarity is lower than a threshold, (e.g., 85%, 90%, or 95% identity) then the subcategory is split and each part of the split is analyzed and further split until the consensus sequence reaches the requisite threshold. It is noted that one tRNA family can result in multiple consensus sequences.

The resulting consensus sequences are each split into two parts at the site of the anticodon. Each part includes at least one nucleotide of the anticodon. For example the 5' part of the consensus sequence may have two nucleotides of the anticodon and the 3' end of the consensus sequence may have one nucleotide of the anticodon.

The reverse complement of both parts of each consensus sequence is used as tRNA probes. The probe with its 5' start at the site of anticodon requires the addition of a 5' phosphate group. A 5' phosphate is added to the 3' probe during synthesis.

Application of this technology in the mitochondrial context is contemplated. Mitochondria have a single tRNA for each codon. A probe-pair for each tRNA sequence in the mitochondrial genome can be designed. Applicants have disclosed probe pairs for human mitochondrial tRNA. See FIG. 9, probe names beginning with "m".

The probes are pooled into a single or multiple pools (based on their Tm). In this way, the PCR protocol can be tailored according to the Tm of the specific pool.

The methods disclosed herein were applied to the mouse and human genomes. The resulting probes are disclosed herein in Tables 2 and 3.

The tRNA/DNA hybrids are then isolated. The isolation step can be performed by any known means, including using the tag applied to the RNA described above. For example, RNA that was previously tagged with biotin could be removed utilizing streptavidin beads.

Once the plurality of DNA probes are hybridized to the tRNA to form DNA/tRNA hybrids, the DNA of the hybrids are ligated to form a single continuous DNA molecule. The ligation of the DNA probes can be performed by any known means. For example, the DNA may be ligated with DNA ligase under conditions that provide ligation. Examples of suitable DNA ligases include T4 DNA ligase, PBCV-1 DNA Ligase or *Chlorella* virus DNA Ligase, and derivatives thereof. Conditions that provide ligation are commonly known in the art. For example, the DNA may be ligated by incubation with T4 DNA ligase 16° C. overnight or room temperature for 2 hours. The T4 DNA ligase may be heat inactivated after ligation to prevent interference with downstream applications. In one example, T4 DNA ligase is inactivated by incubation at 65° C. for 10 minutes. Molecular Cloning, a Laboratory Manual, fourth edition, Cold Spring Harbor Laboratory Press.

After ligation, the tRNA from the ligated hybrids is digested to form ligated DNA. The RNA can be digested by using, for example, ribonuclease (RNase). Examples of suitable ribonucleases include RNase A, RNase H, RNase T1, combinations thereof, and derivatives thereof. Conditions include incubating the material to be digested with an effective amount of nuclease under conditions that provide digestion. For example, an effective amount of nuclease is incubated with the material to be digested at 37° C. for 30 minutes. When the tRNA is removed from the ligated hybrids, the ligated DNA remains. Once the tRNA is digested from the ligated hybrids to form ligated DNA, each ligated DNA corresponds to a particular tRNA to which it was previously hybridized.

The disclosure also provides methods of creating a tRNA profile of a cell of interest. The tRNA profile includes identifying the amount of each type of tRNA in the cell. As defined herein, each type of tRNA to be quantified is identified as having a different anticodon. The DNA is amplified, for example, by polymerase chain reaction (PCR), as is known in the art. The amplified DNA can then be analyzed to identify the types of tRNA present and their abundance.

This information is used to create a profile of the relative amount of each type of tRNA that is present in the cell. This procedure can be performed for the source cell, i.e. the cell in which the protein is naturally expressed, as well as the destination cell, i.e. the cell in which the engineered polynucleotide will be expressed.

In creating the tRNA profile, the species specific probes described above are de-convoluted to enumerate all possible combinations of degenerate nucleotides. Accordingly, this will provide the full scope of all tRNAs obtained by the above-described method. To elaborate, for example, in designing the DNA probes discussed above, the sequences may contain variable positions wherein two or more nucleotides are possible (for example, an "R" can be A or G; "N" can be A, T, C, or G; and "Y" is C or T). In deconvoluting the sequences, all possible sequence combinations are listed. For example, RAGCY, can be AAGCT, AAGCC, GAGCT, and GAGCC.

The resulting sequences are indexed by any suitable alignment software or tool. An example of a suitable tool is Bowtie. (Langmead B, Trapnell C, Pop M, Salzberg S L. Ultrafast and memory-efficient alignment of short DNA sequences to the human genome. Genome Biol 10:R25)

Sequences that do not provide proper alignment with the tRNAs are discarded. As used herein, proper alignment means more than 85%, more than 90%, or more than 95% identity over at least 45 base pairs.

The sequences are quantified by counting the number of times each sequence is read. Degenerate sequences of the same probe-pair are combined. Combining the degenerate sequences provide the total number of tRNAs available for a single codon.

A size factor for the sequence libraries is calculated and the tRNA counts are normalized. The tRNA counts (quantitation data) is used to determine the differential expression of the different tRNAs. The counts, size factors, and dispersions are used to perform statistical comparisons (e.g. using negative binomial-based methods) of the abundance of the tRNAs.

The method described above allows for codon optimization in order to maximize expression of a gene from a source cell in a destination cell.

In one embodiment the amino acids encoded by the engineered gene is selected based upon a comparison of the isoacceptor tRNA abundance in the source cell as compared to the destination cell. In particular, codons for the amino acid isoacceptors that show at least similar average abundance in the destination cell are selected.

Knowing the relative amount of each tRNA in the cell, a polynucleotide (i.e. a gene) can be engineered to optimize the expression of a particular protein in the destination cell. In one embodiment, the methods described herein are used to increase the yield in known protein expression systems.

The gene can be engineered to exclude codons that correlate to anticodons of tRNAs in the destination cell that are present in an amount that is less than in the source cell. Engineering such genes is well known in the art and can be performed by conventional means. For example, DNA for the engineered gene can be synthesized and incorporated into an expression vector for expression in the destination cell. By avoiding less abundant tRNAs in the destination cell, the protein can be more efficiently expressed.

In addition to engineering the gene to avoid less abundant tRNAs in the destination cell, the gene can be engineered to maximize the codons that correlate to anticodons of the most abundant tRNAs present in the destination cell for each amino acid. As mentioned previously, due to the degeneracy of the genetic code, some amino acids are specified by two or more codons. Thus, expression of the protein can be further optimized by selecting through genetic engineering the tRNAs that are present in a higher number in the destination cell for each amino acid required to express the protein of interest.

The methods described above may be used to express any desired gene/protein in a destination cell. The method may be useful in the expression of difficult to express proteins.

In a preferred embodiment, the protein is an antibody, more preferably a monoclonal antibody. Production of monoclonal antibodies (mAbs) involves their expression in mammalian cells. Codon engineering by methods other than those disclosed herein has been previously used for achieving a higher expression than that of hybridoma cells. The methods described herein can further increase the codon optimization of these sequences which, given the widespread use of mAbs in therapeutics and research, can have immense value.

EXAMPLES

The present disclosure may be better understood with reference to the examples, set forth below. The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure.

tRNA Profiling Protocol
MicroRNA Purification
    plate ~175,000 cells per well in 6 well plates (triplicate of each sample)
    collect cells and extract microRNA with Norgen kit
    Nanodrop (~25-50 ng/µL is good, max volume of 90 µL)
Deacylation (Makes tRNAs Able to be Biotinylated)
    turn on heat block to 37° C.
    prepare diluted samples (keep on ice):
        normalize volume to the lowest concentration of RNA 500 ng to 1 µg RNA in 90 µL total volume (90-RNA volume=$H_2O$ volume)
    add 10 µL 1M Tris-HCl (pH 9) to each
    incubate samples at 37° C. for 30 minutes
    add 100 µL 100 mM acetate buffer (pH 4.8) and 100 mM NaCl
    add 400 µL 1:1 ethanol/isopropanol
    add 2 µL glycoblue
    incubate at −20° C. overnight
    put 75% ethanol on ice
    take samples out of −20° C. and spin down at max speed for 20 minutes (4° C.) (keep samples on ice)
    in TC hood, pour off liquid onto paper towel
    resuspend in 300 µL 75% cold ethanol
    spin down at max speed for 5 minutes (4° C.)
    carefully pour off ethanol so as not to dislodge the pellet
    keep tubes open in the hood for 5-10 minutes to allow pellets to air dry
    carefully aspirate excess ethanol around tube to reduce the likelihood of ethanol contamination
    resuspend in a max volume of 50 µL $H_2O$ (if you start with a lower concentration of RNA, use 20-25 µL)
    Nanodrop samples to make sure there is a RNA signal (concentrations may look higher if there is ethanol contamination)
Biotinylation (so tRNA Will Bind to Streptavidin Beads)—
Pierce RNA 3' End Biotinylation Kit
    take out Pierce RNA 3' End Biotinylation Kit reagents to thaw (keep RNase Inhibitor and T4 RNA Ligase on ice)
    label PCR tubes
    set up thermocycler −85° C. 5 minutes→16° C. forever
    add 4 µL DMSO to each PCR tube
    add 12 µL of sample RNA
    run PCR to incubate at 85° C. for 5 minutes
    prepare Master Mix in the following proportions (keep on ice):
        6 µL 10×RNA Ligase Reaction Buffer
        2 µL RNase inhibitor
        2 µL biotinylated cytidine (bis)phosphate
        4 µL T4 RNA ligase
        30 µL 30% PEG
(make a couple samples worth more than needed—PEG is very viscous)
    when thermocycler gets to 16° C., add 44 µL Master Mix to each tube
    vortex and spin down
    incubate at 16° C. overnight
purifying biotinylated RNA
    label MAXTRACT phase lock tubes
    dilute 1M Tris HCl (pH 7.4) stock 1:10 to get 100 mM—add 60 µL to each
    in TC hood, resuspend well in 120 µL chloroform:isoamyl alcohol
    transfer to phase lock tube
    vortex and spin down at max speed for 2 minutes
    label fresh 1.5 mL microcentrifuge tubes
    transfer aqueous phase to new tubes (careful not to touch white part to avoid chloroform contamination)
    add 12 µL 3M sodium acetate (pH 5.2)
    add 240 µL 1:1 ethanol/isopropanol
    add 2 µL glycoblue
    vortex
    incubate at −20° C. overnight Hybridization
  put 75% ethanol on ice
  take samples out of −20° C. and spin down at max speed for 20 minutes (4° C.)
  in TC hood, pour off liquid and resuspend in 300 μL cold 75% ethanol (keep samples on ice)
  spin down at max speed for 5 minutes (4° C.)
  carefully pour off ethanol so as not to dislodge the pellet
  keep tubes open in the hood for 5-10 minutes to allow pellets to air dry
  carefully aspirate excess ethanol around tube
  resuspend in ~20 μL H$_2$O
  Nanodrop (high concentrations and peaks can indicate chloroform contamination)
  prepare PCR tubes
  dilute probes 1:5
  prepare Master Mix in the following proportions:
    0.25 μL 1M Tris HCl
    0.25 μL 5M NaCl
    0.25 μL 0.1M EGTA
    5 μL diluted probe mix
    15 μL H$_2$O
  add 20.75 μL Master Mix to each PCR tube
  add 5 μL RNA
  vortex and spin down
  run Hybridization program in thermocycler (90° C. for 5 minutes, cool down slowly to 50° C. for 1 hour)
Ligation (Ligating Perfectly Matched Probe Pairs)
  take out 10× SPLINTR ligase reaction buffer to thaw (does not have to be on ice)
  calculate Master Mix for Ligation and prepare in these proportions:
    5 μL SPLINTR ligase buffer 10×
    2 μL SPLINTR ligase
    2 μL RNASIN
    16 μL H$_2$O
  after 1 hour, add 25 μL Master Mix to each PCR tube
  spin, vortex, spin
  incubate at 25° C. for 1 hour
  take out T4 ligase buffer early to thaw at room temperature
  prepare Master Mix in the following proportions:
    5 μL T4 ligase buffer 5×
    2 μL T4 DNA ligase
    43 μL H$_2$O
  add 50 μL Master Mix to each PCR tube
  vortex and spin
  incubate at 16° C. overnight
RNA/DNA Hybrid Purification
  prepare 1.5 mL microcentrifuge tubes
  vortex and warm up in hands Dynabeads Myone C Streptavidin before aliquoting to 1.5 mL tube (need 50 μL for each 100 μL sample)
  place aliquoted beads against magnetic strip and pipette off buffer
  make 2λ washing buffer
    10 mM Tris-HCl (pH 7.5)
    1 mM EDTA
    2M NaCl
  wash beads in equal volume (500 μL) of 2× buffer—resuspend beads, place against magnetic strip, and remove liquid (3 times)
  resuspend in 2× buffer to get 1× (500 μL beads in 1000 μL buffer)
  add equal volume of beads (100 μL beads in 100 μL sample) to each PCR tube and transfer to 1.5 mL microcentrifuge tubes
  mix well by resuspending
  shake on block for 15 minutes (room temperature)
  take out RNase H buffer and RNase A from −20° C. to thaw
  make 1× wash buffer (1 mL 2× buffer and 1 mL H$_2$O)
  after shaking, put tubes against magnetic strip and remove supernatant
  set block to 37° C.
  wash 2 times with 100 μL 1× wash buffer
RNA Removal
  prepare Master Mix in the following proportions (keep on ice):
    86 μL H$_2$O
    10 μL RNase H buffer
    2 μL RNase H
    2 μL RNase A
  add 100 μL Master Mix to each sample and resuspend
  put samples in hot block at 37° C. for 30 minutes
  run Zymogen DNA Clean and Concentrator Kit using the ssDNA application (700 μL binding buffer)
  elute DNA in 100 μL elution buffer (or water) for 1:10 dilution
  [OPTIONALLY] prepare Master Mix that will deactivate enzymes in the following proportions:
    5 μL 1M Tris-HCl (pH 8)
    5 μL 500 mM EGTA
    10 μL 10% SDS
  after 30 minutes, take tubes out and set the block to 65° C.
  add 20 μL enzyme-inactivating Master Mix to each tube and vortex
  incubate on block at 65° C. for 30 minutes, vortexing every few minutes
  put tubes against magnetic strip and transfer supernatant to new 1.5 mL microcentrifuge tube
  run Zymogen DNA Clean and Concentrator Kit using the ssDNA application (700 μL binding buffer)
  elute DNA in 100 μL elution buffer (or water) for 1:10 dilution
Amplify DNA Probes by PCR
  prepare PCR tubes
  prepare PCR Master Mix in the following proportions:
    5 μL 10× buffer
    2 μL Mg
    1 μL dNTP
    1 μL forward primer
    38 μL H$_2$O
    0.2 μL enzyme
  (reverse primer is the barcode, so each must be added separately (1 μL) with 2 μL DNA)
  add 47 μL Master Mix to each PCR tube
  add 1 μL reverse primer to each
  add 2 μL DNA sample
  amplify for 15 cycles to keep in linear range on NETFLEX Small RNA Library Prep protocol
  can store products at −20° C. or run gel immediately The inventors have performed an unbiased study of tRNA abundances in malignant and non-malignant human cell lines. Highly metastatic sublines derived from distinct parental cancer cell populations were found to exhibit similar modulations in their tRNA content relative to their isogenic metastatic parental lines. Through loss-of-function and gain-of-function experiments, the inventors establish a causal role for two specific tRNA species as promoters of breast cancer metastasis. Modified expression of these specific tRNAs reshapes protein expression through the direct modulation of ribosome occupancy and/or transcript stability of specific transcripts enriched for codon complementary to these tRNAs. The inventors reveal that increased expression of a specific tRNA enhances the expression of direct targets of the tRNA in a codon-specific manner. These downstream targets constitute novel promoters of metastasis, and in combination with their upstream regulatory tRNA form a tRNA-activated pathway that drives cancer progression.

Metastatic Progression and Modulations in the tRNA Expression Landscape

Figure 1A:
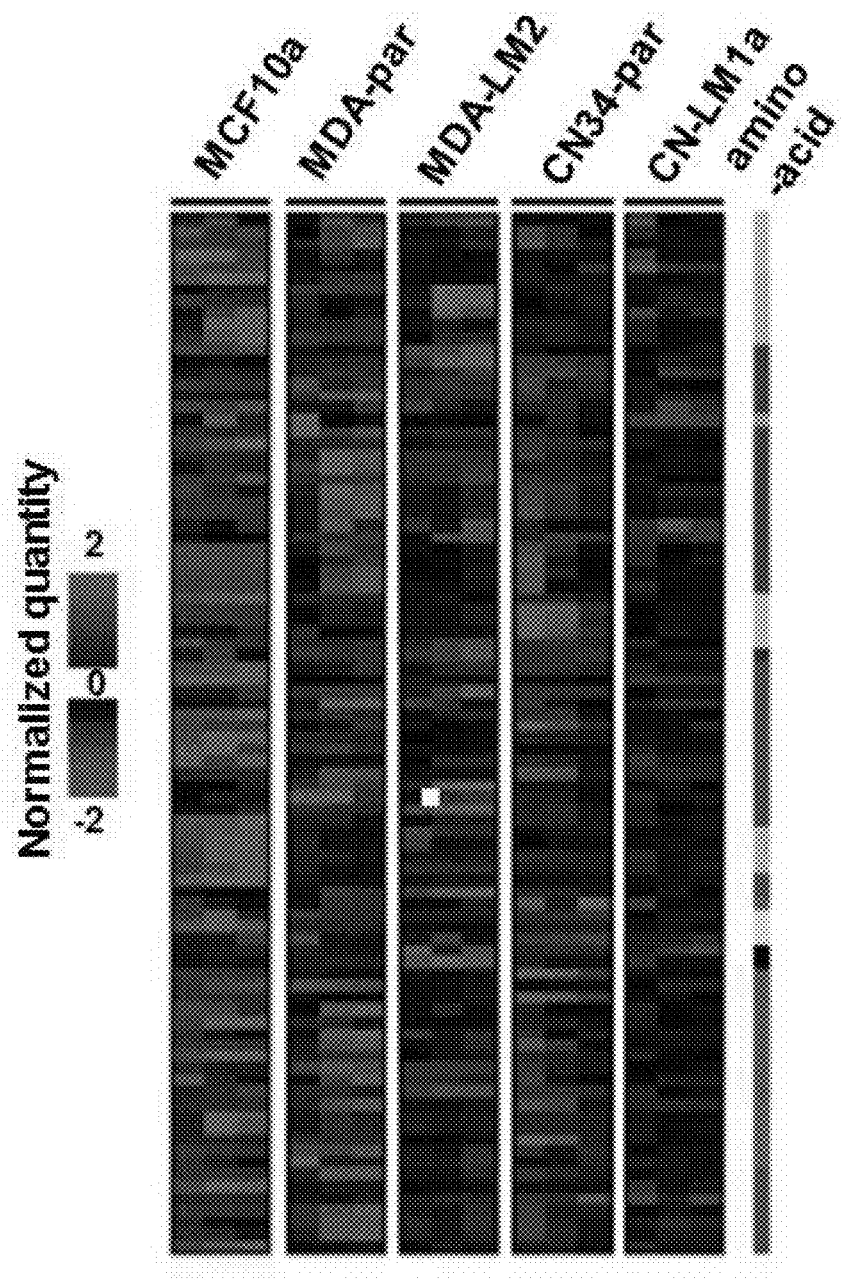
FIGS. 1A-1G| Transfer RNA profiling of metastatic and non-metastatic breast cancer lines.

To create a snapshot of the tRNA landscape in different cellular contexts, we measured the cellular content of various tRNA species in five different human cell lines (Minn et al., 2005; Tavazoie et al., 2008): a non-tumorigenic epithelial cell line (MCF10a), poorly metastatic breast cancer lines MDA-231 and CN34, and their highly metastatic sub-lines MDA-LM2 and CN-LM1a (FIG. 1A). To do this, we developed an approach based on hybridization and subsequent ligation of complementary DNA probes. Due to their strong secondary structures and extensive base modifications, tRNAs are not suitable substrates for reverse transcription. Thus, their quantification using common cDNA-based approaches results in unpredictable biases and spurious measurements (Dittmar et al., 2006). While enzymatic removal of certain tRNA modifications and the application of highly processive reverse transcriptase enzymes provide a promising avenue for tRNA-sequencing and quantification (Zheng et al., 2015), high-quality tRNA profiling is still a need and tRNA content and its regulatory roles remain poorly studied. Here, by relying on the hybridization and quantification of tRNA-specific probes, we have bypassed the first-strand cDNA synthesis step (Nilsson et al., 2000). Briefly, for each tRNA species, a pair of probes were designed that upon hybridization to their cognate tRNAs would provide a nick at the site of the anticodon. The nick was then repaired in a ligation reaction, giving rise to a first-strand cDNA. Biotinylation of the tRNA population and streptavidin-mediated co-precipitation steps were included to achieve a higher signal-to-noise ratio (FIGS. 8A-8E). Following the successful splinted ligation of probes on their cognate tRNAs, high-throughput sequencing or qPCR can be used for relative quantification of tRNA levels (FIG. 1A).

Figure 1B:
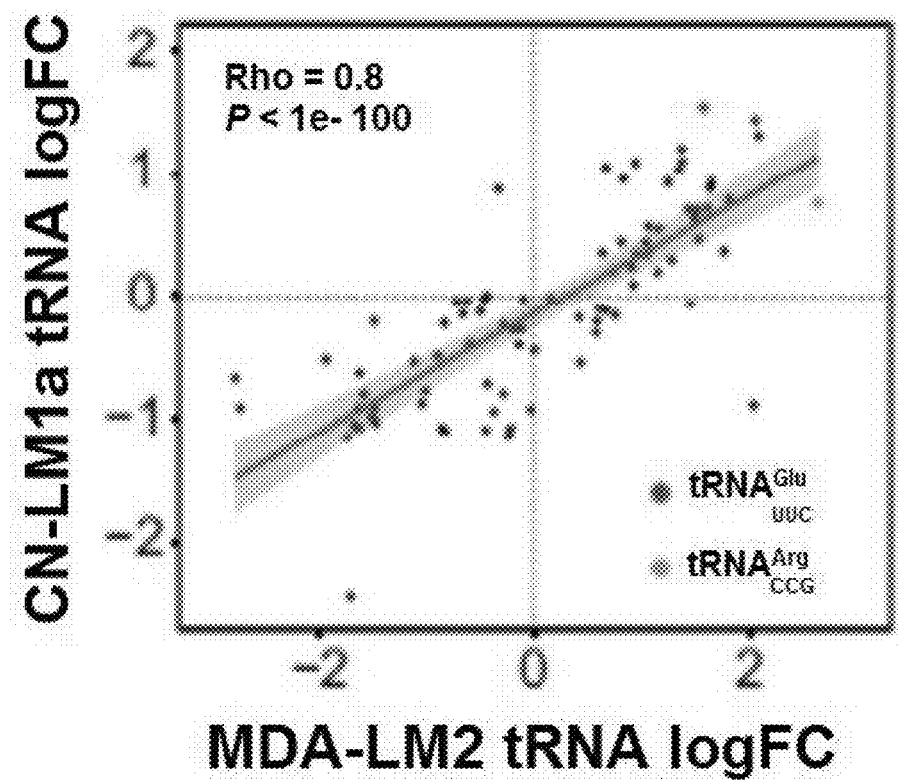

TRNA profiling revealed that tRNA expression levels in breast cancer lines were different from those of non-tumorigenic cells (FIG. 1A). And more importantly, while cells from the MDA-231 and CN34 populations showed distinct tRNA profiles, we observed substantial similarities between the two cell lines with respect to their differential tRNA content when comparing parental and metastatic lines (FIGS. 1A and 1B). In other words, in vivo selection of MDA-231 and CN34 parental cancer cell populations for higher metastatic capacity selected for similar modulations in tRNA abundances. This concerted modulation of tRNA levels suggests a direct role for tRNAs in promoting cancer progression.

Figure 1C:
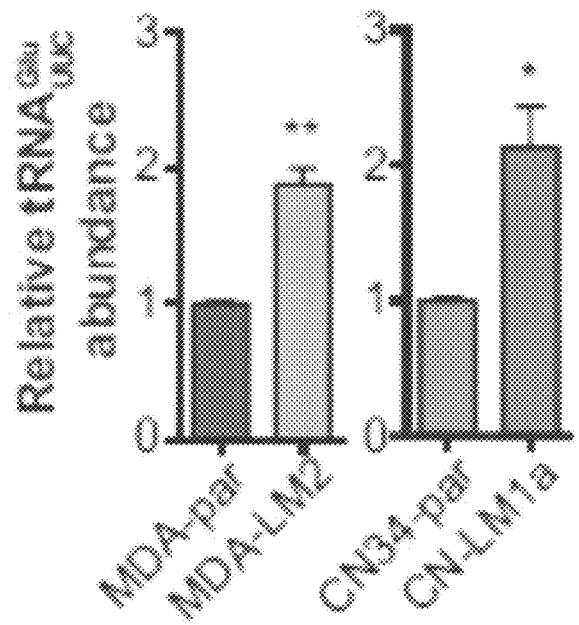
Figure 1D:
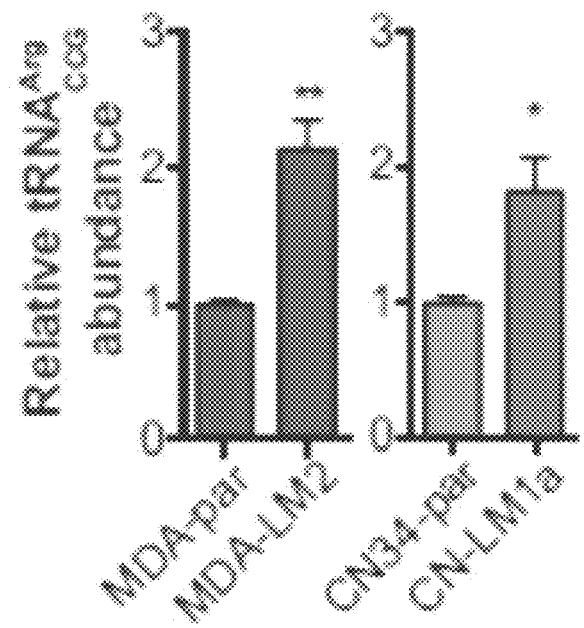
Figure 8A:
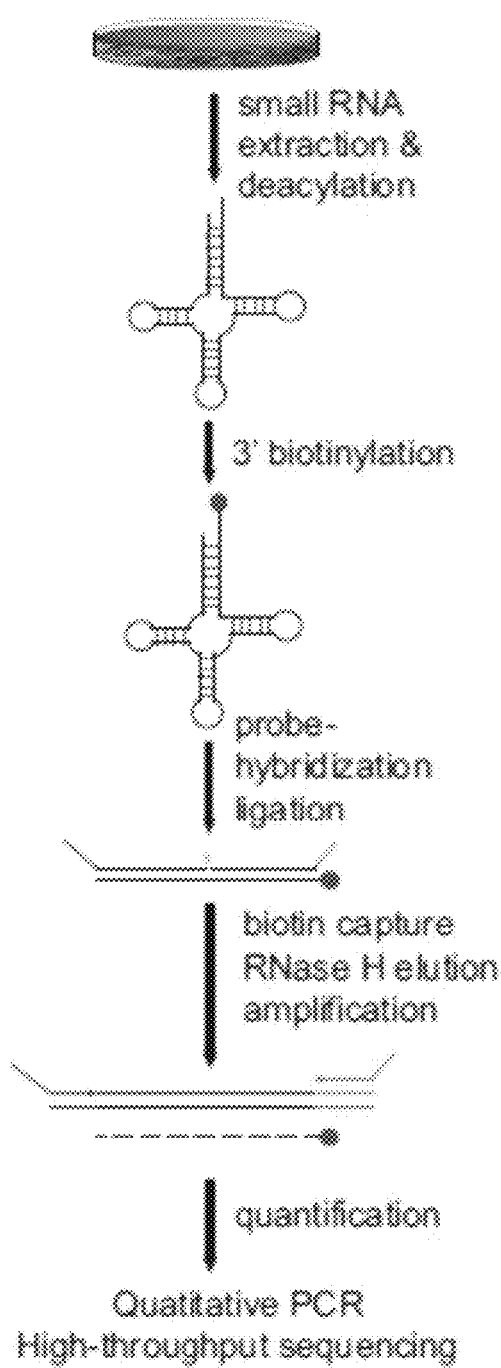
Figure 8B:
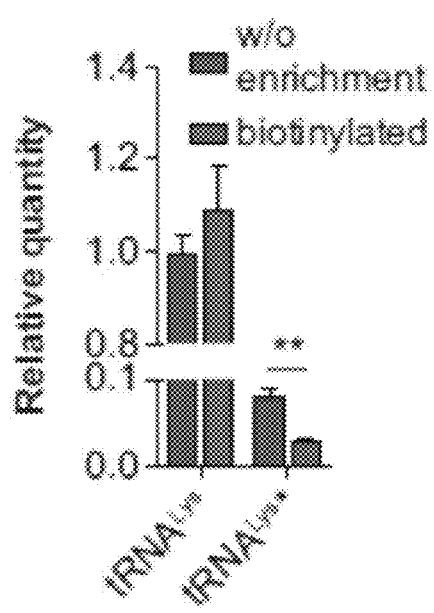
Figure 8C:
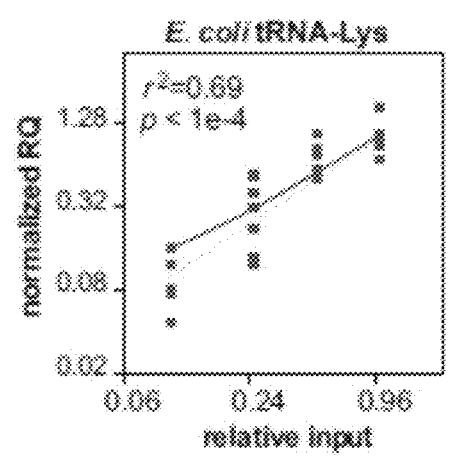
Figure 8D:
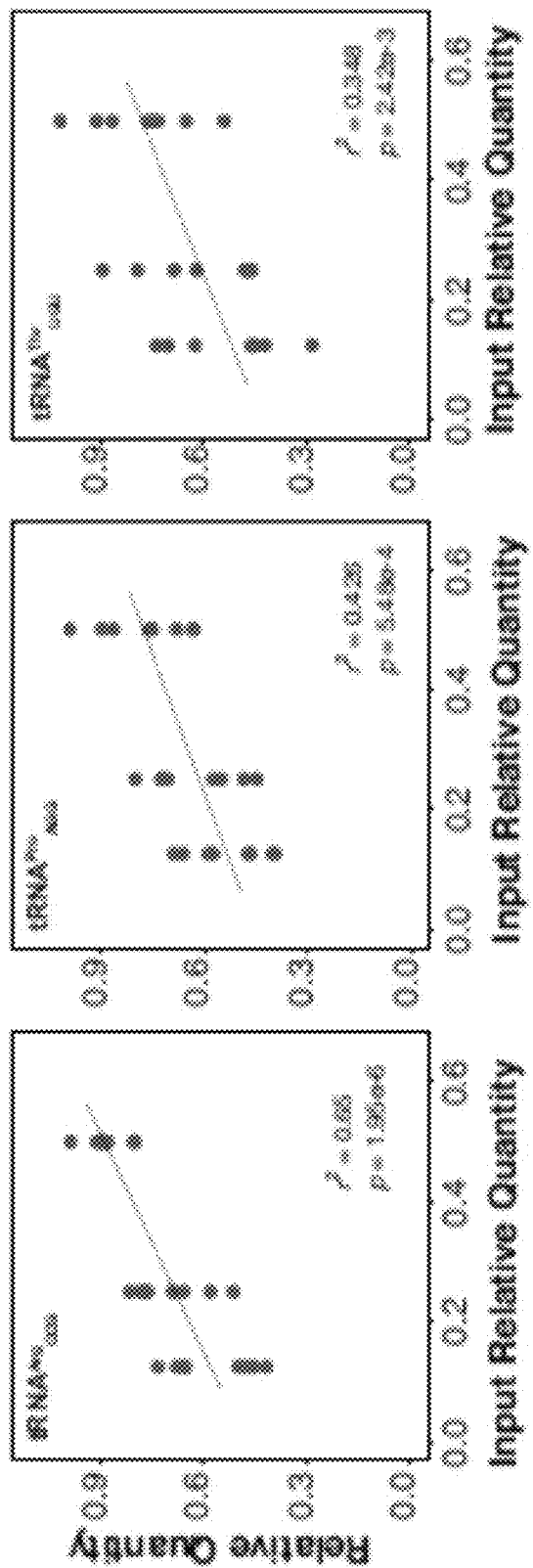
Figure 8E:
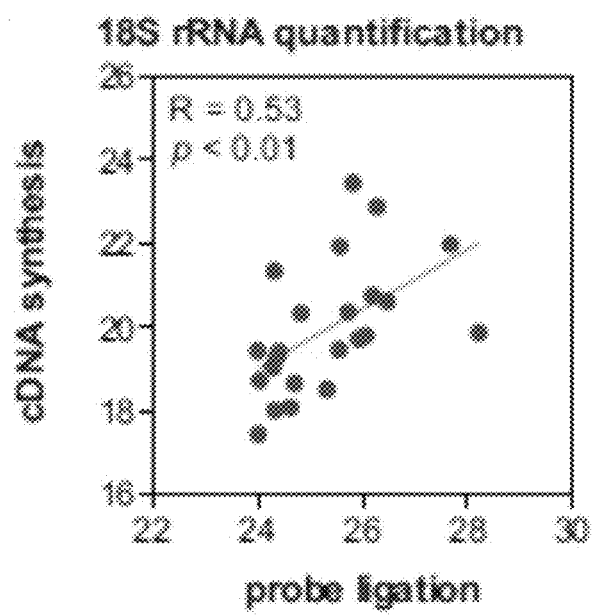
Figure 8F:
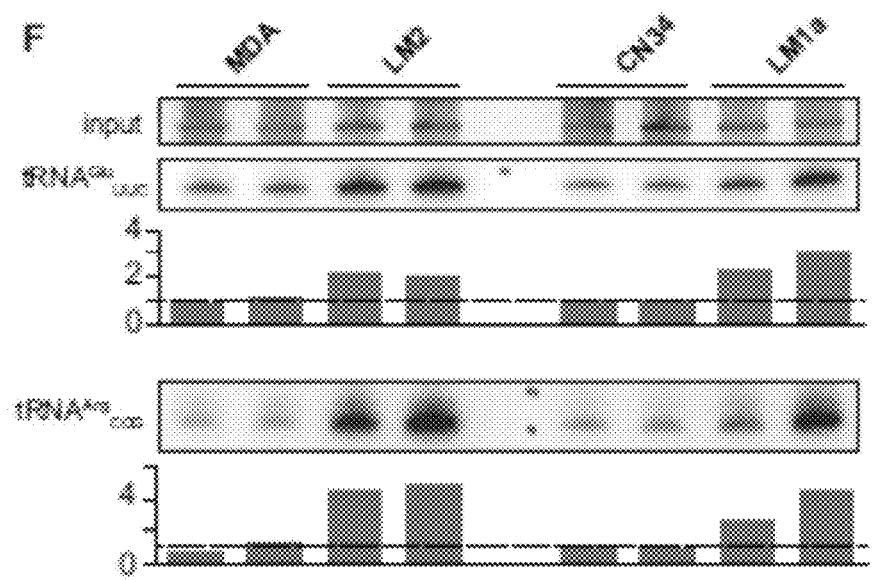
Figure 8G:
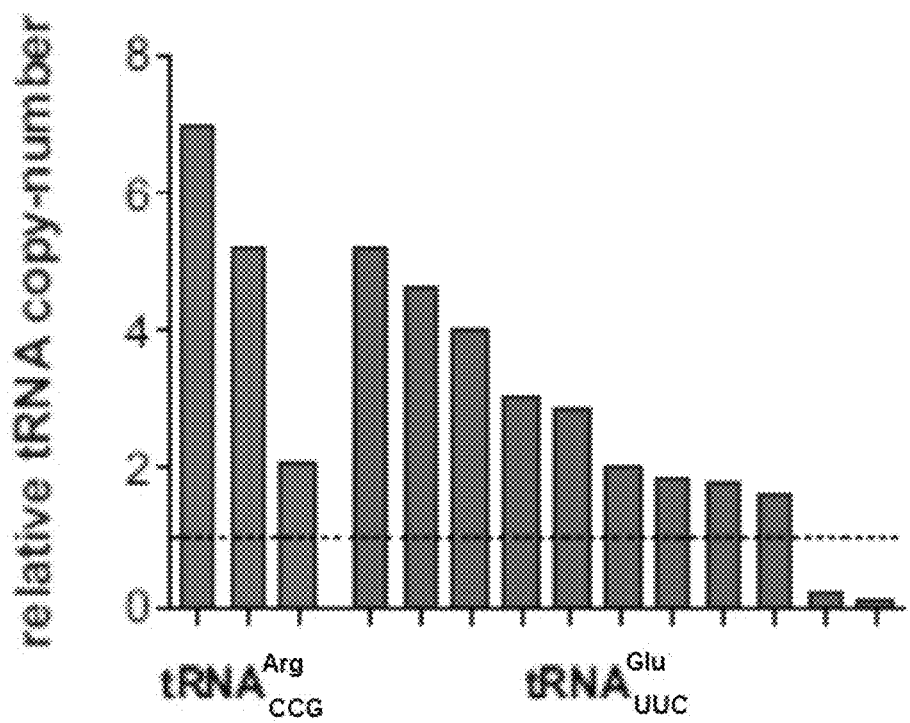

Among the tRNAs deregulated in the metastatic cells, tRNA$^{Arg}_{CCG}$ and tRNA$^{Glu}_{UUC}$ were consistently upregulated in both MDA-LM2 and CN-LM1a highly metastatic cells relative to their parental lines (FIG. 1B). We further validated this up-regulation using both splinted-ligation followed by qPCR and Northern blot analysis (FIGS. 1C and 8F). Importantly, qRT-PCR assays for pre-tRNA$^{Arg}_{CCG}$ and pre-tRNA$^{Glu}_{UUC}$ species revealed a significant up-regulation in the pre-tRNA levels as well (FIG. 1D). Consistent with the increased pre-tRNA and mature tRNA levels expressed in highly metastatic cells, increased genomic copy number of tRNA$^{Arg}_{CCG}$ and tRNA$^{Glu}_{UUC}$ loci were observed in highly metastatic cells (FIG. 8G).

Figure 1E:
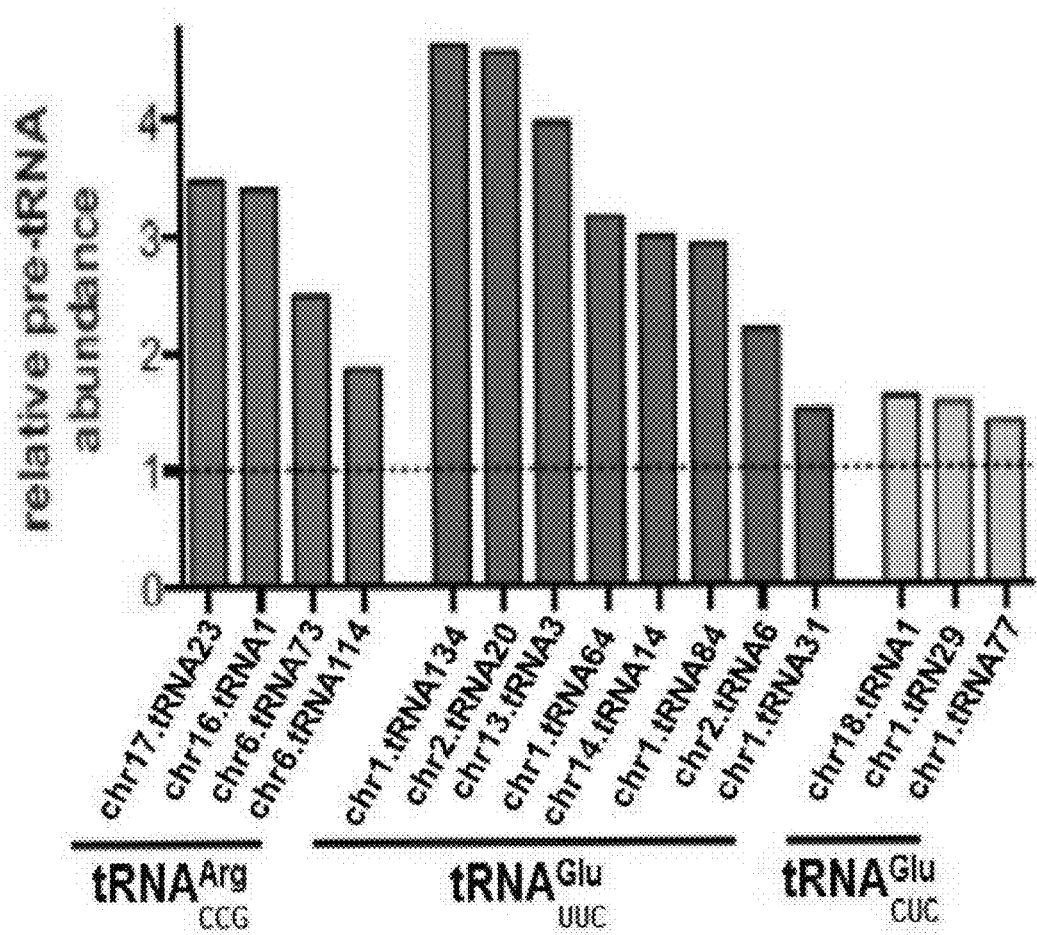
Figure 1F:
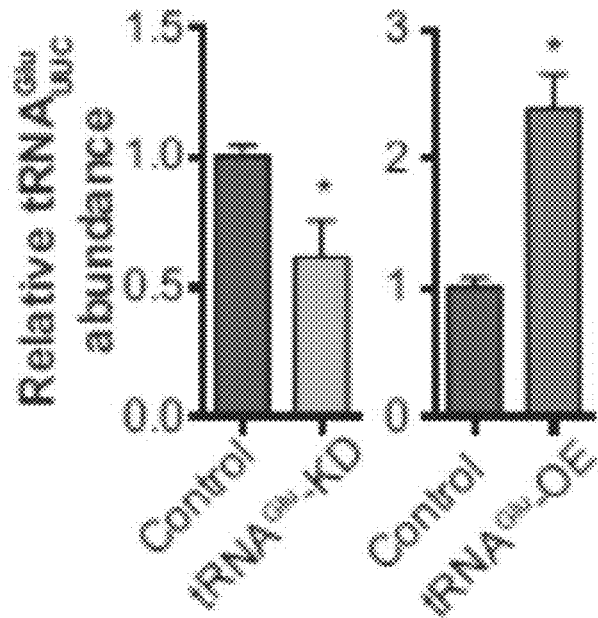
Figure 1G:
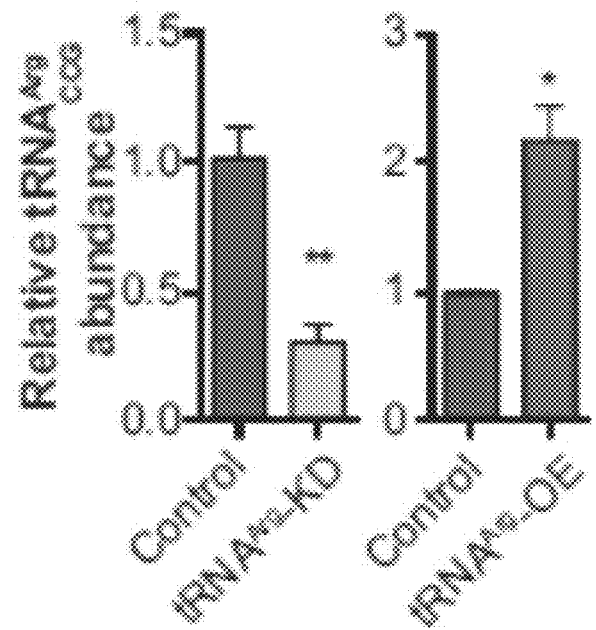

To measure the phenotypic and molecular consequences of modulations in the levels of these tRNAs, we first tested whether stable cell lines over-expressing or knocked-down for these tRNAs could be generated. We found that endogenous levels of tRNA$^{Arg}_{CCG}$ and tRNA$^{Glu}_{UUC}$ in the highly metastatic MDA-LM2 background could be effectively reduced by expressing short hairpins targeting these tRNAs respectively (FIG. 1E). Similarly, the expression levels of these tRNAs in MDA-parental cells were successfully enhanced by stable integration of additional copies of these tRNAs under a U6 promoter (FIG. 1E). It should be noted that these observed over-expression and knockdowns (~2-fold as measured by quantitative PCR-based tRNA quantification) in the levels of these tRNAs were within physiological boundaries of their level of endogenous modulation between the parental and the in vivo-selected highly metastatic cells (FIGS. 1C and 1E).

tRNA$^{Glu}$UUC and tRNA$^{Arg}_{CCG}$ Promote Metastatic Progression

Figure 2A:
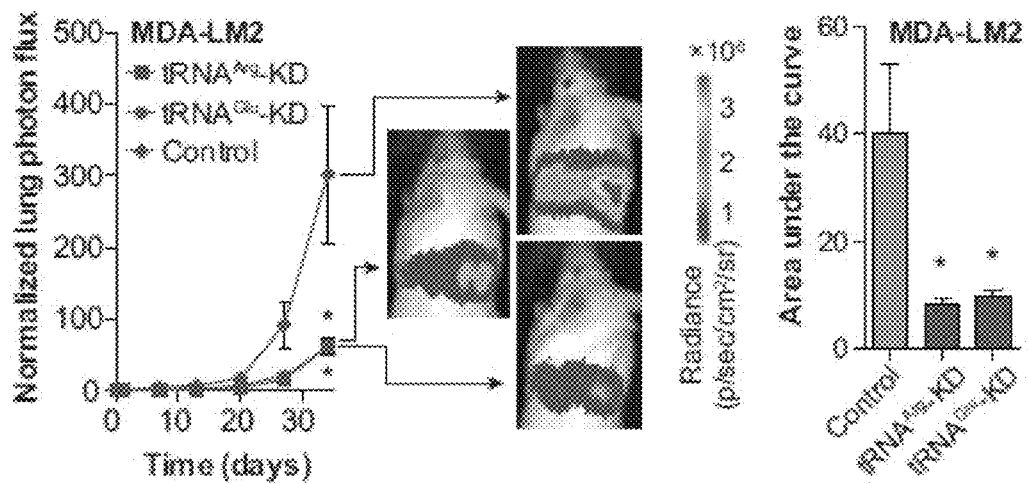
Figure 2B:
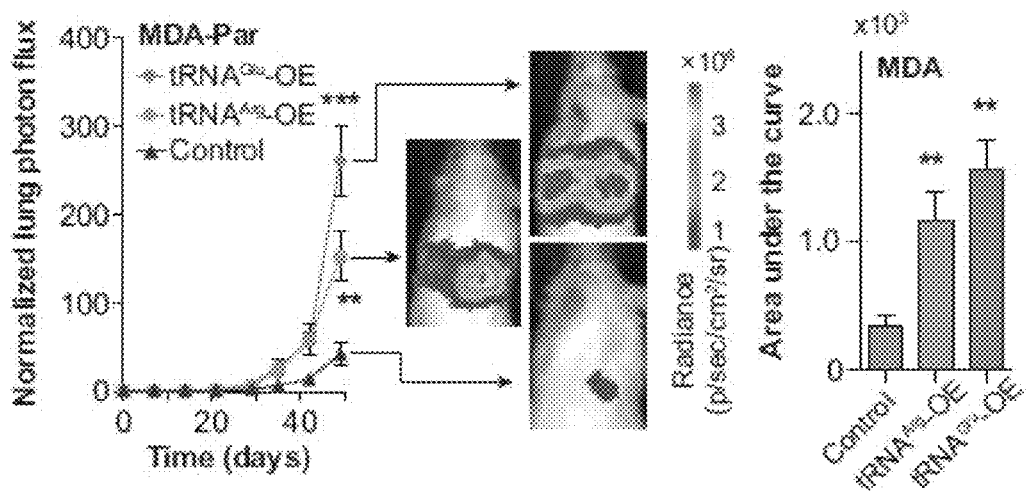
Figure 2C:
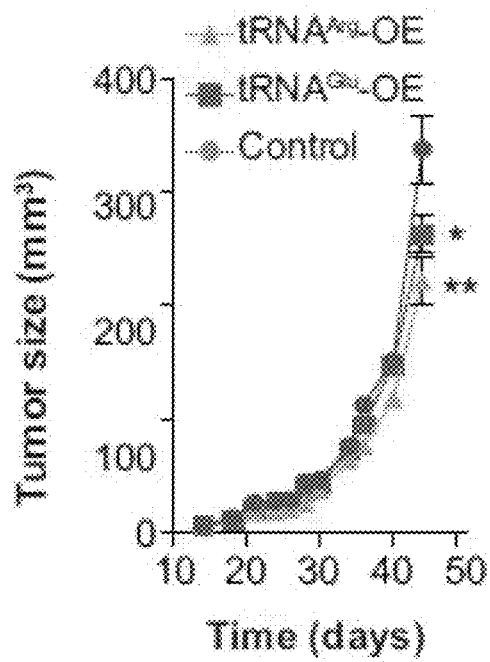
Figure 2D:
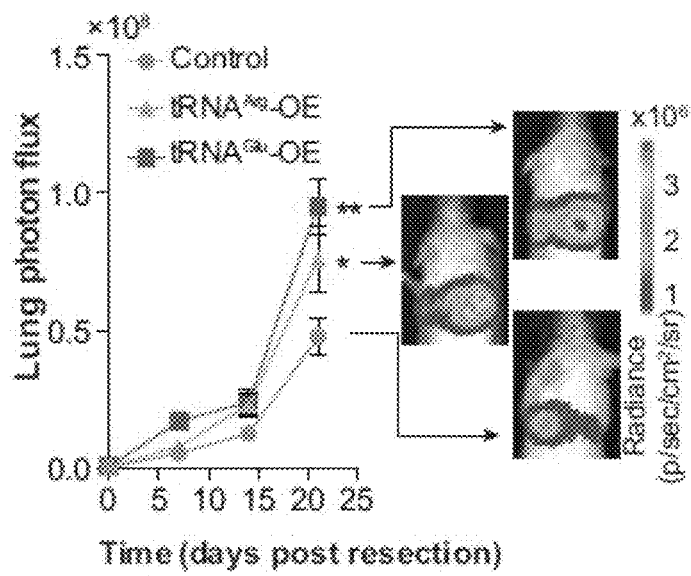
Figure 9A:
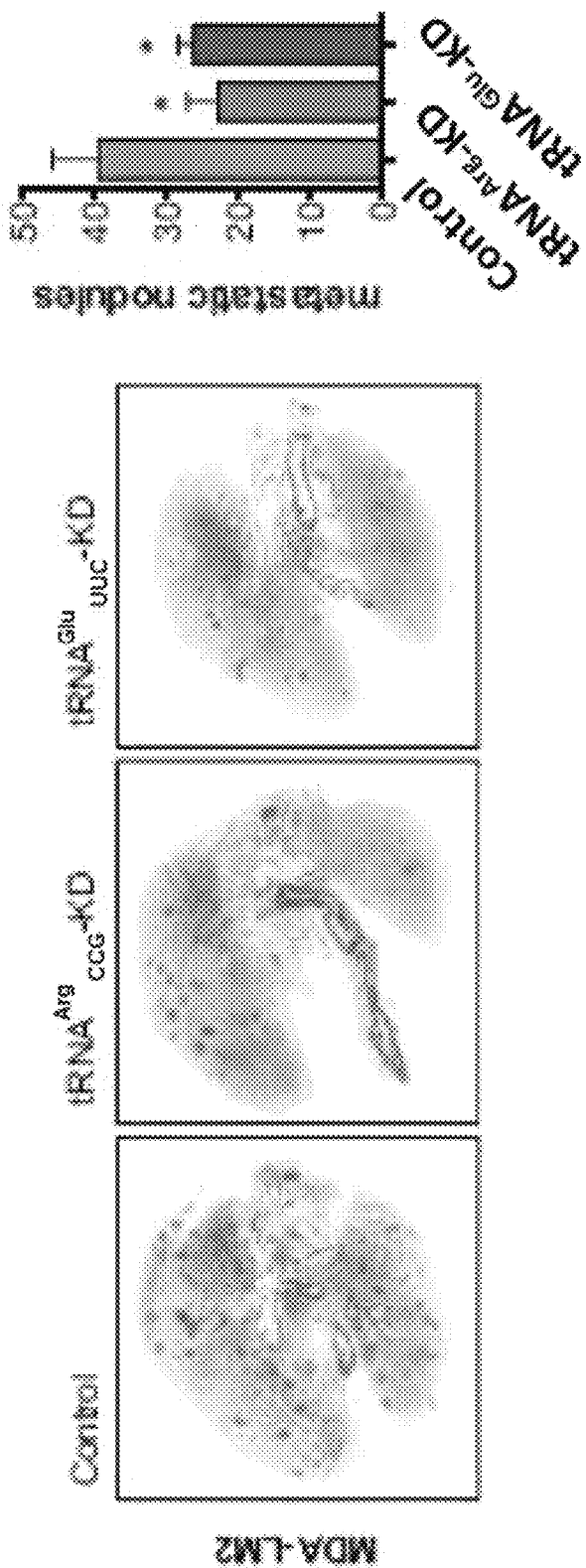
Figure 9B:
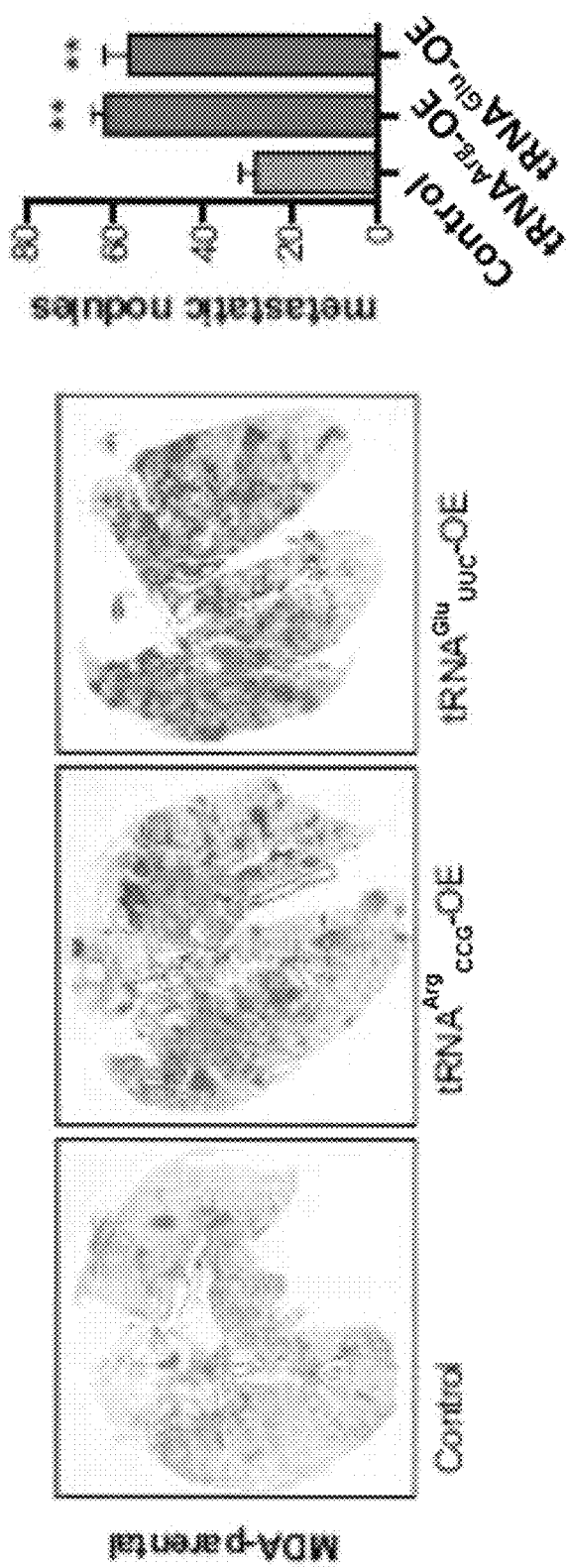

To test whether the increased expression levels of tRNA$^{Arg}_{CCG}$ and tRNA$^{Glu}_{UUC}$ play direct roles in conferring higher metastatic capacity, we employed short hairpins targeting tRNA$^{Arg}_{CCG}$ and tRNA$^{Glu}_{UUC}$ in metastatic MDA-LM2 cells. Reducing the levels of tRNA$^{Glu}_{UUC}$ and tRNA$^{Arg}_{CCG}$ by 40% and 70%, respectively, in metastatic MDA-LM2 cells (FIG. 1E) to physiologically equivalent levels observed in poorly metastatic parental cells, significantly reduced their lung colonization capacity (FIG. 2A). Gross histology of the extracted lungs also showed significantly fewer metastatic nodules relative to MDA-LM2 control cells (FIG. 9A). Consistent with these observations, over-expression of tRNA$^{Glu}_{UUC}$ and tRNA$^{Arg}_{CCG}$ in poorly metastatic MDA-parental cells, significantly enhanced metastatic progression (FIGS. 2B and 9B). More strikingly, tRNA over-expressing cells exhibited enhanced orthotopic metastasis compared to control cells despite their significantly reduced primary tumor growth rates (FIGS. 2C-2D). These results reveal that increased abundance of specific tRNAs can promote the metastatic phenotype of breast cancer cells.

Figure 3B:
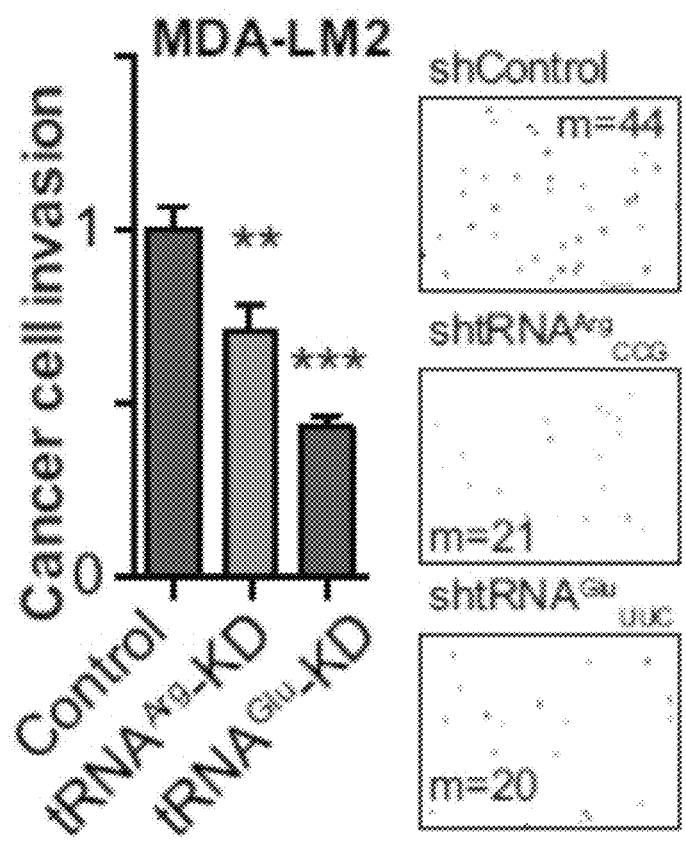
Figure 9C:
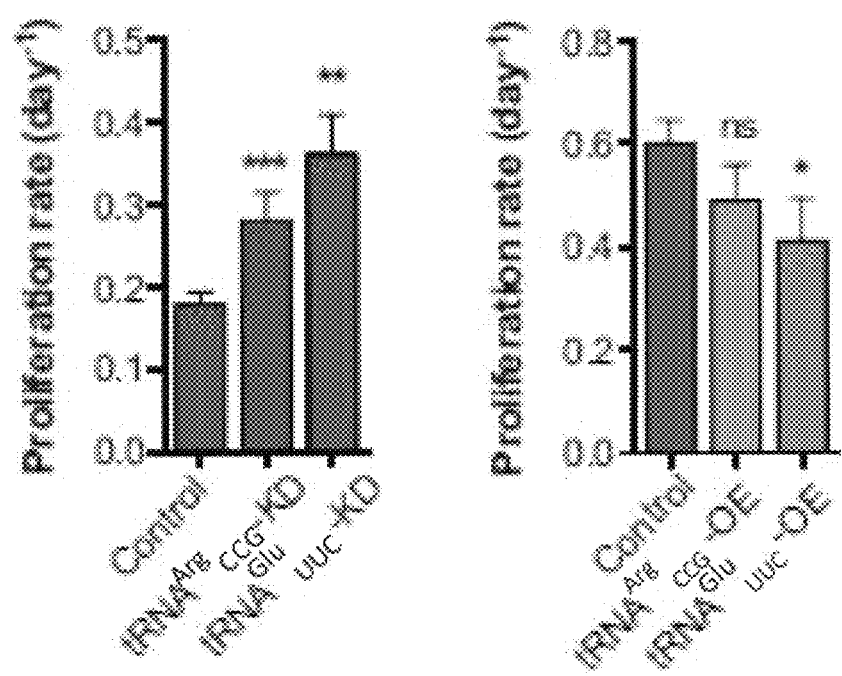
Figure 9D:
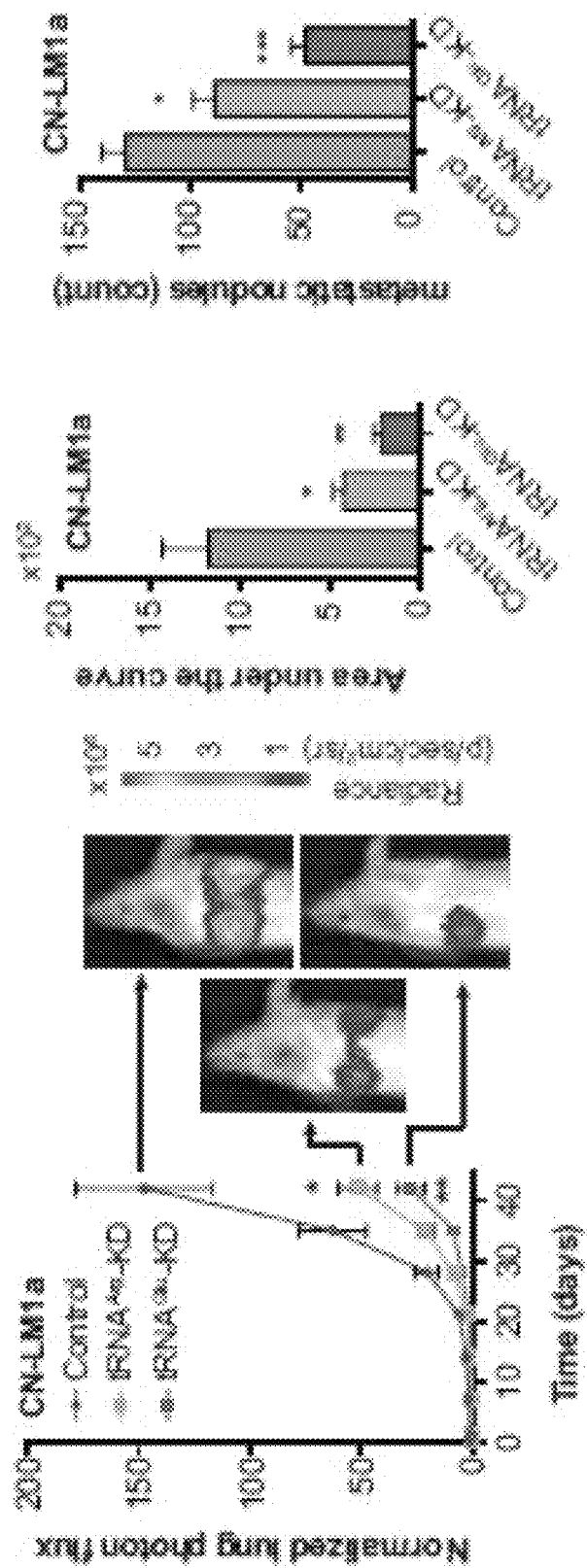
Figure 9E:
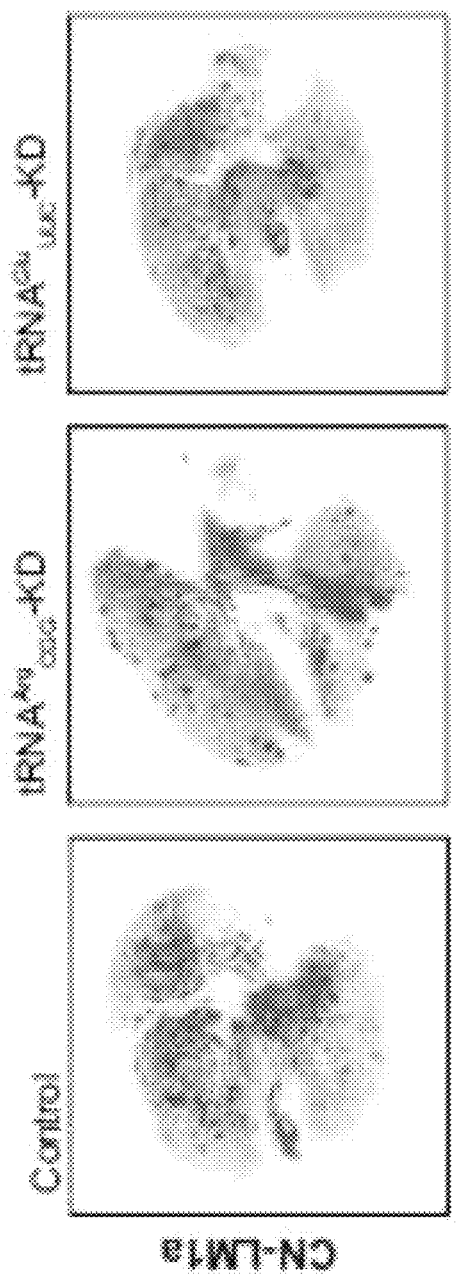

Given that cancer cell invasion is a key phenotypic attribute required for metastatic progression from the mammary gland in vivo, we asked whether modulations in the levels of tRNA$^{Arg}_{CCG}$ and tRNA$^{Glu}_{UUC}$ could affect the invasiveness of these cells. We performed in vitro cancer cell invasion assays for tRNA$^{Arg}_{CCG}$ and tRNA$^{Glu}_{UUC}$ over-expressing cells (FIG. 3A), and observed significant increases in invasion capacity. Conversely, highly metastatic MDA-LM2 cells expressing shRNAs targeting these tRNAs exhibited significantly reduced invasive capacity (FIG. 3B). The observed increase in in vitro invasion upon up-regulation of these tRNAs was not due to a general increase in proliferative capacity, as overexpression of these tRNAs actually slightly decreased in vitro proliferation rates (FIG. 9C). These in vitro findings are consistent with the tumor growth and metastatic phenotypes observed in vivo, and provide further support to the notion that individual tRNAs can have specific, pro-metastatic phenotypic consequences.

To ensure the broad biological relevance of these findings and to rule out off-target effects due to shRNA expression, we performed the following experiments. First, we functionally tested the phenotypic effects of tRNA knock-down in an independent cell line—the metastatic CN-LM1a sub-line. Knock-down of these two tRNAs also reduced metastatic capacity of this breast cancer cell population as well (FIGS. 10D-10E). We then over-expressed and knocked-down each tRNA simultaneously and measured their metastatic capacity in vivo relative to control cells. Consistent with on-target effect of shRNAs, over-expressing each tRNA prevented the reduced metastatic phenotype observed upon depletion of each tRNA (FIG. 10A). Lastly, to ensure that the observed phenotypes were specific to tRNA$^{Arg}_{CCG}$ and tRNA$^{Glu}_{UUC}$ and that varying the levels of another tRNA, which was not observed to be modulated in cancer cells upon selection for enhanced metastatic activity, would not manifest similar effects, we also varied the levels of tRNA$^{Tyr}_{GUA}$. Modulating tRNA$^{Tyr}_{GUA}$ in both knock-down and over-expression experiments did not affect the metastatic activity of MDA-LM2 cells (FIG. 10B).

Figure 3C:
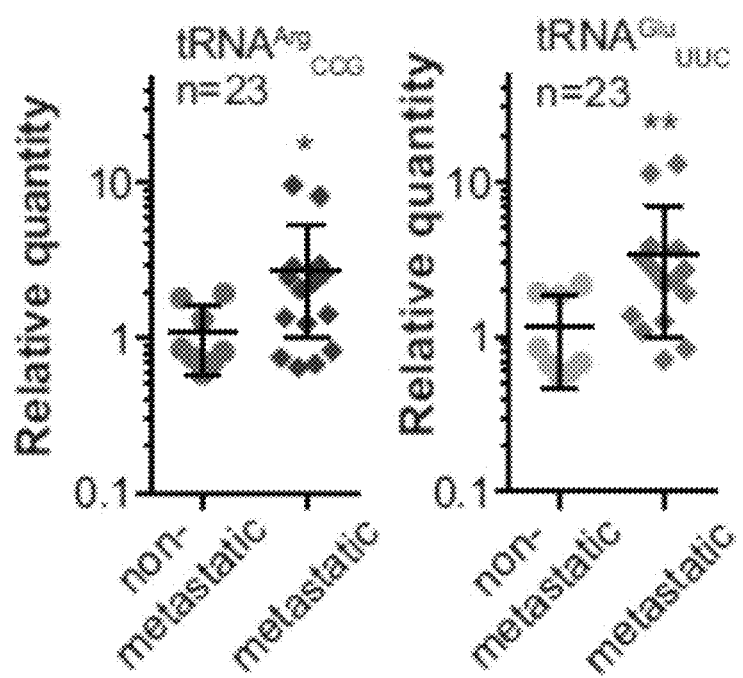
Figure 4A:
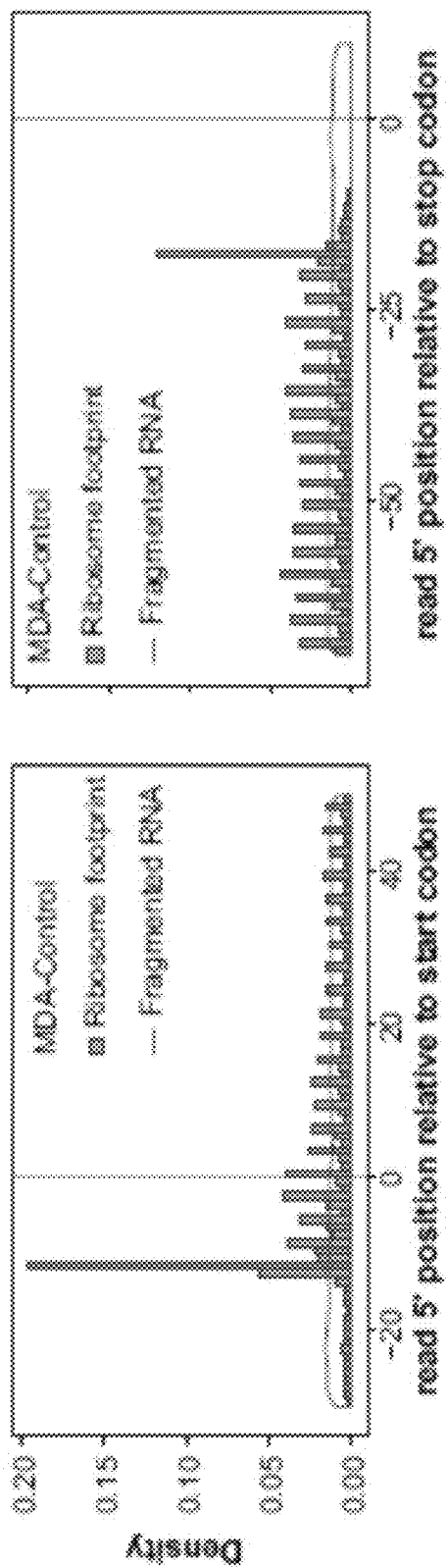
Figure 4B:
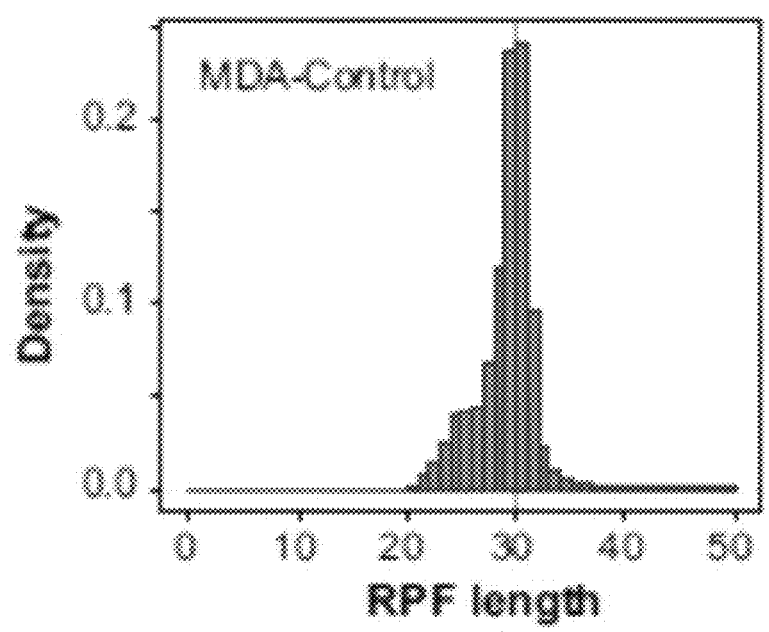
Figure 4C:
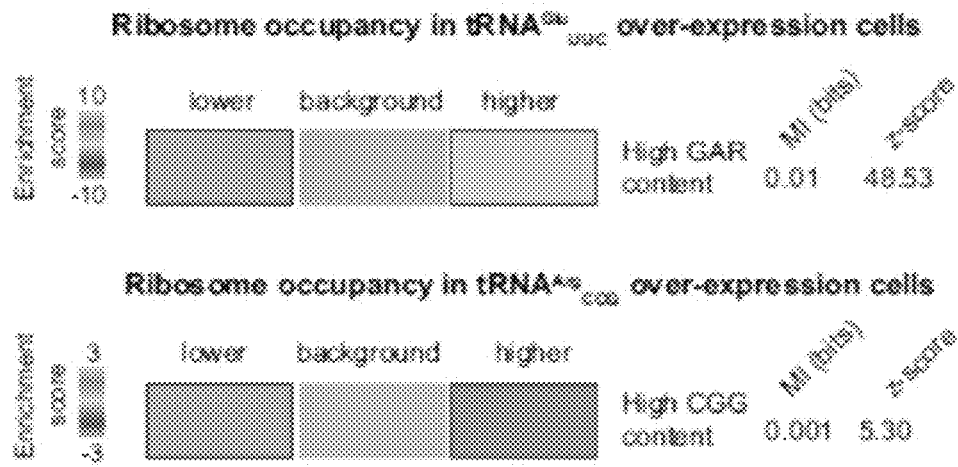
Figure 11A:
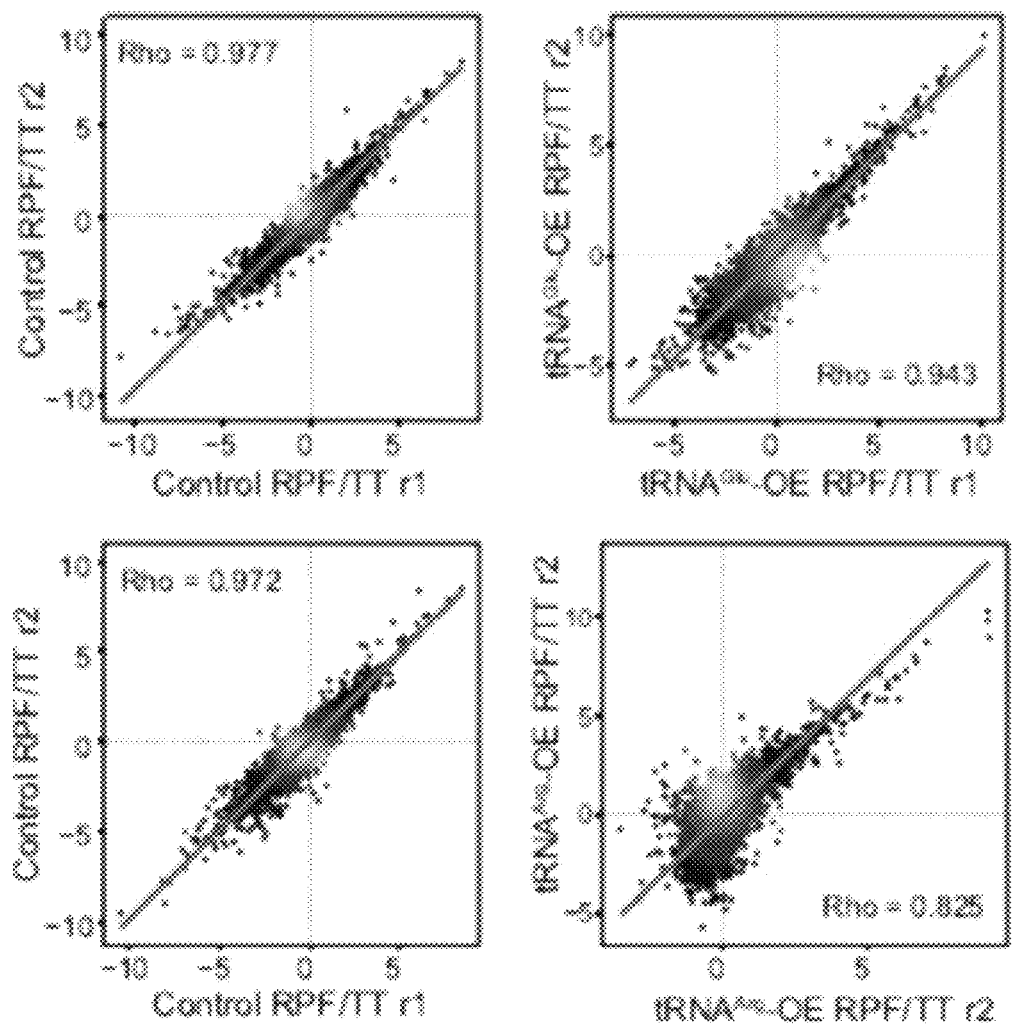
Figure 11B:
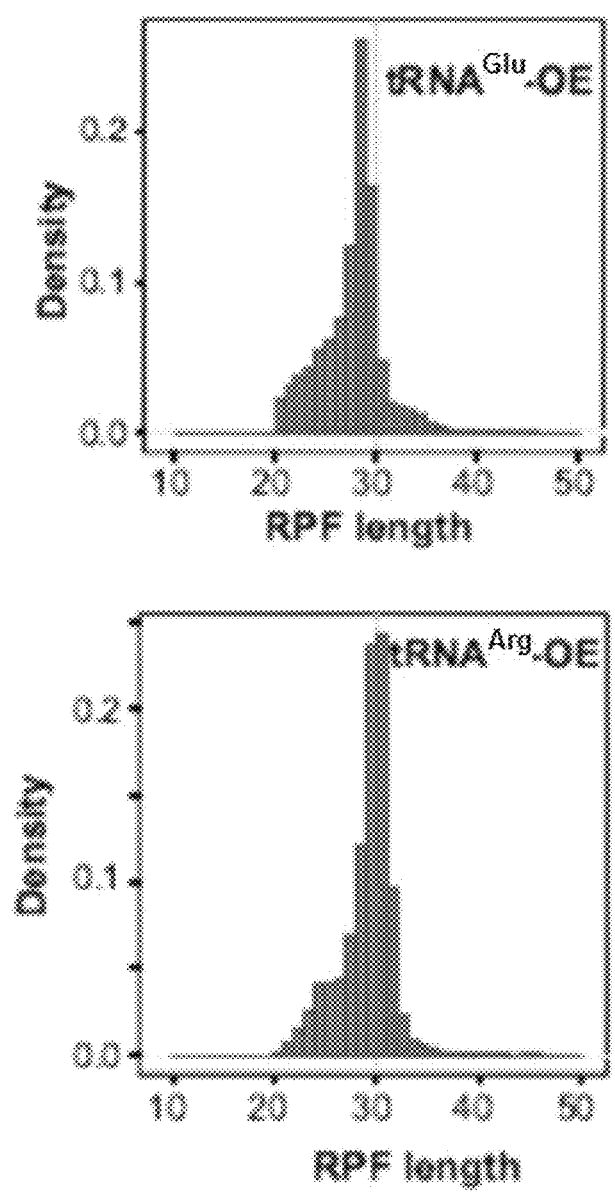
Figure 11C:
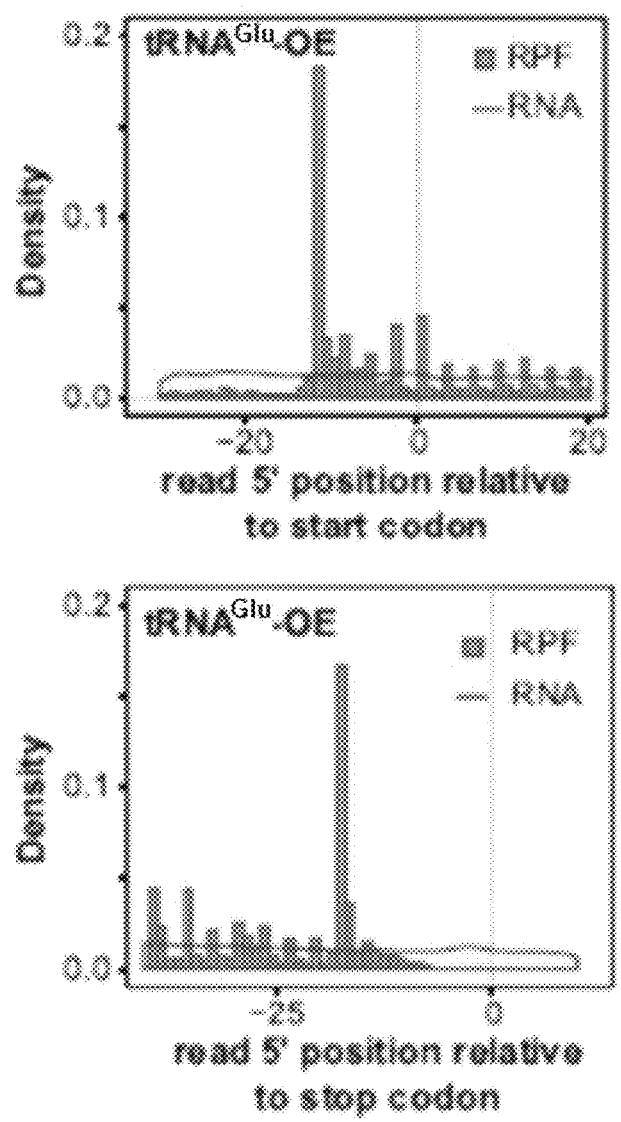
Figure 11D:
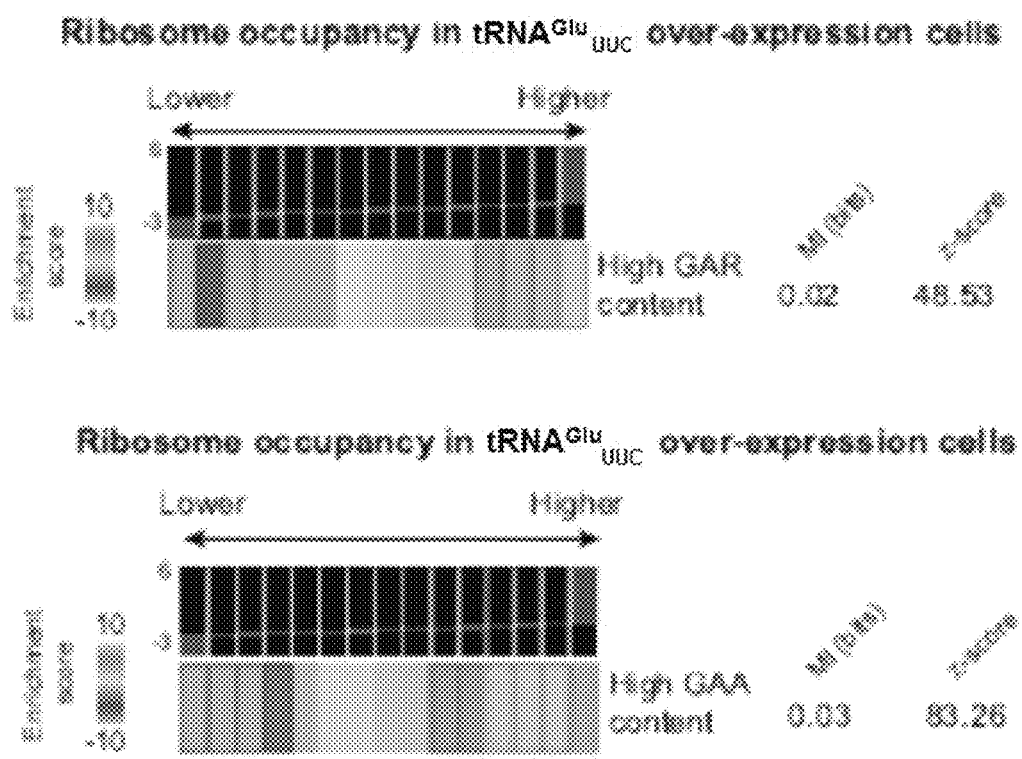

To further ascertain whether these associations are clinically relevant to human breast cancer progression, we quantified the levels of these tRNAs in a cohort of primary tumors that had not metastasized as well as in those that had exhibited clinical metastasis (n=23). We observed significant up-regulations in tRNA$^{Arg}_{CCG}$ and tRNA$^{Glu}_{UUC}$ levels across the metastatic primary tumors relative to non-metastatic primary tumors (FIG. 3C). These findings reveal that the expression levels of tRNA$^{Arg}_{CCG}$ and tRNA$^{Glu}_{UUC}$ in human breast cancers correlate with and predict metastatic propensity.

tRNA$^{Glu}$UUC and tRNA$^{Arg}_{CCG}$ Over-Expression Impacts Transcript Stability and Translation As previously mentioned, modulations in tRNA levels may impact the gene expression landscape of the cell in a variety of ways. To assess the regulatory consequences of up-regulating these tRNAs, we systematically measured their impact on post-transcriptional regulatory processes. First, we performed ribosome profiling in control as well as tRNA$^{Arg}_{CCG}$ and tRNA$^{Glu}_{UUC}$ over-expressing cells to provide a snapshot of changes in active translation (Ingolia et al., 2014). We observed a substantial positive correlation between relative ribosome occupancy of transcripts across biological replicates (FIG. 11A). Importantly, the periodicity and length generally noted for ribosome protected fragments were observed in this dataset as well (FIGS. 4A-4B and 11B-11C). For each gene, we calculated a corrected ribosome-occupancy score to compare active translation in tRNA over-expressing cells relative to control cells (MDA-parental background; see Methods). We subsequently asked whether the frequency of codons cognate to each over-expressed tRNA was informative of the observed changes in active translation. We observed that in tRNA$^{Glu}_{UUC}$ over-expressing cells, genes with high GAR content in their coding sequence (GAA and GAG codons, since tRNA$^{Glu}_{YUC}$ has Wobble-base pairing at the 3$^{rd}$ nucleotide) were significantly enriched among those with higher relative ribosome occupancy (FIGS. 4C and 11D). Similarly, higher CGG content was associated with higher active translation in tRNA$^{Arg}_{CCG}$ over-expressing cells (FIG. 4C).

Figure 4D:
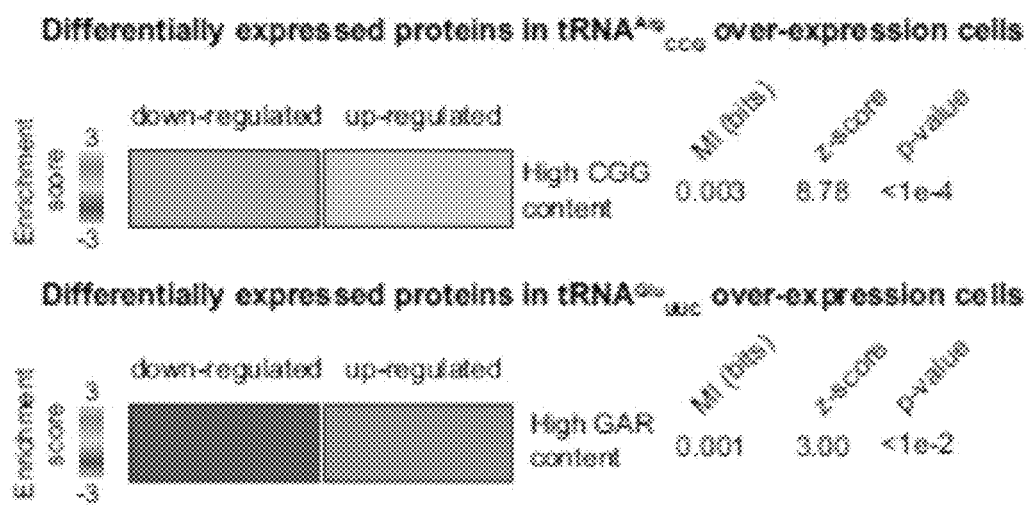
Figure 11E:
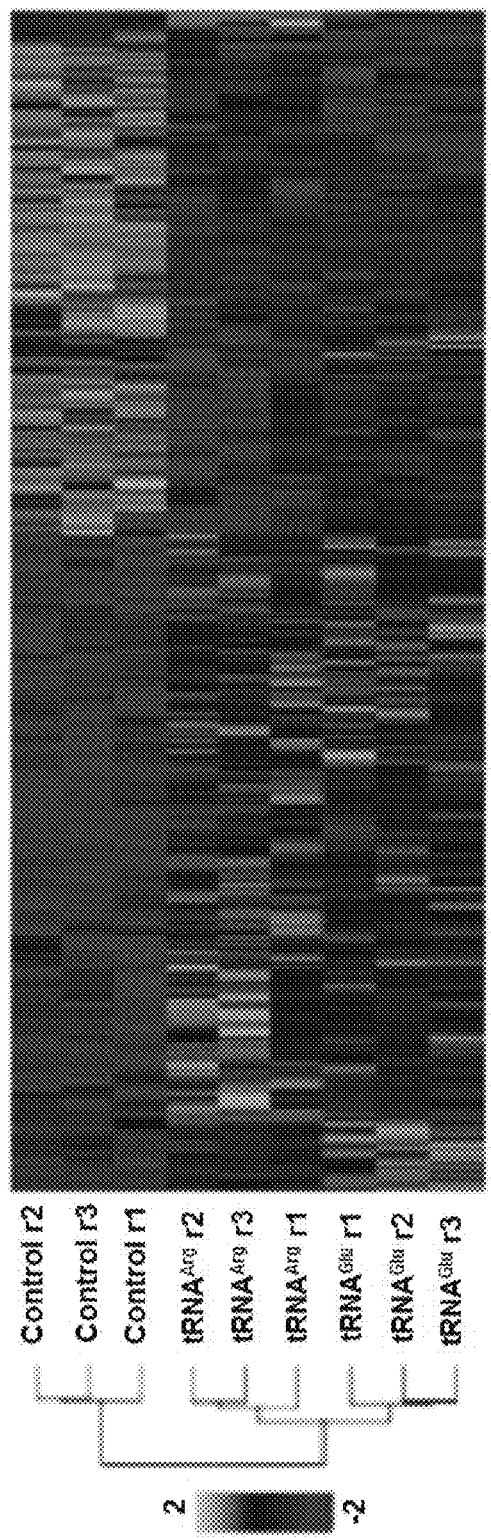
Figure 11F:
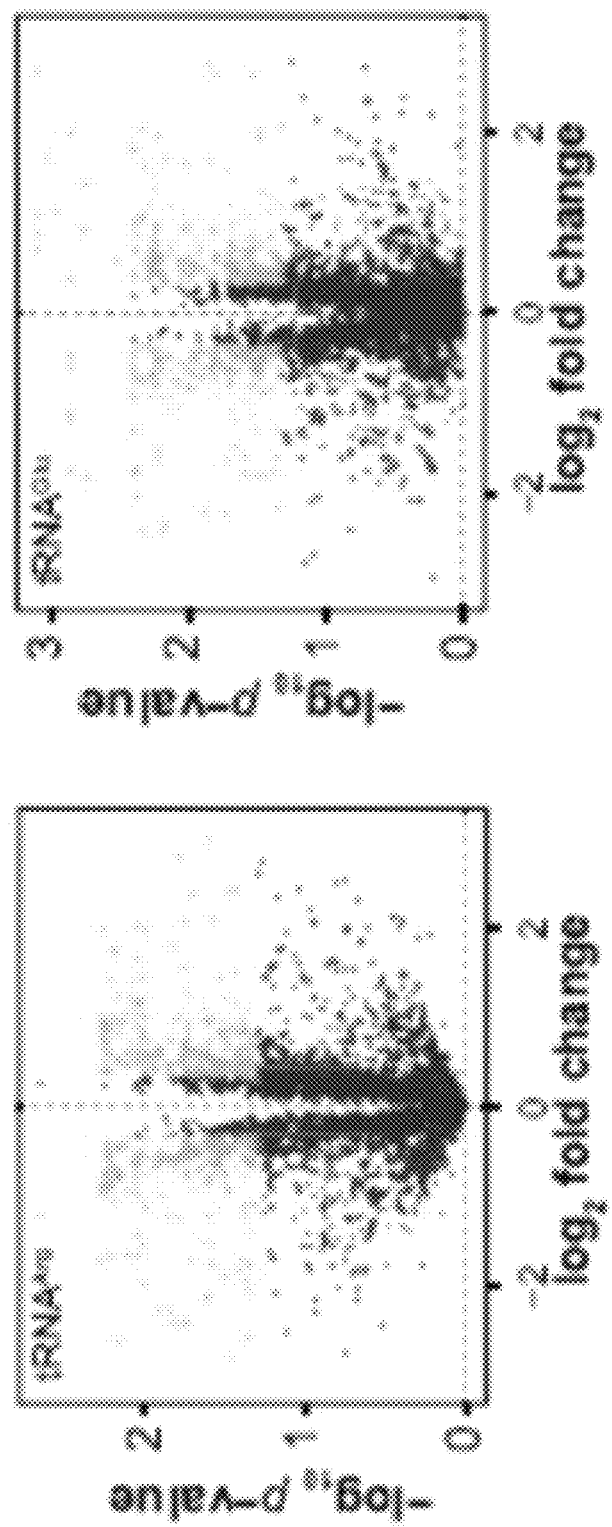
Figure 11G:
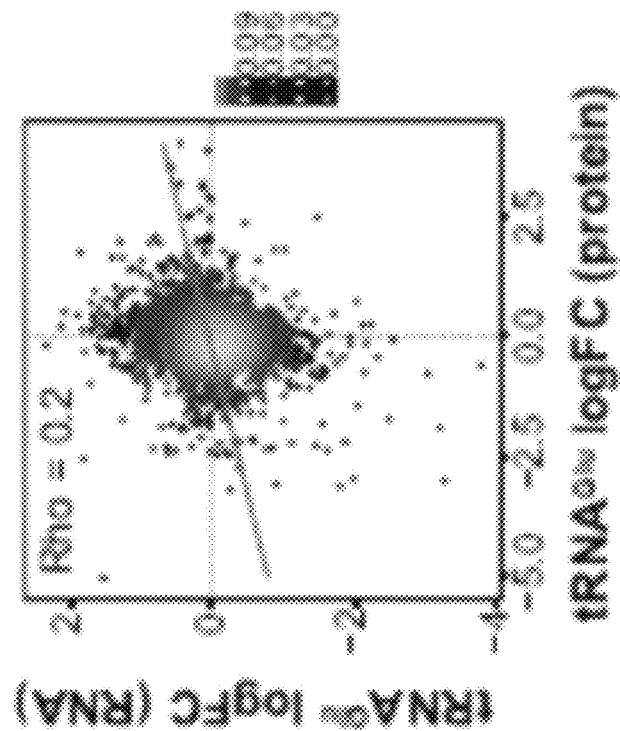
Figure 11G:
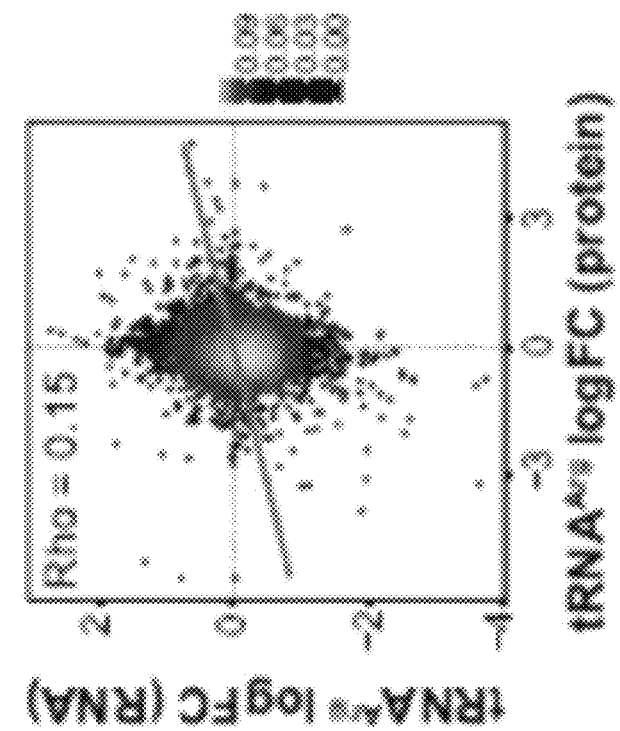

To directly assess the impact of tRNA modulations on proteomic output, we measured the expression levels of roughly 4,000 proteins using mass spectrometry-based quantification in tRNA$^{Arg}_{CCG}$ and tRNA$^{Glu}_{UUC}$ as well as control cells (MDA-parental background). In tRNA over-expressing cells, we identified hundreds of proteins that were significantly altered in their expression levels (FIGS. 11E-11F). To correct for changes in transcript levels, we performed transcriptomic measurements in tRNA$^{Arg}_{CCG}$ and tRNA$^{Glu}_{UUC}$ over-expressing as well as control cells. We then corrected the fold-changes in protein expression levels with those of their corresponding transcripts (FIG. 11G). As shown in FIG. 4D, similar to ribosome profiling results, proteins with high GAR content in their genes (GAA and GAG codons) were significantly enriched among those up-regulated in the tRNA$^{Glu}_{UUC}$ over-expressing cells. Moreover, proteins with high CGG content showed a significant enrichment among the up-regulated genes in the tRNA$^{Arg}_{CCG}$ over-expressing line (FIG. 4D). These observations are consistent with the hypothesis that protein expression levels can be modulated as a function of their codon usage and cellular tRNA content.

Figure 4E:
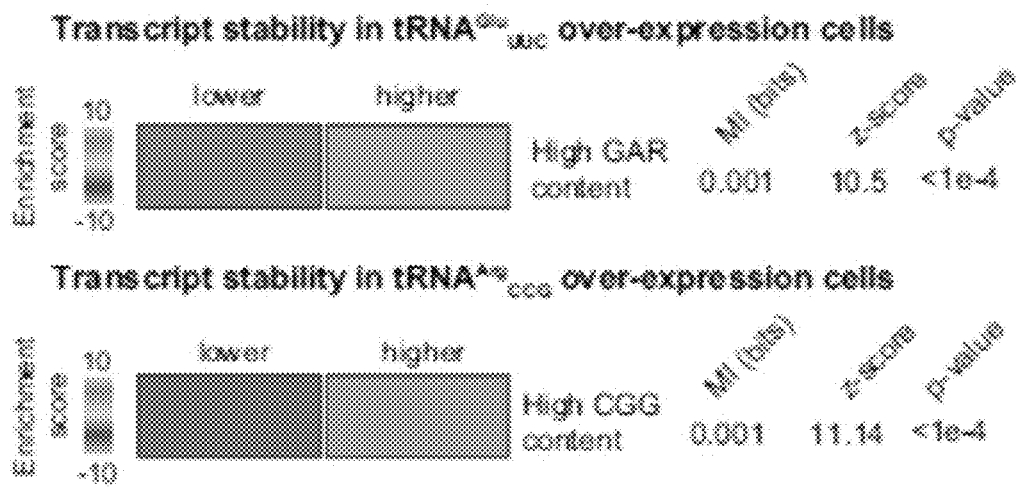
Figure 4F:
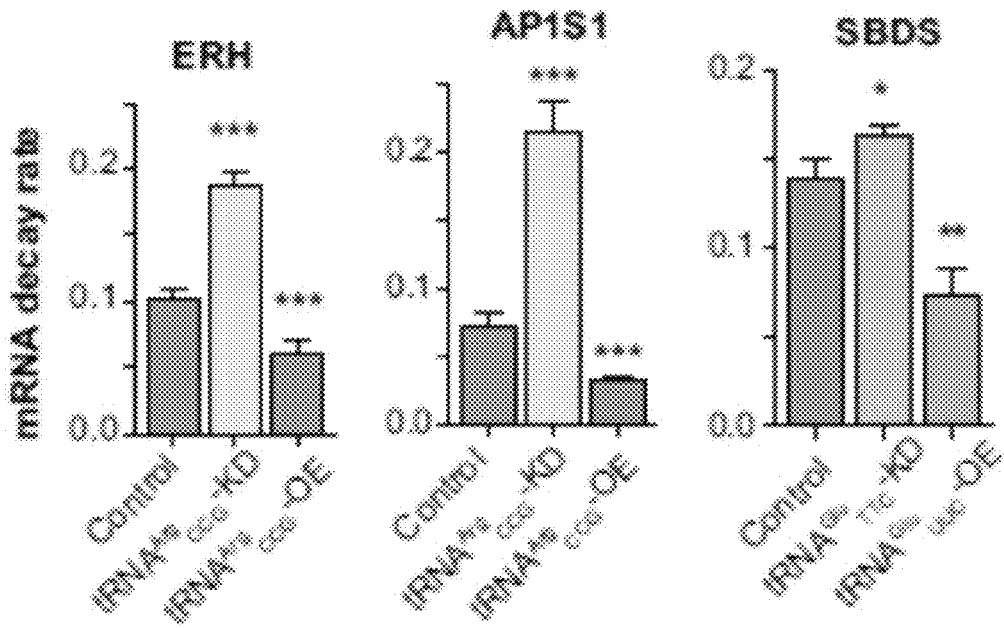

In addition to a direct impact on active translation, differential ribosome occupancy may also affect other aspects of RNA life-cycle, specifically RNA stability (Huch and Nissan, 2014). To test whether tRNA abundance can likewise impact transcript stability, we performed α-amanitin-mediated whole-genome mRNA stability measurements in tRNA over-expressing and control cell lines. Consistent with a positive association between translation and RNA stability (Coller and Parker, 2005; Huch and Nissan, 2014; Muhlrad et al., 1995), we observed a general stabilization of transcripts with higher GAR and CGG content in tRNA$^{Glu}_{UUC}$ and tRNA$^{Arg}_{CCG}$ over-expressing cells respectively (FIG. 4E). We also validated these observations by measuring transcript decay rates using qRT-PCR for a set of mRNAs showing differential stability in tRNA over-expressing cells (FIG. 4F). Taken together, modulations in tRNA levels can have broad regulatory consequences across the proteome of cancer cells, which can partly be explained by variations in codon usage of the target proteins.

Codon-Specific Modulation of tRNA$^{Glu}$ UUC Downstream Targets and Clinical Associations Given the regulatory consequences of tRNA modulations in cancer cells and their impact on metastatic capacity, we hypothesized that a set of core target transcripts may be the major drivers of the metastatic phenotype downstream of tRNA$^{Glu}_{UUC}$ as a global regulator. To identify these targets, we systematically combined the various whole-genome datasets we had compiled as part of this study. We specifically focused on the ribosome profiling data in tRNA$^{Glu}_{UUC}$ over-expressing cell line to identify potential targets that exhibited a higher rate of active translation when tRNA$^{Glu}_{UUC}$ was more abundant. We identified EXOSC2 and GRIPAP1 as such targets. Consistent with their higher ribosome occupancy in tRNA$^{Glu}_{UUC}$ over-expressing cell, these genes also displayed higher protein levels in highly metastatic cells relative to their poorly metastatic parental cells (both MDA- and CN34-backgrounds, data not shown). Quantitative western blots further validate the increased expression of these genes in tRNA$^{Glu}_{UUC}$ over-expressing background (FIG. 5A). It should be emphasized that neither of these genes exhibited a significant up-regulation at the transcript level (log fold-change of <0.1 for both genes in both MDA- and CN34-backgrounds), highlighting that the observed up-regulation for these genes was post-transcriptionally mediated.

To test whether these genes impact metastatic progression downstream of tRNA$^{Glu}_{UUC}$, we took advantage of epistasis experiments in xenograft mouse models. EXOSC2 and GRIPAP1 were stably knocked-down in the context of tRNA$^{Glu}_{UUC}$ overexpression as well as in the control line, and injected into the tail-veins of NSG mice. Reduced EXOSC2 and GRIPAP1 expression levels substantially abrogated the enhanced metastatic outcome caused by tRNA$^{Glu}_{UUC}$ overexpression (FIGS. 5B and 12). Consistent with this, the in vitro invasiveness of tRNA$^{Glu}_{UUC}$ over-expressing line was also dramatically decreased upon silencing of EXOSC2 and GRIPAP1 (FIG. 5C). It should be noted that reduced lung colonization and invasiveness were not observed in the control MDA-parental background upon EXOSC2 or GRIPAP1 depletion. This suggests that EXOSC2 and GRIPAP1 are downstream targets of tRNA$^{Glu}_{UUC}$ overexpression, and that only in the context of elevated tRNA$^{Glu}_{UUC}$ can cancer cells exploit these proteins for a pro-metastatic phenotype. Furthermore, silencing EXOSC2 and GRIPAP1 did not completely abolish the metastatic phenotype of overexpressing tRNA$^{Glu}_{UUC}$, supporting the possibility that additional genes may operate downstream of this tRNA in directing metastasis.

Figure 6A:
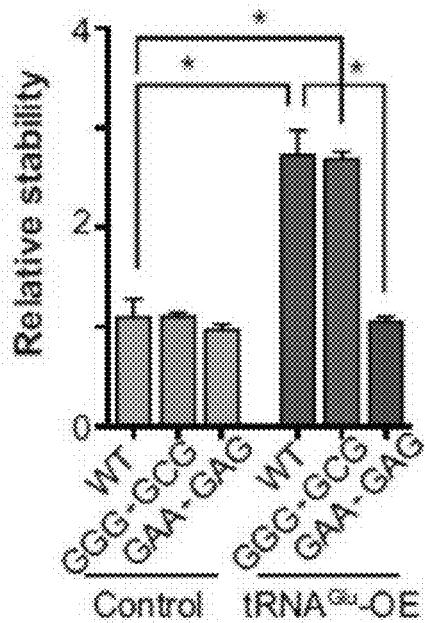
Figure 6B:
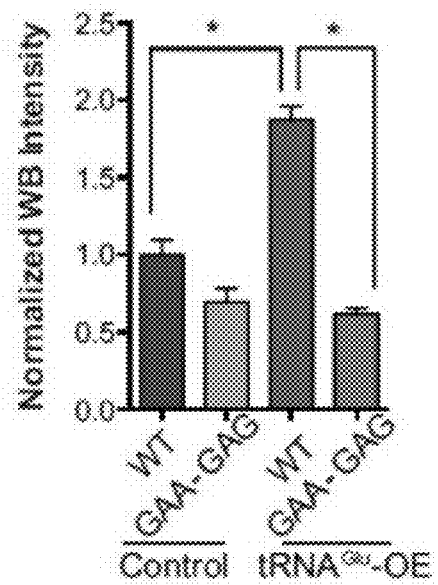

To elucidate the importance of codon specificity on the effect of tRNA$^{Glu}_{UUC}$ on its targets, we performed a codon mutagenesis experiment in which every GAA codon in the EXOSC2 coding sequence was switched to GAG. As a negative control, we instead mutated every instance of a non-deregulated codon, Gly-GGG to Gly-GGC (see FIG. 13A and Methods for details). Transcript stability assays for exogenously transfected wild-type, Gly-mutated, and Glu-mutated versions of EXOSC2 revealed significant loss of the stabilizing effect of tRNA$^{Glu}_{UUC}$ over-expression in the GAA-to-GAG mutant (FIG. 6A). Reduction in protein expression of the GAA-to-GAG (Glu) codon mutated transcript, and not of the GGG-to-GGC (Gly) codon mutated transcript (data not shown), further validates the codon-specific mechanism through which tRNA$^{Glu}_{UUC}$ confers its effect (FIGS. 6B and 13B-13C). These mutagenesis studies establish the direct interaction of a specific tRNA with its downstream targets of regulation.

Figure 6C:
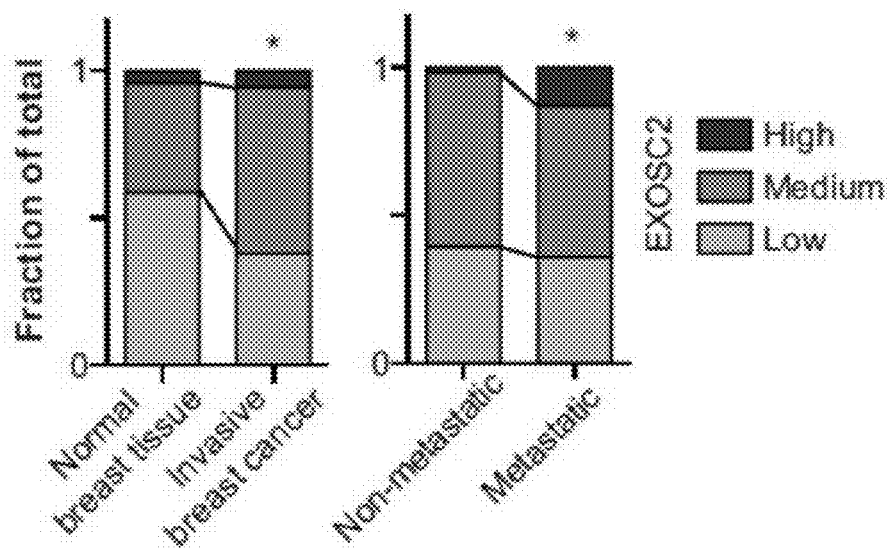
Figure 6D:
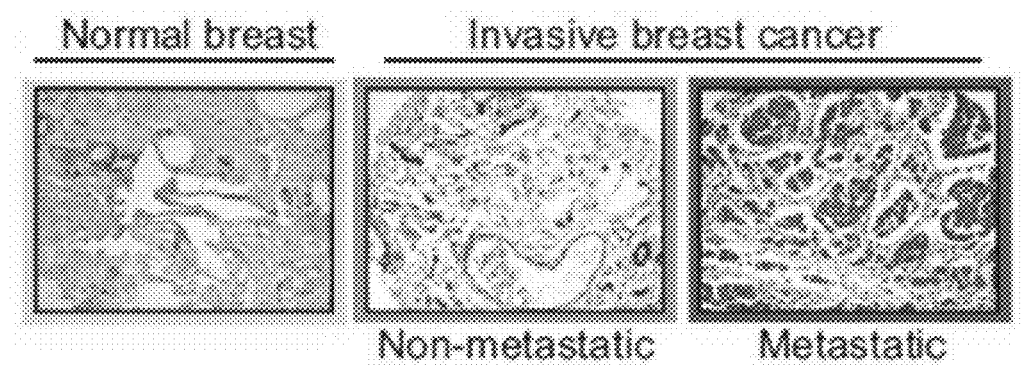
Figure 13D:
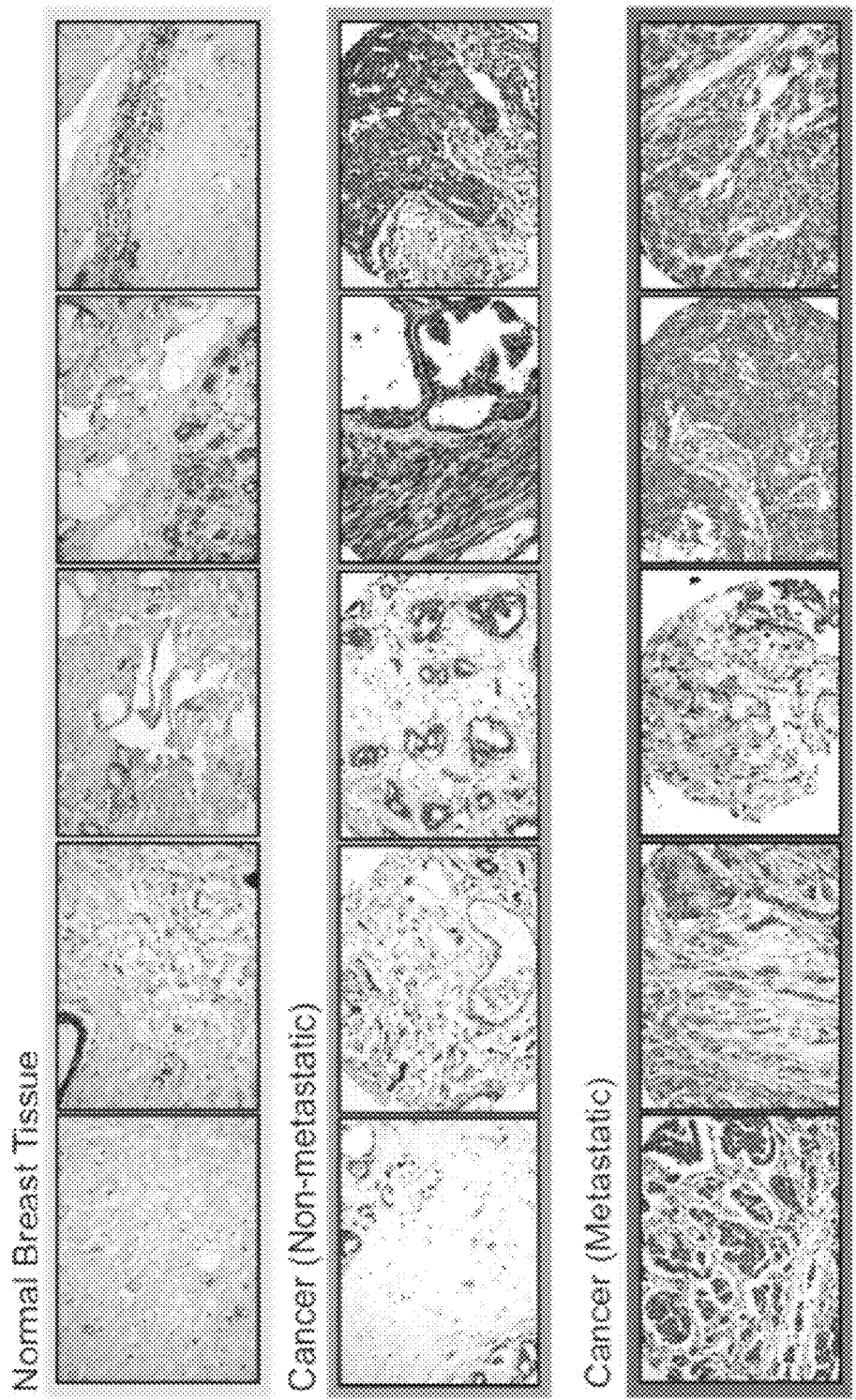

Because EXOSC2 and GRIPAP1 have not been previously implicated in breast cancer metastasis, we sought clinical association evidence for our experimental findings. Although we could not establish specificity for multiple commercially available GRIPAP1 antibodies, we identified an EXOSC2 antibody, which exhibited specificity in fixed tissue immunohistochemistry (IHC). Immunohistochemical staining of breast cancer progression tissue microarrays (TMA) for EXOSC2 revealed a positive association between its expression and clinical breast cancer progression. EXOSC2 protein expression was significantly higher in invasive breast cancer relative to normal breast tissues (FIGS. 6C, 6D, and 13D). More importantly, EXOSC2 protein levels were also significantly higher in primary tumors of patients with distant metastases compared to earlier stage tumors (FIGS. 6C, D, and 13D). These clinical association results not only support our in vitro and in vivo findings regarding the role of tRNA modulation in promoting metastasis, but also support this tRNA-based pathway discovery approach as a means for identifying post-transcriptionally regulated targets that might have been otherwise missed by traditional transcriptomic profiling methods.

Association Among tRNA Preference, Ribosomal Occupancy and Protein Expression

Given their crucial roles in translation, deregulations in tRNA abundance could strongly impact the protein expression landscape of the cell. While tRNA$^{Arg}_{CCG}$ and tRNA$^{Glu}_{UUC}$ were significantly up-regulated in highly metastatic cells, the modifications in the tRNA profiles of highly metastatic cells relative to poorly metastatic cells were not limited to these two tRNAs. To test the consequences of the broader tRNA modulations, we first asked whether the observed changes in tRNA content, across all measured tRNA species, were informative of expression levels of proteins based on their coding sequence alone. As mentioned before, differential tRNA expression levels can impact translational outcome by affecting the abundance of ribosome-bound transcripts. We thus sought to quantify the likely impact of variations in tRNA content on active translation and protein expression given the frequency of each codon for every gene. For this, we defined tRNA preference scores as the sum of changes in the tRNA content in each background (log-ratio in MDA-231 and CN34 backgrounds) across all codons of a given gene (MDA- and CN-preference scores; see Methods). In this scoring scheme, genes whose codons are favored, based on the up-regulation of their cognate tRNAs, are assigned positive scores and those whose codons on average are associated with down-regulated tRNAs are assigned negative scores.

Figure 7A:
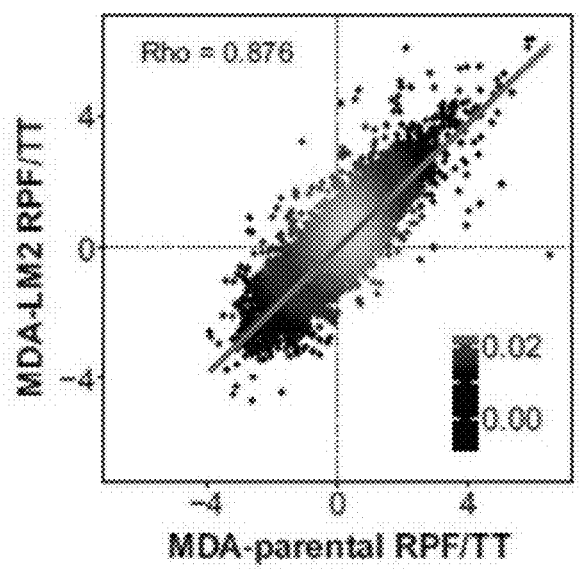
Figure 7B:
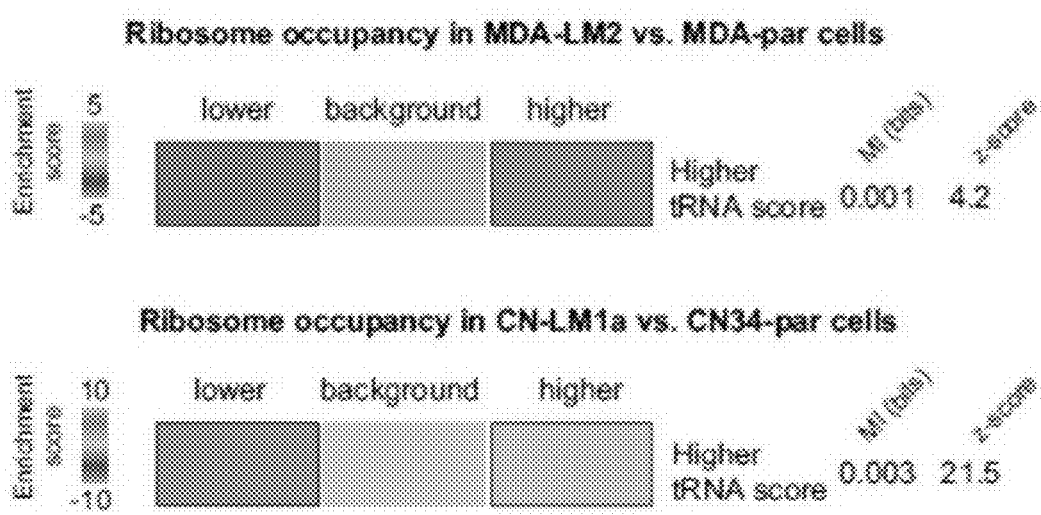
Figure 7C:
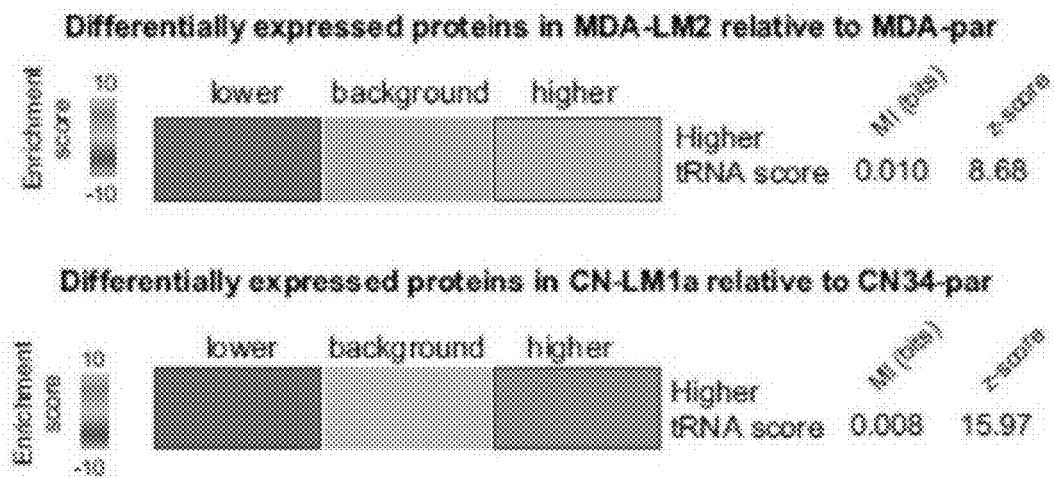

We performed whole-genome ribosome profiling on poorly metastatic parental lines, MDA-par and CN34-par, as well as their highly metastatic derivatives, MDA-LM2 and CN34-LM1a. The ribosome protected fragments (RPF) were normalized to total RNA (TT) for every cell line to account for differences in gene expression. As expected, the RPF/TT ratio between parental and derivative lines, as well as between biological duplicates demonstrated a strong positive correlation. (FIGS. 7A and 14A). tRNA preference scores of every gene were then overlapped with its respective corrected ribosome footprints. Interestingly, transcripts with higher tRNA preference scores were strongly enriched among those bound more by ribosomes (FIG. 7B). We subsequently measured differential protein levels between the metastatic and parental lines using stable-isotope labeling by amino acids in cell culture (SILAC, Ong et al., 2003; also see FIG. 14B). To correct for protein expression changes due to variations in transcript abundances, we normalized the change in protein expression for each gene to its transcript level in each background. In accordance with the increased ribosomal occupancy, we observed a significant enrichment of genes with high tRNA preference scores among those translationally up-regulated in the highly metastatic cells in both MDA-231 and CN34 backgrounds (FIG. 7C). Importantly, consistent with the observed correlation between the changes in tRNA abundance in the MDA and CN34 backgrounds, we also observed a highly significant correlation between tRNA preference scores calculated across all coding sequences (FIG. 14C).

Figure 7D:
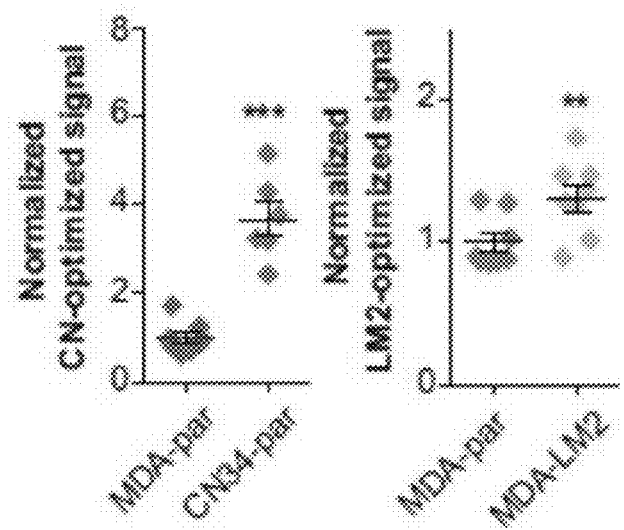

Our findings reveal that differential tRNA expression is informative of changes in translational landscapes. However, to show that there in fact may be a causal link between global tRNA content and protein expression, we took advantage of two synthetic constructs based on the coding sequence of Renilla luciferase. We designed a comparative luciferase coding sequence by scanning the gene and inserting the codon variant whose cognate tRNA had the highest relative expression in CN34 versus MDA-parental cells (CN-optimized luciferase). We should emphasize that the chosen codons were not the ones with highest tRNA levels, but rather the ones with highest CN34 to MDA-231 ratios. We similarly constructed an LM2-optimized luciferase coding sequence comparing MDA-LM2 tRNA levels to those of the parental MDA-231. We then measured luciferase activity of the CN-optimized construct in both MDA- and CN34-parental cells. Interestingly, we observed a substantially higher luciferase signal in CN34-parental cells (FIG. 7D). We next focused on cancer cell populations originating from the same patient (MDA and MDA-LM2 cells). Expression of the LM2-optimized construct similarly showed a higher signal in MDA-LM2 line relative to MDA-parental cells (FIG. 7D). The magnitude of the change also supports the level of variation we had initially observed with the tRNA profile in CN34 being more distinct from the MDA lines and MDA-231 and MDA-LM2 showing more similar tRNA profiles. These findings reveal that even within the same cancer type, the proteomic output of cells obtained from two distinct patients are constrained by the cells' tRNA contents. Moreover, even within a given patient, cancer subpopulations' expression output can be significantly impacted by the tRNA codon landscape within cell sub-populations.

DISCUSSION

Collectively, the inventors' findings demonstrate that changes in tRNA abundance can modulate protein expression in the cell and that cancer cells can evolve to fine-tune the expression of multiple promoters of cancer progression through modulations in tRNA levels. Consistent with previous reports (Pavon-Eternod et al., 2009), we observed that the tRNA profiles of breast cancer lines can markedly differ from non-cancerous epithelial cells. More importantly, the tRNA profile is further modified en route to higher metastatic capacity. TRNA$^{Arg}_{CCG}$ and tRNA$^{Glu}_{UUC}$ were significantly up-regulated in breast cancer lines relative to epithelial cells but this increase was further augmented in metastatic lines relative to their parental population. Moreover, we find that the levels of these tRNAs are higher in metastatic human tumors relative to non-metastatic ones. We have shown that the increased expression of these tRNAs contributes to the metastatic phenotype. We propose that modulations in specific tRNA levels enhance the translational efficiency of genes that are promoters of metastasis in a codon-dependent manner. A detailed analysis of differential protein expression and its relationship to codon preference revealed a modest albeit highly significant correlation between these parameters.

In many organisms, such as bacteria, yeast, and even human, tRNA gene copy number is correlated with codon usage of highly expressed genes (Novoa and de Pouplana, 2012; Novoa et al., 2012). However, in yeast, modulating the levels of a rare tRNA$^{Arg}_{CCU}$ did not impact elongation rate or translational efficiency, while tRNA$^{Thr}_{UGU}$ knock-down, by deleting three of the four copies of the heavily used ACA tRNA, had a modest effect on efficiency (Pop et al., 2014). Thus, the observed correlation between codon bias and efficiency arises from the selection on highly expressed genes to utilize translation machinery efficiently (Pop et al., 2014). Consistent with this observation, the data provided herein, the association between tRNA abundance and codon usage were more pronounced among highly expressed genes. For example, limiting our analysis to roughly 300 genes with one standard deviation above average expression (based on whole-transcriptomic measurement), a significant correlation between codon CGG content and protein levels in tRNA$^{Arg}_{CCG}$ over-expressing cells (Rho=0.12, p=0.03) were observed—a correlation that is otherwise less pronounced across all the detected proteins (Rho=0.06). Another point to consider is that, higher levels of these specific tRNAs were specifically selected for in the context of pathological disease progression. It is possible that modulating other tRNAs, as was the case for tRNA$^{Tyr}$, will not result in significant changes in protein expression levels or may not be tolerated by the cells under study. Furthermore, it is plausible that the link between tRNA levels and translational efficiency is more pronounced in mammalian cells selected in vivo than it is in yeast cells grown in culture. More importantly, in our data, codon usage explains a fraction of protein expression changes, implying that (i) tRNA levels may affect protein expression in ways other than direct translation (Lee et al., 2006) and stability, and/or (ii) positive and negative feedback loops may amplify and propagate the regulatory consequences of modulations in tRNA levels.

Taken together, the data provided herein puts forth the notion that cancer cells, in addition to many known regulatory mechanisms, exhibit tRNA landscape modulations that modify the expression of promoters of cancer progression. Specific tRNAs can form "activatable" pathways with their direct target transcripts, which are enriched for their cognate codons. Such target transcripts can become stabilized in the context of their favored tRNA content or can be more effectively translated—ultimately yielding greater protein output. It should be noted that while we have focused on breast cancer metastasis, this approach based on tRNA profiling is general in concept and can be employed to study other diseases and can be extended to other models and species, as well as to developmental processes where similar tRNA modulations could govern developmental gene expression programs.

Experimental Procedures

Cell Culture

CN34 and MDA-MB-231 cells and their respective sublines, CN-LM1a and MDA-LM2, were propagated in DMEM-based media supplemented with 10% FBS, glutamine, pyruvate, penicillin, streptomycin and fungizone (Life Technologies).

Animal Studies

All mouse studies were conducted according to a protocol approved by the Institutional Animal Care and Use Committee (IACUC) at the Rockefeller University.

Accession Numbers

The data for high-throughput sequencing and microarray profiling experiments are deposited at GEO under the accession number GSE.

Stable Cell Line Generation

For generation of lentivirus, 293T cells were seeded onto 10 cm plates such that cell confluency will be approximately 70% the next day. 3 µg each of pRSV-Rev, pCMV-VSVG-G and pCgpV packaging vectors were co-transfected with 9 µg the appropriate pLKO-backboned targeting plasmid using 45 µL of Lipofectamine 2000 in antibiotic-free media. After 24 hr the media was replaced with fresh antibiotic-free media. After 48 hr virus-containing supernatant was collected and centrifuged for 10 min at 2000 rpm before being filtered through a 0.45 µm filter. For transduction of cells, 2 mL of the appropriate virus was used to transduce 100 k cells in the presence of 8 µg/mL polybrene. Media was replaced 24 hr later. 48 hr after transduction, antibiotic selection was performed with either blasticidin (10 µg/mL) or puromycin (2 µg/mL) for 2-7 days alongside a population of untransduced control cells. For each stable knockdown line, four independent shRNAs were tested and the best two shRNAs in knocking down gene expression (>90% knockdown) for each cell-line were used (except for hairpins against tRNAs). Oligonucleotide sequences used for tRNA knock-down and overexpression are listed in table (Table 1).

Northern Blotting

10 µg of RNA was separated on a Urea-PAGE gel at 300V. After SYBR Gold-based staining and imaging, RNA was transferred to a nylon membrane in 0.5×TBE and UV crosslinked (240mJ/cm$^2$). The membrane was then prehybridized using UltraHyb-Oligo (Ambion) at 40 C. RNA oligos were radiolabeled with [γ-$^{32}$P]ATP (3 µL) and T4 PNK (NEB) at 37° C. for 30 min and purified using G-25/G50 columns. After hybridization overnight, the blot was washed twice and developed.

Western Blotting

Cellular lysates were prepared by lysing cells (5-10 million) in ice-cold RIPA buffer containing protease and phosphatase inhibitors (Roche). Cellular debris was removed by centrifugation (12,000 rpm) for 20 min at 4° C. Samples were denatured in loading buffer separated using SDS-PAGE, transferred to a PVDF membrane (Pierce), blocked and probed using target-specific antibody: EXOSC2 (Proteintech, 14805-1-AP; 1:500), GRIPAP1 (Proteintech, 15806-1-AP; 1:500). Bound antibodies were chemiluminescently detected using horseradish peroxidase-conjugated secondary antibodies (1:10,000), ECL Western Blotting Substrate (Pierce) and the SRX-101A (Konica Minolta) developer, according to the manufacturer's instructions. The membrane was then stripped (Restore Western Blot Stripping Buffer, Pierce) and re-probed (at RT for 1 hr) and re-developed (similar to the previous step) using an alpha-tubulin antibody (1:5,000; Sigma) or GAPDH (1:5,000, Cell signaling) as an internal control.

Quantitative Western Blot

Odyssey™ Quantitative Western Blot (LICOR) was used to quantify protein expression levels. Briefly, the procedure is identical to western blotting, except that instead of using horseradish peroxidase-conjugated secondary antibodies, species-specific fluorescent IRDye® secondary antibodies were used. The membrane was then imaged with Odyssey® Sa Infrared Imaging System at the Rockefeller University Center for High Throughput Screening. Quantification was done using Image Studio™ Lite (LICOR) and statistical significance was determined with unpaired t-test.

Transfer RNA Profiling

For each family of mature tRNAs (with introns removed and containing terminal CCA) with a similar consensus sequence and a common anticodon, a pair of probes is designed so that upon annealing to the complementary tRNA, the resulting nick in the DNA-RNA hybrid is located at the site of the anticodon. We designed a total of 67 probe-pairs to cover the majority of cytosolic tRNAs. The downstream probes were 5'-phosphorylated to enable enzymatic ligation. The 67 probe-pairs were combined into four separate batches based on their melting temperature. The batches were then aliquoted to avoid repeated freeze-thaw cycles and stored at −80° C.

For tRNA profiling, cells were subjected to small-RNA extraction (microRNA Purification Kit, Norgen) and tRNA$^{Lys}$ of E. coli (Sigma) was added at set concentrations as spike-in (varied depending on the RNA concentration). To deacylate the tRNA population, the samples were incubated in 100 mM Tris-HCl (pH 9.0) at 37° C. for 30 min. To stop the reaction, an equal volume of acetate buffer (pH 4.8) and NaCl were added to the final concentration of 50 mM. The samples were then subjected to RNA precipitation at −20° C. overnight. Following re-suspension, RNA samples were 3' biotinylated in 25% DMSO using T4 RNA ligase (RNA 3' End Biotinylation Kit, Thermo Scientific) at 16° C. overnight. The samples were then subjected to chloroform extraction and RNA precipitation. The RNA population was then divided into four batches and each batch was hybridized with one of the four pools of probe-pairs (in 10 mM Tris-HCl, 5 mM NaCl, 100 µM EGTA) by incubating at 90° C. for 5 min followed by slow cool down to 55-60° C. (based on Tm of the pool). The hybridized samples were then subjected to ligation at 16° C. overnight (given the lower efficiency of T4 DNA ligase for DNA/RNA hybrids, overnight ligation is essential). M-270 Streptavidin Dynabeads (Invitrogen) were then used to purify biotinylated DNA/RNA hybrids per the manufacturer's instructions. Ligated probes were then eluted after incubation with RNase H and RNase A (30 min at 37° C.) followed by incubation with an elution buffer (50 mM Tris pH 8, 10 mM EDTA, 1% SDS; incubate at 65° C. for 30 min with intermittent vortexing). Following elution, the samples were ethanol precipitated and minimally amplified (12-15 cycles) with primers against the universal sequences included at the two ends of the ligated probes. This amplification step is required to add the linkers required for high-throughput Illumina sequencing and barcoding. For this study, we prepared libraries in biological triplicate from each cell-line. The samples were then sequences on two lanes of a HISEQ 2000 Illumina sequencer. The obtained reads were then aligned against the fasta file carrying all probe sequences. Sequences containing degenerate positions were multiplied so that all possible versions were present in the reference library. The relative quantity of each probe was calculated by normalizing the number of mapped reads to the total number of reads.

Low-Throughput tRNA Quantification

The preparation of samples for low-throughput tRNA quantification was identical to the protocol described above, with the following exception: (i) instead of using a library of probes, the RNA samples were hybridized to a single probe-pair (matching the tRNA of interest); (ii) the amplification step is replaced with quantitative PCR using SYBR Green (Life Technologies) per manufacturer's instructions. The qPCR primers were CACGACGCTCTTCCGATCT (SEQ ID NO. 3) and TTCTTTGCAGTGTCGTGG (SEQ ID NO. 4) matching the 3' and 5' ends of the probe-pairs respectively. We used tRNA$^{Lys}$ of E. coli or small-RNA populations extracted from cells to benchmark the protocol and create the standard curves and compare the efficiency of T4 DNA ligase in recognizing a mismatch at the location of the nick (FIGS. 8A-8C). This qPCR-based measurements of specific tRNA species was also used to validate tRNA expression changes between cell-lines and also cell-lines generated to test tRNA knock-down and over-expression of tRNA$^{Arg}$ and tRNA$^{Glu}$.

We also used probes against the 18S rRNA to compare quantifications based on probe-hybridization/ligation to those obtained from cDNA synthesis followed by qPCR (FIG. 9B). The following probe sequences were synthesized (IDT) to detect 18S levels:

```
                                     (SEQ ID NO. 5)
/5Phos/GGTAGTAGCGACGGGCGGTGTGTACAAAGGGCAGATCGGAA GAGCGTCGTG
and
                                     (SEQ ID NO. 6)
TTCTTTGCAGTGTCGTGGCCGATCCGAGGGCCTCACTAAACCATCCAA

TC.
```

Whole-Genome Transcript Stability Measurements

Cells were seeded in triplicates at 80% confluence in 6-well plates in DMEM-based media enriched with 10% FBS and. 24 hours later, media was spiked with 10 µg/ml of α-amanitin (Sigma). Total RNA was extracted using the manufacturer's protocol (Norgen) at 0 and 8 hr time points after α-amanitin treatment. Samples were then labeled using TARGETAMP-Nano Labeling Kit for Illumina (Epicenter). Labeled RNA was purified using MINELUTE RNEASY Kit (QIAGEN) and submitted for analysis to the Rockefeller University genomics core facility using Illumina HT-12 v4 Expression BeadChip microarrays. The Lumi package in R was used to transform and normalize signal intensities. The transformed signal at 0 and 8 hr time points was then normalized based on input RNA and used to estimate a decay rate for each transcript. For transcript-specific stability measurements, qRT-PCR was used to determine relative quantities of tRNA-overexpression dependent stabilized targets at different time points using 18S as endogenous control.

Quantitative RT-PCR

Transcript levels were measured using quantitative RT-PCR by first converting total RNA to cDNA (SUPERSCRIPT III, Life Technologies) followed by SYBR Green quantification (Life Technologies) per the manufacturer's instructions. We used the following primers for qRT-PCR: EXOSC2: TGGCTCGCAAGCCTCTTAG (SEQ ID NO. 7), TGTGTCCGTAGTGATTGTATCCC (SEQ ID NO. 8); GRIPAP1: GGACAAACAACTACCAGCTTTCA (SEQ ID NO. 9), GCGACCTTCTGTCGAAGACT (SEQ ID NO. 10); ERH: AATGAATCCCAACAGTCCCTCT (SEQ ID NO. 11), CAGCTCGGTAAACCAGGCAG (SEQ ID NO. 12); AP1S: CGGTTCATGCTATTATTCAGCCG (SEQ ID NO. 13), CCGTTCCTTGTCCGAAGTGG (SEQ ID NO. 14); SBDS: ACCAACCAGATCCGCCTAAC (SEQ ID NO. 15), CGACGACCTTGTTTTTGTAGCA (SEQ ID NO. 16); EXOSC2-FLAG: AACTGCATCATCTCGCTGGTAAC (SEQ ID NO. 17), CTTGTCGTCATCGTCTTTGTAGT (SEQ ID NO. 18); and Luciferase: CTGACCGGCAAGCTGGA (SEQ ID NO. 19), GACTCTAGAATTATTACACGGCGATCT (SEQ ID NO. 20). For pre-tRNA expression level and tRNA copy number, we designed 15-nt long qRT-PCR primers for each tRNA locus (hg19) by including 10-nt from the upstream (forward primer) or downstream (reverse primer) in each primer.

Whole-Genome Ribosomal Occupancy Profiling

The procedure was performed with TRUSEQ Ribo Profile for mammalian cells (Illumina) per manufacturer's instructions. An input of $50 \times 10^6$ cells were harvested for each replicate (biological duplicates for every cell line profiled) and libraries were sequenced using Illumina Nextseq 500 at the Rockefeller Genomics Center. For analysis, we first performed quality trimming and linker removal (Cutadapt v1.8, MARTIN, Marcel. Cutadapt removes adapter sequences from high-throughput sequencing reads. EMBnet.journal, [S.l.], v. 17, n. 1, p. pp. 10-12, May 2011). We then used Bowtie2 (Langmead B, Salzberg S. Fast gapped-read alignment with Bowtie 2. Nature Methods. 2012, 9:357-359) to remove reads that map to contaminating RNAs (e.g. rRNA sequences). Tophat and cufflinks were consequently used to map the resulting reads to the human transcriptome and compare transcript abundances. We normalized the RPKM estimates from ribosome-protected fragments (RPF) to the total RNA from each sample (TT) and used the resulting log FC values to compare control, tRNA$^{Arg}_{CCG}$-OE, and tRNA$^{Glu}_{UUC}$-OE samples. The MDA and CN34 parental cells and their highly metastatic derivatives (MDA-LM2, and CN-LM1a) were similarly analyzed. To correct for GC bias, when present in the resulting datasets, we applied a lowess regression model based on GC content of coding sequences and subtracted the resulting values from the observed log FC values prior to performing enrichment analysis. This step is of especial importance for tRNA$^{Arg}_{CCG}$, whose anticodon has a GC content of 1.

Codon-Specific Mutational Assays

Wild-type and mutated versions of EXOSC2 coding sequences were synthesized by IDT. Every Glu-GAA codon was mutated to Glu-GAG. As a negative control, another construct in which every Gly-GGG codon was mutated to Gly-GGC was used (FIG. 13A). Gly-GGG and Gly-GGC codons were chosen because there was no significant difference in their respective tRNA levels based on our high-throughput tRNA profiling analysis. Each synthetic coding sequence also contained a 3'-FLAG-tag. The constructs were then cloned into the psiCHECK2 backbone (replacing synthetic Renilla Luciferase gene) together with an upstream Tetracycline-response element.

For transcript stability studies, $1 \times 10^6$ MDA-Ctrl and MDA-tRNA$^{Glu}_{UUC}$ overexpressing cells were seeded overnight in biological triplicates in 100 mm tissue culture dishes. 1 µg of psiCHECK2 (containing either wild-type, Gly-mutated, or Glu-mutated versions of EXOSC2) and 1 µg of pTet-OFF (Clontech) were co-transfected into cells using 10 µL of Lipofectamine 2000. 24 hours post-transfection, doxycycline was added to a final concentration of 200 ng/mL to stop transcription. Untreated cells were harvested for the time 0 data point. 8 hours later, doxycycline-treated cells were harvested. RNA and protein was extracted as described before, with one exception: RNA was treated with DNase I (NEB) for 30 minutes at 37° C. to remove any contaminating plasmid DNA.

qRT-PCR primers were designed such that the forward primer targets the EXOSC2 sequence that is identical among the wild-type and mutated versions of the transcript, while the reverse primer mapped to the FLAG-tag. As a control for transfection efficiency, primers were designed against the co-transcribed Firefly luciferase gene on psiCHECK2. To ensure the absence of contaminating plasmid DNA, a reverse transcriptase-free control reaction was run side-by-side, together with qPCR primers that target the ampicillin resistance gene on psiCHECK2. Stability was measured by comparing the relative changes in normalized transcript levels between 0 h and 8 h time point. For protein expression measurement, anti-FLAG antibody (Sigma) was used with anti-Firefly Luciferase (Novus, NB100-1677) as a control.

Lung Colonization Assays

All mouse studies were conducted according to a protocol approved by the Institutional Animal Care and Use Committee (IACUC) at the Rockefeller University. Seven- to eight-week-old age-matched female NOD/SCID gamma mice (Jackson Labs) were used for lung colonization assays. In all cases, $5 \times 10^4$ cells in 100 µL PBS were injected via tail-vein along with cells expressing a neutral hairpin as control. In every case 4-5 mice were included in each cohort. The metastatic growth was tested using both two-way ANOVA as a function of time and sub-line identity and also t-test based comparison of area under the curve for each mouse.

Primary Tumor Growth and Orthotopic Metastasis $1 \times 10^6$ triple-reporter labeled cells were suspended in 100 µL of 1:1 PBS:Matrigel mixture and injected into subcutaneous flanks of mice at two sites. Tumor growth was measured using digital calipers starting 7 days after injection when palpable tumors can be measured accurately. Tumor volumes were calculated using the formula, Volume=(width)$^2$×(length)/2. Tumors were resected as they reached a growth plateau and lung metastasis was measured by bioluminescent signal. Statistical significance was determined as described above.

Histology

For gross macroscopic metastatic nodule visualization, mice lungs (from each cohort) were extracted at specific time-points post-injection and 5 µm thick lung tissue sections were hematoxylin and eosin (H&E) stained. The number of macroscopic nodules was then recorded for each section. Unpaired t-test was used to test for significant variations.

Tissue Microarray and Immunohistochemistry

Breast cancer progression tissue microarrays (TMA) were obtained from the Cancer Diagnosis Program. Immunohistochemistry was performed using an antibody targeting EXOSC2 (Proteintech, 14805-1-AP, 1:100 dilution) and VECTASTAIN ABC (Vectorlabs, PK-4000) per manufacturers' instructions with a citrate buffer (pH 6.0) antigen retrieval step. Staining was assigned a score of either 1, 2, or 3 corresponding to the low, medium, or high intensity of the signal (in a blinded fashion). A score of N/A was assigned to damaged tissues or to those sections for which staining was incomplete as judged by the scorers. The scores were then counted and compared among different clinical stages of interest (i.e., non-invasive vs. invasive, non-metastatic vs. metastatic). $\chi^2$ statistics was used to initially test for the difference in the percentage of each intensity score in each cohort. Hypergeometric p-values were then calculated to assess the increase in the frequency of samples with higher intensity among the metastatic tumors (reported in the bargraphs). Three blinded researchers who were not authors were also asked to independently score the samples to ensure the unbiased nature of the findings. Representative images of stained tissues were taken at the Rockefeller Bio-Imaging Resource Center (Zeiss—field fluorescence/brightfield/DIC microscope).

Cancer Cell Invasion Assays

Invasion assays were performed as previously described (Png et al., 2012). Briefly, cells were starved for 24 hours in DMEM-based media supplemented with 0.2% FBS. $5 \times 10^5$ cells were seeded in the same conditions in trans-well invasion chambers (BD Biosciences) and incubated for 16-18 hours. Inserts stained with DAPI and imaged using an inverted fluorescence microscope (Zeiss Axiovert 40 CFL), sampling five fields per insert. Invading cells were counted in a blinded fashion using ImageJ.

Cancer Cell Proliferation

Roughly 10,000 cells were seeded into three 6-well wells and subsequently were trypsinized and viable cells were counted using a hemocytometer at day 1, day 3, and day 5. An exponential model was then used to fit a growth rate for each sample (1 $n_{(Nt-1}/N_1)$=rt where t is measured in days). The experiment was performed blinded in biological quadruplicates and unpaired t-test was used to test for significant variations.

Codon-Optimized Luciferase Assays

Approximately 200,000 cells were grown in 24-well plates in quadruplicate and were transfected as previously described with vectors codon-optimized luciferase constructs. 48 hours post-transfection, luciferase activity was measured according the manufacturer's protocol. Briefly, cells were washed using 1×PBS and lysed using 500 µL of PLB for 15 min at room temperature. Lysate was then plated in technical quadruplicates onto a 96 well plate. Immediately prior to measuring firefly luciferase activity, 100 µL of LARII solution was added to each sample. Subsequently, 100 µL of STOP&GLO Reagent was added to measure Renilla luciferase activity. Half of the lysate was used to extract and measure luciferase transcript levels using qRT-PCR.

LC-MS/NIS Analysis of Protein Expression

For the label-free quantitation analysis of expression levels of $tRNA^{Arg}_{CCG}$ and $tRNA^{Glu}_{UUC}$ against control MDA cells, 100 µg protein from each sample was acetone precipitated overnight. Precipitates were dissolved in 8M urea (GE Healthcare) with 0.1 M ammonium bicarbonate (Sigma) and 10 mM DTT (Sigma), incubated with shaking at room temperature for 1 h, followed by iodoacetamide (Sigma) alkylation of cysteines. Samples were diluted to below 4M urea before lysyl endopeptidase (Wako) digestion overnight. Samples were then diluted below 2 M urea before adding trypsin (Promega) digestion for 6 h. Peptides were desalted/concentrated using STAGE-type C18 tips (Ishihama et al., 2006) and resuspended in 2% acetonitrile/2% formic acid.

1 µg of each sample was analyzed by nano LC-MS/MS (Dionex 3000 HPLC coupled to a Q-Exactive mass spectrometer, ThermoFisher Scientific). Peptides were separated at 200 nL/min using a gradient increasing from 5% B to 45% B in 133 minutes (A: 0.1% formic acid, B: acetonitrile/0.1% formic acid). Peptides were loaded onto a trap column prior to separation on a packed-in-emitter C18 column (75 µm by 12 cm, 3 µm particles—Nikkyo Technos Co., Ltd. Japan). The mass spectrometer was operated in 'preferred mode' fragmentation up to 20 ions per cycle using an under fill ratio of 1%. MS spectra (m/z range: 300-1400) were recorded at a resolution of 70,000 (AGC: 5e5) and MS/MS spectra at 17,500 (AGC: 2e5) with a lowest m/z of 100. Generated LC-MS/MS data were queried against Uniprot's complete Human Proteome (July 2014) and quantitated using MaxQuant 1.5.0.9 (Cox et al., 2014). In short, Peptide-Spectrum Match false discovery rate and protein false discovery rate was set to 1%. Match between runs were used for label free quantitation (LFQ). A total of 5,096 proteins were matched. Proteins were filtered requiring that a protein was matched in minimum 2 of 3 biological replicates. 3,475 proteins fulfilled this criterion. Excellent correlation (r2~0.99) was observed between replicates. Missing LFQ values was replaced with imputated LFQ values (width: 0.3, down shift: 1.8). Differences between the three conditions were assessed by a multiple ANOVA test using a permutation based FDR cut-off of p<0.05.

For the correlation of tRNA preference scores to protein abundance changes between metastatic and parental cell lines using SILAC quantitation, each cell line was split into two populations of approximately 1e6 cells, each cultured for 10 days in DMEM-Flex based media supplemented with dialyzed FBS (Life Technologies) and either heavy arginine and lysine ($^{10}R,^6K$) or normal arginine and lysine (0.1 mg/ml). Cells were passaged every 2 days to maintain appropriate confluency in 10 cm² plates. After 10 days, heavy-labeled parental cells were mixed with light-labeled derivative cells (and vice versa) in equal numbers and lysed according to the manufacturer's protocol. Briefly, cells were trypsinized and resuspended with cell counting performed twice using a manual cytometer to ensure consistency. 5e5 cells from each population were mixed together and spun down at 1000 rpm for 5 minutes. Cells were lysed using SILAC Phosphoprotein Lysis Buffer A (per manufacturer instructions). Fifty µg of each heavy/light mixture was prepared as above, followed by STAGE-type SAX microfractionation as described previously (Wisniewski et al., 2009). In brief, desalted peptides in a pH 11 buffer were loaded onto STAGE-type SAX tips, collecting the flowthrough, and eluted with decreasing pH: 8, 6, 5, 4, and 3, for a total of 6 fractions. Fractions and an unfractionated sample were analyzed by LC-MS/MS and MaxQuant/Perseus as above, yielding 4,601 protein identifications after filtering contaminants and 3,756 protein ratios based on proteins with at least 2 peptides. Additionally, analysis of unmixed, heavy-only samples demonstrated better than 98% SILAC incorporation for each cell line.

Differential Gene Expression Analysis

Protein expression is a function of mRNA abundance. To correct differential protein expression levels for tRNA$^{Arg}_{CCG}$ and tRNA$^{Glu}_{UUC}$ over-expressing cells against control MDA cells, we performed microarray-based transcriptomic measurements in biological replicates. Sample preparation and data analysis was performed as described before (Goodarzi et al., 2014). The fold-changes in the levels of the detected proteins were then corrected by the fold-change in the transcript levels. We used a similar approach for correcting differential protein expression between parental and highly metastatic lines.

Computational Pipeline for Designing Probe-Pairs Against tRNA Species

The sequence and secondary structure of tRNAs, obtained from GtRNAdb, is the starting material for this process.

Group tRNAs into isodecoders, i.e. group them based on their anticodon sequence.

For each group of isodecoders:
1. Compare the tRNA sequences in a pair-wise manner:
    Use a global sequence alignment algorithm (e.g. Needleman-Wunsch) to get a score for sequence similarities
    Create a symmetric matrix holding all pairwise alignment scores
2. Define tRNA families with high sequence similarity and identical anticodon sequence:
    Use the resulting 'distance' matrix to cluster tRNA isodecoders into smaller groups with high sequence similarity. Any supervised or unsupervised method can be used here.
3. Deriving consensus sequences:
    Use a multiple alignment algorithm (e.g. ClustalW) to derive a consensus sequence for each tRNA family defined in the previous step.
    Compare each tRNA to the consensus sequence of its family; if the sequence similarity was lower than a threshold, split the family and redo this step until the consensus sequence is a good representation of the family.
    In this step, one tRNA family can result in multiple consensus sequences.
4. Designing probe-pairs for each tRNA family:
    Split the consensus sequence into two parts at the site of the third anticodon position
    Reverse complement both sequences
    The probe with its 5' start at the site of anticodon requires the addition of a 5' phosphate group
    Universal linker sequences, compatible with Illumina TRUSEQ sequencing primers are added to these (e.g. GAGTTCTACAGTCCGACGATC (SEQ ID NO. 21) to 5' end of the 5' probe and CCATGGAATTCTCGGGTGC (SEQ ID NO. 22) to the 3' end of the 3' probe).
5. Supplement mitochondrial tRNAs:
    Mitochondria have a single tRNA for each type
    Design a probe-pair for each tRNA sequence in the mitochondrial genome
6. Synthesis:
    Probe-pairs are synthesized en masse (e.g. ~110 pairs for human hg19 tRNAs, used in our study).
    A 5' phosphate is added to the 3' probe during synthesis.

The probes are pooled into a single or multiple pools (based on their Tm).

Computational Pipeline for Analyzing tRNA Profiling Data

Building the reference sequence
1. De-convolute the degenerate consensus sequences used for probe-pair designs by enumerating all possible combination of degenerate nucleotides. For example, a position with R, can be A or G. RAGCY, can be AAGCT, AAGCC, GAGCT, and GAGCC.
2. Index the resulting sequences for the aligner of choice (e.g. bowtie)

Alignment and read counts
1. Align each read to the reference sequences devised above.
2. Remove reads with improper alignments.
3. Count the number of times each sequence is read.
4. Combine counts from degenerate sequences of the same probe-pair Count normalization
1. Calculate the size factor for the sequence libraries
2. Normalized tRNA counts Differential level analysis
1. Use counts from above to calculate dispersion (e.g. using DESeq or other methods)
2. Use counts, size factors, and dispersions to perform statistical comparisons (e.g. using negative binomial-based methods).

Codon optimization
1. The goal is to take a sequence expressed in a source cell, to a destination cell, maximizing its expression in the process
2. We only optimize amino acids whose isoacceptors (i.e. at least two of the codons) show similar average abundance in the destination cells.

For these codons, in every case, we choose the tRNA that is more abundant in the destination cell relative to the source cell (based on our calculations in the previous step).

TABLE 2

Lists of sequences of primers and hairpins.

| Target | Sequence | |
|---|---|---|
| shCtrl | CCGGCAACAAGATGAAGAGCACCAACTCGAGTTGGTGCTCTTCATCTTGTTGTTTTTG | SEQ ID NO. 385 |
| ShtRNA$^{Arg}$CCG | CCGGTTCTGATCCGGAATCAGACGCCTTTCTCGAGAAAGGCGTCTGATTCCGGATCAGA | SEQ ID NO. 386 |
| ShtRNA$^{Glu}$UUC | CCGGAACCCGGGCCGCGGCGGTGAAAGCGCTCGAGCGCTTTCACCGCCGCGGCCCGGGTTTTTTTG | SEQ ID NO. 387 |
| tRNA$^{Arg}$CCG -OE | TTCTTTGCAGTGTCGTGGCGACCACGAAGGGACTCGAACCCTCATCTTCTGATCCG | SEQ ID NO. 388 |

TABLE 2-continued

Lists of sequences of primers and hairpins.

| Target | Sequence | |
|---|---|---|
| tRNA$^{Glu}$UUC -OE | TTCTTTGCAGTGTCGTGGTTCCCTGACCGG GAATCGAACCCGGGCCGCAGGCGGTGA | SEQ ID NO. 389 |
| shEXOSC2 #2 | CCGGCCCACTTTCATGATTTGCCATCTCGA GATGGCAAATCATGAAAGTGGGTTTTTG | SEQ ID NO. 390 |
| shEXOSC2 #3 | CCGGGCTGTATGATACCAGCATCCTCTCGA GAGGATGCTGGTATCATACAGCTTTTTG | SEQ ID NO. 391 |
| shGRIPAP1 -1 | CCGGGCTCAGGTACATTCCATGGATCTCGA GATCCATGGAATGTACCTGAGCTTTTTG | SEQ ID NO. 392 |
| shGRIPAP1-2 | CCGGGAACTTCAAGCTCAGGTACATCTCGA GATGTACCTGAGCTTGAAGTTCTTTTTG | SEQ ID NO. 393 |

TABLE 3

Mouse DNA probes.
DNA probes to generate a tRNA profile in mouse cells. The DNA probes were designed by the methods disclosed herein.

| | | |
|---|---|---|
| mm10_Ala_AGC-1_33_R | GCACCCGAGAATTCCATGGATGGAGATGCTGG GGCTCGAACCCAGRCYBCRHRCAYGC | SEQ ID NO. 23 |
| mm10_Ala_AGC-2_33_R | GCACCCGAGAATTCCATGGTGGAGGATGTGGG CATCGATCCCAWKCCTCDYRCATGC | SEQ ID NO. 24 |
| mm10_Ala_CGC-2_32_R | GCACCCGAGAATTCCATGGTGGAGATGCCGGG AGTCGAACCCGGGCCSCAYACATGC | SEQ ID NO. 25 |
| mm10_Ala_CGC_32_R | GCACCCGAGAATTCCATGGTGGAGATGCCGGG AGTCGAACCCGGGCCSCAYACATGC | SEQ ID NO. 26 |
| mm10_Ala_TGC_32_R | GCACCCGAGAATTCCATGGTGGAGATGCCGGG AATCGAACCCGGKCCYCATRCATGC | SEQ ID NO. 27 |
| mm10_Arg_ACG_32_R | GCACCCGAGAATTCCATGGCGAGCCAGCCAGG AGTCGAACCTGGATCTTCTGATCCG | SEQ ID NO. 28 |
| mm10_Arg_CCG_32_R | GCACCCGAGAATTCCATGGCGACCACGAAGGG ACTCGAACCCTCATCYYCSGMTCCG | SEQ ID NO. 29 |
| mm10_Arg_CCT_32_R | GCACCCGAGAATTCCATGGCACCCCAGGTGGG ACTCGAACCCACATCCCTGGCTTAG | SEQ ID NO. 30 |
| mm10_Arg_TCG_32_R | GCACCCGAGAATTCCATGGCAACCACGAAGGG ATTCGAACCCTCATCTTCTGATCCG | SEQ ID NO. 31 |
| mm10_Arg_TCT_32_R | GCACCCGAGAATTCCATGGCGACTCTGGCGGG ACTCGAACCCACACCTYTGRATTAG | SEQ ID NO. 32 |
| mm10_Asn_GTT_33_R | GCACCCGAGAATTCCATGGCGTCCCTGGGTGG GCTCGAACCACCACCTTYYRGTTAA | SEQ ID NO. 33 |
| mm10_Asp_GTC_32_R | GCACCCGAGAATTCCATGGCTCCCCGTCGGGG AATCGAACCCCGGTWTCCYGYGTGA | SEQ ID NO. 34 |
| mm10_Cys_GCA_32_R | GCACCCGAGAATTCCATGGAGGGGCACCTGG ATTTGAACCAGGGYCYCKTRATCTG | SEQ ID NO. 35 |
| mm10_Gln_CTG_32_R | GCACCCGAGAATTCCATGGAGGTCCACCGAG ATTTGAACTCGGRTCGCTGGATTCA | SEQ ID NO. 36 |
| mm10_Gln_TTG_32_R | GCACCCGAGAATTCCATGGAGGTCCACCGAG ATTTGAACTCGGATYGCTGGAYTCA | SEQ ID NO. 37 |
| mm10_Glu_CTC_32_R | GCACCCGAGAATTCCATGGTTCCCTGACCGGG AATCGAACCCGGGcMRYGWHGGTGA | SEQ ID NO. 38 |
| mm10_Glu_TTC-1_32_R | GCACCCGAGAATTCCATGGTTCCCACACCGGG AGTCGAACCCGGGCCGCCTGGGTGA | SEQ ID NO. 39 |

TABLE 3-continued

Mouse DNA probes.
DNA probes to generate a tRNA profile in mouse cells. The DNA probes
were designed by the methods disclosed herein.

| | | |
|---|---|---|
| mm10_Glu_TTC-2_32_R | GCACCCGAGAATTCCATGGTTCCCTGACCGGG AATCGAACCCGGGCCGCGGCGGTGA | SEQ ID NO. 40 |
| mm10_Gly_ACC_33_R | GCACCCGAGAATTCCATGGTGTTTCCGCCCGG TTTCGAACCGGGGCCTTTCGCTTGG | SEQ ID NO. 41 |
| mm10_Gly_CCC-1_32_R | GCACCCGAGAATTCCATGGTGCGCCGCCCGGG AATCGAACCCGGGTCGCAAGAATGG | SEQ ID NO. 42 |
| mm10_Gly_CCC-2_32_R | GCACCCGAGAATTCCATGGTGCATTGGCCGGG AATCGAACCCGGGTCMCCCRHGTGG | SEQ ID NO. 43 |
| mm10_Gly_CCC-3_32_R | GCACCCGAGAATTCCATGGTGCGCCGCCCGGG AATCGAACCCGGGTCGCAAGAATGG | SEQ ID NO. 44 |
| mm10_Gly_CCC_32_R | GCACCCGAGAATTCCATGGTGCATTGGCCGGG AATCGAACCCGGGTCMCCCRHGTGG | SEQ ID NO. 45 |
| mm10_Gly_GCC_32_R | GCACCCGAGAATTCCATGGTGCATTGGCCGGG AATCGAACCCGGGCCTCCCGWGTGG | SEQ ID NO. 46 |
| mm10_Gly_TCC_32_R | GCACCCGAGAATTCCATGGTGCGTTGGCCGGG AATCGAACCCGGGTCAACTGCTTGG | SEQ ID NO. 47 |
| mm10_His_ATG_33_R | GCACCCGAGAATTCCATGGCGAGCCAGACAGG AGTCGAACCTAGATCTTCTGATCCA | SEQ ID NO. 48 |
| mm10_His_GTG_32_R | GCACCCGAGAATTCCATGGTGCCGTGACTCGG ATTCGAACCGAGGTTGCTGCRGCCA | SEQ ID NO. 49 |
| mm10_Ile_AAT_33_R | GCACCCGAGAATTCCATGGTGGCCCGTACGGG GATCGAACCCGYRCCTTGGCGTTAT | SEQ ID NO. 50 |
| mm10_Ile_GAT_34_R | GCACCCGAGAATTCCATGGTGACCTGTACGGG GAACGAACCCACGACTTGGCATTAT | SEQ ID NO. 51 |
| mm10_Ile_TAT-1_33_R | GCACCCGAGAATTCCATGGTGCTCCAGGTGAG GCTCGAACTCACACCTCGGCATTAT | SEQ ID NO. 52 |
| mm10_Ile_TAT-2_33_R | GCACCCGAGAATTCCATGGTAGTTCCACTGGG GCTCAAACTCAGGCCTTCTGCAT | SEQ ID NO. 53 |
| mm10_Leu_AAG-1_32_R | GCACCCGAGAATTCCATGGGACTCGTCCAAG CTTTGAACCCAGGCTTCTCAGACCT | SEQ ID NO. 54 |
| mm10_Leu_AAG-2_32_R | GCACCCGAGAATTCCATGGCGGTGGGATTCGA ACCCACGCCCCCGAAGAGACTGGAGCCT | SEQ ID NO. 55 |
| mm10_Leu_CAA_32_R | GCACCCGAGAATTCCATGGGTGGGATTCGAAC CCACGCCTCCABDcGGAGACCAGAACTT | SEQ ID NO. 56 |
| mm10_Leu_CAG_32_R | GCACCCGAGAATTCCATGGAGTGGGATTCGAA CCCACGCCTCCAGGGGAGACTGCGACCT | SEQ ID NO. 57 |
| mm10_Leu_TAA-1_32_R | GCACCCGAGAATTCCATGGGTGGGGTTCGAAC CCACGCAGRYASMHRYCCATTGGATCTT | SEQ ID NO. 58 |
| mm10_Leu_TAA-2_34_R | GCACCCGAGAATTCCATGGTATTAGGGAGAGG ATTTGAACCTCTGGAACAAGGTTTT | SEQ ID NO. 59 |
| mm10_Leu_TAG_32_R | GCACCCGAGAATTCCATGGCGGTGGGATTCGA ACCCACGCCSYCGAARSGACTGGAGCCT | SEQ ID NO. 60 |
| mm10_Lys_CTT-1_33_R | GCACCCGAGAATTCCATGGTGCCCAACGTGGG GCTTGAACCCAYGCYCTGRGATTAA | SEQ ID NO. 61 |
| mm10_Lys_CTT-2_33_R | GCACCCGAGAATTCCATGGCGCCCAACGTGGG GCTCGAACCCAYGCCCTRRGAYTAA | SEQ ID NO. 62 |
| mm10_Lys_CTT_33_R | GCACCCGAGAATTCCATGGCGCCCAACGTGGG GCTCGAACCCAYGCYCTRRGAYTAA | SEQ ID NO. 63 |
| mm10_Lys_TTT-1_32_R | GCACCCGAGAATTCCATGGTGCTCGATGTGGG GCTTGAACCTTWRWCCTWAGATTAA | SEQ ID NO. 64 |
| mm10_Lys_TTT-2_32_R | GCACCCGAGAATTCCATGGCGCCCGAACAGGG ACTTGAACCCTGRCCCTCAGATTAA | SEQ ID NO. 65 |

TABLE 3-continued

Mouse DNA probes.
DNA probes to generate a tRNA profile in mouse cells. The DNA probes
were designed by the methods disclosed herein.

| | | |
|---|---|---|
| mm10_Lys_TTT_32_R | GCACCCGAGAATTCCATGGCGCCCGAACAGGG ACTTGAACCCTWRWCCTWAGATTAA | SEQ ID NO. 66 |
| mm10_Met_CAT-1_32_R | GCACCCGAGAATTCCATGGTAGCAGAGGATG GTTTCGATCCATCGCCTCTGGGTTAT | SEQ ID NO. 67 |
| mm10_Met_CAT-2_33_R | GCACCCGAGAATTCCATGGTGCCCCTCTGAG GTTCGAACTCAWGYCTYCSGSTTAT | SEQ ID NO. 68 |
| mm10_Phe_GAA_33_R | GCACCCGAGAATTCCATGGTGCCGAAACCCGG GATCGAACCAGGGCCTTTAGATCTT | SEQ ID NO. 69 |
| mm10_Pro_AGG_32_R | GCACCCGAGAATTCCATGGGGGCTCGTCCGGG ATTTGAACCCGGGCCTCTCRCACCC | SEQ ID NO. 70 |
| mm10_Pro_CGG_32_R | GCACCCGAGAATTCCATGGGGGCTCGTCCGGG ATTTGAACCCGGGCCTCTCGCACCC | SEQ ID NO. 71 |
| mm10_Pro_TGG_32_R | GCACCCGAGAATTCCATGGGGGCTCGTCCGGG ATTTGAACCCGGGCCTCTCDVACCC | SEQ ID NO. 72 |
| mm10_SeC(e)_TCA_36_R | GCACCCGAGAATTCCATGGGTGGAATTGAACC ACTCTGTCGCTAAACAGCTACAGGTTTG | SEQ ID NO. 73 |
| mm10_SeC_TCA_32_R | GCACCCGAGAATTCCATGGCGCCCAATGTGGG GCTCGAACCCACACCCTGAGATTG | SEQ ID NO. 74 |
| mm10_Ser_AGA_32_R | GCACCCGAGAATTCCATGGGGCAGGATTCGAA CCTGCGCgGGGARACCCCAATGGATTTC | SEQ ID NO. 75 |
| mm10_Ser_CGA_32_R | GCACCCGAGAATTCCATGGAGCAGGATTCGAA CCTGCGCGGGRARAMCCCATTGGATTTC | SEQ ID NO. 76 |
| mm10_Ser_GCT_32_R | GCACCCGAGAATTCCATGGGATGGGATTCGAA CCCACGCRTRCSRAGCACARTGGATTAG | SEQ ID NO. 77 |
| mm10_Ser_GGA_34_R | GCACCCGAGAATTCCATGGTGCCGAAACCCGG GATCAAACCAGGGCCTTTAGATCTC | SEQ ID NO. 78 |
| mm10_Ser_TGA_32_R | GCACCCGAGAATTCCATGGGGCAGGATTCGAA CCTGCGCGGGGARACCCCASTGGATTTC | SEQ ID NO. 79 |
| mm10_Sup_TTA_33_R | GCACCCGAGAATTCCATGGGTGGGGTTTGAAC CCACGCAGGCATCCGCCCATTGGATCTA | SEQ ID NO. 80 |
| mm10_Thr_AGT_33_R | GCACCCGAGAATTCCATGGAGGCACCGCTGGG ATTCGAACCCAGGTCTCCTGTTTAC | SEQ ID NO. 81 |
| mm10_Thr_CGT-1_33_R | GCACCCGAGAATTCCATGGAGGCCCGGCTGGG GTTCGAACCCGBGTCTCYCKGTTTAC | SEQ ID NO. 82 |
| mm10_Thr_CGT-2_33_R | GCACCCGAGAATTCCATGGAAGGGGCACTAGG AACTGAACCTAGACCTCCAACCTAC | SEQ ID NO. 83 |
| mm10_Thr_TGT_33_R | GCACCCGAGAATTCCATGGAGGCCCCAGCGAG ATTTGAACTCGWGYCYCYKGTTTAC | SEQ ID NO. 84 |
| mm10_Trp_CCA_32_R | GCACCCGAGAATTCCATGGTGACCCCGACGTG ATTTGAACACGCACCTTCTGATCTG | SEQ ID NO. 85 |
| mm10_Tyr_GTA_33_R | GCACCCGAGAATTCCATGGTCCTTCGAGCCGG ATTCGAACCAGCGCCTAAGGATCTA | SEQ ID NO. 86 |
| mm10_Val_AAC-1_32_R | GCACCCGAGAATTCCATGGTGTTTCCGCCCGG TTTCGAACCGGGGCCTYTCGCGTGT | SEQ ID NO. 87 |
| mm10_Val_AAC-2_33_R | GCACCCGAGAATTCCATGGCTATGGTACTGGG AATTGAACCCAGGCTTTTGCATGT | SEQ ID NO. 88 |
| mm10_Val_CAC-1_32_R | GCACCCGAGAATTCCATGGTGTTTCTGCTGGG TTTTGAACCGGGGCCTYTYGCRTGT | SEQ ID NO. 89 |
| mm10_Val_CAC-2_32_R | GCACCCGAGAATTCCATGGTGTTTCCGCCCGG TTTCGAACCGGGGCCTYTYGCRTGT | SEQ ID NO. 90 |

TABLE 3-continued

Mouse DNA probes.
DNA probes to generate a tRNA profile in mouse cells. The DNA probes
were designed by the methods disclosed herein.

| Name | Sequence | SEQ ID NO. |
|---|---|---|
| mm10_Val_CAC_32_R | GCACCCGAGAATTCCATGGTGTTTCCGCCCGG TTTCGAACCGGGGCCTYTYGCRTGT | SEQ ID NO. 91 |
| mm10_Val_GAC_34_R | GCACCCGAGAATTCCATGGCATAAACACTGGG GTTTGAACCCAGACTTTCTGCAGGT | SEQ ID NO. 92 |
| mm10_Val_TAC_32_R | GCACCCGAGAATTCCATGGTGGTTCCACTGGG GCTCGAACCCAGGCCTTCTGCGTGT | SEQ ID NO. 93 |
| mm10_Ala_AGC-1_33_L | /5Phos/TARRCRMRCRCTCTACCAACTGAGC CACATCCCCGATCGTCGGACTGTAGAACTC | SEQ ID NO. 94 |
| mm10_Ala_AGC-2_33_L | /5Phos/TAAGCRHGCGCTCTACCATTTGAGC TAATCCCCCGATCGTCGGACTGTAGAACTC | SEQ ID NO. 95 |
| mm10_Ala_CGC-2_32_L | /5Phos/GAAGCRYGYGCTCTACCTCTGAGCT ACATCCCCGATCGTCGGACTGTAGAACTC | SEQ ID NO. 96 |
| mm10_Ala_CGC_32_L | /5Phos/GAAGCAYGYGCTCTACCTCTGAGCT ACATCCCCGATCGTCGGACTGTAGAACTC | SEQ ID NO. 97 |
| mm10_Ala_TGC_32_L | /5Phos/AAAGCATGYGCTCTACCACTGAGCT ACATCCCCGATCGTCGGACTGTAGAACTC | SEQ ID NO. 98 |
| mm10_Arg_ACG_32_L | /5Phos/TAGTCAGACGCGTTTCCATTGCGCC ACTGGCCCGATCGTCGGACTGTAGAACTC | SEQ ID NO. 99 |
| mm10_Arg_CCG_32_L | /5Phos/GARKCSGAYGCCTTTCCATTAGGCC ACGCGGCCGATCGTCGGACTGTAGAACTC | SEQ ID NO. 100 |
| mm10_Arg_CCT_32_L | /5Phos/GAGGCCARTGCCTTTCCATTAGGCC ACTGGGGCGATCGTCGGACTGTAGAACTC | SEQ ID NO. 101 |
| mm10_Arg_TCG_32_L | /5Phos/AAGTCAGACGCCTTTCCATTAGGCC ACGTGGTCGATCGTCGGACTGTAGAACTC | SEQ ID NO. 102 |
| mm10_Arg_TCT_32_L | /5Phos/AAGTCCARYGCGCTTCCATTGCGCC ACAGAGCCGATCGTCGGACTGTAGAACTC | SEQ ID NO. 103 |
| mm10_Asn_GTT_33_L | /5Phos/CAGCWRAACRCGCTACCGATTGCGC CACAGAGACGATCGTCGGACTGTAGAACTC | SEQ ID NO. 104 |
| mm10_Asp_GTC_32_L | /5Phos/CAGGCRGGGATACTACCACTATACT AACGAGGAGATCGTCGGACTGTAGAACTC | SEQ ID NO. 105 |
| mm10_Cys_GCA_32_L | /5Phos/CAKYCAAATRCTCTACCCCTGAGCT ATACCCCCGATCGTCGGACTGTAGAACTC | SEQ ID NO. 106 |
| mm10_Gln_CTG_32_L | /5Phos/GAGTCCAGAGTGCTACCATTACACC ATGGAACCGATCGTCGGACTGTAGAACTC | SEQ ID NO. 107 |
| mm10_Gln_TTG_32_L | /5Phos/AAGTCCAGSGTGCTACCATTACACC ATGGGACCGATCGTCGGACTGTAGAACTC | SEQ ID NO. 108 |
| mm10_Glu_CTC_32_L | /5Phos/GAWCRMYRAVTCCTACCACTAGACC ACCAGGGAGATCGTCGGACTGTAGAACTC | SEQ ID NO. 109 |
| mm10_Glu_TTC-1_32_L | /5Phos/AAACCAGGAATCCTACCGCTAGACC ATGTGGGAGATCGTCGGACTGTAGAACTC | SEQ ID NO. 110 |
| mm10_Glu_TTC-2_32_L | /5Phos/AAGCGCCGAATCCTGCCACTAGACC ACCAGGGAGATCGTCGGACTGTAGAACTC | SEQ ID NO. 111 |
| mm10_Gly_ACC_33_L | /5Phos/TAGGCGAACGCGCTACCACTACACT ACGGAAACGATCGTCGGACTGTAGAACTC | SEQ ID NO. 112 |
| mm10_Gly_CCC-1_32_L | /5Phos/GAATCTTGCATGATACCACTACACC AGCGGCGCGATCGTCGGACTGTAGAACTC | SEQ ID NO. 113 |
| mm10_Gly_CCC-2_32_L | /5Phos/GAGGCGAGAATTCTACCATTGAACC ACCAATGCGATCGTCGGACTGTAGAACTC | SEQ ID NO. 114 |
| mm10_Gly_CCC-3_32_L | /5Phos/GAATCTTGCATGATACCACTACACC AGCGGCGCGATCGTCGGACTGTAGAACTC | SEQ ID NO. 115 |

TABLE 3-continued

Mouse DNA probes.
DNA probes to generate a tRNA profile in mouse cells. The DNA probes
were designed by the methods disclosed herein.

| Name | Sequence | SEQ ID NO. |
|---|---|---|
| mm10_Gly_CCC_32_L | /5Phos/GAGGCGAGAATTCTACCATTGAACCACCAATGCGATCGTCGGACTGTAGAACTC | SEQ ID NO. 116 |
| mm10_Gly_GCC_32_L | /5Phos/CAGGCRAGAATTCTACCACTGAACCACCAATGCGATCGTCGGACTGTAGAACTC | SEQ ID NO. 117 |
| mm10_Gly_TCC_32_L | /5Phos/AAGGCAGCTATGCTACCACTATACCACCAACGCGATCGTCGGACTGTAGAACTC | SEQ ID NO. 118 |
| mm10_His_ATG_33_L | /5Phos/TAGTCAGACGTGTTTCCATTGCACCACTGGTCCGATCGTCGGACTGTAGAACTC | SEQ ID NO. 119 |
| mm10_His_GTG_32_L | /5Phos/CAAYGCAGAGTACTACCACTATACGATCACGGCGATCGTCGGACTGTAGAACTC | SEQ ID NO. 120 |
| mm10_Ile_AAT_33_L | /5Phos/TAGCACCAYRCTCTACCAACTGAGCTAACCGGCCGATCGTCGGACTGTAGAACTC | SEQ ID NO. 121 |
| mm10_Ile_GAT_34_L | /5Phos/CAGCACCATGCTCTACCAACTGAGCTAACTGGCCGATCGTCGGACTGTAGAACTC | SEQ ID NO. 122 |
| mm10_Ile_TAT-1_33_L | /5Phos/AAGTACCGCGCGCTACCGATTGCGCCACTGGAGCGATCGTCGGACTGTAGAACTC | SEQ ID NO. 123 |
| mm10_Ile_TAT-2_33_L | /5Phos/ATAAAGCAGATGTGATACCACTACCCTATGGAACCGATCGTCGGACTGTAGAACTC | SEQ ID NO. 124 |
| mm10_Leu_AAG-1_32_L | /5Phos/TAAGTGAGAATCATACCCCTAGACCAACAAGCCGATCGTCGGACTGTAGAACTC | SEQ ID NO. 125 |
| mm10_Leu_AAG-2_32_L | /5Phos/TAATCCAGCGCCTTACCGCTCGGCCACGCTACCGATCGTCGGACTGTAGAACTC | SEQ ID NO. 126 |
| mm10_Leu_CAA_32_L | /5Phos/GAGTCTGGCGCCTTACCACTCGGCCATCCTGACGATCGTCGGACTGTAGAACTC | SEQ ID NO. 127 |
| mm10_Leu_CAG_32_L | /5Phos/GAACRAGCGCCTTACCGCTCGGCCATCCTGACGATCGTCGGACTGTAGAACTC | SEQ ID NO. 128 |
| mm10_Leu_TAA-1_32_L | /5Phos/AAGTCCAACGCCTTACCACTCGGCCATCCTGGTGATCGTCGGACTGTAGAACTC | SEQ ID NO. 129 |
| mm10_Leu_TAA-2_34_L | /5Phos/AAGTCTTACGCAATTCCGGCTCTGCCACCCTAATGATCGTCGGACTGTAGAACTC | SEQ ID NO. 130 |
| mm10_Leu_TAG_32_L | /5Phos/AAATCCAGCGCCTTACCGCTCGGCCACGCTACCGATCGTCGGACTGTAGAACTC | SEQ ID NO. 131 |
| mm10_Lys_CTT-1_33_L | /5Phos/GAGTCYCATGCTGTACCGACTGAGCTAGCTGGGCGATCGTCGGACTGTAGAACTC | SEQ ID NO. 132 |
| mm10_Lys_CTT-2_33_L | /5Phos/GAKTCYCAHGCTCTACCGACTGAGCTAGCCGGGCGATCGTCGGACTGTAGAACTC | SEQ ID NO. 133 |
| mm10_Lys_CTT_33_L | /5Phos/GAKTCYCAHGCTCTACCGACTGAGCTAGCCGGGCGATCGTCGGACTGTAGAACTC | SEQ ID NO. 134 |
| mm10_Lys_TTT-1_32_L | /5Phos/AAGTYTWATRCTCTACTGACTGAGCTATCCAGGTGATCGTCGGACTGTAGAACTC | SEQ ID NO. 135 |
| mm10_Lys_TTT-2_32_L | /5Phos/AAGTCTGATGCTCTACCGACTGAGCTATCCGGGCGATCGTCGGACTGTAGAACTC | SEQ ID NO. 136 |
| mm10_Lys_TTT_32_L | /5Phos/AAGTYTWATRCTCTACCGACTGAGCTATCCGGGCGATCGTCGGACTGTAGAACTC | SEQ ID NO. 137 |
| mm10_Met_CAT-1_32_L | /5Phos/GGGCCCAGCACGCTTCCGCTGCGCCACTCTGCTGATCGTCGGACTGTAGAACTC | SEQ ID NO. 138 |
| mm10_Met_CAT-2_33_L | /5Phos/GAGACSGRCRCGCTGCCTACTGCGCTAAGGAGGCGATCGTCGGACTGTAGAACTC | SEQ ID NO. 139 |
| mm10_Phe_GAA_33_L | /5Phos/CAGTCTAACGCTCTCCCAACTGAGCTATTTCGGCGATCGTCGGACTGTAGAACTC | SEQ ID NO. 140 |

TABLE 3-continued

Mouse DNA probes.
DNA probes to generate a tRNA profile in mouse cells. The DNA probes
were designed by the methods disclosed herein.

| Name | Sequence | SEQ ID |
|---|---|---|
| mm10_Pro_AGG_32_L | /5Phos/TAAGYGAGAATCATACCCCTAGACCAACGAGCCGATCGTCGGACTGTAGAACTC | SEQ ID NO. 141 |
| mm10_Pro_CGG_32_L | /5Phos/GAAGCGAGAATCATACCCCTAGACCAACGAGCCGATCGTCGGACTGTAGAACTC | SEQ ID NO. 142 |
| mm10_Pro_TGG_32_L | /5Phos/AAAWHGAGAATCATACCCCTAGACCAACGAGCCGATCGTCGGACTGTAGAACTC | SEQ ID NO. 143 |
| mm10_SeC(e)_TCA_36_L | /5Phos/AAGCCTGCACCCCAGACCACTGAGGATCATCCGGGCGATCGTCGGACTGTAGAACC | SEQ ID NO. 144 |
| mm10_SeC_TCA_32_L | /5Phos/AGTCTCATGCTCTCCCACTGAGCTAGCTGGGTGATCGTCGGACTGTAGAACTC | SEQ ID NO. 145 |
| mm10_Ser_AGA_32_L | /5Phos/TAGTCCATCGCCTTACCACTCGGCCACGACTACGATCGTCGGACTGTAGAACTC | SEQ ID NO. 146 |
| mm10_Ser_CGA_32_L | /5Phos/GAGTCCAACGCCTTACCACTCGGCCATCACAGCGATCGTCGGACTGTAGAACTC | SEQ ID NO. 147 |
| mm10_Ser_GCT_32_L | /5Phos/CAGTCCATCGCCTTACCACTCGGCCACCTCGTCGATCGTCGGACTGTAGAACTC | SEQ ID NO. 148 |
| mm10_Ser_GGA_34_L | /5Phos/CAGTCTAATGCTCTCCCAACTGAGCTATTTCAGCGATCGTCGGACTGTAGAACTC | SEQ ID NO. 149 |
| mm10_Ser_TGA_32_L | /5Phos/AAGTCCATCGCCTTACCACTCGGCCACGACTACGATCGTCGGACTGTAGAACTC | SEQ ID NO. 150 |
| mm10_Sup_TTA_33_L | /5Phos/AAGTCCAAGGCCTTACCACTCAGCCATCCCAGTGATCGTCGGACTGTAGAACTC | SEQ ID NO. 151 |
| mm10_Thr_AGT_33_L | /5Phos/TAGACAGGCGCTTTACCAGCTAAGCCACGGCGCCGATCGTCGGACTGTAGAACTC | SEQ ID NO. 152 |
| mm10_Thr_CGT-1_33_L | /5Phos/GAGACMGRCGCTTTACCAGCTTGGCCACGGCGCCGATCGTCGGACTGTAGAACTC | SEQ ID NO. 153 |
| mm10_Thr_CGT-2_33_L | /5Phos/GAGGCAAGTGTTCATCCACTGAACTACATCCCTGATCGTCGGACTGTAGAACTC | SEQ ID NO. 154 |
| mm10_Thr_TGT_33_L | /5Phos/AAGACMRGYGCTCTACCACCTGAGCTATGGAGCCGATCGTCGGACTGTAGAACTC | SEQ ID NO. 155 |
| mm10_Trp_CCA_32_L | /5Phos/GAGTCAGACGCGCTACCGTTGCGCCACGAGGTCGATCGTCGGACTGTAGAACTC | SEQ ID NO. 156 |
| mm10_Tyr_GTA_33_L | /5Phos/CAGTCCTCCGCTCTACCAACTGAGCTATCGAAGGGATCGTCGGACTGTAGAACTC | SEQ ID NO. 157 |
| mm10_Val_AAC-1_32_L | /5Phos/TAGGCGARYGTGATACCACTACACTACGGAAACGATCGTCGGACTGTAGAACTC | SEQ ID NO. 158 |
| mm10_Val_AAC-2_33_L | /5Phos/TAGGCAAATGCTCTACCACTGAGCTATATCACCGATCGTCGGACTGTAGAACTC | SEQ ID NO. 159 |
| mm10_Val_CAC-1_32_L | /5Phos/GAGGCRARYGTGATACCGCTACACTACAGAAACGATCGTCGGACTGTAGAACTC | SEQ ID NO. 160 |
| mm10_Val_CAC-2_32_L | /5Phos/GAGGCGARCGTGATACCACTACACTACGGAAACGATCGTCGGACTGTAGAACTC | SEQ ID NO. 161 |
| mm10_Val_CAC_32_L | /5Phos/GAGGCRARYGTGATACCACTACACTACGGAAACGATCGTCGGACTGTAGAACTC | SEQ ID NO. 162 |
| mm10_Val_GAC_34_L | /5Phos/CAAGCAAGCACTTTACCAATTGAGCTATATCCACGATCGTCGGACTGTAGAACTC | SEQ ID NO. 163 |
| mm10_Val_TAC_32_L | /5Phos/AAAGCAGACGTGATACCGCTACACTATGGAACCGATCGTCGGACTGTAGAACTC | SEQ ID NO. 164 |

TABLE 4

Human DNA probes.
DNA probes to generate a tRNA profile in human cells. The DNA
probes were designed by the methods disclosed herein.

| | | |
|---|---|---|
| Ala_AGC-1_32_R | GCACCCGAGAATTCCATGGTGGAGGTGCTGG GGATTGAACCCGGGCCTCRTRCATGC | SEQ ID NO. 165 |
| Ala_AGC-2_33_R | GCACCCGAGAATTCCATGGTGGAGAATGCGG GCATCGATCCCGCTCCTCTYGCRTGC | SEQ ID NO. 166 |
| Ala_AGC-3_32_R | GCACCCGAGAATTCCATGGTGGAGGTGCTGG GGATTGAACCCGGGCCTCRTGCATGC | SEQ ID NO. 167 |
| Ala_CGC_32_R | GCACCCGAGAATTCCATGGTGGAGATGCCGG GGATCGAACCCGGGCCTCRYACATGC | SEQ ID NO. 168 |
| Ala_TGC_32_R | GCACCCGAGAATTCCATGGTGGAGGTGCCGG GGATCGAACCCGGRYCTCAYACRTGC | SEQ ID NO. 169 |
| Arg_ACG_32_R | GCACCCGAGAATTCCATGGCGAGCCAGCCAG GAGTCGAACCTAGATCTTCTGATCCG | SEQ ID NO. 170 |
| Arg_CCG-1_32_R | GCACCCGAGAATTCCATGGCGACCACGAAGG GACTCGAACCCTCATCTTCTGATCCG | SEQ ID NO. 171 |
| Arg_CCG-2_33_R | GCACCCGAGAATTCCATGGCGACCCAGATGG GACTCGAACCCACATCCCCAGCTCCG | SEQ ID NO. 172 |
| Arg_CCT_32_R | GCACCCGAGAATTCCATGGTACCCCAGGTGG GACTCGAACCCACATCCCTGGCTTAG | SEQ ID NO. 173 |
| Arg_TCG_32_R | GCACCCGAGAATTCCATGGCGACCACGGAGG GATTCGAACCCTCATCTTYTGATCCG | SEQ ID NO. 174 |
| Arg_TCT_32_R | GCACCCGAGAATTCCATGGCGACTCTGGTGG GACTCGAACCCGCACCTYTGRATTAG | SEQ ID NO. 175 |
| Asn_ATT_34_R | GCACCCGAGAATTCCATGGCGTCCCTGGGTG GTCTTGAACTACTCCCGTTCGGTTAA | SEQ ID NO. 176 |
| Asn_GTT-1_33_R | GCACCCGAGAATTCCATGGCGTCCCTGGGTG GGCTCGAACCACCACYTTHYGKTTAA | SEQ ID NO. 177 |
| Asn_GTT-2_33_R | GCACCCGAGAATTCCATGGCGTCCCTGGGTG GGCTCGAACCACYABYTTHYRGTTAA | SEQ ID NO. 178 |
| Asn_GTT-3_33_R | GCACCCGAGAATTCCATGGCATCCCTGGATG GGCTTGCACCACCACCTTTCAGTTAA | SEQ ID NO. 179 |
| Asp_GTC-1_32_R | GCACCCGAGAATTCCATGGCTCCCTGTTGGG GACTCGACCTCCTWTCTCaYRCATGA | SEQ ID NO. 180 |
| Asp_GTC-2_32_R | GCACCCGAGAATTCCATGGCTCCCCGTCGGG GAATCGAACCCCGWTCTCCCGCGTGA | SEQ ID NO. 181 |
| Cys_GCA_32_R | GCACCCGAGAATTCCATGGAGGGGGCACCCG GATTTGAACCGGGGCYTYTTGATYTG | SEQ ID NO. 182 |
| Gln_CTG-1_33_R | GCACCCGAGAATTCCATGGTGACAGAACCAG ATTCAAATCAAGTTCTCTGACTTCA | SEQ ID NO. 183 |
| Gln_CTG-2_32_R | GCACCCGAGAATTCCATGGAGGTTCCACCGA GACTTGAACTCGGRTBRCYGKATTCA | SEQ ID NO. 184 |
| Gln_CTG-3_32_R | GCACCCGAGAATTCCATGGAAGCAGTGCCGG GATTTGAACCCAGCCCTTCTGACCA | SEQ ID NO. 185 |
| Gln_TTG-1_33_R | GCACCCGAGAATTCCATGGCTGGGACTATAG GAATTGAACCTAYCCCTGAGAMTCCA | SEQ ID NO. 186 |
| Gln_TTG-2_32_R | GCACCCGAGAATTCCATGGAGGTCCCACCGA GATTTGAACTCGGATYGCTGGATTCA | SEQ ID NO. 187 |
| Gln_TTG-3_33_R | GCACCCGAGAATTCCATGGTGACCATGAAAG GACTTGAACCCTCATCTTCTGACCCA | SEQ ID NO. 188 |
| Glu_CTC-1_32_R | GCACCCGAGAATTCCATGGTTCCCTGACCGG GAATCGAGTCTGGGYMRYRGTGGTGA | SEQ ID NO. 189 |

TABLE 4-continued

Human DNA probes.
DNA probes to generate a tRNA profile in human cells. The DNA
probes were designed by the methods disclosed herein.

| Name | Sequence | SEQ ID |
|---|---|---|
| Glu_CTC-2_33_R | GCACCCGAGAATTCCATGGTCCCTGATCTG GAATCAACCAGTCCCGGCGGTGA | SEQ ID NO. 190 |
| Glu_CTC-3_32_R | GCACCCGAGAATTCCATGGTTCCCTGACCGG GAATCGAACCCGGGCMGCRGCGGTGA | SEQ ID NO. 191 |
| Glu_TTC-1_32_R | GCACCCGAGAATTCCATGGTTCCCATACCGG GAGTCGAACCCGGGCCRCCTGGGTGA | SEQ ID NO. 192 |
| Glu_TTC-2_31_R | GCACCCGAGAATTCCATGGTCTCTAACCAGG AATTGAACCTGGGCTGTCATGACGA | SEQ ID NO. 193 |
| Glu_TTC-3_32_R | GCACCCGAGAATTCCATGGTTCCCTGATCTG GAATCGAACTCGAGYYWCGGCGGTGA | SEQ ID NO. 194 |
| Glu_TTC-4_31_R | GCACCCGAGAATTCCATGGTTCCCTGACTGG GAATTGAACCTGGRcTRWAGCAMTGA | SEQ ID NO. 195 |
| Glu_TTC-5_32_R | GCACCCGAGAATTCCATGGTTCCCTGACCGG GAATCGAACCCGGGCCGCGGCGGTGA | SEQ ID NO. 196 |
| Gly_CCC-1_32_R | GCACCCGAGAATTCCATGGTGCGCCGCCCGG GAATCGAACCCGGGTCGCAAGAATGG | SEQ ID NO. 197 |
| Gly_CCC-2_32_R | GCACCCGAGAATTCCATGGTGCATTGGCCGG GAATTGAACCCGGGTCTCCYRCRTGG | SEQ ID NO. 198 |
| Gly_CCC-3_33_R | GCACCCGAGAATTCCATGGTGCATTGGCCGG GAATTGAACCCGGGTCTCCCGCGTGG | SEQ ID NO. 199 |
| Gly_GCC_32_R | GCACCCGAGAATTCCATGGTGCATTGGCCGG GAATCGAACCCGGGCCKCCYGCRTGG | SEQ ID NO. 200 |
| Gly_TCC_32_R | GCACCCGAGAATTCCATGGTGCGTTGGCCGG GAATCGAACCCGGGTCAACTGCTTGG | SEQ ID NO. 201 |
| His_GTG_32_R | GCACCCGAGAATTCCATGGTGCCGTGACTCG GATTCGAACCGAGGTTGCTGYGGCCA | SEQ ID NO. 202 |
| Ile_AAT_33_R | GCACCCGAGAATTCCATGGTGGCCCGTACGG GGATCGAACCCGCGCCTTRGCGTTAT | SEQ ID NO. 203 |
| Ile_GAT_33_R | GCACCCGAGAATTCCATGGTGGCCGGTGCGG GAGTCGAGCCCGCGCCTTGGTGTTAT | SEQ ID NO. 204 |
| Ile_TAT_33_R | GCACCCGAGAATTCCATGGTGCTCCAGGTGA GGCTCGAACTCACACCTCGGCATTAT | SEQ ID NO. 205 |
| Leu_AAG-1_32_R | GCACCCGAGAATTCCATGGCGGTGGGATTGA AACCCATGCCYCYRAAGAGACTGGAGSCT | SEQ ID NO. 206 |
| Leu_AAG-2_32_R | GCACCCGAGAATTCCATGGCGGTGGGATTCG AACCCACGCCYCCGAAGAGACTGGAGCCT | SEQ ID NO. 207 |
| Leu_AAG-3_33_R | GCACCCGAGAATTCCATGGTGAGCCAGCCAG GAGTCAAGGCTGGATCTTCTGATTCT | SEQ ID NO. 208 |
| Leu_CAA-1_34_R | GCACCCGAGAATTCCATGGTGCCCCTCTGA GGCTTGAACTCAGGCCTTCAGATTTT | SEQ ID NO. 209 |
| Leu_CAA-2_32_R | GCACCCGAGAATTCCATGGGTGGGATTCGAA CCCACGCCTCCATvYGGAGACCAGAACTT | SEQ ID NO. 210 |
| Leu_CAG-1_32_R | GCACCCGAGAATTCCATGGAGTGGGATTCGA ACCCACGCCTCCAGGGGAGACTGCGACCT | SEQ ID NO. 211 |
| Leu_CAG-2_32_R | GCACCCGAGAATTCCATGGGCCAGGGCTAGG GTTTGAACCCAGATCTACCTACCTGTTCT | SEQ ID NO. 212 |
| Leu_TAA-1_32_R | GCACCCGAGAATTCCATGGGTGGGGTTCGAA CCCACGCGGRYAYVSRYCCATTGGATCTT | SEQ ID NO. 213 |
| Leu_TAA-2_33_R | GCACCCGAGAATTCCATGGTGTTAATGAGAG GAGTTGAACCTCTGTTATAAARTTTT | SEQ ID NO. 214 |

TABLE 4-continued

Human DNA probes.
DNA probes to generate a tRNA profile in human cells. The DNA probes were designed by the methods disclosed herein.

| Name | Sequence | SEQ ID |
|---|---|---|
| Leu_TAA-3_33_R | GCACCCGAGAATTCCATGGGTGGGGTTTAAACCCACACAGCCACTACTCCATTGGATCTT | SEQ ID NO. 215 |
| Leu_TAG_32_R | GCACCCGAGAATTCCATGGCGGTGGGATTCGAACCCACGCCHYCGAARSGACTGGAGCCT | SEQ ID NO. 216 |
| Lys_CTT-1_33_R | GCACCCGAGAATTCCATGGTGTCCAATGTGGGGCTTGAACCCAYKCCCTGAGATTAA | SEQ ID NO. 217 |
| Lys_CTT-2_33_R | GCACCCGAGAATTCCATGGCGCCCAACGTGGGGCTCGAACCCAYRCCCTGRGATKAA | SEQ ID NO. 218 |
| Lys_TTT-1_32_R | GCACCCGAGAATTCCATGGCGCCCGAACAGGGACTTGAACCCTRWCCWTCARATTAA | SEQ ID NO. 219 |
| Lys_TTT-2_32_R | GCACCCGAGAATTCCATGGCACCCAAACAGGGACTTGAACCCTRGCCCTCARATTAA | SEQ ID NO. 220 |
| Met_CAT-1_33_R | GCACCCGAGAATTCCATGGTGCCCTCTCTGAGGCTCGAACTCAWGCYTTCAGATTAT | SEQ ID NO. 221 |
| Met_CAT-2_32_R | GCACCCGAGAATTCCATGGTAGCAGAGGATGGTTTCGATCCATCRCCTCTGGGTTAT | SEQ ID NO. 222 |
| Phe_GAA_33_R | GCACCCGAGAATTCCATGGTGCCGAAACCCGGGATCGAACCAGRGCYTKHAGASCTT | SEQ ID NO. 223 |
| Pro_AGG_32_R | GCACCCGAGAATTCCATGGGGGCTCGTCCGGGATTTGAACCCGGGCCTCTCGCAYCC | SEQ ID NO. 224 |
| Pro_CGG_32_R | GCACCCGAGAATTCCATGGGGGCTCGTCCGGGATTTGAACCCGGGCCTCTCRCACCC | SEQ ID NO. 225 |
| Pro_TGG_32_R | GCACCCGAGAATTCCATGGGGGCTCGTCCGGGATTTGAACCCGGGCCTCTCGWACCC | SEQ ID NO. 226 |
| SeC(e)_TCA_35_R | GCACCCGAGAATTCCATGGGTGGAATTGAACCACTCTGTCRCTAGACAGCTACAGGTTTG | SEQ ID NO. 227 |
| SeC_TCA_33_R | GCACCCGAGAATTCCATGGTGACCACAAAGGGACTCAAACCCTCATCTTCTGATCTG | SEQ ID NO. 228 |
| Ser_AGA-1_33_R | GCACCCGAGAATTCCATGGAGCAGGATTCAAACCTGCACAGAGAGAAACCAACGAATTTC | SEQ ID NO. 229 |
| Ser_AGA-2_32_R | GCACCCGAGAATTCCATGGGGCAGGATTCGAACCTGCGCGGGGARACCCCAATGGRTTTC | SEQ ID NO. 230 |
| Ser_AGA-3_33_R | GCACCCGAGAATTCCATGGAGGGGGCACCTGGATTTGAACCAGGGGCCTCTTGATC | SEQ ID NO. 231 |
| Ser_CGA_32_R | GCACCCGAGAATTCCATGGAGCAGGATTTGAACCTGCGCGGGGARMCCCCATTGGATTTC | SEQ ID NO. 232 |
| Ser_GCT_32_R | GCACCCGAGAATTCCATGGGATGGGATTCGAACCCACGCGTGCARAGCACAATGGATTAG | SEQ ID NO. 233 |
| Ser_TGA-1_32_R | GCACCCGAGAATTCCATGGGGCAGGATTCGAACCTGCGCGGGGARACCCCASTGGATTTC | SEQ ID NO. 234 |
| Ser_TGA-2_30_R | GCACCCGAGAATTCCATGGTGAAAAAGGAGGGAATCGAACCCCCCCAGACTGGTTTC | SEQ ID NO. 235 |
| Thr_AGT_33_R | GCACCCGAGAATTCCATGGAGGCCCGCTGGGATTCGAACCCAGGTCTCCTGTTTAC | SEQ ID NO. 236 |
| Thr_CGT-1_32_R | GCACCCGAGAATTCCATGGTGGCCCTGGTTGGCTTTGATCTCTTGCCYCTGGKTTAC | SEQ ID NO. 237 |
| Thr_CGT-2_33_R | GCACCCGAGAATTCCATGGAGGCCCGGCTGGGGTTCGAACCCGBGTCTYCKGTTTAC | SEQ ID NO. 238 |
| Thr_TGT_33_R | GCACCCGAGAATTCCATGGAGGCCCCAGCGAGATTTGAACTCGWGyCYCYKGTTTAC | SEQ ID NO. 239 |

TABLE 4-continued

Human DNA probes.
DNA probes to generate a tRNA profile in human cells. The DNA
probes were designed by the methods disclosed herein.

| Name | Sequence | SEQ ID |
|---|---|---|
| Trp_CCA-1_34_R | GCACCCGAGAATTCCATGGATGCAGAACTGG GAATTGAACCCAGGCACATGACTGTG | SEQ ID NO. 240 |
| Trp_CCA-2_32_R | GCACCCGAGAATTCCATGGTGACCCCGACGT GATTTGAACACGCACCTTCTGATCTG | SEQ ID NO. 241 |
| Trp_CCA-3_33_R | GCACCCGAGAATTCCATGGTGACCCCGACGT GATTTGAACACGCACCTTCTGATCTG | SEQ ID NO. 242 |
| Tyr_ATA_34_R | GCACCCGAGAATTCCATGGTCCTTCAAGCTG GAATCGAACCAGCACCTAAGGACCTA | SEQ ID NO. 243 |
| Tyr_GTA-1_33_R | GCACCCGAGAATTCCATGGTCCTTCGAGCCG GAATCGAACCAGCRCCTAAGRATCTA | SEQ ID NO. 244 |
| Tyr_GTA-2_32_R | GCACCCGAGAATTCCATGGAGGGAGAACCTG GATTTGAACCAGGGCCTCTTGCTCTA | SEQ ID NO. 245 |
| Val_AAC-1_33_R | GCACCCGAGAATTCCATGGTGTTTCTGCCTG GTTTCAAACCAAGGCCTTTCGCGTGT | SEQ ID NO. 246 |
| Val_AAC-2_32_R | GCACCCGAGAATTCCATGGTGTTTCCGCCCG GTTTCGAACCGGGGCCTTTCGCGTGT | SEQ ID NO. 247 |
| Val_AAC-3_33_R | GCACCCGAGAATTCCATGGTGGAAGTGCTGG GGATCGAACCCAGACCTCATGAATGT | SEQ ID NO. 248 |
| Val_CAC-1_33_R | GCACCCGAGAATTCCATGGCGTTTCCACCTG GTTTCGAACCAGRGCYTTSMDCGT | SEQ ID NO. 249 |
| Val_CAC-2_32_R | GCACCCGAGAATTCCATGGTGTTTCCGCCCG GTTTCGAACCGGGGCYTTTCGCGT | SEQ ID NO. 250 |
| Val_TAC-1_32_R | GCACCCGAGAATTCCATGGTGTTTCCGCTGG GTTTTGACCCGAGGCCTTYYGCGTGT | SEQ ID NO. 251 |
| Val_TAC-2_32_R | GCACCCGAGAATTCCATGGTGGTTCCACTGG GGCTCGAACCCAGGCCTTCTGCGTGT | SEQ ID NO. 252 |
| mAla-TGC_31_R | GCACCCGAGAATTCCATGGTAAGGACTGCAA AACCCCACTCTGCATCAACTGAACGC | SEQ ID NO. 253 |
| mArg-TCG_31_R | GCACCCGAGAATTCCATGGTTGGTAAATATG ATTATCATAATTTAATGAGTCG | SEQ ID NO. 254 |
| mAsn-GTT_34_R | GCACCCGAGAATTCCATGGCTAGACCAATGG GACTTAAACCCACAAACACTTAGTTAA | SEQ ID NO. 255 |
| mAsp-GTC_31_R | GCACCCGAGAATTCCATGGTAAGATATATAG GATTTAGCCTATAATTTAACTTTGA | SEQ ID NO. 256 |
| mCys-GCA_29_R | GCACCCGAGAATTCCATGGAAGCCCCGGCAG GTTTGAAGCTGCTTCTTCGAATTTG | SEQ ID NO. 257 |
| mGlu-TTC_31_R | GCACCCGAGAATTCCATGGTATTCTCGCACG GACTACAACCACGACCAATGATATGA | SEQ ID NO. 258 |
| mGln-TTG_34_R | GCACCCGAGAATTCCATGGCTAGGACTATGA GAATCGAACCCATCCCTGAGAATCCA | SEQ ID NO. 259 |
| mGly-TCC_31_R | GCACCCGAGAATTCCATGGTACTCTTTTTTG AATGTTGTCAAAACTAGTTAATTGG | SEQ ID NO. 260 |
| mHis-GTG_31_R | GCACCCGAGAATTCCATGGGTAAATAAGGG GTCGTAAGCCTCTGTTGTCAGATTCA | SEQ ID NO. 261 |
| mIle-GAT_30_R | GCACCCGAGAATTCCATGGTAGAAATAAGGG GGTTTAAGCTCCTATTATTTACTCTAT | SEQ ID NO. 262 |
| mLeu-TAG_33_R | GCACCCGAGAATTCCATGGTACTTTTATTTG GAGTTGCACCAAAATTTTTGGGGCCT | SEQ ID NO. 263 |
| mLeu-TAA_36_R | GCACCCGAGAATTCCATGGTGTTAAGAAGAG GAATTGAACCTCTGACTGTAAAGTTTT | SEQ ID NO. 264 |

TABLE 4-continued

Human DNA probes.
DNA probes to generate a tRNA profile in human cells. The DNA
probes were designed by the methods disclosed herein.

| Name | Sequence | SEQ ID |
|---|---|---|
| mLys-TTT_28_R | GCACCCGAGAATTCCATGGTCACTGTAAAGAGGTGTTGGTTCTCTTAATCTTTAACTTAA | SEQ ID NO. 265 |
| mMet-CAT_31_R | GCACCCGAGAATTCCATGGTAGTACGGGAAGGGTATAACCAACATTTTCGGGGTAT | SEQ ID NO. 266 |
| mPhe-GAA_35_R | GCACCCGAGAATTCCATGGTGTTTATGGGTGATGTGAGCCCGTCTAAACATTTT | SEQ ID NO. 267 |
| mPro-TGG_32_R | GCACCCGAGAATTCCATGGTCAGAGAAAAGTCTTTAACTCCACCATTAGCACCC | SEQ ID NO. 268 |
| mSer-GCT_20_R | GCACCCGAGAATTCCATGGTGAGAAAGCCATGTTGTTAGACATGGGGGCATGAGTTAG | SEQ ID NO. 269 |
| mSer-TGA_31_R | GCACCCGAGAATTCCATGGCAAAAAAGGAAGGAATCGAACCCCCCAAAGCTGGTTTC | SEQ ID NO. 270 |
| mThr-TGT_32_R | GCACCCGAGAATTCCATGGTGTCCTTGGAAAAAGGTTTTCATCTCCGGTTTAC | SEQ ID NO. 271 |
| mTrp-TCA_33_R | GCACCCGAGAATTCCATGGCAGAAATTAAGTATTGCAACTTACTGAGGGCTTTG | SEQ ID NO. 272 |
| mTyr-GTA_30_R | GCACCCGAGAATTCCATGGTGGTAAAAAGAGGCCTAACCCCTGTCTTTAGATTTA | SEQ ID NO. 273 |
| mVal-TAC_32_R | GCACCCGAGAATTCCATGGTCAGAGCGGTCAAGTTAAGTTGAAATCTCCTAAGTGT | SEQ ID NO. 274 |
| Ala_AGC-1_32_L | /5Phos/TAAGCAYGCGCTCTACCACTGAGCTACACCCCCGATCGTCGGACTGTAGAACTC | SEQ ID NO. 275 |
| Ala_AGC-2_33_L | /5Phos/TAAGWRRGCRCTCTACCACTTGAGCTAATTCCCCGATCGTCGGACTGTAGAACTC | SEQ ID NO. 276 |
| Ala_AGC-3_32_L | /5Phos/TAAGCRYGCGCTCTACCACTGATCTACACCCCCGATCGTCGGACTGTAGAACTC | SEQ ID NO. 277 |
| Ala_CGC_32_L | /5Phos/GAAGCRYGCGCTCTACCACTGAGCTACATCCCCGATCGTCGGACTGTAGAACTC | SEQ ID NO. 278 |
| Ala_TGC_32_L | /5Phos/AAAGCATWYGCTCTACCACTGAGCTACACCCCCGATCGTCGGACTGTAGAACTC | SEQ ID NO. 279 |
| Arg_ACG_32_L | /5Phos/TAGTCAGACGCGTTTCCATTGCGCCACTGGCCCGATCGTCGGACTGTAGAACTC | SEQ ID NO. 280 |
| Arg_CCG-1_32_L | /5Phos/GAATCAGACGCCTTTCCATTAGGCCACGCGGCCGATCGTCGGACTGTAGAACTC | SEQ ID NO. 281 |
| Arg_CCG-2_33_L | /5Phos/GAGGCTGATGCCTTTCCATTAGGCCACTGGGTCGATCGTCGGACTGTAGAACTC | SEQ ID NO. 282 |
| Arg_CCT_32_L | /5Phos/GAGGCCARTRCCTTTCCATTAGGCCACTGGGGCGATCGTCGGACTGTAGAACTC | SEQ ID NO. 283 |
| Arg_TCG_32_L | /5Phos/AAGTCAGACGCCTTTCCATTAGGCCACGTGGTCGATCGTCGGACTGTAGAACTC | SEQ ID NO. 284 |
| Arg_TCT_32_L | /5Phos/AAGTCCARYGCGCTTCCATTGCGCCACAGAGCCGATCGTCGGACTGTAGAACTC | SEQ ID NO. 285 |
| Asn_ATT_34_L | /5Phos/TAGCCGAACGCTCTACCGATTGCGCCACAGAGACGATCGTCGGACTGTAGAACTC | SEQ ID NO. 286 |
| Asn_GTT-1_33_L | /5Phos/CRGCCGAAWGCGCTACCGATTGCGCCACAGAGACGATCGTCGGACTGTAGAACTC | SEQ ID NO. 287 |
| Asn_GTT-2_33_L | /5Phos/CAGCWRAAYGCGCTACCGATTGCGCCACAGAGACGATCGTCGGACTGTAGAACTC | SEQ ID NO. 288 |
| Asn_GTT-3_33_L | /5Phos/CAGTCAAACGCGCTACCGATTGCGCCACAGAGACGATCGTCGGACTGTAGAACTC | SEQ ID NO. 289 |

TABLE 4-continued

Human DNA probes.
DNA probes to generate a tRNA profile in human cells. The DNA
probes were designed by the methods disclosed herein.

| Name | Sequence | SEQ ID NO. |
|---|---|---|
| Asp_GTC-1_32_L | /5Phos/CAGGCAGARATACTACCACTATAGTAACAAGGAGATCGTCGGACTGTAGAACTC | SEQ ID NO. 290 |
| Asp_GTC-2_32_L | /5Phos/CAGRCRGGGATACTACCACTATACTAACGAGGAGATCGTCGGACTGTAGAACTC | SEQ ID NO. 291 |
| Cys_GCA_32_L | /5Phos/CAGTCAARTGCTCTACCCCTGAGCTATACCCCCGATCGTCGGACTGTAGAACTC | SEQ ID NO. 292 |
| Gln_CTG-1_33_L | /5Phos/GAGTTCATGATCTTACCACTCTACCATACTGCCGATCGTCGGACTGTAGAACTC | SEQ ID NO. 293 |
| Gln_CTG-2_32_L | /5Phos/GAGTCCARRGTGCTACCATTACACCATGGAACCGATCGTCGGACTGTAGAACTC | SEQ ID NO. 294 |
| Gln_CTG-3_32_L | /5Phos/GAGCGAATGCCCTACCTCTGGGCTACACTGCCGATCGTCGGACTGTAGAACTC | SEQ ID NO. 295 |
| Gln_TTG-1_33_L | /5Phos/AAATTCTCYRTGCTACCTATTACACCATGTCCTAGATCGTCGGACTGTAGAACTC | SEQ ID NO. 296 |
| Gln_TTG-2_32_L | /5Phos/AAGYCCAGAGTGCTACCATTACACCATGGGGCCGATCGTCGGACTGTAGAACTC | SEQ ID NO. 297 |
| Gln_TTG-3_33_L | /5Phos/AAGTGAGATGTCTTTCCCTTAGGCCACATGGTCGATCGTCGGACTGTAGAACTC | SEQ ID NO. 298 |
| Glu_CTC-1_32_L | /5Phos/GAGWKCYRAATCCTTCCGCTAGACCACCCGGGGATCGTCGGACTGTAGAACTC | SEQ ID NO. 299 |
| Glu_CTC-2_33_L | /5Phos/GAGCGCCAAACTTTGCCACTAGACTACCAGGGAGATCGTCGGACTGTAGAACTC | SEQ ID NO. 300 |
| Glu_CTC-3_32_L | /5Phos/GAGCRCCGAATCCTACCACTAGACCACCAGGGAGATCGTCGGACTGTAGAACTC | SEQ ID NO. 301 |
| Glu_TTC-1_32_L | /5Phos/AAACCAGGAATCCTACCGCTAGACCATGTGGGAGATCGTCGGACTGTAGAACTC | SEQ ID NO. 302 |
| Glu_TTC-2_31_L | /5Phos/AAGCACCAACTCCTACCACTAGACCACAGGGGATCGTCGGACTGTAGAACTC | SEQ ID NO. 303 |
| Glu_TTC-3_32_L | /5Phos/AAGCGCCRAATTTTGCCACTAGACTACCAGGGAGATCGTCGGACTGTAGAACTC | SEQ ID NO. 304 |
| Glu_TTC-4_31_L | /5Phos/AARCACSRAGTTTTGCCACTAGACCACAGGGTGATCGTCGGACTGTAGAACTC | SEQ ID NO. 305 |
| Glu_TTC-5_32_L | /5Phos/AAGCGCCGAATCCTGCCACTAGACCACCAGGGAGATCGTCGGACTGTAGAACTC | SEQ ID NO. 306 |
| Gly_CCC-1_32_L | /5Phos/GAATCTTGCATGATACCACTACACCAGCGGCGCGATCGTCGGACTGTAGAACTC | SEQ ID NO. 307 |
| Gly_CCC-2_32_L | /5Phos/GAGGCGAGAATTCTACCACTGAACCACCAATGCGATCGTCGGACTGTAGAACTC | SEQ ID NO. 308 |
| Gly_CCC-3_33_L | /5Phos/GAGGCGAGAATTCTACCACTGAACCACCAATGCGATCGTCGGACTGTAGAACTC | SEQ ID NO. 309 |
| Gly_GCC_32_L | /5Phos/CAGGCRAGAATTCTACCACTGAACCACCAATGCGATCGTCGGACTGTAGAACTC | SEQ ID NO. 310 |
| Gly_TCC_32_L | /5Phos/AAGGCARCTATGCTACCACTATACCACCAACGCGATCGTCGGACTGTAGAACTC | SEQ ID NO. 311 |
| His_GTG_32_L | /5Phos/CARCRCAGAGTACTACCACTATACGATCACGGCGATCGTCGGACTGTAGAACTC | SEQ ID NO. 312 |
| Ile_AAT_33_L | /5Phos/TAGCRCCACGCTCTACCAACTGAGCTAACCGGCCGATCGTCGGACTGTAGAACTC | SEQ ID NO. 313 |
| Ile_GAT_33_L | /5Phos/CAGCACCACGCTCTACCAACTGAGCTAACCGGCCGATCGTCGGACTGTAGAACTC | SEQ ID NO. 314 |

TABLE 4-continued

Human DNA probes.
DNA probes to generate a tRNA profile in human cells. The DNA
probes were designed by the methods disclosed herein.

| Name | Sequence | SEQ ID |
|---|---|---|
| Ile_TAT_33_L | /5Phos/AAGTACCGCGCGCTACCGATTGCG CCACTGGAGCGATCGTCGGACTGTAGAACTC | SEQ ID NO. 315 |
| Leu_AAG-1_32_L | /5Phos/TAATSCAGTGTCTTACCGCTCGGC CATGCTACCGATCGTCGGACTGTAGAACTC | SEQ ID NO. 316 |
| Leu_AAG-2_32_L | /5Phos/TAATCCAGCGCCTTACCGCTCGGC CACGCTACCGATCGTCGGACTGTAGAACTC | SEQ ID NO. 317 |
| Leu_AAG-3_33_L | /5Phos/TAGTCAGACGCATTTCCATTGAGC CACTGGCCCGATCGTCGGACTGTAGAACTC | SEQ ID NO. 318 |
| Leu_CAA-1_34_L | /5Phos/GAGACTGATGCGCTACCTACTGCA CTAAGGAGGCGATCGTCGGACTGTAGAACTC | SEQ ID NO. 319 |
| Leu_CAA-2_32_L | /5Phos/GAGTCTGGCGCCTTACCACTCGGC CCATCTGACGATCGTCGGACTGTAGAACTC | SEQ ID NO. 320 |
| Leu_CAG-1_32_L | /5Phos/GAACGCAGCGCCTTACCGCTCGGC CATCCTGACGATCGTCGGACTGTAGAACTC | SEQ ID NO. 321 |
| Leu_CAG-2_32_L | /5Phos/GAGCAGGTCCTTAACCACTAAACT CCACTGCCGATCGTCGGACTGTAGAACTC | SEQ ID NO. 322 |
| Leu_TAA-1_32_L | /5Phos/AAGTCCAACGCCTTACCACTCGGC CATCCTGGTGATCGTCGGACTGTAGAACTC | SEQ ID NO. 323 |
| Leu_TAA-2_33_L | /5Phos/AAGTYTTATGCAATGCCGGCTCTG CCATCTTAACGATCGTCGGACTGTAGAACTC | SEQ ID NO. 324 |
| Leu_TAA-3_33_L | /5Phos/AAGTCCAATGCCTTACCACTCAGC CAAATGAGTGATCGTCGGACTGTAGAACTC | SEQ ID NO. 325 |
| Leu_TAG_32_L | /5Phos/AAATCCAGCGCCTTACCGCTCGGC CACGCTACCGATCGTCGGACTGTAGAACTC | SEQ ID NO. 326 |
| Lys_CTT-1_33_L | /5Phos/GAGTCTCAYGCTTTATCGACTGAG CTATTTGGTTGATCGTCGGACTGTAGAACTC | SEQ ID NO. 327 |
| Lys_CTT-2_33_L | /5Phos/GRGTCYYATGCTCTACCGACTGAG CTAGCCGGGCGATCGTCGGACTGTAGAACTC | SEQ ID NO. 328 |
| Lys_TTT-1_32_L | /5Phos/AAGTCYRATGCTCTACCGACTGAG CTATCCGGGCGATCGTCGGACTGTAGAACTC | SEQ ID NO. 329 |
| Lys_TTT-2_32_L | /5Phos/AAGTCYRATGCTCTACCTACTGAG CTACCCAGGTGATCGTCGGACTGTAGAACTC | SEQ ID NO. 330 |
| Met_CAT-1_33_L | /5Phos/GARACTGACGCGCTGCCTGCTGCG CTAAGAGGGCGATCGTCGGACTGTAGAACTC | SEQ ID NO. 331 |
| Met_CAT-2_32_L | /5Phos/GGGCCCAGYACGCTTCCGCTGCGC CACTCTGCTGATCGTCGGACTGTAGAACTC | SEQ ID NO. 332 |
| Phe_GAA_33_L | /5Phos/CRGTCTAACRCTCTCCCAACTGAG CTATTTCGGCGATCGTCGGACTGTAGAACTC | SEQ ID NO. 333 |
| Pro_AGG_32_L | /5Phos/TAAGCGAGAATCATACCCCTAGAC CAACGAGCCGATCGTCGGACTGTAGAACTC | SEQ ID NO. 334 |
| Pro_CGG_32_L | /5Phos/GAAGCGAGAATCATACCCCTAGAC CAACGAGCCGATCGTCGGACTGTAGAACTC | SEQ ID NO. 335 |
| Pro_TGG_32_L | /5Phos/AAAWCGAGAATCATACCCCTAGAC CAACGAGCCGATCGTCGGACTGTAGAACTC | SEQ ID NO. 336 |
| SeC(e)_TCA_35_L | /5Phos/AAGCCTGCACCCCAGACCACTGAG GATCATCCGGGCGATCGTCGGACTGTAGAAC TC | SEQ ID NO. 337 |
| SeC_TCA_33_L | /5Phos/AAGTCAGACACCTTTCCATTAGGC CACACGGTCGATCGTCGGACTGTAGAACTC | SEQ ID NO. 338 |
| Ser_AGA-1_33_L | /5Phos/TAGCTCGTTGCCTTACCACTCAGC TACAACTCAGATCGTCGGACTGTAGAACTC | SEQ ID NO. 339 |

TABLE 4-continued

Human DNA probes.
DNA probes to generate a tRNA profile in human cells. The DNA probes were designed by the methods disclosed herein.

| Name | Sequence | SEQ ID |
|---|---|---|
| Ser_AGA-2_32_L | /5Phos/TAGTCCATCGCCTTACCACTCGGCCACGACTACGATCGTCGGACTGTAGAACTC | SEQ ID NO. 340 |
| Ser_AGA-3_33_L | /5Phos/TCTAGTCAAATTCTCTACCCCTGAGCCATACACCCGATCGTCGGACTGTAGAACTC | SEQ ID NO. 341 |
| Ser_CGA_32_L | /5Phos/GAGTCCAACGCCTTACCACTCGGCCATCACAGCGATCGTCGGACTGTAGAACTC | SEQ ID NO. 342 |
| Ser_GCT_32_L | /5Phos/CAGTCCATCGCCTTACCACTCGGCCACCTCGTCGATCGTCGGACTGTAGAACTC | SEQ ID NO. 343 |
| Ser_TGA-1_32_L | /5Phos/AAGTCCATCGCCTTACCACTCGGCCACGACTACGATCGTCGGACTGTAGAACTC | SEQ ID NO. 344 |
| Ser_TGA-2_30_L | /5Phos/AAGCCAATCCCATACCTCTGTGACCTTCTCGATCGTCGGACTGTAGAACTC | SEQ ID NO. 345 |
| Thr_AGT_33_L | /5Phos/TAGACAGGYGCTTTACCAGCTAAGCCACGGCGCCGATCGTCGGACTGTAGAACTC | SEQ ID NO. 346 |
| Thr_CGT-1_32_L | /5Phos/GRGMCCAGCRCTCTTCCGCTGCGCTACTGTGCCGATCGTCGGACTGTAGAACTC | SEQ ID NO. 347 |
| Thr_CGT-2_33_L | /5Phos/GAGACMGRCGCTTTACCAACTTGGCCACCGCGCCGATCGTCGGACTGTAGAACTC | SEQ ID NO. 348 |
| Thr_TGT_33_L | /5Phos/AAGACMRGYGCTCTACCACCTGAGCTATGGAGCCGATCGTCGGACTGTAGAACTC | SEQ ID NO. 349 |
| Trp_CCA-1_34_L | /5Phos/GAGCCCACAGGCTTTCCAGCTTGGCCATCCTTCCGATCGTCGGACTGTAGAACTC | SEQ ID NO. 350 |
| Trp_CCA-2_32_L | /5Phos/GAGTCAGACGCGCTACCGTTGCGCCACGAGGTCGATCGTCGGACTGTAGAACTC | SEQ ID NO. 351 |
| Trp_CCA-3_33_L | /5Phos/GAGTCAGACGCGCTGCCGTTGCGCCACGAGGTCGATCGTCGGACTGTAGAACTC | SEQ ID NO. 352 |
| Tyr_ATA_34_L | /5Phos/TAGTCCTCTGCTCTACCAGCTGAACTATTGAAGGGATCGTCGGACTGTAGAACTC | SEQ ID NO. 353 |
| Tyr_GTA-1_33_L | /5Phos/CAGTCCTCCGCTCTACCAGCTGAGCTATCGAAGGGATCGTCGGACTGTAGAACTC | SEQ ID NO. 354 |
| Tyr_GTA-2_32_L | /5Phos/CAGTCAAAAGCTCTGCCCTGAGCTATACCCCCGATCGTCGGACTGTAGAACTC | SEQ ID NO. 355 |
| Val_AAC-1_33_L | /5Phos/TAGGTGAATGTGATACCAGTACACTATGGAAACGATCGTCGGACTGTAGAACTC | SEQ ID NO. 356 |
| Val_AAC-2_32_L | /5Phos/TAGGCRAACGTGATACCACTACACTACGGAAACGATCGTCGGACTGTAGAACTC | SEQ ID NO. 357 |
| Val_AAC-3_33_L | /5Phos/TAAGCATACGCTCTACCACTGAGCTACACCCCCGATCGTCGGACTGTAGAACTC | SEQ ID NO. 358 |
| Val_CAC-1_33_L | /5Phos/GTGAGRCKAACRTGATAACCACTACACTACAGAAACGATCGTCGGACTGTAGAACTC | SEQ ID NO. 359 |
| Val_CAC-2_32_L | /5Phos/GTGAGGCGAAYRTGATACCACTACACTACGGAAACGATCGTCGGACTGTAGAACTC | SEQ ID NO. 360 |
| Val_TAC-1_32_L | /5Phos/AARGCRRATGTGATACCACTACACTATGGAACCGATCGTCGGACTGTAGAACTC | SEQ ID NO. 361 |
| Val_TAC-2_32_L | /5Phos/AAAGCAGACGTGATACCACTACACTATGGAACCGATCGTCGGACTGTAGAACTC | SEQ ID NO. 362 |
| mAla-TGC_31_L | /5Phos/AAATCAGCCACTTTAATTAAGCTAAGCCCTTGATCGTCGGACTGTAGAACTC | SEQ ID NO. 363 |

TABLE 4-continued

Human DNA probes.
DNA probes to generate a tRNA profile in human cells. The DNA probes were designed by the methods disclosed herein.

| Name | Sequence | SEQ ID |
|---|---|---|
| mArg-TCG_31_L | /5Phos/AAATCATTCGTTTTGTTTAAACTATATACCAGATCGTCGGACTGTAGAACTC | SEQ ID NO. 364 |
| mAsn-GTT_34_L | /5Phos/CAGCTAAGCACCCTAATCAACTGGCTTCAATCTAGATCGTCGGACTGTAGAACTC | SEQ ID NO. 365 |
| mAsp-GTC_31_L | /5Phos/CAAAGTTATGAAATGGTTTTTCTAATACCTTGATCGTCGGACTGTAGAACTC | SEQ ID NO. 366 |
| mCys-GCA_29_L | /5Phos/CAATTCAATATGAAAATCACCTCGGAGCTGATCGTCGGACTGTAGAACTC | SEQ ID NO. 367 |
| mGlu-TTC_31_L | /5Phos/AAAACCATCGTTGTATTTCAACTACAAGAACGATCGTCGGACTGTAGAACTC | SEQ ID NO. 368 |
| mGln-TTG_34_L | /5Phos/AAATTCTCCGTGCCACCTATCACACCCCATCCTAGATCGTCGGACTGTAGAACTC | SEQ ID NO. 369 |
| mGly-TCC_31_L | /5Phos/AAGTTAACGGTACTATTTATACTAAAAGAGTGATCGTCGGACTGTAGAACTC | SEQ ID NO. 370 |
| mHis-GTG_31_L | /5Phos/CAATCTGATGTTTTGGTTAAACTATATTTACGATCGTCGGACTGTAGAACTC | SEQ ID NO. 371 |
| mIle-GAT_30_L | /5Phos/CAAAGTAACTCTTTTATCAGACATATTTCTGATCGTCGGACTGTAGAACTC | SEQ ID NO. 372 |
| mLeu-TAG_33_L | /5Phos/AAGACCAATGGATAGCTGTTATCCTTTAAAAGTGATCGTCGGACTGTAGAACTC | SEQ ID NO. 373 |
| mLeu-TAA_36_L | /5Phos/AAGTTTTATGCGATTACCGGGCTCTGCCATCTTAACGATCGTCGGACTGTAGAACTC | SEQ ID NO. 374 |
| mLys-TTT_28_L | /5Phos/AAGGTTAATGCTAAGTTAGCTTTACAGTGGATCGTCGGACTGTAGAACTC | SEQ ID NO. 375 |
| mMet-CAT_31_L | /5Phos/GGGCCCGATAGCTTATTTAGCTGACCTTACTGATCGTCGGACTGTAGAACTC | SEQ ID NO. 376 |
| mPhe-GAA_35_L | /5Phos/CAGTGTATTGCTTTGAGGAGGTAAGCTACATAAACGATCGTCGGACTGTAGAACTC | SEQ ID NO. 377 |
| mPro-TGG_32_L | /5Phos/AAAGCTAAGATTCTAATTTAAACTATTCTCTGGATCGTCGGACTGTAGAACTC | SEQ ID NO. 378 |
| mSer-GCT_20_L | /5Phos/CAGTTCTTGTGAGCTTTCTCGATCGTCGGACTGTAGAACTC | SEQ ID NO. 379 |
| mSer-TGA_31_L | /5Phos/AAGCCAACCCCATGGCCTCCATGACTTTTTCGATCGTCGGACTGTAGAACTC | SEQ ID NO. 380 |
| mThr-TGT_32_L | /5Phos/AAGACTGGTGTATTAGTTTATACTACAAGGACGATCGTCGGACTGTAGAACTC | SEQ ID NO. 381 |
| mTrp-TCA_33_L | /5Phos/AAGGCTCTTGGTCTGTATTTAACCTAAATTTCTGATCGTCGGACTGTAGAACTC | SEQ ID NO. 382 |
| mTyr-GTA_30_L | /5Phos/CAGTCCAATGCTTCACTCAGCCATTTTACCGATCGTCGGACTGTAGAACTC | SEQ ID NO. 383 |
| mVal-TAC_32_L | /5Phos/AAGTTGGGTGCTTTGTGTTAAGCTACACTCTGGATCGTCGGACTGTAGAACTC | SEQ ID NO. 384 |

REFERENCES

1 Begley, U., Dyavaiah, M., Patil, A., Rooney, J. P., DiRenzo, D., Young, C. M., Conklin, D. S., Zitomer, R. S., and Begley, T. J. (2007). Trm9-catalyzed tRNA modifications link translation to the DNA damage response. Molecular cell 28, 860-870.

2 Chan, C. T., Dyavaiah, M., DeMott, M. S., Taghizadeh, K., Dedon, P. C., and Begley, T. J. (2010). A quantitative systems approach reveals dynamic control of tRNA modifications during cellular stress. Plos Genet 6, e1001247.

3. Coller, J., and Parker, R. (2005). General translational repression by activators of mRNA decapping. Cell 122, 875-886.

4. Comeron, J. M. (2004). Selective and mutational patterns associated with gene expression in humans: influences on synonymous composition and intron presence. Genetics 167, 1293-1304.
5. Dever, T. E., and Green, R. (2012). The elongation, termination, and recycling phases of translation in eukaryotes. Cold Spring Harbor perspectives in biology 4, a013706.
6. Dittmar, K. A., Goodenbour, J. M., and Pan, T. (2006). Tissue-specific differences in human transfer RNA expression. Plos Genet 2, e221.
7. dos Reis, M., Savva, R., and Wernisch, L. (2004). Solving the riddle of codon usage preferences: a test for translational selection. Nucleic acids research 32, 5036-5044.
8. Drummond, D. A., and Wilke, C. O. (2008). Mistranslation-induced protein misfolding as a dominant constraint on coding-sequence evolution. Cell 134, 341-352.
9. Fredrick, K., and Ibba, M. (2010). How the Sequence of a Gene Can Tune Its Translation. Cell 141, 227-229.
10. Gingold, H., Tehler, D., Christoffersen, N. R., Nielsen, M. M., Asmar, F., Kooistra, S. M., Christophersen, N. S., Christensen, L. L., Borre, M., Sorensen, K. D., et al. (2014). A dual program for translation regulation in cellular proliferation and differentiation. Cell 158, 1281-1292.
11. Goodarzi, H., Elemento, O., and Tavazoie, S. (2009). Revealing global regulatory perturbations across human cancers. Molecular cell 36, 900-911.
12. Gustafsson, C., Govindarajan, S., and Minshull, J. (2004). Codon bias and heterologous protein expression. Trends Biotechnol 22, 346-353.
13. Han, K., Jaimovich, A., Dey, G., Ruggero, D., Meyuhas, O., Sonenberg, N., and Meyer, T. (2014). Parallel measurement of dynamic changes in translation rates in single cells. Nat Methods 11, 86-93.
14. Huch, S., and Nissan, T. (2014). Interrelations between translation and general mRNA degradation in yeast. Wiley Interdiscip Rev RNA 5, 747-763.
15. Ingolia, N. T., Brar, G. A., Stern-Ginossar, N., Harris, M. S., Talhouarne, G. J., Jackson, S. E., Wills, M. R., and Weissman, J. S. (2014). Ribosome profiling reveals pervasive translation outside of annotated protein-coding genes. Cell Rep 8, 1365-1379.
16. Kirchner, S., and Ignatova, Z. (2015). Emerging roles of tRNA in adaptive translation, signalling dynamics and disease. Nature reviews Genetics 16, 98-112.
17. Lee, J. W., Beebe, K., Nangle, L. A., Jang, J., Longo-Guess, C. M., Cook, S. A., Davisson, M. T., Sundberg, J. P., Schimmel, P., and Ackerman, S. L. (2006). Editing-defective tRNA synthetase causes protein misfolding and neurodegeneration. Nature 443, 50-55.
18. Li, G. W., Burkhardt, D., Gross, C., and Weissman, J. S. (2014). Quantifying absolute protein synthesis rates reveals principles underlying allocation of cellular resources. Cell 157, 624-635.
19. Minn, A. J., Gupta, G. P., Siegel, P. M., Bos, P. D., Shu, W., Giri, D. D., Viale, A., Olshen, A. B., Gerald, W. L., and Massague, J. (2005). Genes that mediate breast cancer metastasis to lung. Nature 436, 518524.
20. Muhlrad, D., Decker, C. J., and Parker, R. (1995). Turnover mechanisms of the stable yeast PGK1 mRNA. Molecular and cellular biology 15, 2145-2156.
21. Nilsson, M., Barbany, G., Antson, D. O., Gertow, K., and Landegren, U. (2000). Enhanced detection and distinction of RNA by enzymatic probe ligation. Nature biotechnology 18, 791-793.
22. Novoa, E. M., and de Pouplana, L. R. (2012). Speeding with control: codon usage, tRNAs, and ribosomes. Trends Genet 28, 574-581.
23. Novoa, E. M., Pavon-Eternod, M., Pan, T., and Ribas de Pouplana, L. (2012). A role for tRNA modifications in genome structure and codon usage. Cell 149, 202-213.
24. Ong, S. E., Kratchmarova, I., and Mann, M. (2003). Properties of 13C-substituted arginine in stable isotope labeling by amino acids in cell culture (SILAC). Journal of proteome research 2, 173-181.
25. Pavon-Eternod, M., Gomes, S., Geslain, R., Dai, Q., Rosner, M. R., and Pan, T. (2009). tRNA over-expression in breast cancer and functional consequences. Nucleic acids research 37, 7268-7280.
26. Plotkin, J. B., and Kudla, G. (2011). Synonymous but not the same: the causes and consequences of codon bias. Nature reviews Genetics 12, 32-42.
27. Pop, C., Rouskin, S., Ingolia, N. T., Han, L., Phizicky, E. M., Weissman, J. S., and Koller, D. (2014). Causal signals between codon bias, mRNA structure, and the efficiency of translation and elongation. Mol Syst Biol 10, 770.
28. Presnyak, V., Alhusaini, N., Chen, Y. H., Martin, S., Morris, N., Kline, N., Olson, S., Weinberg, D., Baker, K. E., Graveley, B. R., et al. (2015). Codon optimality is a major determinant of mRNA stability. Cell 160, 1111-1124.
29. Qian, W., Yang, J. R., Pearson, N. M., Maclean, C., and Zhang, J. (2012). Balanced codon usage optimizes eukaryotic translational efficiency. Plos Genet 8, e1002603.
30. Shah, P., and Gilchrist, M. A. (2011). Explaining complex codon usage patterns with selection for translational efficiency, mutation bias, and genetic drift. Proceedings of the National Academy of Sciences of the United States of America 108, 10231-10236.
31. Subramaniam, A. R., Pan, T., and Cluzel, P. (2013). Environmental perturbations lift the degeneracy of the genetic code to regulate protein levels in bacteria. Proceedings of the National Academy of Sciences of the United States of America 110, 2419-2424.
32. Tavazoie, S. F., Alarcon, C., Oskarsson, T., Padua, D., Wang, Q., Bos, P. D., Gerald, W. L., and Massague, J. (2008). Endogenous human microRNAs that suppress breast cancer metastasis. Nature 451, 147-152.
33. Zhang, G., and Ignatova, Z. (2011). Folding at the birth of the nascent chain: coordinating translation with co-translational folding. Curr Opin Struc Biol 21, 25-31.
34. Zheng, G., Qin, Y., Clark, W. C., Dai, Q., Yi, C., He, C., Lambowitz, A. M., and Pan, T. (2015). Efficient and quantitative high-throughput tRNA sequencing. Nat Methods 12, 835-837.
35. Zouridis, H., and Hatzimanikatis, V. (2008). Effects of codon distributions and tRNA competition on protein translation. Biophys J 95, 1018-1033.
36. Cox, J., Hein, M. Y., Luber, C. A., Paron, I., Nagaraj, N., and Mann, M. (2014). Accurate proteome-wide label-free quantification by delayed normalization and maximal peptide ratio extraction, termed MaxLFQ. Molecular & cellular proteomics: MCP 13, 2513-2526.
37. Goodarzi, H., Zhang, S., Buss, C. G., Fish, L., Tavazoie, S., and Tavazoie, S. F. (2014). Metastasis-suppressor transcript destabilization through TARBP2 binding of mRNA hairpins. Nature 513, 256260.
38. Ishihama, Y., Rappsilber, J., and Mann, M. (2006). Modular stop and go extraction tips with stacked disks for parallel and multidimensional Peptide fractionation in proteomics. Journal of proteome research 5, 988-994.

39. Png, K. J., Halberg, N., Yoshida, M., and Tavazoie, S. F. (2012). A microRNA regulon that mediates endothelial recruitment and metastasis by cancer cells. Nature 481, 190-194.
40. Wisniewski, J. R., Zougman, A., and Mann, M. (2009). Combination of FASP and StageTip-based fractionation allows in-depth analysis of the hippocampal membrane proteome. Journal of proteome research 8, 5674-5678

INCORPORATION OF SEQUENCE LISTING

Incorporated herein by reference in its entirety is the Sequence Listing for the application. The Sequence Listing is disclosed on a computer-readable ASCII text file titled, "1119-43_Updated_Sequence_Listing.txt", created on Nov. 19, 2018. The sequence-listing.txt file is 74.1 KB in size.

The invention claimed is:

1. A method for creating a tRNA profile of a cell, said method comprising:
   a) removing RNA from said cell,
   b) hybridizing said RNA with a plurality of DNA probes specific for a portion of tRNA to form DNA/tRNA hybrids, wherein two DNA probes collectively hybridize to the full length of the tRNA, and wherein said probes each hybridize to at least one ribonucleotide of the anticodon of said tRNA,
   c) ligating the DNA of said hybrids,
   d) digesting the tRNA from said ligated hybrids to form ligated DNA,
   e) sequencing said ligated DNA to obtain sequences that correlate to the tRNA present in the cell, and
   f) analyzing said sequences to identify the amount of each tRNA in said cell.

2. The method of claim 1, wherein said method further comprises deacylating said RNA removed from the cell.

3. The method of claim 2, wherein said method further comprises tagging said deacylated RNA.

4. The method of claim 3, wherein said tagging comprises biotinylating said deacylated RNA.

5. The method of claim 3, wherein said method further comprises purifying said tagged RNA.

6. The method of claim 3, wherein said method further comprises isolating said DNA/tRNA hybrids by binding said tagged RNA.

7. The method according to claim 6, wherein said RNA is tagged with biotin and wherein said isolating step comprises binding said biotinylated RNA to streptavidin beads.

8. The method according to claim 1, wherein said removing step comprises isolating short RNA.

9. The method according to claim 1, wherein said method comprises isolating tRNA.

10. A method for optimizing cell-type specific protein expression, said method comprising:
    a) removing RNA from a source cell of said protein,
    b) hybridizing said RNA with a plurality of DNA probes specific for a portion of tRNA to form DNA/tRNA hybrids, wherein two DNA probes collectively hybridize to the full length of the tRNA, and wherein said probes each hybridize to at least one ribonucleotide of the anticodon of said tRNA, c) ligating the DNA of said hybrids, d) digesting the tRNA from said ligated hybrids to form ligated DNA, e) sequencing said ligated DNA to obtain sequences that correlate to the tRNA present in the cell, f) repeating steps a-e for a destination cell in which the protein is to be expressed, g) analyzing said sequences to identify tRNAs that are present in an amount at least as abundant in said destination cell compared to said source cell, and h) engineering a polynucleotide sequence for the expression of said protein in said destination cell, wherein said engineering excludes codons that correlate to anticodons of tRNAs in the destination cell that are present in an amount that is less than in said source cell.

11. The method of claim 1, wherein said method further comprises deacylating said RNA removed from the cell.

12. The method of claim 11, wherein said method further comprises tagging said deacylated RNA.

13. The method of claim 12, wherein said tagging comprises biotinylating said deacylated RNA.

14. The method of claim 12, wherein said method further comprises purifying said tagged RNA.

15. The method of claim 12, wherein said method further comprises isolating said DNA/tRNA hybrids by binding said tagged RNA.

16. The method according to claim 15, wherein said RNA is tagged with biotin and wherein said isolating step comprises binding said biotinylated RNA to streptavidin beads.

17. The method according to claim 10, wherein said removing step comprises isolating short RNA.

18. The method according to claim 10, wherein said removing step comprises isolating tRNA.

19. The method according to claim 10, further comprising engineering the polynucleotide to maximize the codons that correlate to anticodons of the most abundant tRNAs present in the destination cell for each amino acid.

* * * * *

UNITED STATES PATENT AND TRADEMARK OFFICE
CERTIFICATE OF CORRECTION

PATENT NO. : 10,337,065 B2
APPLICATION NO. : 15/487192
DATED : July 2, 2019
INVENTOR(S) : Sohail Tavazoie and Hani Goodarzi It is certified that error appears in the above-identified patent and that said Letters Patent is hereby corrected as shown below:

In the Specification

Column 4, Line 15:
Now reads: "(5A) EXSOC2"
Should read: --"(5A) EXOSC2"--

Column 15, Line 56:
Now reads: "make 2λ washing buffer"
Should read: --make 2X washing buffer--

Column 19, Line 50:
Now reads: "tRNA$^{Glu}_{YUC}$"
Should read: --tRNA$^{Glu}_{UUC}$--

Column 26, Line 63:
Now reads: "using MINELUTE RNEASY Kit"
Should read: --using RNEASY MINELUTE Kit--

Signed and Sealed this
Twenty-third Day of June, 2020

Andrei Iancu
*Director of the United States Patent and Trademark Office*